(12) United States Patent
Chen et al.

(10) Patent No.: US 8,288,373 B2
(45) Date of Patent: Oct. 16, 2012

(54) MODULATORS OF CXCR7

(75) Inventors: Xi Chen, Palo Alto, CA (US); Pingchen Fan, Fremont, CA (US); Mark M. Gleason, Redwood City, CA (US); Juan C. Jaen, Burlingame, CA (US); Lianfa Li, Palo Alto, CA (US); Jeffrey P. McMahon, Mountain View, CA (US); Jay Powers, Pacifica, CA (US); Yibin Zeng, Foster City, CA (US); Penglie Zhang, Foster City, CA (US)

(73) Assignee: Chemocentryx, Inc., Mountain View, CA (US)

( * ) Notice: Subject to any disclaimer, the term of this patent is extended or adjusted under 35 U.S.C. 154(b) by 171 days.

(21) Appl. No.: 12/612,638

(22) Filed: Nov. 4, 2009

(65) Prior Publication Data
US 2010/0150831 A1 Jun. 17, 2010

Related U.S. Application Data

(60) Provisional application No. 61/219,341, filed on Jun. 22, 2009, provisional application No. 61/111,251, filed on Nov. 4, 2008.

(51) Int. Cl.
*A61K 31/497* (2006.01)
*C07D 403/00* (2006.01)
(52) U.S. Cl. ......................................... 514/218; 540/575
(58) Field of Classification Search .................. 540/575; 514/218
See application file for complete search history.

(56) References Cited

U.S. PATENT DOCUMENTS

| | | | |
|---|---|---|---|
| 3,920,636 A * | 11/1975 | Takahashi et al. | 540/575 |
| 6,225,312 B1 * | 5/2001 | Feenstra et al. | 514/230.5 |
| 7,557,213 B2 | 7/2009 | Melikian et al. | |
| 2005/0074826 A1 | 4/2005 | Burns et al. | |
| 2005/0214287 A1 | 9/2005 | Burns et al. | |
| 2006/0069102 A1 | 3/2006 | Leban et al. | |
| 2006/0247253 A1 | 11/2006 | Leban et al. | |
| 2007/0254886 A1 | 11/2007 | Habashita et al. | |
| 2007/0275965 A1 | 11/2007 | Thomas et al. | |
| 2010/0150831 A1 | 6/2010 | Chen et al. | |

FOREIGN PATENT DOCUMENTS

| | | |
|---|---|---|
| AU | 2006-230674 A1 | 11/2006 |
| WO | WO 02/08221 A2 | 1/2002 |
| WO | WO 03/076400 A1 | 9/2003 |
| WO | WO 2004/009587 A1 | 1/2004 |
| WO | WO 2005/074535 A2 | 8/2005 |
| WO | WO 2007/126935 A2 | 11/2007 |
| WO | WO 2008/008518 A1 | 1/2008 |
| WO | 2008/112156 A1 | 9/2008 |

OTHER PUBLICATIONS

Konishi et al. (Yakugaku Zasshi (1973), 93(5), 684-7). Abstract.*
Miao et al., "CXCR7 (RDC1) promotes breast and lung tumor growth in vivo and is expressed on tumor-associated vasculature," 2007, PNAS, vol. 104., No. 40, pp. 15735-15740.
Zabel et al., "Elucidation of CXCR-7-Mediated Signaling Events and Inhibition of CXCR4-Mediated Tumor Cell Transendothelial Migration by CXCR7 Ligands," The Journal of Immunology, 2009, vol. 183, Issue 5, pp. 3204-3211.
International Search Report mailed on Jan. 27, 2010, for International Application No. PCT/US09/63298 filed on Nov. 4, 2009, 1 page.
Supplementary European Search Report, date May 31, 2012, EP Application No. 09 82 5370, 4 pages.

* cited by examiner

*Primary Examiner* — Bruck Kifle
(74) *Attorney, Agent, or Firm* — Kilpatrick Townsend & Stockton LLP

(57) ABSTRACT

Compounds having formula I,

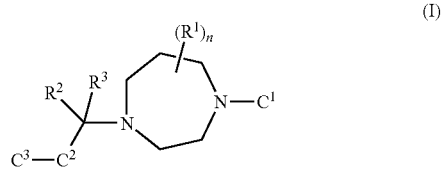

or pharmaceutically acceptable salts, hydrates or N-oxides thereof are provided and are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

42 Claims, 41 Drawing Sheets

| Structure | Avg Bind IC50 (nM) | Structure | Avg Bind IC50 (nM) |
|---|---|---|---|
| 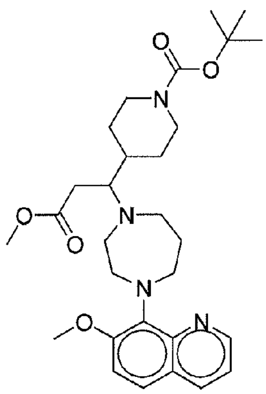 | ++ | 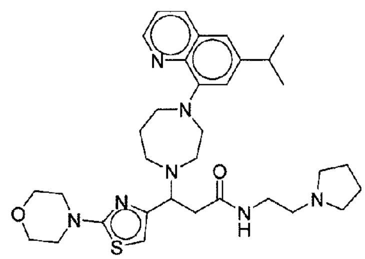 | +++ |
|  | +++ |  | +++ |
|  | +++ |  | +++ |
|  | +++ |  | +++ |

| Structure | Avg Bind IC50 (nM) | Structure | Avg Bind IC50 (nM) |
|---|---|---|---|
|  | ++ |  | ++ |
|  | ++ |  | +++ |
|  | ++ |  | ++ |
| 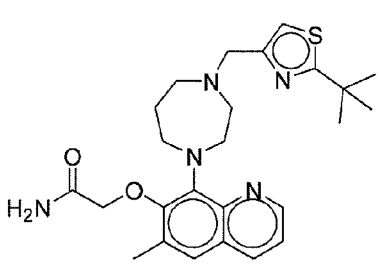 | +++ | 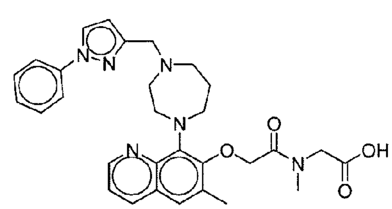 | +++ |

FIG. 2L

| Structure | Avg Bind IC50 (nM) | Structure | Avg Bind IC50 (nM) |
|---|---|---|---|
| | +++ | | + |
| | +++ | | +++ |
| | +++ | | +++ |
| 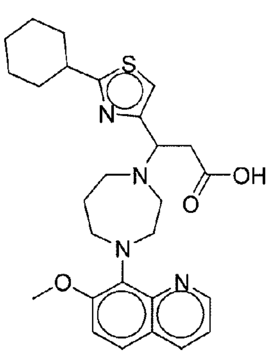 | ++ | 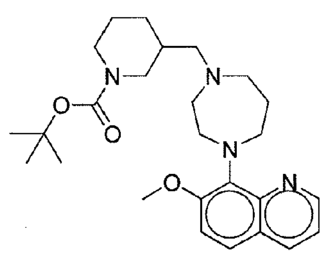 | ++ |

| Structure | Avg Bind IC50 (nM) | Structure | Avg Bind IC50 (nM) |
|---|---|---|---|
|  | +++ |  | +++ |
| 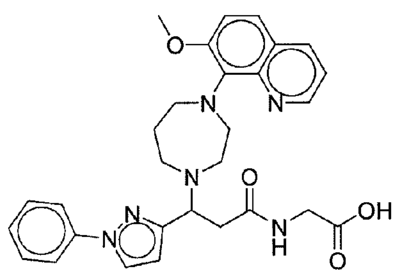 | ++ | 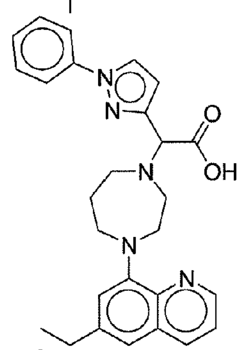 | +++ |
|  | +++ |  | +++ |
|  | +++ |  | +++ |

FIG. 2O

| Structure | Avg Bind IC50 (nM) | Structure | Avg Bind IC50 (nM) |
|---|---|---|---|
| 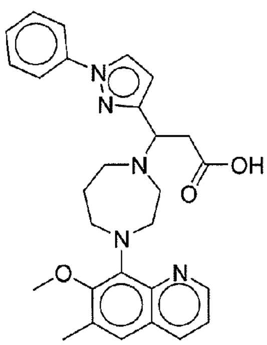 | ++ | 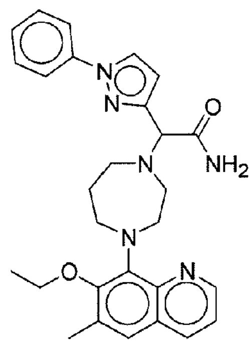 | +++ |
|  | +++ |  | +++ |
|  | +++ |  | +++ |

| Structure | Avg Bind IC50 (nM) | Structure | Avg Bind IC50 (nM) |
|---|---|---|---|
|  | +++ |  | +++ |
|  | +++ |  | ++ |
|  | +++ |  | +++ |

| Structure | Avg Bind IC50 (nM) | Structure | Avg Bind IC50 (nM) |
|---|---|---|---|
|  | +++ |  | +++ |
|  | +++ |  | +++ |
|  | +++ |  | +++ |

| stucture | Avg Bind IC50 (nM) | stucture | Avg Bind IC50 (nM) |
|---|---|---|---|
| | + | | + |
| | +++ | | ++ |
| | ++ | | ++ |
| | +++ | | +++ |
| | + | | +++ |

| stucture | Avg Bind IC50 (nM) | stucture | Avg Bind IC50 (nM) |
|---|---|---|---|
|  | +++ |  | +++ |
|  | + |  | +++ |
|  | +++ |  | +++ |
|  | ++ |  | +++ |
|  | ++ |  | +++ |

| stucture | Avg Bind IC50 (nM) | stucture | Avg Bind IC50 (nM) |
|---|---|---|---|
|  | + |  | +++ |
|  | +++ |  | +++ |
|  | + |  | +++ |
|  | +++ |  | +++ |
|  | +++ |  | +++ |

FIG. 3F

| stucture | Avg Bind IC50 (nM) | stucture | Avg Bind IC50 (nM) |
|---|---|---|---|
| | +++ | | +++ |
| | +++ | | +++ |
| | +++ | | +++ |
| | ++ | | +++ |
| | +++ | | +++ |

| stucture | Avg Bind IC50 (nM) | stucture | Avg Bind IC50 (nM) |
|---|---|---|---|
|  | +++ |  |  |

MODULATORS OF CXCR7

CROSS-REFERENCES TO RELATED APPLICATIONS

This application claims the benefit of U.S. Provisional applications Ser. Nos. 61/111,251, filed Nov. 4, 2008 and 61/219,341, filed Jun. 22, 2009, the disclosures of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Attached below.

BACKGROUND OF THE INVENTION

The present invention is directed to novel compounds and pharmaceutical compositions that inhibit the binding of the SDF-1 chemokine (also known as the CXCL12 chemokine) or I-TAC (also known as CXCL11) to the chemokine receptor CXCR7. These compounds are useful in preventing tumor cell proliferation, tumor formation, tumor vascularization, metastasis, inflammatory diseases including, but not limited to arthritis, renal inflammatory disorders and multiple sclerosis, conditions of improper vascularization including, but not limited to wound healing, treatment of HIV infectivity, and treatment of stem cell differentiation and mobilization disorders (see also, co-pending U.S. Ser. No. 10/912,638 and 11/050,345).

Chemokines are a superfamily of small, cytokine-like proteins that induce cytoskeletal rearrangement, firm adhesion to endothelial cells, and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CXCR7, may also be a target in the treatment of cancer. CXCR7 is preferentially expressed in transformed cells over normal cells, with detectable expression in a number of human cancers. In vitro studies indicate that proliferation of CXCR7 expressing cells can be inhibited by an antagonist of CXCR7. In vivo studies in mice indicate that CXCR7 antagonists can inhibit tumor formation and tumor growth.

The potential importance of CXCR7 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both CXCR4 and CXCR7. SDF-1 is the only ligand for CXCR4. SDF-1 and I-TAC both bind CXCR7. Using anti-SDF-1 antibody, it has now been shown that antagonists of CXCR7 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. As a result, CXCR7 is the likely target, as the continued activity appears due to the interactions of the second ligand, I-TAC, with CXCR7.

Until recently, the possible importance of CXCR7 in tumor cell proliferation, tumor growth, and metastasis was unknown. Now, recent evidence points to the ability of certain CXCR7 antagonists to prevent the growth and spread of cancer, and expression patterns indicate a limited tissue distribution for the CXCR7 receptor which correlates to tumorigenesis.

Moreover, recently it has been discovered that CXCR7 can serve as a co-receptor for certain genetically divergent human immunodeficiency virus (HIV) and simian immunodeficiency virus (SIV), in particular for the HIV-2-ROD, an X4-tropic isolate (Shimizu, N. et al., *J. Virol.*, (2000) 74: 619-626; Balabanian, K., et al., *J. Biol. Chem.*, in press; published on Aug. 17, 2005 as Manuscript M508234200).

Still further, SDF-1, has been described to have a role in the mobilization of hematopoietic progenitor cells and stem cells, and in particular of those cells bearing the CXCR4 receptor, from specific hematopoietic tissues including bone marrow has been described (Hattori, K., et al., *Blood*, (2000) 97:3354-3360; WO 2005/000333, the disclosure of which are incorporated herein by reference). More recent studies suggest that the CXCR7 receptor may also play a part in stem cell mobilization processes.

In view of the above, it is apparent that compounds that are able to bind specifically to CXCR7 receptors can be useful for treating diseases and other biological conditions that may benefit from such interactions. The present invention provides such compounds along with pharmaceutical compositions and related methods for treatment.

BRIEF SUMMARY OF THE INVENTION

The present invention provides, in one aspect, compounds having formula I,

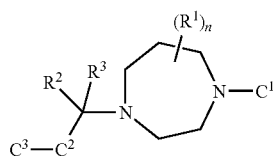

or pharmaceutically acceptable salts, hydrates or N-oxides thereof. The various groups (e.g., $R^1$, $R^2$, $R^3$, $C^1$, $C^2$, $C^3$ and the subscript n) are described in the Detailed Description of the Invention.

The compounds provided herein are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

In still another aspect, the present invention provides methods for treating various diseases, discussed further herein, comprising administering to a subject in need to such treatment a therapeutically effective amount of a compound of the above formula for a period of time sufficient to treat the disease.

In yet another aspect, the present invention provides methods of diagnosing disease in an individual. In these methods, the compounds provided herein are administered in labeled form to a subject, followed by diagnostic imaging to determine the presence or absence of CXCR7. In a related aspect, a method of diagnosing disease is carried out by contacting a tissue or blood sample with a labeled compound as provided herein and determining the presence, absence, or amount of CXCR7 in the sample.

BRIEF DESCRIPTION OF THE DRAWINGS

FIGS. 1A-1I, 2A-2X and 3A-3H provide structures and activity for compounds of the invention prepared by methods illustrated in the Examples or by methods related to those in the Examples.

DETAILED DESCRIPTION OF THE INVENTION

I. Abbreviation and Definitions

Figure 1A:
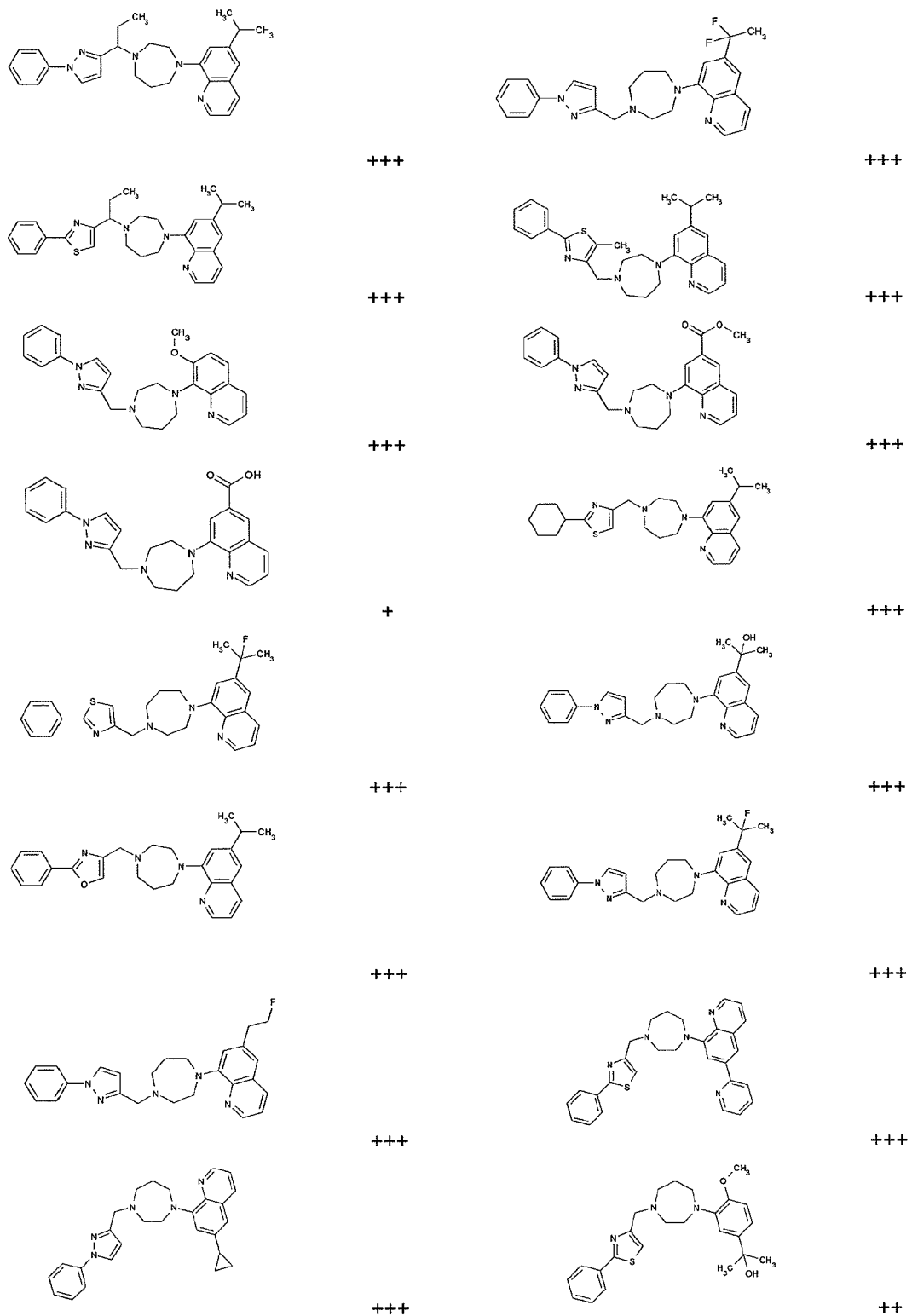

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "〜〜〜", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$R^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroarylalkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R'—NR'—C(O)NR"R'", —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

As used herein, the term "progenitor cells" and "stem cells" are used interchangeably. "Progenitor cells" and "stem cells" refer to cells that, in response to certain stimuli, can form differentiated cell lineages, including but not limited to hematopoietic, mesenchymal, epithelial or myeloid cells. The presence of progenitor/stem cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols. Hematopoetic progenitor/stem cells are often positive for CD34. Some stem cells do not contain this marker, however. These CD34+ cells can be assayed using fluorescence activated cell sorting (FACS) and thus their presence can be assessed in a sample using this technique. Alternatively, such cells can be assayed by FACS for the presence of c-kit receptor (CD117), absence of lineage specific markers (e.g., CD2, CD3, CD4, CD5, CD8, NK1.1, B220, TER-119, and Gr-1 in mice and CD3, CD14, CD16, CD19, CD20 and CD56 in humans).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical fauns are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the invention are present in an enantiomerically enriched form, wherein the amount of enantiomeric excess for a particular enantiomer is calculated by known methods. The preparation of enantiomerically enriched forms is also well known in the art and can be accomplished using, for example, chiral resolution via chromatography or via chiral salt formation. Still further, the compounds of the present invention may also contain unnatural proportions of atomic isotopes at one or more of the atoms that constitute such compounds. Accordingly, in some embodiments, the compounds of the invention are present in isotopically enriched form. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"CXCR7" also referred to as "RDC1" or "CCXCKR2" refers to a seven-transmembrane domain presumed G-protein coupled receptor (GPCR). The CXCR7 dog ortholog was originally identified in 1991. See, Libert et al. *Science* 244: 569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide. "CXCR7" includes sequences that are substantially similar to or conservatively modified variants of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

II. General

Compounds of the present invention can inhibit the binding of ligands to the CXCR7 receptor and are useful in the treatment of various diseases, including cancer, particularly solid tumor cancers and lymphomas. More recently, the inhibition of ligand binding to CXCR7 was noted to reduce the severity of rheumatoid arthritis in an animal model.

III. Embodiments of the Invention

A. Compounds

The present invention provides, in one aspect, compounds having formula I,

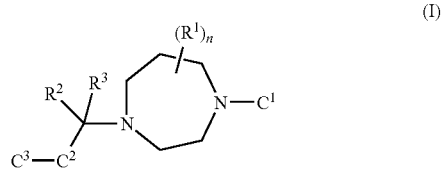

or pharmaceutically acceptable salts, hydrates or N-oxides thereof, wherein the subscript n is an integer of from 0 to 2; each $R^1$, when present, is independently selected from $C_{1-4}$ alkyl, —$CO_2R^a$, —X—$CO_2R^a$, —$CONR^aR^b$ and —X—$CONR^aR^b$; and $R^2$ and $R^3$ are each members independently selected from H, —$R^a$, —$XR^a$, —$XNR^aR^b$, —XNH-$CONR^aR^b$, —$XNHCOR^a$, —X—O—$CONR^aR^b$, —$XNHSO_2R^a$, —$CO_2R^a$, —X—$CO_2R^a$, —$CONR^aR^b$ and —X—$CONR^aR^b$, or taken together are oxo.

Additionally, $C^1$ is a member selected from the group consisting of monocyclic or fused-bicyclic aryl and heteroaryl, wherein the heteroaryl group has from 1-3 heteroatoms as ring members selected from N, O and S; and wherein said aryl and heteroaryl groups are optionally substituted with from 1 to 3 $R^4$ substituents;

$C^2$ is a monocyclic four-, five-, six- or seven-membered ring selected from the group consisting of benzene, heteroaromatic, cycloalkane, and heterocycloalkane, wherein the heteroaromatic and heterocycloalkane rings have from 1-3 heteroatoms as ring members selected from N, O and S; and wherein each of said monocyclic $C^2$ rings are optionally substituted with from 1 to 3 $R^5$ substituents;

$C^3$ is a member selected from the group consisting of hydrogen, $C_{1-8}$ alkyl, $C_{3-8}$ cycloalkyl, aryl, aryl-$C_{1-4}$ alkyl, heteroaryl, heteroaryl-$C_{1-4}$ alkyl, and four- to six-membered heterocycloalkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^6$ substituents;

each $R^4$ is independently selected from the group consisting of halogen, —CN, —NO$_2$, —$R^e$, —CO$_2$$R^a$, —NR$^a$R$^b$, —OR$^a$, —X—CO$_2$R$^a$, —CONR$^a$R$^b$ and —X—CONR$^a$R$^b$;

and within each of $R^1$, $R^2$, $R^3$ and $R^4$, each $R^a$ and $R^b$ is independently selected from hydrogen, $C_{1-8}$ alkyl, $C_{3-7}$ cycloalkyl, $C_{1-8}$haloalkyl, and four- to six-membered heterocycloalkyl, or when attached to the same nitrogen atom can be combined with the nitrogen atom to form a four-, five- or six-membered ring having from 0 to 2 additional heteroatoms as ring members selected from N, O or S; each $R^c$ is independently selected from the group consisting of $C_{1-8}$ alkyl, $C_{1-8}$haloalkyl, $C_{3-6}$ cycloalkyl, aryl and heteroaryl, and wherein the aliphatic and cyclic portions of $R^a$, $R^b$ and $R^c$ are optionally further substituted with from one to three halogen, hydroxy, methyl, alkoxy, amino, alkylamino, dialkylamino, carboxamide, carboxy alkyl ester, carboxylic acid, heteroaryl, and four- to six-membered heterocycloalkyl groups; and wherein the heterocycloalkyl portions of $R^2$, $R^3$, and $R^4$ are optionally substituted with oxo; and optionally when two $R^4$ substituents are on adjacent atoms, are combined to form a fused five or six-membered ring having carbon and oxygen atoms as ring members;

each $R^5$ is independently selected from the group consisting of halogen, —CN, —NO$_2$, —$R^f$, —CO$_2$$R^d$, —COR$^d$, —NR$^d$R$^e$, —OR$^d$, —X—CO$_2$R$^d$, —CONR$^d$R$^e$ and —X—CONR$^d$R$^e$; wherein each $R^d$ and $R^e$ is independently selected from hydrogen, $C_{1-8}$ alkyl, $C_{1-8}$ haloalkyl, $C_{3-6}$ cycloalkyl, $C_{3-6}$ cycloalkylalkyl, and four- to six-membered heterocycloalkyl or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, and $C_{3-6}$ cycloalkyl, and wherein the aliphatic and cyclic portions of $R^d$, $R^e$ and $R^f$ are optionally further substituted with from one to three halogen, hydroxy, methyl, alkoxy, amino, alkylamino, dialkylamino, carboxamide, carboxy alkyl ester, carboxylic acid, heteroaryl, four- to six-membered heterocycloalkyl groups;

each $R^6$ is independently selected from the group consisting of halogen, —CN, —NO$_2$, —$R^i$, —CO$_2$R$^g$, —COR$^g$, —NR$^g$R$^h$, —X—CO$_2$R$^g$, —X—COR$^g$, —CONR$^g$R$^h$ and —X—CONR$^g$R$^h$, wherein each $R^g$ and $R^h$ is independently selected from hydrogen, $C_{1-8}$ alkyl and $C_{1-8}$ haloalkyl; each $R^i$ is independently selected from the group consisting of $C_{1-8}$ alkyl and $C_{1-8}$ haloalkyl; and each X is a $C_{1-4}$ alkylene linking group or a linking group having the formula —(CH$_2$)$_m$O(CH$_2$)$_p$—, wherein the subscripts m and p are independently integers of from 0 to 5, and m+p is from 0 to 6, wherein the alkylene or methylene groups are optionally substituted with one or two methyl groups. In one group of embodiments, each X is independently selected from —OCH$_2$—, —OCH$_2$CH$_2$—, —OCH$_2$CH$_2$CH$_2$—, —OC(CH$_3$)$_2$—, —OCH$_2$C(CH$_3$)$_2$—, —OCH$_2$CH$_2$C(CH$_3$)$_2$—, —CH$_2$—, —C(CH$_3$)$_2$— and —CH$_2$CH$_2$—. In another group of embodiments, each X is selected from —O—, —CH$_2$—, —OCH$_2$—, —OCH$_2$CH$_2$—, —C(CH$_3$)$_2$— and —CH$_2$CH$_2$—.

A number of embodiments are provided in the present invention.

(A) In one group of embodiments, $C^1$ is phenyl, optionally substituted with from 1 to 3 $R^4$ substituents. In another group of embodiments, $C^1$ is pyridyl, optionally substituted with from 1 to 3 $R^4$ substituents. In still another group of embodiments, $C^1$ is naphthyl, optionally substituted with from 1 to 3 $R^4$ substituents. In yet another group of embodiments, $C^1$ is a fused-bicyclic heteroaryl selected from the group consisting of quinolinyl, benzofuranyl and benzopyrazolyl, optionally substituted with from 1 to 3 $R^4$ substituents.

Within any of the embodiments provided in (A) or with reference to formula I, are other selected embodiments.

(B) In one group of embodiments, $C^2$ is a monocyclic five-membered heteroaromatic ring selected from the group consisting of thiazole, triazole, imidazole, pyrazole and oxazole, each of which is optionally substituted with from 1 to 3 $R^5$ substituents. In other embodiments, $C^2$ is selected from the group consisting of cyclobutane, cyclopentane, cyclohexane, cycloheptane, azetidine, pyrrolidine and piperidine, each of which is optionally substituted with from 1 to 3 $R^5$ substituents. In still other embodiments, $C^2$ is selected from the group consisting of benzene and pyridine, each of which is optionally substituted with from 1 to 3 $R^5$ substituents.

Within any of the embodiments provided in (A), (B) or with reference to formula I, are still other selected embodiments.

(C) In one group of embodiments, $C^3$ is selected from the group consisting of $C_{1-8}$ alkyl and $C_{3-8}$ cycloalkyl, each of which is optionally substituted with from 1 to 3 $R^6$ substituents. In other embodiments, $C^3$ is selected from the group consisting of phenyl and phenyl-$C_{1-4}$ alkyl, each of which is optionally substituted with from 1 to 3 $R^6$ substituents. In still other embodiments, $C^3$ is heteroaryl, which is optionally substituted with from 1 to 3 $R^6$ substituents. In yet other embodiments, $C^3$ is a four- to six-membered heterocycloalkyl, each of which is optionally substituted with from 1 to 3 $R^6$ substituents.

In one specific group of embodiments of the invention, $C^1$ is selected from the group consisting of phenyl, pyridyl and quinolinyl, each of which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-8}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

In another specific group of embodiments, $C^1$ is selected from the group consisting of phenyl and quinolinyl, each of which is optionally substituted with from 1 to 3 $R^4$ substituents; $C^2$ is selected from the group consisting of thiazole, oxazole and pyrazole, each of which is optionally substituted with from 1 to 2 $R^5$ substituents; and $C^3$ is phenyl, which is optionally substituted with from 1 to 2 $R^6$ substituents.

In yet another specific group of embodiments, $C^1$ is pyridyl, which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-8}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

In still another specific group of embodiments, $C^1$ is quinolinyl, which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-4}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

In yet another specific group of embodiments, $C^1$ is phenyl, which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-8}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

Within any of the embodiments provided in (A), (B), (C) or with reference to formula I, or any of the specific groups of embodiments, are still other selected embodiments:

(a) wherein the subscript n is 0;
(b) wherein n is 1, and $R^1$ is methyl;
(c) wherein n is 1, and $R^1$ is methyl and each of $R^2$ and $R^3$ is hydrogen;
(d) wherein n is 0, and each of $R^2$ and $R^3$ is hydrogen;
(e) wherein n is 0, $R^2$ is hydrogen and $R^3$ is selected from the group consisting of methyl, ethyl, —$CO_2H$ and —$CH_2CO_2H$; and
(f) wherein $R^2$ is hydrogen and $R^3$ is selected from the group consisting of

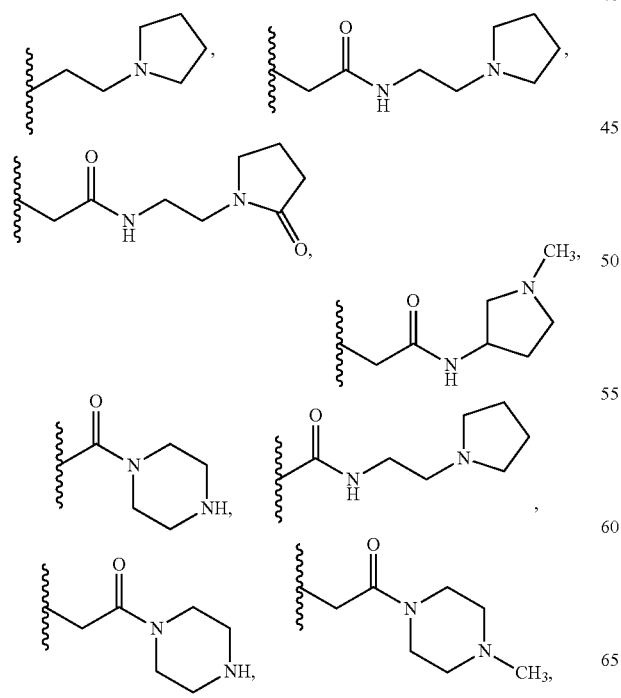

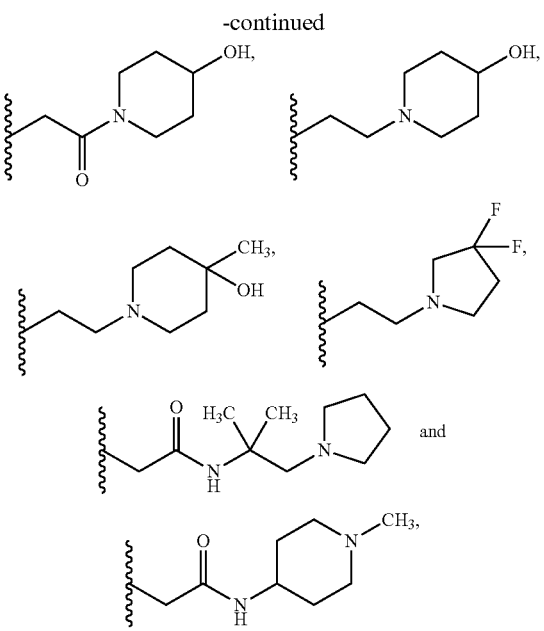

wherein the wavy line indicates the point of attachment to the remainder of the compound.

Within any of the embodiments provided in (A), (B), (C) or with reference to formula I, or any of the specific groups of embodiments, and the selected embodiments, are still other embodiments:

(g) wherein each $R^4$, when present, is selected from methyl, ethyl, isopropyl, 2-fluoroethyl, 2-fluoroisopropyl, 2-hydroxyisopropyl, methoxy, chloro, —$CO_2H$, —$CH_2CO_2H$, oxazolyl and pyridyl;

(h) wherein each $R^5$, when present, is selected from methyl, fluoro, chloro, —$CO_2H$ and —$CH_2CO_2H$; and (i) wherein each $R^6$, when present, is selected from methyl, fluoro, chloro, —$CO_2H$ and —$CH_2CO_2H$.

The present invention is also directed to those embodiments wherein selections from each of (g), (h) and (i) are combined with the frameworks provided for formula I, embodiments provided for (A), (B), (C), the specific groups of embodiments, and the selected embodiments (a) through (f).

In one selected embodiment, the compound is:

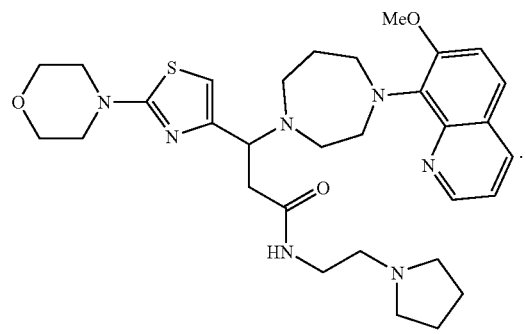

In other selected embodiments, the compound is selected from:
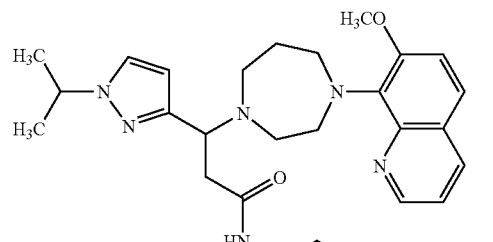
and
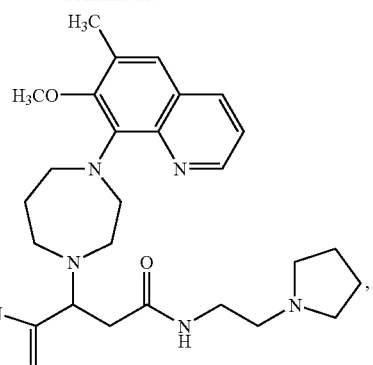
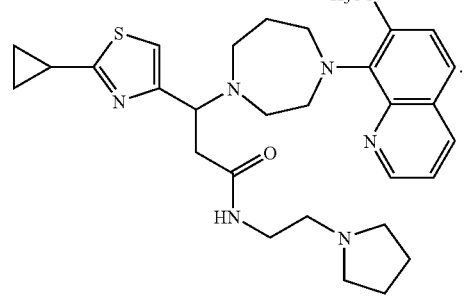
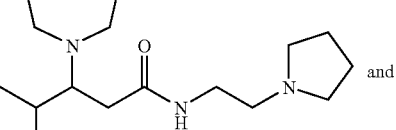
In yet other selected embodiments, the compound is selected from:
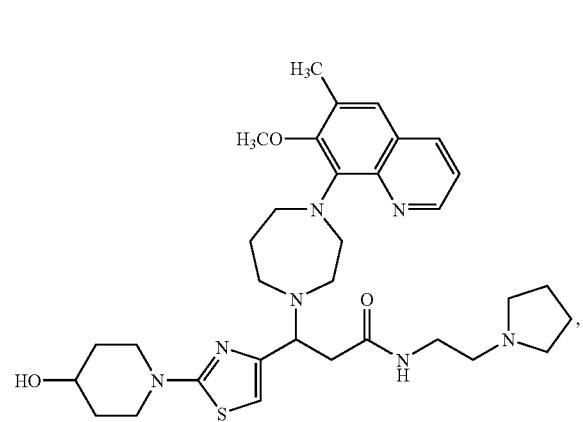
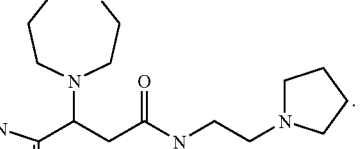
and
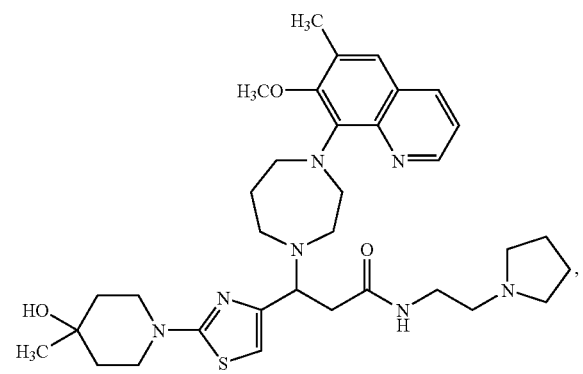

In yet other selected embodiments, the compound is selected from the group consisting of:
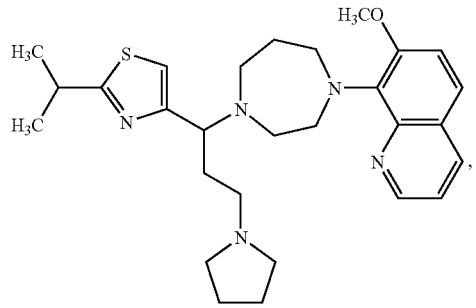
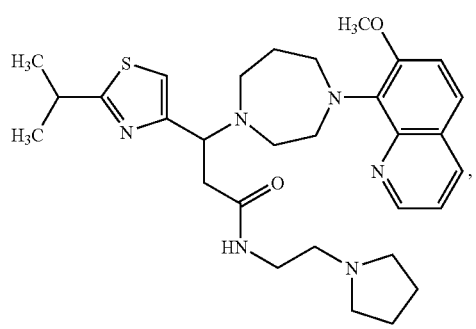
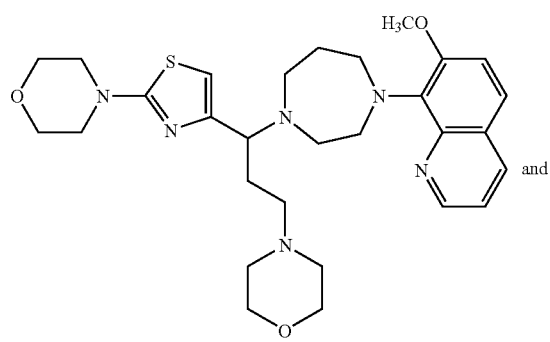
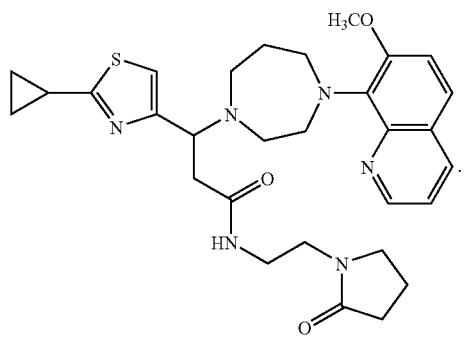
In other selected embodiments, the compounds is selected from:
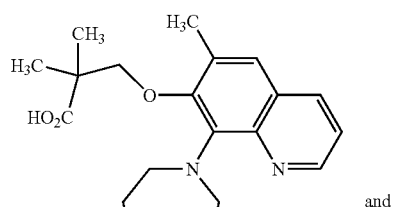
and
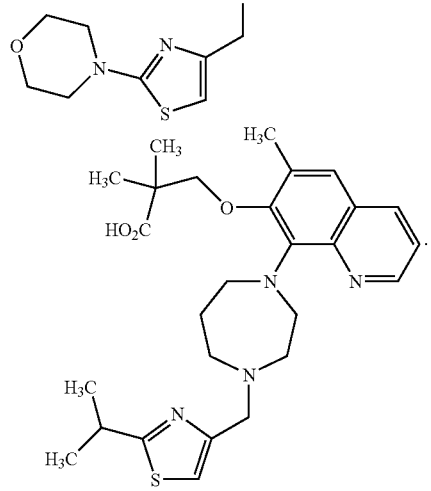
In still another selected embodiment, the compound is:
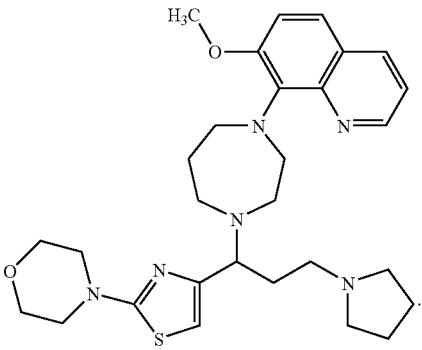
In yet other selected embodiments, the compound is selected from:
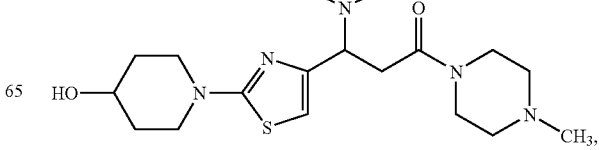

-continued

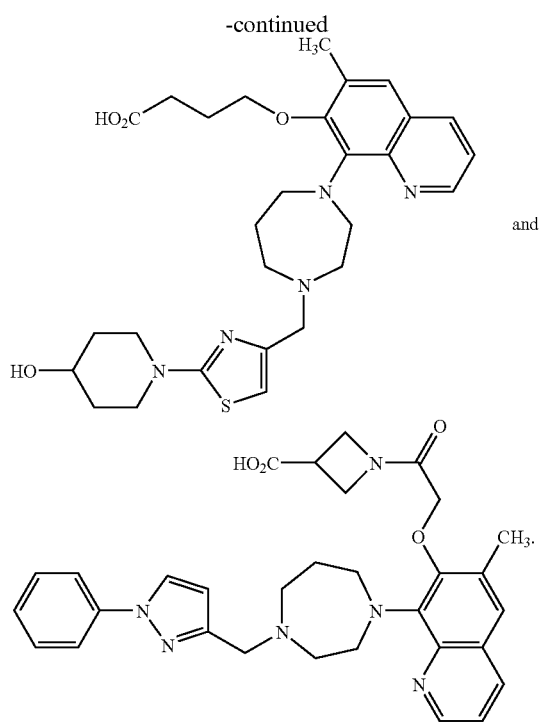

In yet other selected embodiments, the compound is selected from:

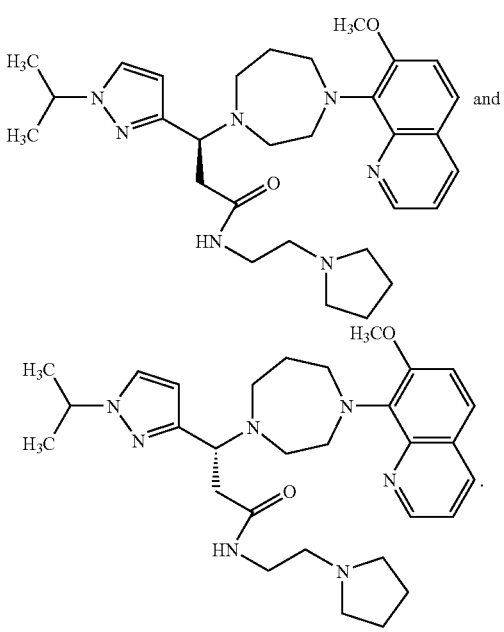

In each of the selected embodiments, the noted compounds may be present in a pharmaceutically acceptable salt or hydrate form.

Still further, for those compounds shown above without stereochemistry, the present invention is also directed to chiral forms of each of the compounds, as well as enantiomerically enriched forms of the noted compounds. Enantiomerically enriched forms can be prepared using chiral chromatography according to well known methods practiced in the art or, for example, by chiral resolution with a chiral salt form. In some embodiments, the enantiomeric excess for an enantiomerically enriched form is at least 10%, 20%, 30%, 40%, 50%, 60% or more. In still other embodiments, an enantiomerically enriched form is provided that is at least 70%, 80%, 90%, 95%, or more.

Preparation of Compounds

Certain compounds of the invention can be prepared following methodology as described below. Compounds can also be prepared as shown in the synthetic procedures outlined in the Examples section of this document. In addition the syntheses of certain inter mediate compounds that are useful in the preparation of compounds of the invention are described below.

Scheme 1

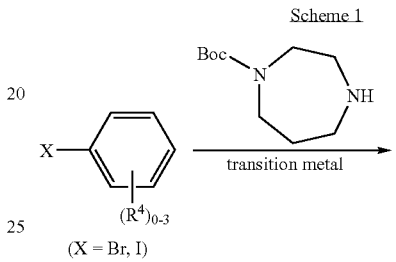

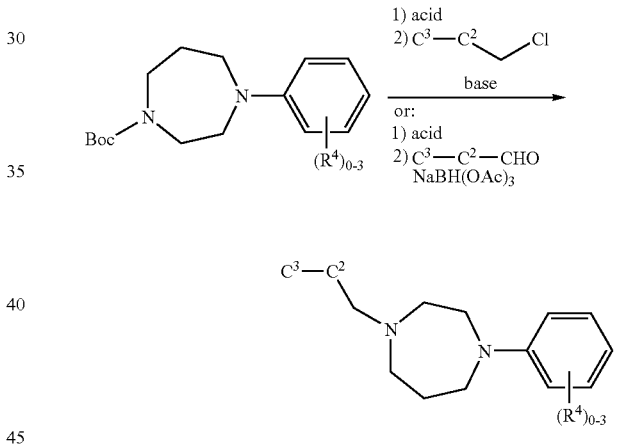

In Scheme 1, a substituted bromo or iodobenzene is coupled with BOC-homopiperazine using a transition metal catalyst. The BOC protecting group is then removed under acidic conditions. The desired product can be obtained from the resulting amine via a nucleophilic substitution or reductive alkylation reaction.

Scheme 2

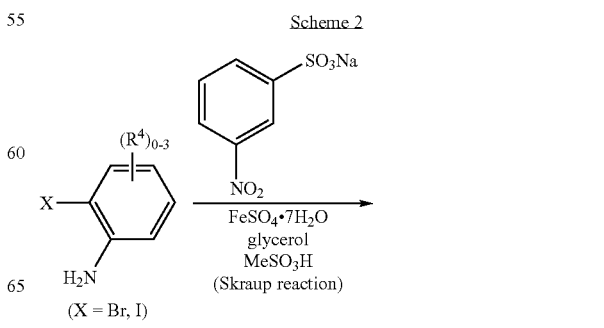

Scheme 2 (continued)

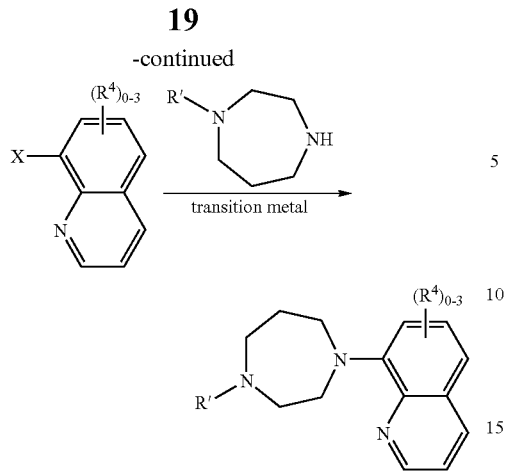

In Scheme 2, a substituted aniline is subjected to the Skraup conditions to give the quinoline intermediate, which can then be coupled with an appropriately derivatized homopiperazine using a transition metal catalyst.

Scheme 3

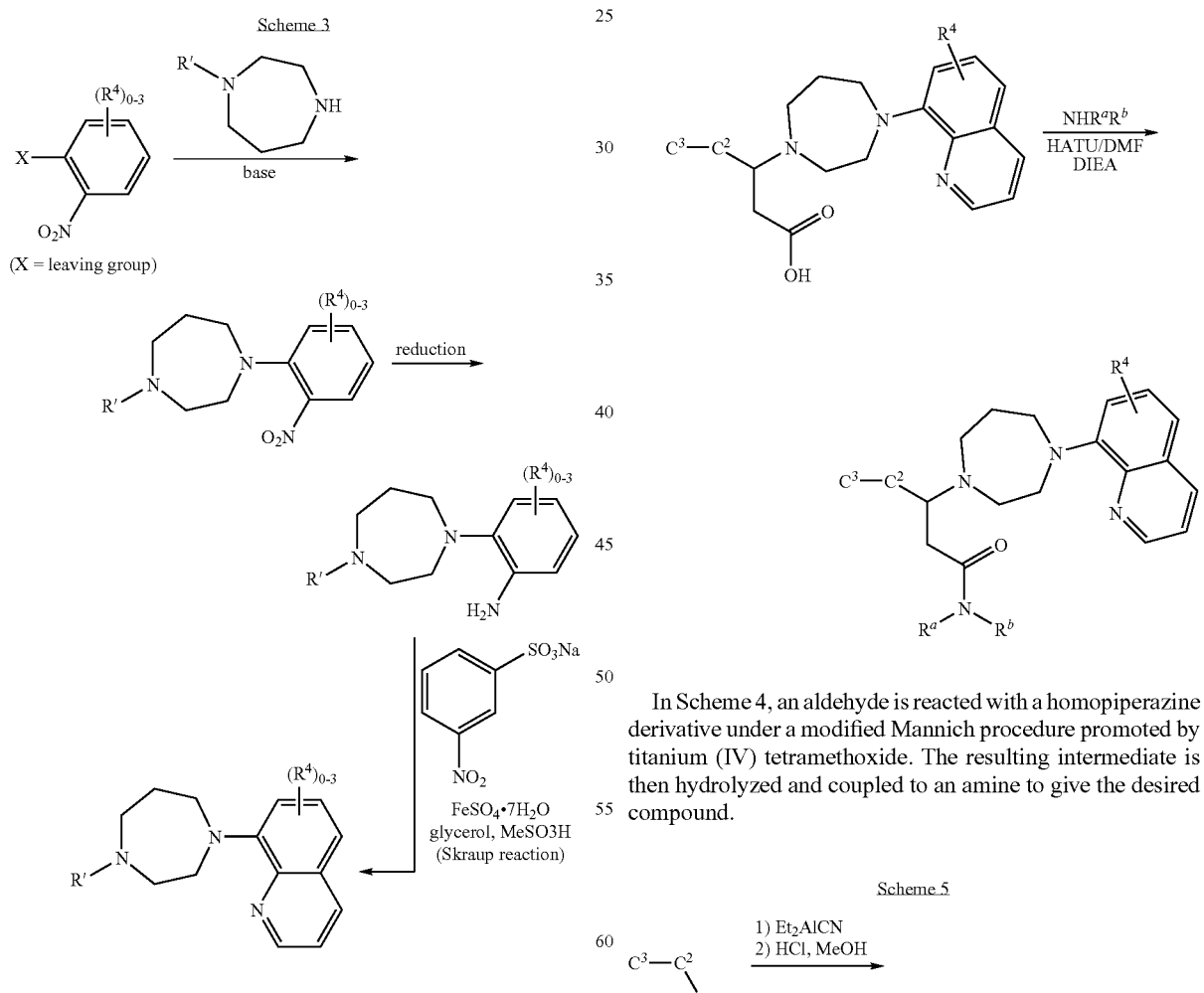

In Scheme 3, an appropriately derivatized homopiperazine is reacted with a substituted nitrobenzene via a SNAr mechanism. The resulting intermediate is then reduced to give an aniline derivative, which can be subjected to the Skraup conditions to give the desired compound.

Scheme 4

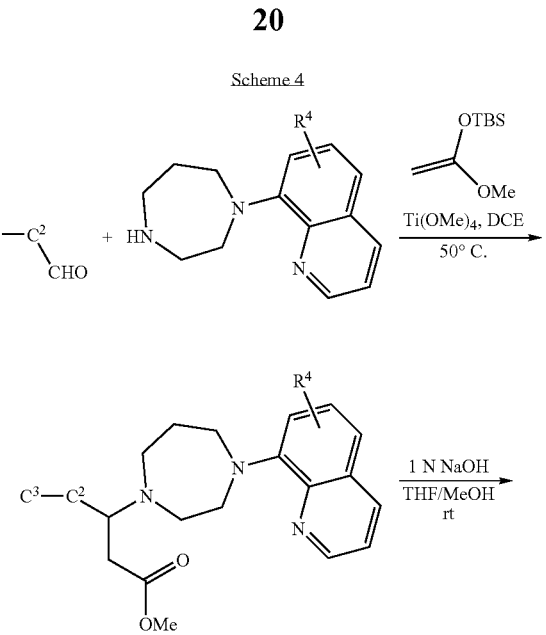

In Scheme 4, an aldehyde is reacted with a homopiperazine derivative under a modified Mannich procedure promoted by titanium (IV) tetramethoxide. The resulting intermediate is then hydrolyzed and coupled to an amine to give the desired compound.

Scheme 5

21
-continued

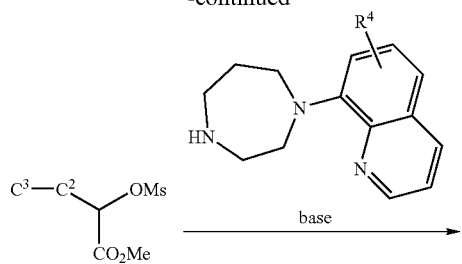

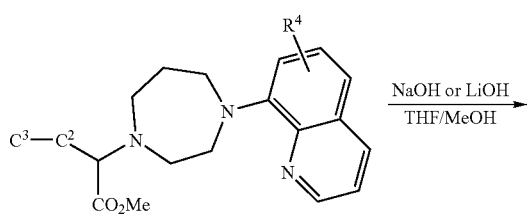

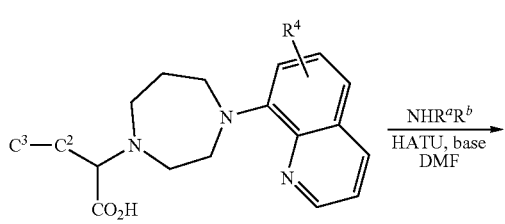

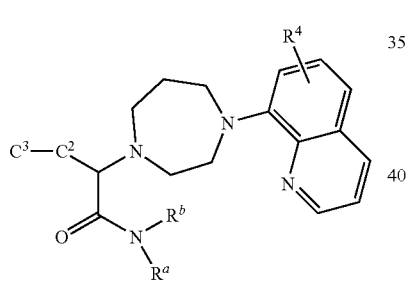

In Scheme 5, a modified Strecker reaction is employed to convert an aldehyde to the corresponding α-hydroxy methyl ester, which is then treated with methanesulfonic acid anhydride. A substitution reaction with a homopiperazine derivative is carried out, and the resulting intermediate is hydrolyzed and coupled to an amine to give the desired compound.

Scheme 6

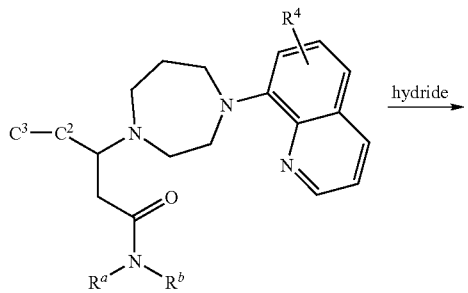

22
-continued

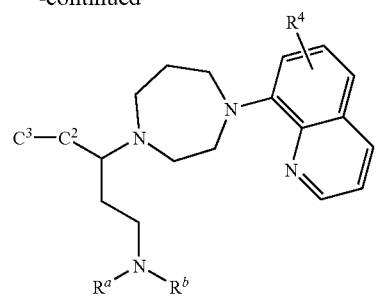

In Scheme 6, an amide intermediate is reduced with a reactive hydride reagent to give the corresponding amine analogue.

Scheme 7

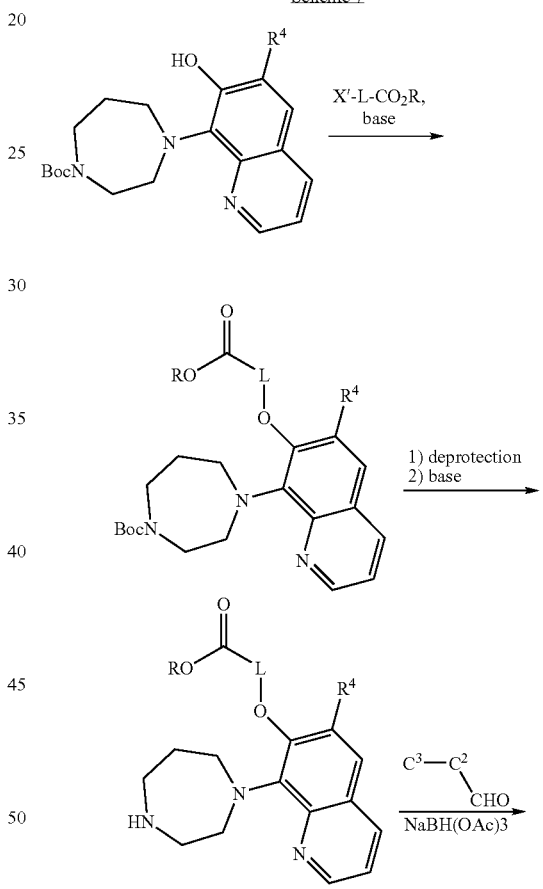

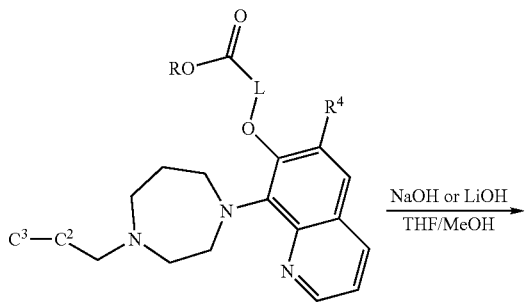

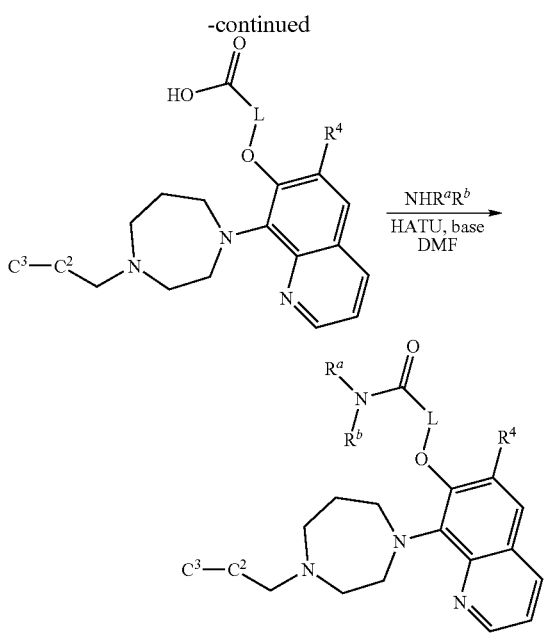

In Scheme 7, the hydroxyl substituted quinoline intermediate is reacted with X'-L-CO$_2$R (X'=leaving group, L=alkylene linker, R=Me or Et) under basic conditions. After the Boc protecting group is removed under acidic conditions, the free base of the homopiperazine derivative is subjected to a reductive alkylation reaction. The resulting ester intermediate is hydrolyzed and coupled to an amine to give the desired compound.

B. Compositions

In addition to the compounds provided above, compositions for modulating CXCR7 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage faun and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

C. Methods of Use

While not wishing to be bound by any particular theory, the compounds and compositions of the present invention are considered to provide a therapeutic effect by inhibiting the binding of SDF-1 and/or I-TAC to the CXCR7 receptor. Therefore, the compounds and compositions of the present invention can be used in the treatment or prevention of diseases or disorders in a mammal in which the inhibition of binding of SDF-1 and/or I-TAC to the CXCR7 receptor would provide a therapeutic effect.

In one embodiment, a preferred method of inhibiting the binding of the chemokines SDF-1 and/or I-TAC to a CXCR7 receptor includes contacting one or more of the previously mentioned compounds with a cell that expresses the CXCR7 receptor for a time sufficient to inhibit the binding of these chemokines to the CXCR7 receptor.

In some embodiments, the compounds and compositions of the invention are administered to a subject having cancer. In some cases, CXCR7 modulators are administered to treat cancer, e.g., carcinomas, gliomas, mesotheliomas, melanomas, lymphomas, leukemias (including acute lymphocytic leukemias), adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, renal cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease, multiple sclerosis and demyelinating diseases; kidney dysfunction; renal dysfunction; rheumatoid arthritis; allograft rejection; atherosclerosis; asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma.

The present invention also encompasses decreasing angiogenesis in any subject in need thereof by administering the compounds and compositions of the invention. For example, decreasing CXCR7 activity by contacting CXCR7 with a compound of the invention, thereby decreasing angiogenesis, is useful to inhibit formation, growth and/or metastasis of tumors, especially solid tumors. Description of embodiments relating to modulated CXCR7 and angiogenesis are described in, e.g., U.S. patent application Ser. No. 11/050,345.

Other disorders involving unwanted or problematic angiogenesis include rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, skin diseases such as psoriasis, excema, and scleroderma, diabetes, diabetic retinopathy, retinopathy of prematurity, age-related macular degeneration, atherosclerosis, scleroderma, wound granulation and hypertrophic scars, i.e., keloids, and diseases that have angiogenesis as a pathologic consequence such as cat scratch disease and ulcers (*Helicobacter pylori*), can also be treated with antibodies of the invention. Angiogenic inhibitors can be used to prevent or inhibit adhesions, especially intra-peritoneal or pelvic adhesions such as those resulting after open or laproscopic surgery, and bum contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophyy, as well as obesity, may also be treated by inhibition of angiogenesis. These disorders may involve increases in size or growth of other types of normal tissue, such as uterine fibroids, prostatic hypertrophy, and amyloidosis. Compounds and compositions of the present invention may be used prophylactically or therapeutically for any of the disorders or diseases described herein.

Decreasing CXCR7 activity with the compounds and compositions of the present invention can also be used in the prevention of neovascularization to effectively treat a host of disorders. Thus, for example, the decreasing angiogenesis can be used as part of a treatment for disorders of blood vessels (e.g., hemangiomas and capillary proliferation within atherosclerotic plaques), muscle diseases (e.g., myocardial angiogenesis, myocardial infarction or angiogenesis within smooth muscles), joints (e.g., arthritis, hemophiliac joints, etc.), and other disorders associated with angiogenesis. Promotion of angiogenesis can also aid in accelerating various physiological processes and treatment of diseases requiring increased vascularization such as the healing of wounds, fractures, and burns, inflammatory diseases, ischeric heart, and peripheral vascular diseases.

The compounds and compositions of the present invention may also be used to enhance wound healing. Without intending to limit the invention to a particular mechanism of action, it may be that antagonism of CXCR7 allows for endogenous ligands to instead bind to lower affinity receptors, thereby triggering enhanced wound healing. For example, SDF-1 binds to both CXCR7 and CXCR4, but binds to CXCR4 with a lower affinity. Similarly, I-TAC binds to CXCR3 with a lower affinity than I-TAC binds to CXCR7. By preventing binding of these ligands to CXCR7, CXCR7 antagonists may allow the ligands to bind to the other receptors, thereby enhancing wound healing. Thus, the antagonism of CXCR7 to enhance wound healing may be mediated by a different mechanism than enhancing wound healing by stimulating CXCR7 activity with an agonist.

Aside from treating disorders and symptoms associated with neovascularization, the inhibition of angiogenesis can be used to modulate or prevent the occurrence of normal physiological conditions associated with neovascularization. Thus, for example the compounds and compositions can be used as a birth control. In accordance with the present invention, decreasing CXCR7 activity within the ovaries or endometrium can attenuate neovascularization associated with ovulation, implantation of an embryo, placenta formation, etc.

Inhibitors of angiogenesis have yet other therapeutic uses. For example, the compounds and compositions of the present invention may be used for the following:
(a) Adipose tissue ablation and treatment of obesity. See, e.g. Kolonin et al., *Nature Medicine* 10(6):625-632 (2004);
(b) Treatment of preclampsia. See, e.g., Levine et al., *N. Engl. J. Med.* 350(7): 672-683 (2004); Maynard, et al.,*J. Clin. Invest.* 111(5): 649-658 (2003); and
(c) Treatment of cardiovascular disease. See, e.g., March, et al., *Am. J. Physiol. Heart Circ. Physiol.* 287:H458-H463 (2004); Rehman et al., *Circulation* 109: 1292-1298 (2004).

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood, No. 1, Vol. 96, pp. 282-87 (1 Jul. 2000); Pengnian, L., *Antiangiogenic gene therapy targeting the endothelium-specific receptor tyrosine kinase Tie2*. Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CXCR7 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Inducing Progenitor/Stem Cell Mobilization

Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound he Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound healing and treatment of bacterial infections. Optionally, following administration of the compounds of the invention, and following progenitor/stem cell mobilization, blood comprising the mobilized cells is collected and optionally, the mobilized cells are purified and optionally expanded, and where desired, reintroduced into the same person or into a second person (e.g., a matched donor).

A number of different types of cells can be mobilized as desired. In some embodiments, hematopoietic progenitor cells (HSCs) are mobilized following administration of the compounds or compositions of the invention, and optionally harvested and purified from other blood components. Optionally, HSC mobilization is induced by administration of at least one compound of the invention in conjunction with one or more of granulocyte-colony stimulating factor (G-CSF) or AMD3100 (1,1'-[1,4-Phenylenebis(methylene)]bis[1,4,8,11-tetraazacyclotetradecane]octohydrobromide dihydrate) or salts, racemates, or isomers thereof.

In some embodiments, endothelial progenitor cells (EPCs) are mobilized following administration of the compounds or compositions of the invention, and optionally harvest and purified from other blood components. Optionally, EPC mobilization is induced by administration of at least one compound of the invention in conjunction with one or more of vascular endothelial growth factor (VEGF), a VEGF agonist (including but not limited to a VEGF agonist antibody) or AMD3100 or salts, racemates, or isomers thereof.

In some embodiments, mesenchymal stem cells (MSCs) or stromal progenitor cells (SPCs) are mobilized following administration of the compounds or compositions of the invention, and optionally harvest and purified from other blood components. Optionally, such mobilization is induced by administration of at least one compound of the invention in conjunction with one or more of G-CSF, VEGF, a VEGF agonist (including but not limited to a VEGF agonist antibody), AMD3100, or salts, racemates, or isomers thereof.

For immobilizing progenitor or stem cells, an appropriate dosage level will generally be about 0.001 to 100 mg per kg patient body weight per day which can be administered in single or multiple doses. The compounds may be administered as a single dose, a dose over time, as in i.v., or transdermal administration, or in multiple doses. The compounds of the invention can also be used in ex vivo treatment protocols to prepare cell cultures which are then used to replenish the blood cells of the subject. Ex vivo treatment can be conducted on autologous cells harvested from the peripheral blood or bone marrow or from allografts from matched donors.

The present compounds can be combined with other compounds and compositions that induce activation, proliferation or mobilization of progenitor/stem cells. In addition to those described above, these include but are not limited to Fms-related tyrosine kinase 3 ligand (Flt3 ligand), interleukin 3 (IL-3), interleukin 7 (IL-7), interleukin 20 (IL-20), Steel factor (SF) and granulocyte macrophage colony-stimulating factor (GM-CSF) and may provide therapeutic utilities that may require or benefit from treatment either before, after or simultaneously with mobilization of progenitor/stem cells. Accordingly, combination methods and compositions are also a component of the present invention to prevent and treat the condition or disease of interest.

Method of Diagnosing Diseases and Disorders Associated with CXCR7

Still further, the compounds and compositions of the present invention are useful for the diagnosis of diseases and disorders associated with CXCR7. In particular, the compounds of the present invention can be prepared in a labeled form (e.g., radiolabeled) and used for the diagnosis of, for example, cancer. Labeled compounds of the present invention that bind to CXCR7 (e.g., antagonists or agonists) can be used to determine levels of CXCR7 in a mammalian subject. In some embodiments, the CXCR7 modulators are administered to a subject having cancer. In some cases, labeled compounds are administered to detect developing cancers, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis; asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma. Since CXCR7 is often expressed in cancer cells but not non-cancer cells, it is typically desirable to administer antagonists of CXCR7 to subjects at risk of having cancer.

A variety of imaging and detection methods can be used for the detection of cancers. In some embodiments, direct methods are available to evaluate CXCR7 biodistribution in the body such as magnetic resonance imaging ("MRI"), positron emission tomography ("PET"), and single photon emission computed tomography ("SPECT"). Each of these methods can detect the distribution of a suitably labeled compound (generally as bound to CXCR7) within the body if that compound contains an atom with the appropriate nuclear properties. MRI detects paramagnetic nuclei; PET and SPECT detect the emission of particles from the decay of radionuclei.

For methods involving PET, it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Another useful isotope, $^{18}F$, has a half-life of 110 minutes. This allows sufficient time for incorporation into a radiolabeled tracer, for purification and for administration into a human or animal subject. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K. F. Hubner, et al., Chapter 2).

SPECT imaging employs isotope tracers that are γ-emitters. While the range of useful isotopes is greater than for PET, imaging with SPECT provides lower three-dimensional resolution. However, in some instances, SPECT is used to obtain clinically significant information about compound binding, localization and clearance rates. One useful isotope for SPECT imaging is $^{123}I$, a γ-emitter with a 13.3 hour half life. Compounds labeled with $^{123}I$ can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include $^{75}Br$, $^{76}Br$, $^{77}Br$ and $^{82}Br$ as having usable half-lives and emission characteristics.

In view of the above, the present invention provides methods for imaging a tumor, organ, or tissue, said method comprising:
 (a) administering to a subject in need of such imaging, a radiolabeled or detectable faun of a compound of Formula I; and
 (b) detecting said compound to determine where said compound is concentrated in said subject.

Additionally, the present invention provides methods for detecting elevated levels of CXCR7 in a sample, said method comprising:
 (a) contacting a sample suspected of having elevated levels of CXCR7 with a radiolabeled or detectable form of a compound of Formula I;
 (b) determining a level of compound that is bound to CXCR7 present in said sample to determine the level of CXCR7 present in said sample; and
 (c) comparing the level determined in step (b) with a control sample to determine if elevated levels of CXCR7 are present in said sample.

As with the treatment methods described herein, administration of the labeled compounds can be by any of the routes normally used for introducing a compound into ultimate contact with the tissue to be evaluated and is well known to those of skill in the art. Although more than one route can be used to administer a particular composition, a particular route can often provide a more immediate and more effective diagnosis than another route.

IV. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; Pd$_2$dba$_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

1-(2,4-Dimethoxyphenyl)-4-(2-phenylthiazol-4-ylmethyl)-[1,4]diazepane

Step 1: 4-(2,4-Dimethoxyphenyl)-[1,4]diazepane-1-carboxylic acid tert-butyl ester

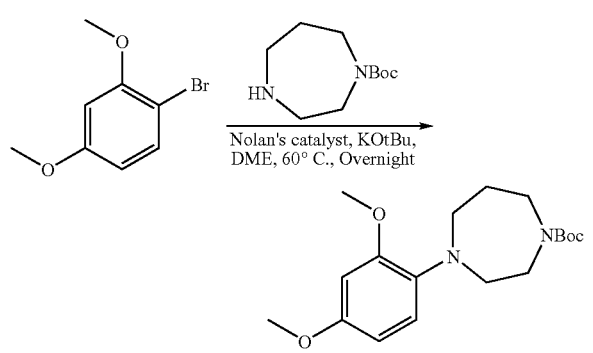

A mixture of 1-bromo-2,4-dimethoxybenzene (433 mg, 1.99 mmol, 1 equiv), [1,4]diazepane-1-carboxylic acid tert-butyl ester (400 mg, 1.99 mmol, 1 equiv), t-BuOK (313.7 mg, 2.79 mmol, 1.4 equiv) and allylchloro[1,3-(2,6-di-isopropylphenyl)imidazol-2-ylidene]palladium (II) (Nolan's catalyst, 11.4 mg, 0.02 mmol, 0.01 equiv) in 4 mL of DME was degassed with compressed nitrogen gas for 5 min. The resulting mixture was stirred at 60° C. overnight and cooled down to room temperature. EtOAc (~30 mL) was added and the mixture was filtered through celite. The filtrate was washed with saturated aqueous NaHCO$_3$ (20 mL) and brine (20 mL) sequentially and then dried over magnesium sulfate. The residue was purified by flash column chromatograph using 30 to 100% EtOAc in hexane to afford the title compound as yellowish liquid (300 mg) after evaporation and dried in vacuo. MS (ES) m/z 337.2 (M+H$^+$).

Step 2: 1-(2,4-Dimethoxyphenyl)-[1,4]diazepane HCl salt

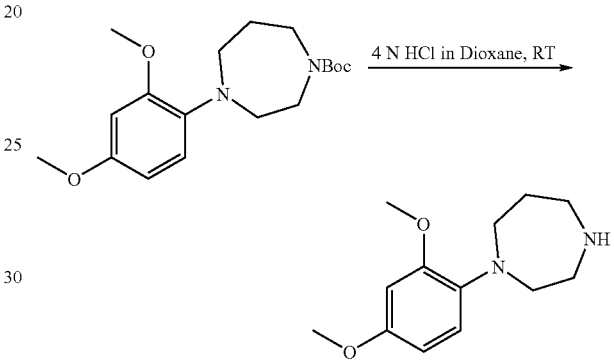

300 mg of 4-(2,4-dimethoxyphenyl)-[1,4]diazepane-1-carboxylic acid tert-butyl ester was dissolved in 10 mL of 4 N HCl in dioxane. The mixture was stirred at room temperature for 2 hrs and evaporated to dryness to give the desired product (270 mg) as a hydrochloride salt. MS (ES) m/z 237.2 (M+H$^+$).

Step 3: 1-(2,4-Dimethoxyphenyl)-4-(2-phenylthiazol-4-ylmethyl)-[1,4]diazepane

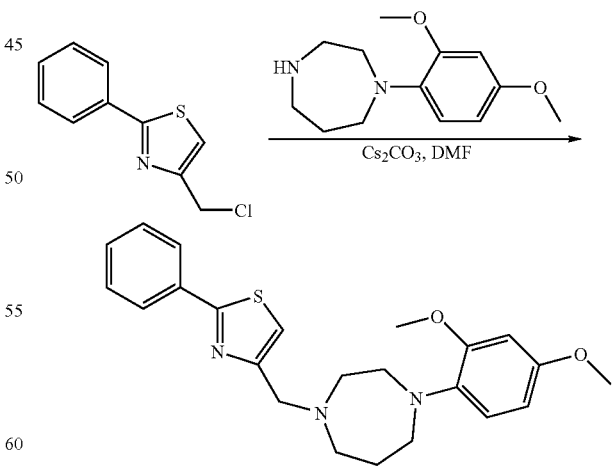

A mixture of 4-chloromethyl-2-phenylthiazole (80 mg, 0.38 mmol, 1 equiv), 1-(2,4-dimethoxyphenyl)-[1,4]diazepane HCl salt (117 mg, 0.38 mmol, 1 equiv) and Cs$_2$CO$_3$ (619 mg, 5 equiv) in 1 mL of DMF was stirred at room temperature overnight. The mixture was diluted with EtOAc 30 mL), washed with saturated aqueous NaHCO$_3$ (20 mL) and brine (20 mL) sequentially and then dried over magnesium sulfate. The residue was purified by flash column chromatograph using 30 to 100% EtOAc in hexane to afford the title compound as light tan solid (50 mg) after evaporation and drying in vacuo. $^1$H NMR (400 MHz, CDCl$_3$) δ 7.90 (d, 2H, J=8.0 Hz), 7.39 (m, 3H), 7.15 (s, 1H), 6.88 (d, 1H, J=8.8 Hz), 6.42 (s, 1H), 6.39 (d, 1H, J=8.8 Hz), 3.91 (s, 2H), 3.79 (s, 3H), 3.74 (s, 3H), 3.25 (m, 4H), 2.92 (m, 4H), 1.98 (m, 2H). MS (ES) m/z 410.2 (M+H$^+$).

Example 2

1-(3-Methoxypyridin-2-yl)-4-(2-phenylthiazol-4-ylmethyl)-[1,4]diazepane

Step 1. 4-(3-Methoxypyridin-2-yl)-[1,4]diazepane-1-carboxylic acid tert-butyl ester

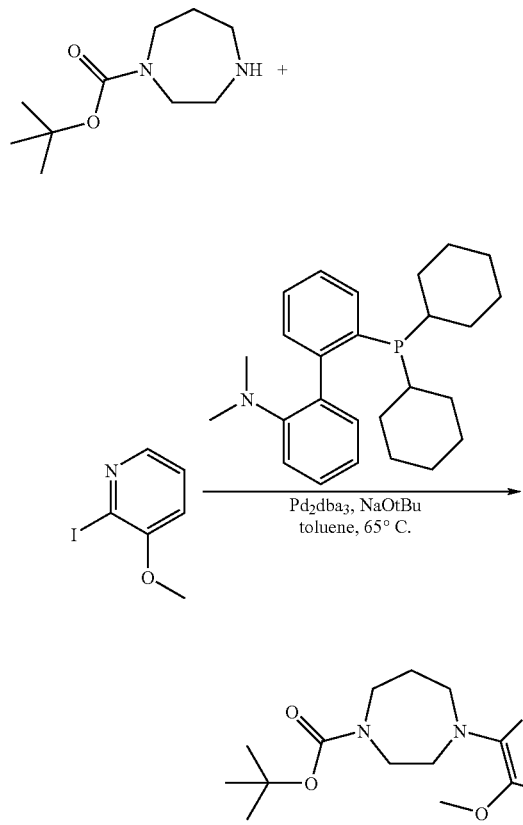

Toluene (1.5 mL) was added to a mixture of 2-iodo-3-methoxypyridine (350 mg, 1.49 mmol), BOC-homopiperazine (0.410 mL, 2.09 mL), 2-dicyclohexylphosphino-2'-(N, N-dimethylamino)biphenyl (26 mg, 0.07 mmol), and trisdibenzylideneacetone dipalladium (20 mg, 0.02 mmol). To this suspension was added sodium t-butoxide (201 mg, 2.09 mmol) and the mixture was heated to 65° C. for 15 h. The mixture was filtered through celite, and the filter cake was washed with EtOAc. The resulting solution was washed with H$_2$O, then brine, and dried over MgSO$_4$. After removal of the solvent, the residue was purified on silica to give 335 mg of the title compound as a dark oil. MS (ES) m/z 308 (M+H$^+$).

Step 2. 1-(3-Methoxypyridin-2-yl)-[1,4]diazepane dihydrochloride

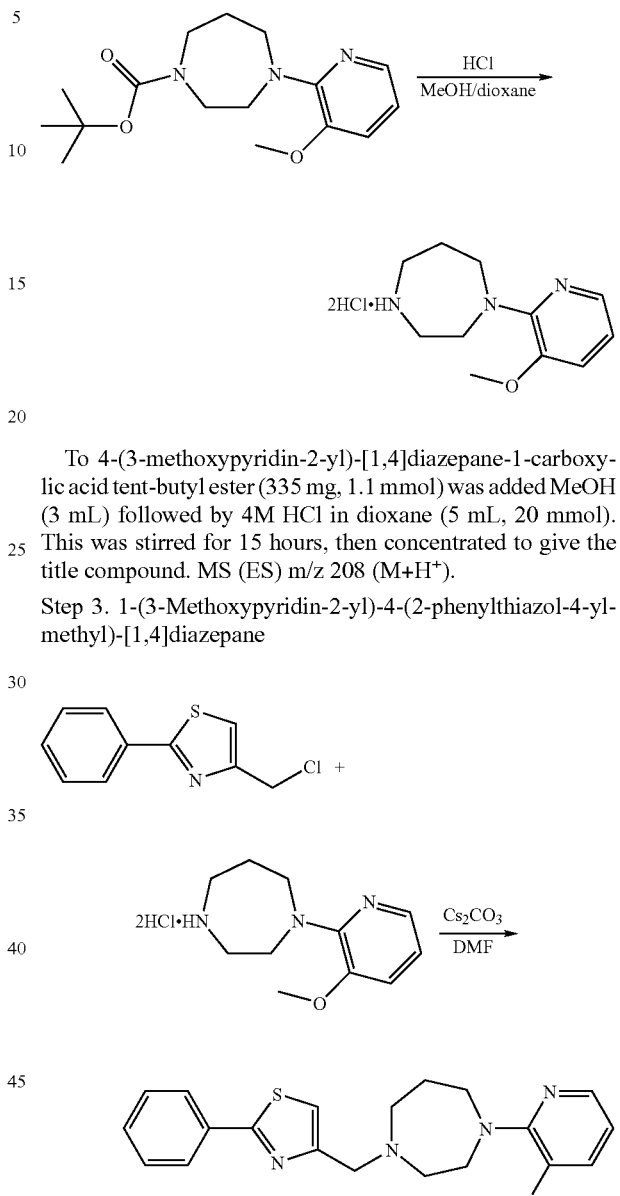

To 4-(3-methoxypyridin-2-yl)-[1,4]diazepane-1-carboxylic acid tert-butyl ester (335 mg, 1.1 mmol) was added MeOH (3 mL) followed by 4M HCl in dioxane (5 mL, 20 mmol). This was stirred for 15 hours, then concentrated to give the title compound. MS (ES) m/z 208 (M+H$^+$).

Step 3. 1-(3-Methoxypyridin-2-yl)-4-(2-phenylthiazol-4-ylmethyl)-[1,4]diazepane 4-(Chloromethyl)-2-phenyl-1,3-thiazole (52 mg, 0.25 mmol), 1-(3-methoxy-pyridin-2-yl)-[1,4]diazepane dihydrochloride (70 mg, 0.25 mmol), and Cesium carbonate (325 mg, 1.0 mmol) were suspended in anhydrous DMF (1.25 mL). The mixture was stirred at room temperature for 18 hours. The reaction was diluted with EtOAc and washed with H$_2$O (3×25 mL), then brine (25 mL). The organic layer was dried over MgSO$_4$, filtered, and concentrated. The residue was purified on silica (CH$_2$Cl$_2$:MeOH+1% NH$_4$OH) to afford the product. $^1$H NMR (400 MHz, CDCl$_3$) δ 7.94 (m, 2H), 7.79 (dd, 1H, J=1.6, 4.8 Hz), 7.40 (m, 3H), 7.15 (s, 1H), 6.96 (dd, 1H, J=1.4, 8.2 Hz), 6.66 (dd, 1H, J=4.8, 7.6 Hz), 3.93 (s, 2H), 3.80 (s, 3H), 3.71 (m, 4H), 2.98 (t, 2H, J=5.0 Hz), 2.85 (t, 2H, J=5.6 Hz), 2.04 (quin., 2H, J=5.9 Hz). MS (ES) m/z 381.1 (M+H$^+$).

Example 3

6-Ethyl-8-[4-(2-phenylthiazol-4-ylmethyl)-[1,4]diazepan-1-yl]-quinoline

Step 1: 2-Bromo-4-ethylphenylamine

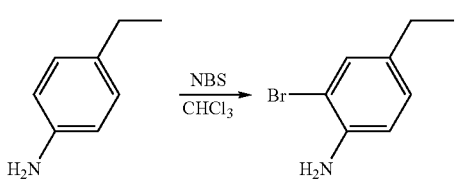

4-Ethylphenylamine (1.00 g, 7.52 mmol, 1 equiv) was dissolved in chloroform (40 mL) and placed into an ice bath. NBS (1.34 g, 1 equiv) was then added into the solution in small portions. The mixture was warmed to room temperature and stirred for 2 hours. EtOAc (~200 mL) was added and the mixture was filtered. The filtrate was washed with saturated aqueous $K_2CO_3$ (200 mL), saturated aqueous $NaHCO_3$ (200 mL), and brine (200 mL), dried over magnesium sulfate and concentrated. The residue was purified by silica gel flash column chromatography using 5% to 20% EtOAc in hexanes to afford the title compound as light brown oil (1 g). MS (ES) m/z 200.0 (M+H$^+$).

Step 2: 8-Bromo-6-ethylquinoline

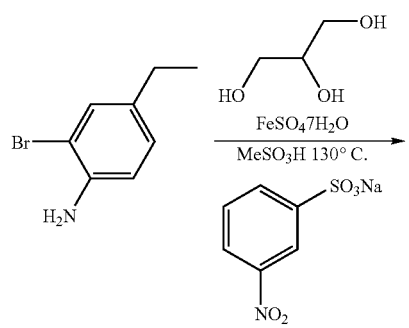

A mixture of 2-bromo-4-ethylphenylamine (1.6 g, 8.0 mmol), propane-1,2,3-triol (1.84 g, 2.5 equiv), $FeSO_4$ (0.067 g, 0.30 equiv), 3-nitrobenzenesulfonic acid sodium salt (1.13 g, 0.63 equiv) in 4.5 mL of methanesulfonic acid was heated at 135° C. for 3 hours and then cooled to room temperature. 2 N Aqueous NaOH (~40 mL) was added and the mixture was extracted with EtOAc (3×50 mL). The organic layer was washed with saturated aqueous $NaHCO_3$ (200 mL) and brine (200 mL), dried over magnesium sulfate and concentrated. The residue was purified by silica gel flash column chromatography using 5% to 20% EtOAc in hexane to afford the title compound as a black solid (1.3 g). MS (ES) m/z 235.9 (M+H$^+$).

Step 3: 4-(6-Ethylquinolin-8-yl)-[1,4]-diazepan-1-carboxylic acid tert-butyl ester

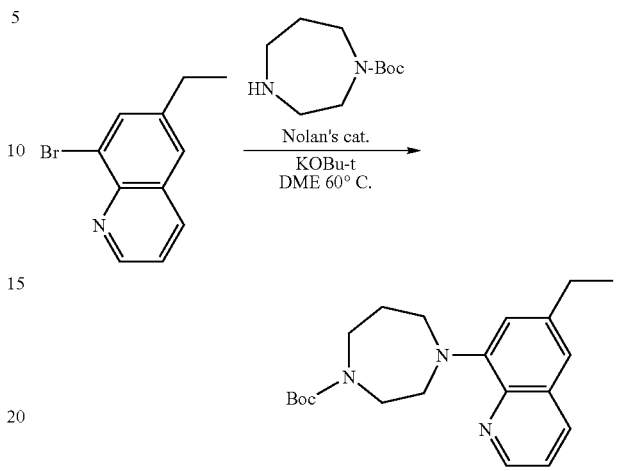

A mixture of 8-bromo-6-ethylquinoline (1.3 g, 5.51 mmol, 1.04 equiv) and 1-(tert-butoxycarbonyl)homopiperazine (1.06 g, 1.0 equiv) in 5.5 mL of DME was degassed with compressed nitrogen gas for 5 minutes. To the mixture was added t-BuOK (0.83 g, 1.4 equiv). After degassing for another 2 minutes, allylchloro[1,3-(2,6-di-isopropylphenyl)imidazol-2-ylidene]palladium (II) (61 mg, 0.02 equiv) was added and the resulting mixture was heated at 60° C. overnight and cooled down to room temperature. EtOAc 70 mL) was added and the mixture was filtered through celite. The filtrate was washed with saturated aqueous $NaHCO_3$ (70 mL) and brine (70 mL), dried over magnesium sulfate and concentrated. The residue was purified by silica gel flash column chromatography using 5% to 20% EtOAc in hexane to afford the title compound (1.0 g). MS (ES) z 356.2 (M+H$^+$).

Step 4: 8-[1,4]-Diazepan-1-yl-6-ethylquinoline dihydrochloride

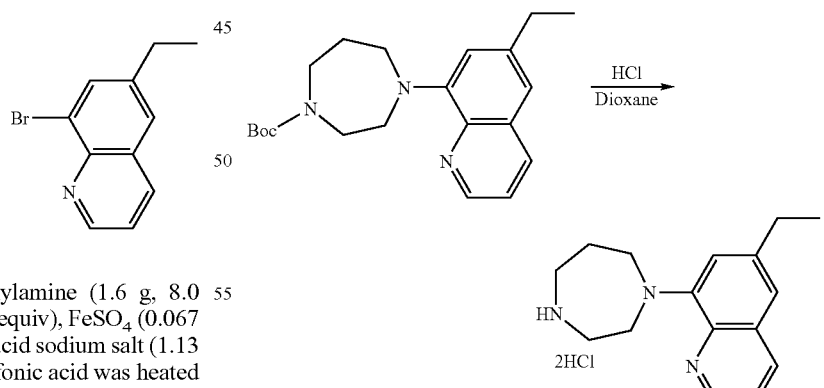

4-(6-Ethylquinolin-8-yl)[1,4]-diazepan-1-carboxylic acid tert-butyl ester (1.0 g, 1.0 equiv) was dissolved in MeOH (5 mL) and 1.0 M HCl in 1,4-dioxane (10 mL) was added to the mixture. After stirring at room temperature for 1 hour, the mixture was concentrated to dryness to afford the title compound (1.0 g). MS (ES) m/z 256.1 (M+H$^+$).

Step 5: 6-Ethyl-8-[4-(2-phenylthiazol-4-ylmethyl)-[1,4]diazepan-1-yl]-quinoline

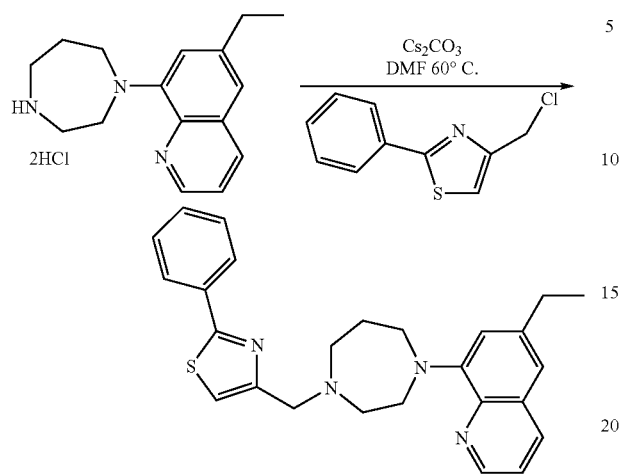

A mixture of 8-[1,4]-diazepan-1-yl-6-ethylquinoline dihydrochloride (0.32 g, 1 mmol, 1 equiv), 4-chloromethyl-2-phenylthiazole (0.21 g, 1 equiv) and Cs$_2$CO$_3$ (1.63 g, 5 equiv) in 5 mL of DMF was heated at 60° C. for 3 hours and then cooled to room temperature. EtOAc (~70 mL) was added and the mixture washed with saturated aqueous NaHCO$_3$ (70 mL) and brine (70 mL), dried over magnesium sulfate and concentrated. The residue was purified by silica gel flash column chromatography using 5% to 40% EtOAc in hexanes. Silica gel chromatography was repeated using 5% to 10% MeOH in EtOAc to afford the title compound as a light tan solid (0.22 g). $^1$H NMR (400 MHz, CD$_3$OD) δ 8.65 (dd, 1H, J=1.8 and 4 Hz), 8.04 (dd. 1H, J=1.5 and 8.4 Hz), 7.91 (m, 1H), 7.90 (d, 1H, J=2.2 Hz), 7.41 (m, 3H), 7.36 (s, 1H), 7.31 (dd, 1H, J=4 and 8 Hz), 7.11 (s, 1H), 6.98 (s, 1H), 3.89 (s, 2H), 3.69 (m, 2H), 3.57 (t, 2H, J=5.87 Hz), 3.11 (m, 2H), 2.92 (t, 2H, J=5.3 Hz), 2.72 (q, 2H, J=7.0 Hz), 2.10 (m, 2H), 1.28 (t, 3H, J=7.0 Hz). MS (ES) m/z 429.2 (M+H$^+$).

Example 4

6-Isopropyl-8-{4-[1-(1-phenyl-1H-pyrazol-3-yl)-propyl]-[1,4]diazepan-1-yl}-quinoline hydrochloride Step 1: 1-(1-Phenyl-1H-pyrazol-3-yl)-propan-1-ol

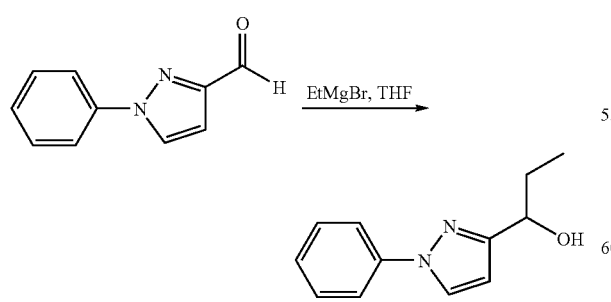

1-Phenyl-1H-pyrazole-3-carbaldehyde (779 mg, 4.53 mmol) was dissolved in anhydrous THF (9 mL) and chilled in an ice bath. EtMgBr (3.0 M in Et$_2$O, 4.5 mL) was added dropwise. After 1.5 hours, the reaction mixture was allowed to warm to ambient temperature. TLC (2:1 hexanes:EtOAc) indicated complete consumption of aldehyde starting material. The reaction mixture was quenched with water and extracted with EtOAc (2×). The EtOAc layers were washed with brine (1×), dried over Na$_2$SO$_4$ and concentrated. The residue was purified by silica gel chromatography (2:1 hexanes:EtOAc) to provide the title compound (631 mg, 69%) as a yellow oil. $^1$H NMR (400 MHz, CDCl$_3$) δ 7.85 (d, 1H, J=2.4 Hz), 7.65 (d, 2H, J=7.6 Hz), 7.42 (t, 2H, J=7.6 Hz), 7.27 (d, 1H, J=7.2 Hz), 6.38 (d, 1H, J=2.4 Hz), 4.79 (dd, 1H, J=12, 5.6 Hz), 2.38 (d, 1H, J=4.8 Hz), 1.98-1.81 (m, 2H), 1.01 (t, 3H, J=7.2 Hz). MS (ES) m/z 203.1 (M+H$^+$).

Step 2: 1-(1-Phenyl-1H-pyrazol-3-yl)-propan-1-one

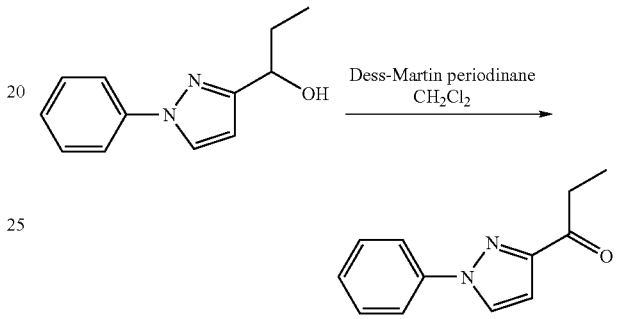

1-(1-Phenyl-1H-pyrazol-3-yl)-propan-1-ol (631 mg, 3.12 mmol) was dissolved in CH$_2$Cl$_2$ (16 mL) and Dess-Martin periodinane (1.6 g, 3.8 mmol) was added in one portion. After 40 minutes, TLC (2:1 hexanes:EtOAc) indicated a mixture of starting material and product. Additional Dess-Martin periodinane (800 mg, 1.88 mmol) was added and the mixture was stirred at ambient temperature. After 30 minutes, TLC indicated no further conversion to product. The reaction mixture was diluted with CH$_2$Cl$_2$ and washed with aqueous Na$_2$S$_2$O$_3$ (1×) and saturated NaHCO$_3$ (2×). The CH$_2$Cl$_2$ layer was dried over Na$_2$SO$_4$ and concentrated. The residue was purified by silica gel chromatography (2:1 hexanes:EtOAc) to provide the title compound as a colorless solid (487 mg, 78%). $^1$H NMR (400 MHz, CDCl$_3$) δ 7.91 (d, 1H, J=2.4 Hz), 7.73 (d, 2H, J=8.8 Hz), 7.48 (t, 2H, J=7.2 Hz), 7.35 (t, 1H, J=7.6 Hz), 6.96 (d, 1H, J=2.8 Hz), 3.13 (q, 2H, J=7.2 Hz), 1.24 (t, 3H, J=7.2 Hz). MS (ES) m/z 201.0 (M+H$^+$).

Step 3: 6-Isopropyl-8-{4-[1-(1-phenyl-1H-pyrazol-3-yl)-propyl]-[1,4]diazepan-1-yl}-quinoline hydrochloride

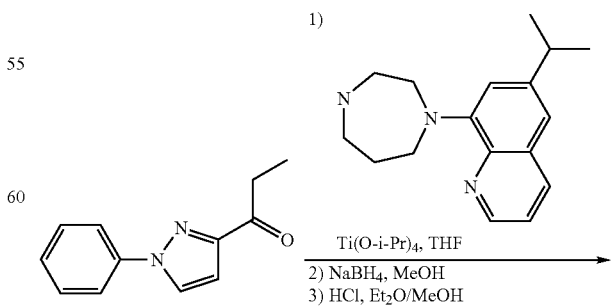

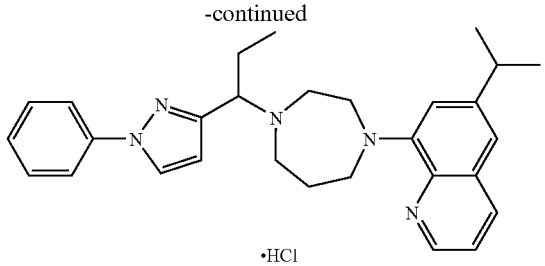
•HCl 1-(1-Phenyl-1H-pyrazol-3-yl)-propan-1-one (97.4 mg, 0.486 mmol) and 8-[1,4]diazepan-1-yl-6-isopropylquinoline (131 mg, 0.486 mmol) were combined and dried by evaporation from toluene (2×2 mL). The mixture was dissolved in anhydrous THF (1.8 mL) and Ti(O$^i$Pr)$_4$ (0.29 mL, 0.97 mmol) was added. The mixture was stirred at ambient temperature for 18 hours, and then chilled to ca. −20° C. Sodium borohydride (74 mg) was added in one portion. MeOH (1.0 mL) was then added dropwise. The reaction mixture was allowed to warm to ambient temperature over 4 hours and was quenched with 1 M NaOH (1 mL) and EtOAc (3 mL). The cloudy suspension was filtered through celite and the EtOAc layer was washed with brine (1×), dried over Na$_2$SO$_4$ and concentrated. The residue was purified by silica gel chromatography (4% to 6% MeOH in CHCl$_3$). The purified product was dissolved in MeOH (ca. 0.5 mL) and 1 M HCl in Et$_2$O (0.5 mL) was added. The clear solution was concentrated and dried under high vacuum to provide the title compound as a yellow solid (27 mg). $^1$H NMR (400 MHz, d$^6$-DMSO) δ 10.20-9.85 (m, 1H), 8.83-8.65 (m, 1H), 8.61 (d, 1H, J=2.4 Hz), 8.30-8.15 (m, 1H), 7.84 (d, 2H, J=8.4 Hz), 7.52-7.46 (m, 3H), 7.33 (t, 1H, J=7.6 Hz), 7.32-7.22 (m, 1H), 6.89 (d, 1H, J=2.4 Hz), 4.68-4.59 (m, 1H), 4.15-3.49 (m, 5H), 3.26-3.00 (m, 4H), 2.37-2.28 (m, 4H), 1.26 (d, 6H, J=6.8 Hz), 0.89-0.83 (m, 3H). MS (ES) m/z 454.2 (M+H$^+$).

Example 5

7-Methoxy-8-[4-(2-phenylthiazol-5-ylmethyl)-[1,4]diazepan-1-yl]-quinoline

Step 1: N-(2-Methoxy-6-nitrophenyl)-N'-methyl-N-propylthane-1,2-diamine hydrochloride

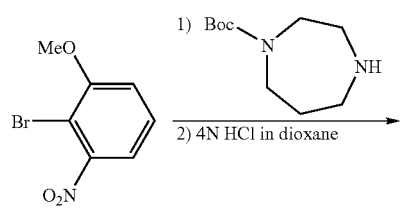

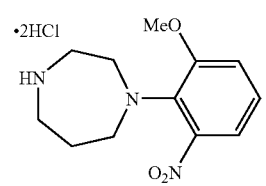

A mixture of BOC-homopiperazine (1.0 g, 5 mmol, 1 equiv), 2-bromo-1-methoxy-3-nitrobenzene (1.16 g, 1 equiv), cesium carbonate (1.7 g, 1 equiv) in 10 mL of DMF was heated at 60° C. over 72 hrs. After cooling down to room temperature, ethyl acetate (100 mL) and water (50 mL) were added. The organic layer was subjected to flash chromatography (5 to 40% ethyl acetate in hexane) to give 4-(2-methoxy-6-nitrophenyl)-[1,4]diazepane-1-carboxylic acid tert-butyl ester (0.50 g, 25%), which was then treated with 50 mL of 4N HCl in dioxane at 60° C. for 2 hrs. The mixture was then evaporated to dryness and used in the next step directly. MS (ES) m/z 252.1 (M+H$^+$).

Step 2: 1-(2-Methoxy-6-nitrophenyl)-4-(2-phenylthiazol-5-ylmethyl)-[1,4]diazepane

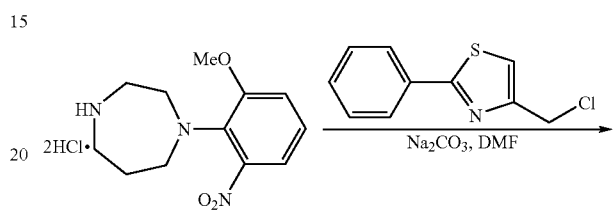

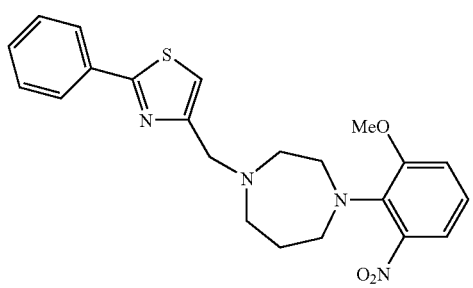

4-(Chloromethyl)-2-phenyl-1,3-thiazole (300 mg, 1.5 mmol, 1 equiv), N-(2-methoxy-6-nitrophenyl)-N'-methyl-N-propylethane-1,2-diamine hydrochloride (all from step 1, 1 equiv), and sodium carbonate (300 mg, 2 equiv) were suspended in 5 mL of anhydrous DMF. The mixture was stirred at 45° C. for 2 hours. After cooling down to room temperature, ethyl acetate (100 mL) and water (50 mL) were added. The organic layer was subjected to flash chromatography (0 to 5% MeOH in ethyl acetate) to give 1-(2-methoxy-6-nitrophenyl)-4-(2-phenylthiazol-5-ylmethyl)-[1,4]diazepane (250 mg, 40%). MS (ES) m/z 425.1 (M+H$^+$).

Step 3: 3-Methoxy-2-[4-(2-phenylthiazol-5-ylmethyl)-[1,4]diazepan-1-yl]-phenylamine

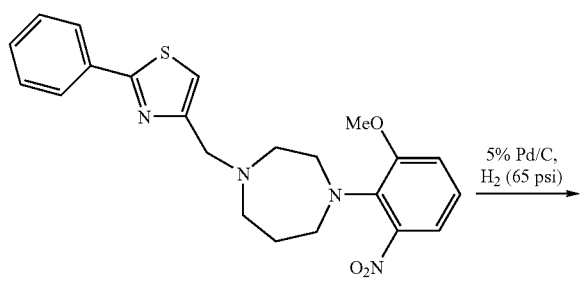

-continued

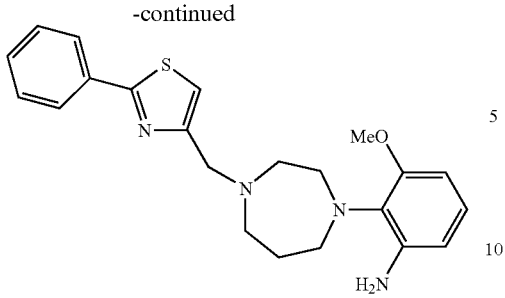

A mixture of 1-(2-methoxy-6-nitrophenyl)-4-(2-phenylthiazol-5-ylmethyl)-[1,4]diazepane (250 mg), 5% Pd/C (20 mg) in 50 mL of ethyl acetate was subjected to a Parr shaker at 65 psi of hydrogen for 16 hours. More 5% Pd/C (10 mg) was added and the reaction continued for another 16 hours. Filtration through celite followed by flash chromatography (0 to 10% MeOH in ethyl acetate) gave 3-methoxy-2-[4-(2-phenylthiazol-5-ylmethyl)-[1,4]diazepan-1-yl]-phenylamine (210 mg, 90%). MS (ES) m/z 395.1 (M+H$^+$).

Step 4: 7-Methoxy-8-[4-(2-phenylthiazol-5-ylmethyl)-[1,4]diazepan-1-yl]quinoline

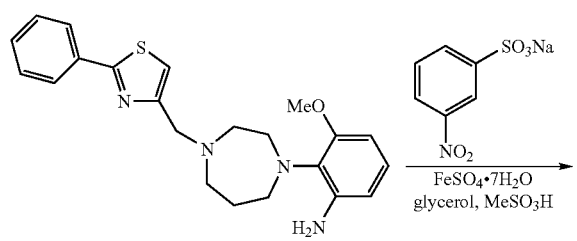

A mixture of 3-methoxy-2-[4-(2-phenylthiazol-5-ylmethyl)-[1,4]diazepan-1-yl]-phenylamine (210 mg, 0.53 mmol, 1 equiv), sodium 3-nitrophenylsulfonate (78 mg, 0.65 equiv), FeSO$_4$.7H$_2$O (7.5 mg, 0.05 equiv) and glycerol (122 mg, 2.5 equiv) in 2 mL of methanesulfonic acid was heated at 130° C. for 2 hours. After cooling down to room temperature, the mixture was diluted with water, neutralized with 10 N NaOH to pH ~10. Ethyl acetate was added and the mixture was filtered through celite. The organic layer was subjected to reverse phase HPLC purification. The combined fractions with the desired product were evaporated to remove acetonitrile, treated with saturated sodium bicarbonate and extracted with ethyl acetate to give the pure title compound (130 mg, 56%). $^1$H NMR (400 MHz, CDCl$_3$) δ 8.85 (dd, 1H, J=4.1, 2 Hz), 8.05 (dd, 1H, J=7.8, 2 Hz), 7.95 (d, 1H, J=2 Hz), 7.90 (d, 1H, J=2 Hz), 7.50 (d, 1H, 8.6 Hz), 7.42-7.35 (m, 3H), 7.30-7.20 (m, 3H), 7.20 (dd, 1H, J=7.8, 4.1 Hz), 4.08 (s, 2H), 3.85 (s, 3H), 3.62-3.50 (m, 4H), 3.10-3.00 (m, 2H), 3.00-2.80 (m, 2H), 2.20-2.00 (m, 2H). MS (ES) m/z 431.1 (M+H$^+$).

Example 6

7-Methyl-8-[4-(2-phenylthiazol-5-ylmethyl)-[1,4]diazepan-1-yl]-quinoline

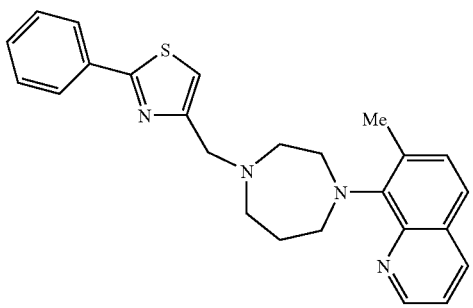

The title compound was prepared according to a sequence similar to that used for the synthesis of Example 5. The final compound was purified by flash chromatography (80 to 100% ethyl acetate in hexane). $^1$H NMR (400 MHz, CDCl$_3$) δ 8.85 (dd, 1H, J=4, 2 Hz), 8.05 (dd, 1H, J=8, 2 Hz), 7.96 (d, 1H, J=2 Hz), 7.95 (d, 1H, J=2 Hz), 7.49 (d, 1H, 8.4 Hz), 7.44-7.36 (m, 4H), 7.27 (dd, 1H, J=8, 4 Hz), 7.24 (s, 1H), 4.02 (s, 2H), 3.80-3.20 (m, 4H), 3.15-3.05 (m, 2H), 3.00-2.90 (m, 2H), 2.60 (s, 3H), 2.20-2.00 (m, 2H). MS (ES) m/z 415.1 (M+H$^+$).

Example 7

7-Chloro-8-[4-(2-phenylthiazol-5-ylmethyl)-[1,4]diazepan-1-yl]-quinoline

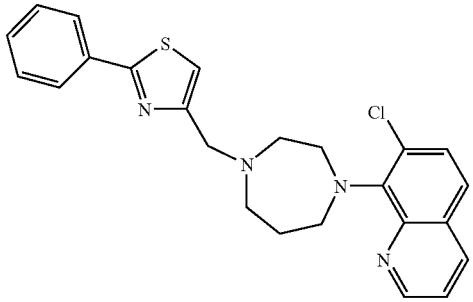

The title compound was prepared according to a sequence similar to that used for the synthesis of Example 5. The final compound was purified by flash chromatography (40 to 100% ethyl acetate in hexane). $^1$H NMR (400 MHz, CDCl$_3$) δ 8.87 (dd, 1H, J=4.2, 2 Hz), 8.10 (dd, 1H, J=7.9, 2 Hz), 7.94 (m, 2H), 7.50-7.42 (m, 2H), 7.42-7.30 (m, 2H), 7.35 (dd, 1H, J=7.9, 4.2 Hz), 7.35-7.30 (m, 1H), 7.22 (s, 1H), 4.03 (s, 2H), 3.70-3.50 (m, 4H), 3.20-2.90 (m, 4H), 2.15-2.00 (m, 2H). MS (ES) m/z 435.1 (M+H$^+$).

Example 8

(±)-3-[4-(7-Methoxyquinolin-8-yl)-[1,4]-diazepan-1-yl]-3-(2-morpholinothiazol-4-yl)-N-[2-(pyrrolidin-1-yl)ethyl]propanamide Step 1: 2-Morpholinothiazole-4-carbaldehyde

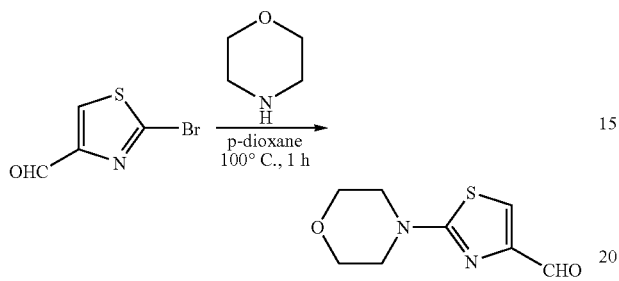

To a slurry of 2-bromothiazole-4-carbaldehyde (1.0 g, 5.21 mmol) in p-dioxane (5 mL) was added morpholine (1.36 g, 15.61 mmol) over 1 min. The mixture was heated to 100° C. for 1 h (monitored by TLC, EtOAc/hexane 1:1) and cooled to room temperature. EtOAc (20 mL) was added and the solid residue filtered off and washed with EtOAc (30 mL). The combined organic layer was washed with brine (30 mL) and concentrated. The residue was purified by silica gel flash column chromatography using 20 to 75% EtOAc in hexane to afford the title compound as a light tan solid (780 mg, 75%): $^1$H NMR (400 MHz, CDCl$_3$) δ 9.70 (s, 1H), 7.49 (s, 1H), 3.82 (t, 4H, J=4.8 Hz), 3.56 (t, 4H, J=4.8 Hz). MS (ES) m/z 199.1 (M+H$^+$).

Step 2: 8-Bromo-7-hydroxyquinoline

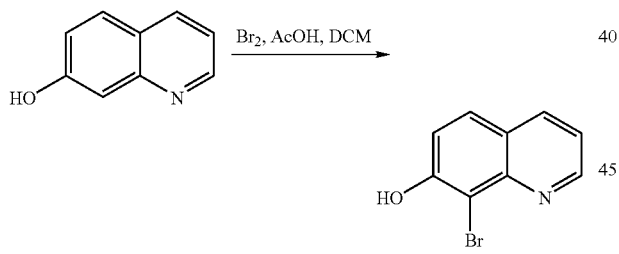

To a stirred solution of 7-hydroxyquinoline (59.0 g, 0.406 mol) in AcOH (120 mL) and CH$_2$Cl$_2$ (240 mL) was slowly added bromine (22.9 ml, 0.444 mol) in AcOH (120 ml) while keeping the internal temperature at 0-5° C. The resulting suspension was stirred for 2 h at 0-5° C., and then diluted with EtOAc (100 mL) and filtered. The solid was washed with EtOAc (2×20 mL) and dried in vacuo to give 8-bromo-7-hydroxyquinoline (65 g, 76%).

Step 3: 8-Bromo-7-methoxyquinoline

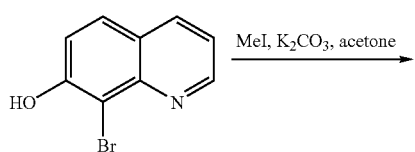

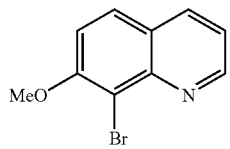

A mixture of 8-bromo-7-hydroxyquinoline (65 g, 0.29 mol), potassium carbonate (120 g, 0.87 mol), and methyl iodide (82 g, 0.58 mol) in acetone (500 mL) was heated to reflux for 4 hrs. The mixture was then cooled to rt and filtered. The filtrate was concentrated, dissolved in ethyl acetate (1 L), washed with water (300 mL×2) and saline (200 mL), dried over Na$_2$SO$_4$ and concentrated. The residue was recrystallized in ethyl acetate and hexane (1:1) to give 8-bromo-7-methoxyquinoline (40 g).

Step 4: 8-[1,4]Diazepan-1-yl-7-methoxy-quinoline

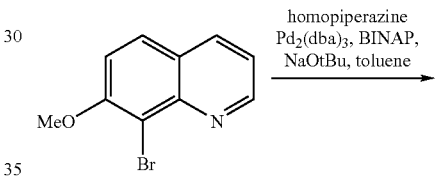

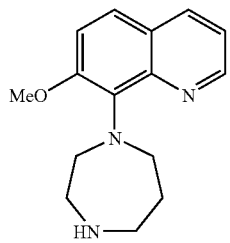

A mixture of 8-bromo-7-hydroxyquinoline (126 g, 0.488 mol), homopiperazine (201 g, 2.0 mol), (±)-BINAP (19.8 g, 31.8 mmol), and sodium tert-butoxide (75.6 g, 0.786 mol) was suspended in 900 mL of toluene and purged with nitrogen gas for an hour. Tris-benzylidineacetone dipalladium(0) (9.7 g, 10.6 mmol) was added. The mixture was purged for another hour, heated to reflux under nitrogen for 4 hr, cooled to rt, carefully diluted with 1300 mL of 20% AcOH in water and filtered through 100 g of celite. The celite pad was washed with 20% AcOH in water (1 L×2) and ethyl acetate (1 L×1). The aqueous phase was extracted with ethyl acetate (1 L×4), adjusted to pH 10-11 with NaOH (10 N, 500 mL), and then extracted with a mixture of CH$_2$Cl$_2$ and iPrOH (80:20, 1 L×2 and 0.5 L×4). The combined organic phase was washed with saline (400 mL), dried over Mg$_2$SO$_4$ and evaporated to give the desired product (98 g).

Step 5: (±)-Methyl 3-[4-(7-methoxyquinolin-8-yl)-[1,4]-diazepan-1-yl]-3-(2-morpholinothiazol-4-yl)-N-[2-(pyrrolidin-1-yl)ethyl]propanoate

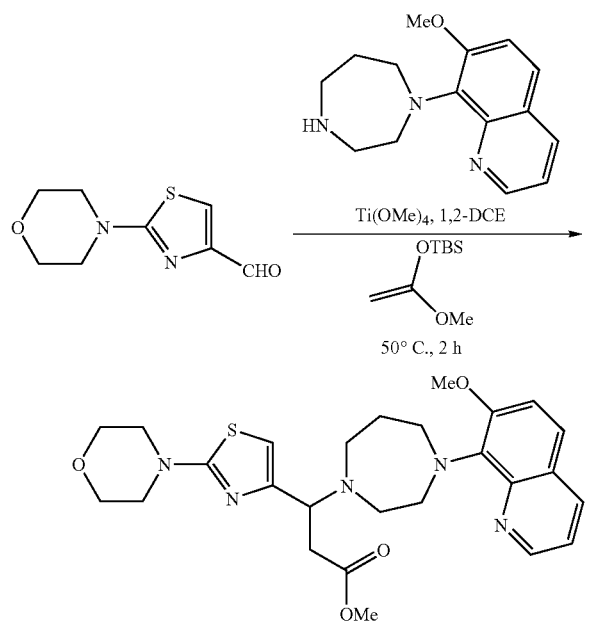

A 35 mL scintillation vial equipped with a magnetic stirrer was charged with 2-morpholinothiazole-4-carbaldehyde (200 mg, 1.01 mmol), 8-([1,4]-diazepan-1-yl)-7-methoxyquinoline (260 mg, 1.01 mmol), Ti(OMe)$_4$ (230 mg, 1.33 mmol) and 1,2-DCE (6 mL). The suspension was heated to 50° C. for 20 min. tert-Butyl (1-methoxyvinyloxy)-dimethylsilane (230 mg, 1.22 mmol) was added and the mixture stirred at 50° C. for 2 h and cooled to room temperature. The mixture was diluted with 20% MeOH in DCM (ca. 30 mL) and filtered through Celite and washed with 10% MeOH in DCM (2×30 mL). The combined organic layer was washed with saturated aqueous NaHCO$_3$, brine and concentrated. The residue was purified by silica gel flash column chromatography using 2 to 15% MeOH in DCM with 0.5% aqueous NH$_4$OH to afford the title compound as a light yellow foam (380 mg, 74%): $^1$H NMR (400 MHz, CDCl$_3$) δ 8.83 (dd, 1H, J=1.2 and 4 Hz), 8.01 (dd, 1H, J=2 and 8 Hz), 7.48 (d, 1H, J=8 Hz), 7.28 (d, 1H, J=8 Hz), 7.20 (dd, 1H, J=4 and 8 Hz), 6.47 (s, 1H), 4.56 (m, 1H), 3.94 (s, 3H), 3.80 (t, 4H, J=4.8 Hz), 3.69 (s, 3H), 3.51 (t, 4H, J=5.2 Hz), 3.43 (t, 4H, J=4.8 Hz), 3.08-2.82 (m, 5H), 2.32-1.90 (m, 3H). MS (ES) m/z 512.2 (M+H$^+$).

Step 6: (±)-Methyl 3-[4-(7-methoxyquinolin-8-yl)-[1,4]-diazepan-1-yl]-3-(2-morpholinothiazol-4-yl)-N-[2-(pyrrolidin-1-yl)ethyl]propanoic acid

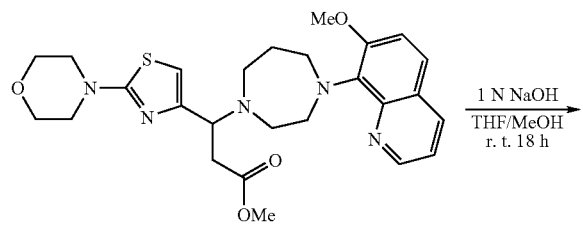

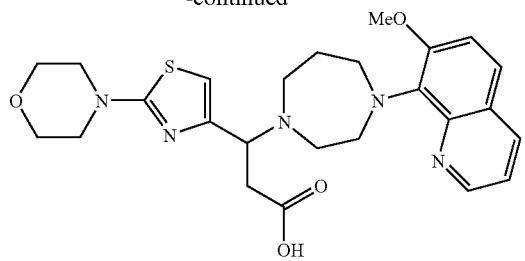

A 35 mL scintillation vial equipped with a magnetic stirrer was charged with (±)-methyl 3-[4-(7-methoxyquinolin-8-yl)-[1,4]-diazepan-1-yl]-3-(2-morpholinothiazol-4-yl)-N-[2-(pyrrolidin-1-yl)ethyl]propanoate (380 mg, 0.74 mmol), THF (5 mL), MeOH (5 mL) and 1 N NaOH solution (2 mL, 2.00 mmol). The resulting suspension was stirred at room temperature overnight (18 h, monitored by LC-MS/TLC). 2 N HCl (ca. 1 mL) was added to bring the pH to 7 and the mixture extracted with 15% MeOH in DCM with 0.5% aqueous NH$_4$OH (3×50 mL). The combined organic layer was concentrated and dried in vacuo to afford the title compound as a light yellow solid (280 mg, 76%). MS (ES) m/z 498.2 (M+H$^+$).

Step 7: (±)-3-[4-(7-Methoxyquinolin-8-yl)-[1,4]-diazepan-1-yl]-3-(2-morpholinothiazol-4-yl)-N-[2-(pyrrolidin-1-yl)ethyl]propanamide

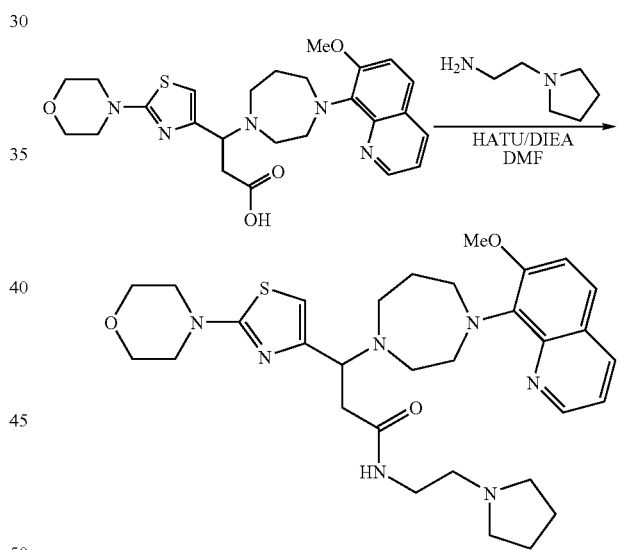

(±)-Methyl 3-[4-(7-methoxyquinolin-8-yl)-[1,4]-diazepan-1-yl]-3-(2-morpholinothiazol-4-yl)-N-[2-(pyrrolidin-1-yl)ethyl]propanoic acid (90 mg, 0.19 mmol), and 2-(pyrrolidin-1-yl)ethanamine (33 mg, 0.29 mmol) were suspended in anhydrous DMF (6 mL). N,N-Diisopropylethylamine (0.20 mL, 1.15 mml) was added and the mixture was stirred at ambient temperature for 5 min followed by addition of HATU (100 mg, 0.26 mmol). After 1 h at ambient temperature, LC-MS and TLC indicated complete reaction (LC/MS [M+H]$^+$594.3). Water (5 mL) was added and the mixture extracted with EtOAc (100 mL). The organic layer was washed with brine (3×30 mL) and concentrated. The residue was purified by silica gel flash column chromatograph using 2 to 5% MeOH in DCM with 0.5% aqueous NH$_4$OH to afford the title compound as a light yellow solid (60 mg, 53%): $^1$H NMR (400 MHz, CDCl$_3$) δ 9.00 (br s, 1H), 8.82 (dd, 1H, J=1.6 and 4 Hz), 8.05 (d, 1H, J=8 Hz), 7.53 (d, 1H, J=8.8 Hz), 7.29 (d, 1H, J=8.8 Hz), 7.22 (dd, 1H, J=4 and 8 Hz), 6.46 (s, 1H), 4.25 (m, 1H), 3.93 (s, 3H), 3.78 (t, 4H, J=4.8 Hz), 3.58 (m, 2H), 3.52 (t, 2H, J=5.6 Hz), 3.40 (t, 4H, J=4.8 Hz), 3.22 (m, 2H), 3.05-2.98 (m, 3H), 2.64 (br, 1H), 2.62 (t, 2H, J=6.4 Hz), 2.53 (br s, 4H), 2.45 (br s, 2H), 2.02 (m, 2H), 1.78 (br s, 4H). MS (ES) m/z 594.3 (M+H$^+$).

Example 9

(±)-3-[1-(Cyclopentanecarbonyl)piperidin-4-yl]-3-[4-(7-methoxyquinolin-8-yl)-[1,4]-diazepan-1-yl]-N-[2-(pyrrolidin-1-yl)ethyl]propanamide Step 1: (±)-tert-Butyl-{3-methoxy-1-[4-(7-methoxyquinolin-8-yl)-[1,4]-diazepan-1-yl]-3-oxopropyl}piperidine-1-carboxylate

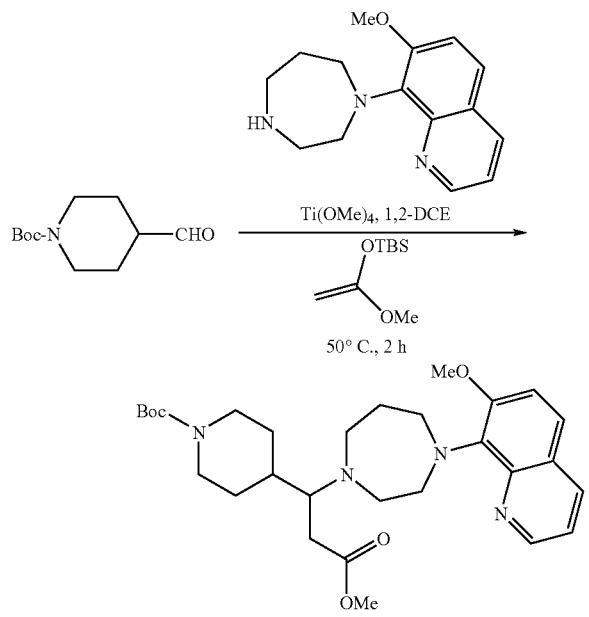

A 35 mL scintillation vial equipped with a magnetic stirrer was charged with the N-Boc-4-formylpiperidine (400 mg, 1.88 mmol), 8-([1,4]-diazepan-1-yl)-7-methoxyquinoline (500 mg, 1.94 mmol), Ti(OMe)$_4$ (400 mg, 2.32 mmol) and 1,2-DCE (10 mL). The suspension was heated to 50° C. for 15 min. tent-Butyl (1-methoxyvinyloxy)-dimethylsilane (400 mg, 2.13 mmol) was added and the mixture stirred at 50° C. for 2 h and cooled to room temperature. The mixture was diluted with 20% MeOH in DCM (ca. 30 mL) and filtered through Celite and washed with 10% MeOH in DCM (2×30 mL). The combined organic layer was washed with saturated aqueous NaHCO$_3$, brine and concentrated. The residue was purified by silica gel flash column chromatograph using 2 to 5% MeOH in DCM with 0.5% aqueous NH$_4$OH to afford the title compound as a light tan foam (400 mg, 40%): $^1$H NMR (400 MHz, CDCl$_3$) δ 8.83 (dd, 1H, J=1.2 and 4 Hz), 8.01 (dd, 1H, J=2 and 8 Hz), 7.47 (d, 1H, J=8.8 Hz), 7.28 (d, 1H, J=8.8 Hz), 7.20 (dd, 1H, J=4 and 8 Hz), 4.11 (br s, 2H), 3.96 (s, 3H), 3.71 (s, 3H), 3.51 (m, 4H), 2.95-2.78 (m, 5H), 2.70-2.58 (m, 3H), 2.37 (dd, 1H, J=6 and 14.8 Hz), 2.15 (d, 1H, J=13.2 Hz), 1.94 (m, 2H), 1.57 (m, 1H), 1.47 (s, 9H), 1.30-1.10 (m, 3H). MS (ES) m/z 527.6 (M+H$^+$).

Step 2: (±)-3-[(tert-Butoxycarbonyl)piperidin-4-yl]-3-[4-(7-methoxyquinolin-8-yl)-[1,4]-diazepan-1-yl]propanoic acid

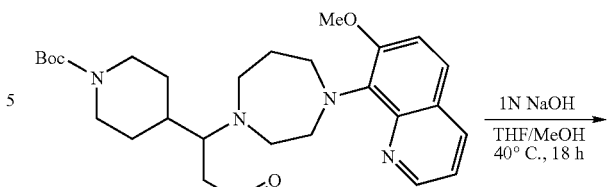

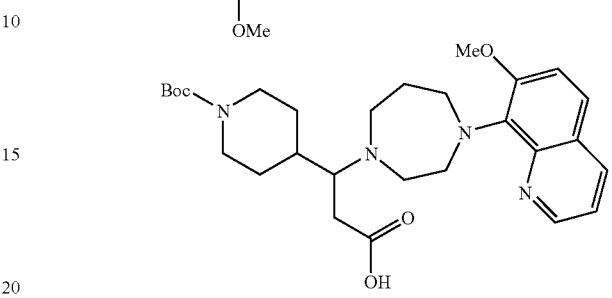

A 35 mL scintillation vial equipped with a magnetic stirrer was charged (±)-tert-butyl-{3-methoxy-1-[4-(7-methoxyquinolin-8-yl)-[1,4]-diazepan-1-yl]-3-oxopropyl}piperidine-1-carboxylate (400 mg, 0.76 mmol), THF (5 mL), MeOH (5 mL) and 1 N NaOH solution (6 mL, 6.00 mmol). The resulting suspension was stirred at 40° C. overnight (18 h). 2 N HCl (ca. 3 mL) was added to bring the pH to 7 and the mixture extracted with 10% MeOH in DCM with 0.5% aqueous NH$_4$OH (3×50 mL). The combined organic layer was concentrated and dried in vacuo to afford the title compound as a light yellow foam (350 mg, 90%). MS (ES) m/z 513.5 (M+H$^+$).

Step 3: (±)-tert-Butyl 4-{1-[4-(7-methoxyquinolin-8-yl)-[1,4]-diazepan-1-yl]-3-oxo-3-[2-(pyrrolidin-1-yl)ethylamino]propyl}piperidine-1-carboxylate

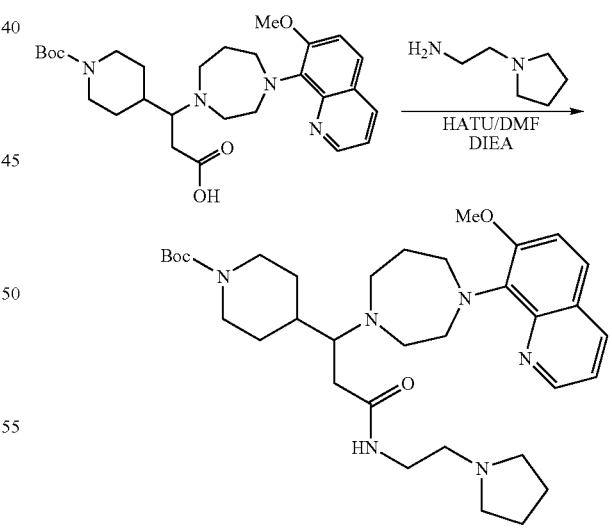

(±)-3-[(tert-Butoxycarbonyl)piperidin-4-yl]-3-[4-(7-methoxyquinolin-8-yl)-[1,4]-diazepan-1-yl]propanoic acid (800 mg, 1.56 mmol), and 2-(pyrrolidin-1-yl)ethanamine (250 mg, 2.19 mmol) were suspended in anhydrous DMF (6 mL). N,N-Diisopropylethylamine (0.5 mL, 2.88 mmol) was added and the mixture was stirred at ambient temperature for 5 min followed by addition of HATU (761 mg, 2.00 mmol).

After 1 h at ambient temperature, LC-MS and TLC indicated complete reaction (LC/MS [M+H]+609.7). Water (5 mL) was added and the mixture extracted with EtOAc (100 mL). The organic layer was washed with brine (3×30 mL) and concentrated. The residue was purified by silica gel flash column chromatograph using 2 to 5% MeOH in DCM with 0.5% aqueous NH$_4$OH to afford the title compound as a light yellow oil (480 mg, 50%): $^1$H NMR (400 MHz, CDCl$_3$) δ 8.81 (dd, 1H, J=1.6 and 4 Hz), 8.03 (dd, 2H, J=1.6 and 8 Hz), 7.51 (d, 1H, J=8.8 Hz), 7.29 (d, 1H, J=8.8 Hz), 7.22 (dd, 1H, J=4 and 8 Hz), 4.12 (br s, 2H), 3.96 (s, 3H), 3.51 (m, 4H), 3.38 (m, 3H), 3.20-2.80 (m, 4H), 2.70-2.40 (m, 5H), 2.24 (m, 1H), 1.98 (br, 1H), 1.80-1.55 (m, 11H), 1.46 (s, 9H), 1.34-1.16 (m, 3H). MS (ES) m/z 609.7 (M+H+).

Step 4: (±)-3-[1-(Cyclopentanecarbonyl)piperidin-4-yl]-3-[4-(7-methoxyquinolin-8-yl)-[1,4]-diazepan-1-yl]-N-[2-(pyrrolidin-1-yl)ethyl]propanamide

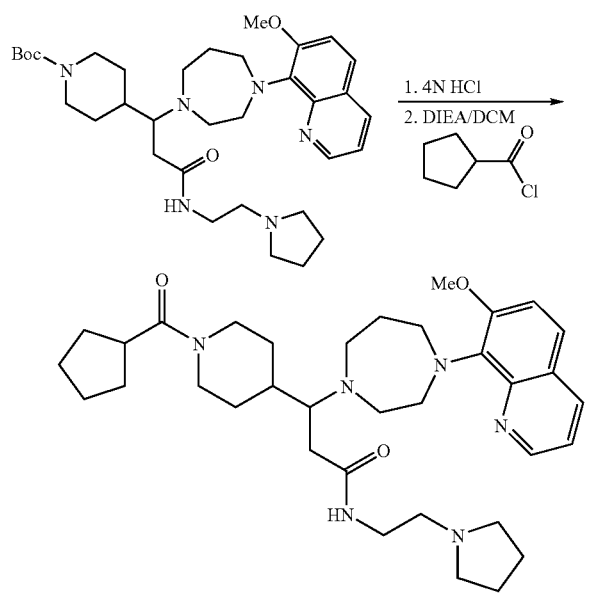

(±)-tert-Butyl 4-{1-[4-(7-methoxyquinolin-8-yl)-[1,4]-diazepan-1-yl]-3-oxo-3-[2-(pyrrolidin-1-yl)ethylamino]propyl}piperidine-1-carboxylate (300 mg, 0.49 mmol) was dissolved in DCM (5 mL). 4 N HCl in dioxane (5 mL, 20.0 mmol) was added and the mixture was stirred at ambient temperature for 2 h. LC-MS and TLC indicated complete reaction (LC/MS [M+H]+509.6). The mixture was concentrated and dried in vacuo to afford the intermediate hydrochloride salt (300 mg, quantitative).

The compound obtained in the previous step (85 mg, ca. 0.14 mmol) was suspended in DCM (5 mL) and DIEA (0.5 mL, 2.88 mmol) was added. After stirring at ambient temperature for 10 min, cyclopentane carbonyl chloride (30 mg, 0.23 mmol) was added. After 1 h at ambient temperature, LC-MS and TLC indicated reaction complete (LC/MS [M+H]+605.7). 1 N NaOH (3 mL) was added and the mixture extracted with EtOAc (100 mL). The organic layer was washed with brine (3×30 mL) and concentrated. The residue was purified by silica gel flash column chromatograph using 2 to 5% MeOH in DCM with 0.5% aqueous NH$_4$OH to afford the title compound as a light yellow oil (10 mg, 12%): $^1$H NMR (400 MHz, CDCl$_3$) δ 8.81 (dd, 1H, J=1.6 and 4 Hz), 8.02 (dd, H, J=1.6 and 8 Hz), 7.88 (br, 1H), 7.50 (d, 1H, J=8.8 Hz), 7.29 (d, 1H, J=8.8 Hz), 7.21 (dd, 1H, J=4 and 8.4 Hz), 4.65 (br s, 1H), 4.00 (m, 1H), 3.96 (s, 3H), 3.54 (t, 4H, J=5.2 Hz), 3.37 (m, 3H), 3.20-2.80 (m, 7H), 2.70-2.40 (m, 7H), 2.24 (m, 1H), 1.98 (br s, 1H), 1.80-1.50 (m, 15H), 1.34-1.16 (m, 3H). MS (ES) m/z 605.7 (M+H+).

Example 10

(±)-3-(1-Isopropyl-1H-pyrazol-3-yl)-3-[4-(7-methoxyquinolin-8-yl)-1,4-diazepan-1-yl]-N-[2-(pyrrolidin-1-yl)ethyl]propanamide Step 1: 4-Dimethylamino-2-oxo-but-3-enoic acid ethyl ester

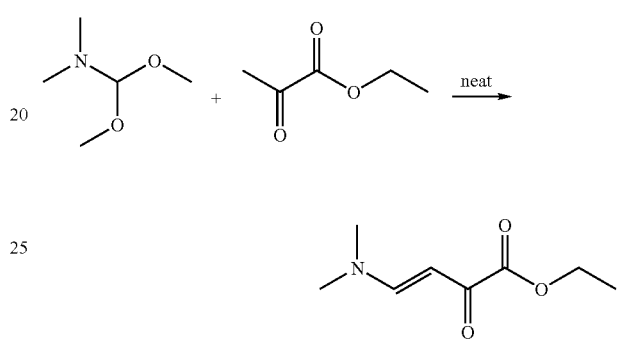

1,1-Dimethoxy-n,n-dimethylmethanamine (153 g, 1.29 mol, 1 equiv) and 2-oxo-propionic acid ethyl ester (152 g, 1.31 mol, 1.02 equiv) were mixed and stirred at room temperature overnight. The mixture was concentrated under vacuum to give the product (197 g, 89% yield) as a dark brown oil.

Step 2: 1H-Pyrazole-3-carboxylic acid ethyl ester

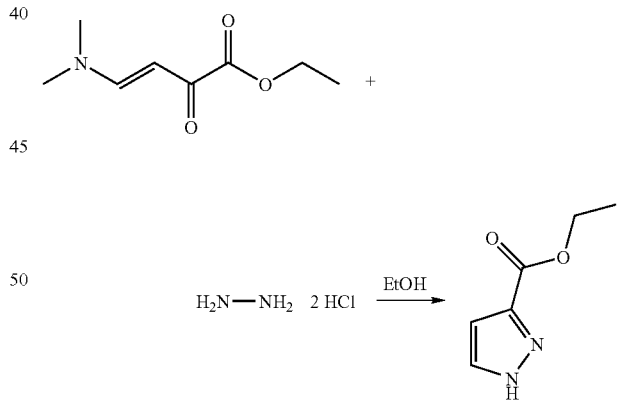

4-Dimethylamino-2-oxo-but-3-enoic acid ethyl ester (195 g, 1.14 mol) and hydrazine dihydrochloride (119.7 g, 1 eq) were dissolved in EtOH (1 L) and stirred at room temperature overnight. The mixture was then heated to reflux for 2 hours. The reaction mixture was allowed to cool to room temperature and filtered. The solid was washed with water three times and dried. The filtrate was concentrated to a thick oil and added dropwise into a flask with stirred EtOAc (200 mL). The resulting solid was filtered and rinsed with a small amount of EtOAc. The filtered solids were combined to give the product (62 g, 39% yield). MS (ES) m/z 141.1 (M+H+).

Step 3: 1-Isopropyl-1H-pyrazole-3-carboxylic acid ethyl ester

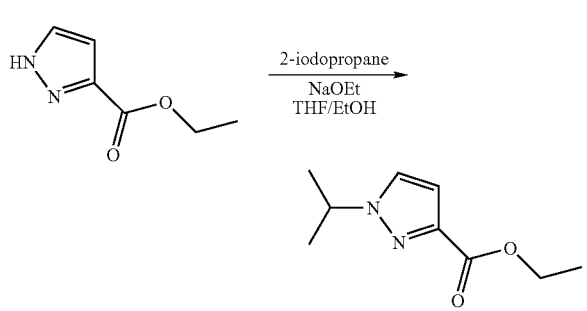

To 1H-pyrazole-3-carboxylic acid ethyl ester (23.1 g, 165 mmol) in THF (330 mL) was added 2-iodopropane (33.0 mL, 330 mmol) followed by NaOEt (21% in EtOH, 65.0 mL, 174 mmol). This solution was then heated to reflux for 16 h. The reaction was then allowed to cool to room temperature. AcOH (10.5 mL, 183 mmol) was added and the reaction was stirred for 5 min. $H_2O$ (400 mL) was added to the solution, and this mixture was extracted with EtOAc (3×150 mL). The combined organic was washed with sat. aq. $NaHCO_3$, then brine. The organic was dried over $MgSO_4$, filtered, and concentrated to give the product (28.70 g, 96%) as a brown oil containing a 98:2 mixture of regioisomers by $^1$H NMR.

Step 4: (1-Isopropyl-1H-pyrazol-3-yl)-methanol

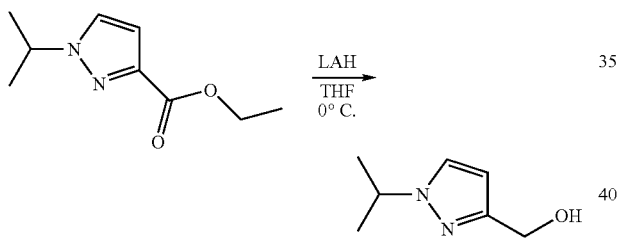

A solution of 1-Isopropyl-1H-pyrazole-3-carboxylic acid ethyl ester (41.1 g, 226 mmol) in THF (678 mL) was cooled to 0° C. under $N_2$. $LiAlH_4$ (1M in THF, 226 mL, 226 mmol) was added dropwise to this solution over 20 min. The reaction was stirred for 1 h, at which point the ester starting material was not detectable by LCMS. $H_2O$ (8.58 mL) was added to the reaction dropwise, followed by dropwise addition of 15% NaOH (8.58 mL), followed by $H_2O$ (8.57 mL). Celite was then added to the solution and this was allowed to stir overnight. The mixture was then filtered through celite, washing the filter cake to remove all the product (1× with EtOAc, then 2× with 90:10 $CH_2Cl_2$:MeOH, then 2× with 1:1 $CH_2Cl_2$:MeOH, then 1× with MeOH.) The solvent was then concentrated to give a mixture of solid and oil. The oil was dissolved in EtOAc and filtered through celite, then concentrated. The resulting oil was a mixture of ~1:1 product with aluminum complexed product. The oil was dissolved in THF (400 mL), 15% NaOH (300 mL) was added and this solution was stirred vigorously for 3 h. The layers were separated, and the aqueous was extracted with EtOAc (6×200 mL) then 2:1 $CHCl_3$:iPrOH (2×300 mL). The combined organic was dried over $MgSO_4$, filtered, and concentrated. The resulting oil was carried on without further purification.

Step 5: 1-Isopropyl-1H-pyrazole-3-carbaldehyde

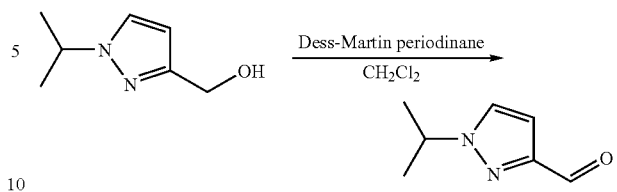

To the (1-Isopropyl-1H-pyrazol-3-yl)-methanol from the above reaction was added $CH_2Cl_2$ (1.10 L). Dess-Martin periodinane (144 g, 339 mmol) was then added portionwise. The reaction was stirred at room temperature. After 1 h, more Dess-Martin periodinane (16.0 g, 37.7 mmol) was added. The reaction was allowed to stir for 11 h, at which point starting material was no longer detectable by LCMS. The reaction mixture was filtered through celite. The filtrate was then washed with sat. aq. $NaHCO_3$ (3×300 mL) followed by brine (150 mL). The organic was dried over $MgSO_4$, filtered, and concentrated. This crude product was then dry loaded onto the ISCO and eluted with $CH_2Cl_2$ to give the purified product (18.8 g, 61%) as a pale yellow oil.

Step 6: (±)-3-(1-Isopropyl-1H-pyrazol-3-yl)-3-[4-(7-methoxy-quinolin-8-yl)-[1,4]diazepan-1-yl]-propionic acid methyl ester

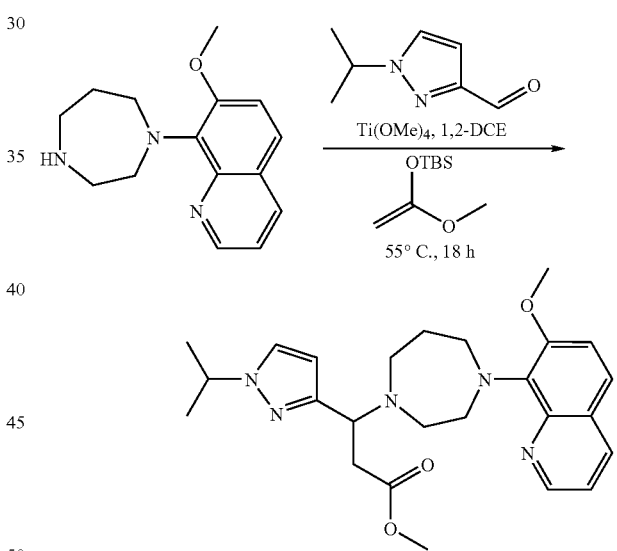

1,2-Dichloroethane (39 mL) was added to a mixture of homopiperazine (2.00 g, 7.78 mmol) and aldehyde (1.07 g, 7.78 mmol). This mixture was heated to 55° C. and stirred until homogeneous. Freshly crushed Ti(OMe)$_4$ (1.61 g, 9.34 mmol) was added and the reaction was stirred for 1 h at 55° C. The solution was then concentrated under vacuum. The resulting brown oil was dissolved in 1,2-Dichloroethane (39 mL), and the silyl ketene acetal (2.04 mL, 9.34 mmol) was added. The reaction was heated to 55° C. and stirred for 15 h. The solution was then diluted with $CH_2Cl_2$, and sat. aq. $NaHCO_3$ was added, followed by 1 N aq. NaOH. This was allowed to stir for 5 min, then filtered through celite, washing the filter cake with $CH_2Cl_2$. The filtrate was transferred to a sep funnel and washed with $H_2O$. To the organic was added AcOH (3.0 mL), and the product was extracted twice with $H_2O$. The combined aqueous was washed once with $CH_2Cl_2$, then Et₃N (7.0 mL) was added. The product was then extracted twice with CH₂Cl₂. The combined organic was dried over MgSO₄, filtered, and concentrated to give the product (1.688 g, 48% yield) as a brown oil.

Step 7: (±)-3-(1-Isopropyl-1H-pyrazol-3-yl)-3-[4-(7-methoxyquinolin-8-yl)-1,4-diazepan-1-yl]propanoic acid

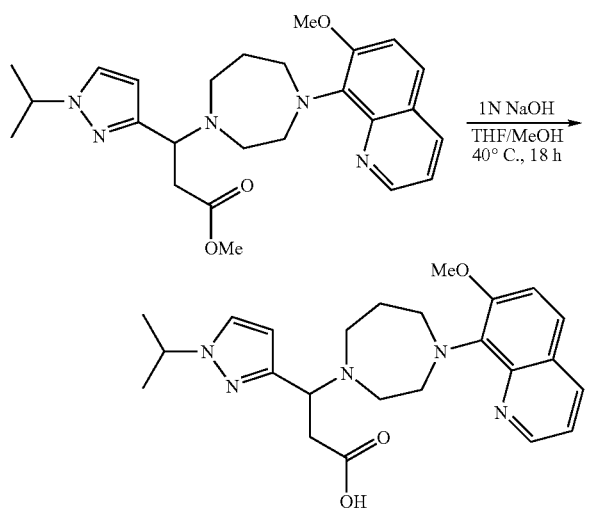

A 35 mL scintillation vial equipped with a magnetic stirrer was charged with (±)-methyl 3-(1-isopropyl-1H-pyrazol-3-yl)-3-[4-(7-methoxyquinolin-8-yl)-1,4-diazepan-1-yl]propanoic acid (450 mg, 1.0 mmol), THF (5 mL), MeOH (5 mL) and 1 N NaOH solution (6 mL, 6.0 mmol). The resulting suspension was stirred at 40° C. overnight (18 h). 2 N HCl (ca. 3 mL) was added to bring the pH to 7 and the mixture extracted with 10% MeOH in CH₂Cl₂ containing 0.5% aqueous NH₄OH (3×50 mL). The combined organic layer was concentrated and dried in vacuo to afford the title compound (360 mg, 82%) as a light yellow foam. MS (ES) m/z 438.4 (M+H⁺).

Step 8: (±)-3-(1-Isopropyl-1H-pyrazol-3-yl)-3-[4-(7-methoxyquinolin-8-yl)-1,4-diazepan-1-yl]-N-[2-(pyrrolidin-1-yl)ethyl]propanamide

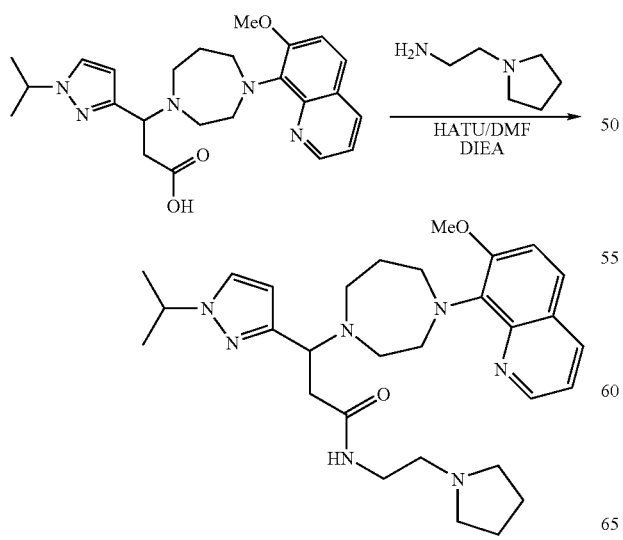

(±)-3-(1-Isopropyl-1H-pyrazol-3-yl)-3-[4-(7-methoxyquinolin-8-yl)-1,4-diazepan-1-yl]propanoic acid (220 mg, 0.50 mmol) and 2-(pyrrolidin-1-yl)ethanamine (114 mg, 1.0 mmol) were suspended in anhydrous DMF (6 mL). N,N-Diisopropylethylamine (0.2 mL, 1.2 mmol) was added and the mixture was stirred at ambient temperature for 5 min followed by addition of HATU (300 mg, 0.79 mmol). After 1 h at ambient temperature, LC-MS and TLC indicated completion of reaction (LC/MS [M+H]⁺ 534.6). Water (5 mL) was added and the mixture extracted with EtOAc (100 mL). The organic layer was washed with brine (3×30 mL) and concentrated. The residue was purified by silica gel chromatography using 2 to 5% MeOH in CH₂Cl₂ containing 0.5% aqueous NH₄OH to afford the title compound (230 mg, 86%) as a light yellow solid. ¹H NMR (400 MHz, CDCl₃) δ 9.20 (br, 1H), 8.81 (d, 1H, J=2.8 Hz), 8.03 (d, 1H, J=8.4 Hz), 7.51 (d, 1H, J=8.4 Hz), 7.34 (d, 1H, J=2.8 Hz), 7.27 (d, 1H, J=8.8 Hz), 7.21 (dd, 1H, J=4.0 and 8.0 Hz), 6.16 (s, 1H), 4.52 (septet, 1H, J=6.8 Hz), 4.34 (br, 1H), 3.90 (s, 3H), 3.58 (m, 2H), 3.52-3.40 (m, 4H), 3.20-2.80 (m, 4H), 2.63 (t, 2H, J=6.8 Hz), 2.54 (br s, 4H), 2.20 (br s, 2H), 2.02 (m, 2H), 1.78 (br s, 4H), 1.47 (d, 6H, J=6.8 Hz). MS (ES) m/z 534.6 (M+H⁺).

Example 11

(+)-3-(1-Isopropyl-1H-pyrazol-3-yl)-3-[4-(7-methoxyquinolin-8-yl)-1,4-diazepan-1-yl]-N-[2-(pyrrolidin-1-yl)ethyl]propanamide and (−)-3-(1-Isopropyl-1H-pyrazol-3-yl)-3-[4-(7-methoxyquinolin-8-yl)-1,4-diazepan-1-yl]-N-[2-(pyrrolidin-1-yl)ethyl]propanamide

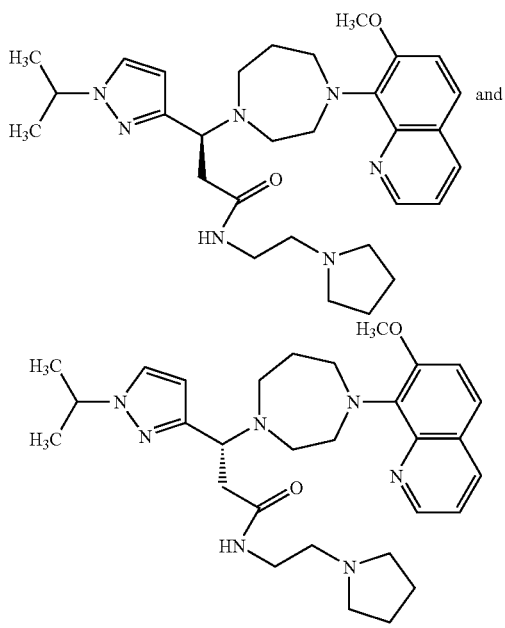

Step 1 (resolution): The 1:2 salt of (±)-3-(1-isopropyl-1H-pyrazol-3-yl)-3-[4-(7-methoxy-quinolin-8-yl)-[1,4]diazepan-1-yl]-propionic acid methyl ester and di-p-toluoyl-L-tartaric acid (1.0 g) in 5 mL of acetone was heated to 60° C. and then cooled to room temperature. After 12 h the mixture was filtered to give 0.4 g of solid, which was re-dissolved in 8 mL of DCM. After addition of 3.6 mL of EtOAc, the mixture was left at room temperature overnight and filtered to give 0.3 g of solid, which was again dissolved in 7.5 mL of DCM. After addition of 1.5 mL of EtOAc, the mixture was left at room temperature overnight and filtered to give 0.25 g of solid. HPLC analysis using a chiral column (RegisCell, catalog #784104) indicated a ratio of >30:1 of the two enantiomers, with the major isomer eluted slower when using 10% iPrOH in hexane containing 0.1% diethylamine at a flow rate of 1 mL/min. Neutralization of the final salt with saturated aq. NaHCO$_3$ followed by extraction with EtOAc and concentration gave the free base.

A similar procedure was carried out using the 1:1 salt of (±)-3-(1-isopropyl-1H-pyrazol-3-yl)-3-[4-(7-methoxyquinolin-8-yl)-[1,4]diazepan-1-yl]-propionic acid methyl ester and di-p-toluoyl-D-tartaric acid. The first resolution cycle used a 1:1.2 mixture of DCM/toluene as the solvent. The major isomer eluted faster on a RegisCell chiral column (catalog #784104) when using 10% iPrOH in hexane containing 0.1% diethylamine at a flow rate of 1 mL/min.

Step 2: The title compounds were obtained, separately, from the two free bases obtained in Step 1 according to the hydrolysis and amide formation procedures described in Example 10.

Example 12

(±)-3-(2-Cyclopropylthiazol-4-yl)-3-[1,4]-methoxyquinolin-8-yl)-[1,4'-diazepan-1-yl]-N-[2-(pyrrolidin-1-yl)ethyl]propanamide Step 1: 4-(Chloromethyl)-2-cyclopropylthiazole

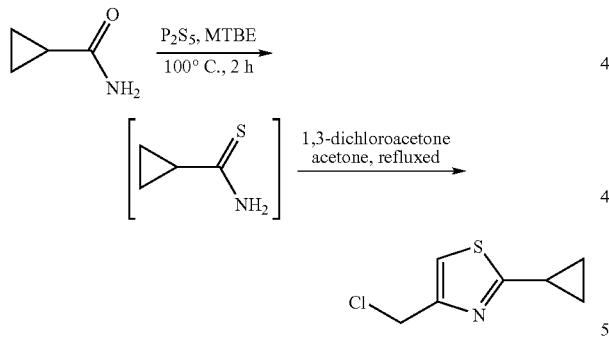

To a slurry of cyclopropanecarboxamide (10 g, 0.12 mol) in MTBE (150 mL) was charged P$_2$S$_5$ (5 g, 12 mmol). The mixture was heated to 100° C. for 2 h (monitored by TLC, EtOAc/hexane 1:1) and cooled to room temperature. Supernatant was decanted and concentrated to afford the intermediate thioamide (6 g, 56%) as a light yellow solid. MS (ES) m/z 102.1 (M+H$^+$)). This was suspended in acetone (100 mL) and charged with 1,3-dichloroacetone (7.0 g, 0.055 mol). The mixture was heated to reflux for 8 h (monitored by TLC, EtOAc/hexane 1:1), cooled to room temperature and concentrated. The residue was purified by silica gel chromatography using 2 to 10% EtOAc in hexane to afford the title compound (8.0 g, 79%) as a light brown oil. $^1$H NMR (400 MHz, CDCl$_3$) δ 7.02 (s, 1H), 4.62 (s, 2H), 2.32 (m, 1H), 1.16 (m, 2H), 1.05 (m, 2H). MS (ES) m/z 174.1 (M+H$^+$).

Step 2: 2-Cyclopropylthiazole-4-carbaldehyde

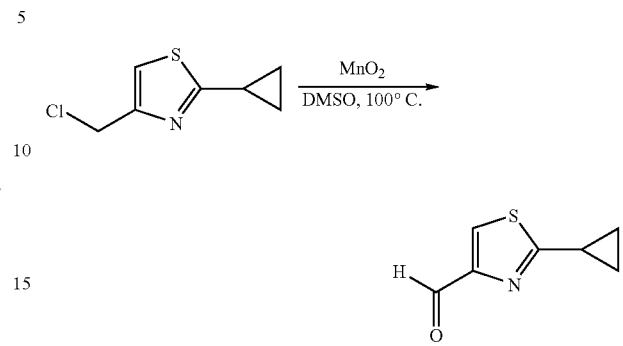

To a solution of 4-(chloromethyl)-2-cyclopropylthiazole (3.0 g, 17.2 mmol) in DMSO (10 mL) was charged MnO$_2$ (1.5 g, 17.2 mmol). The mixture was heated to 100° C. overnight, cooled to room temperature and diluted with EtOAc (30 mL). The mixture was filtered through Celite and washed with EtOAc (3×30 mL). The combined organic layer was washed with brine (3×40 mL) and concentrated. The residue was purified by silica gel chromatography using 2 to 5% EtOAc in hexane to afford the title compound (1.0 g, 38%) as a light brown oil, which solidified upon standing in a refrigerator overnight. $^1$H NMR (400 MHz, CDCl$_3$) δ 9.91 (s, 1H), 7.93 (s, 1H), 2.36 (m, 1H), 1.20 (m, 2H), 1.16 (m, 2H). MS (ES) m/z 154.1 (M+H$^+$).

Step 3: (±)-3-(2-Cyclopropylthiazol-4-yl)-3-[4-(7-methoxyquinolin-8-yl)-[1,4]-diazepan-1-yl]-N-[2-(pyrrolidin-1-yl)ethyl]propanamide

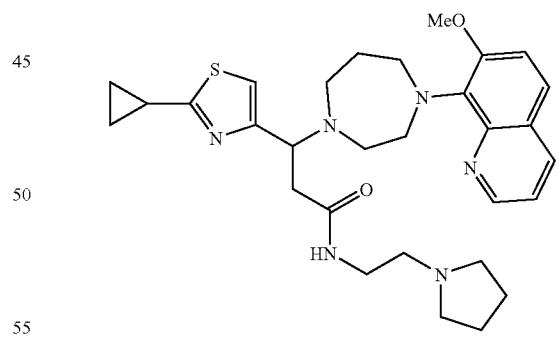

The title compound was prepared according the general procedure described in Example 8 as a light yellow solid. $^1$H NMR (400 MHz, CDCl$_3$) δ 8.81 (dd, 1H, J=2.0 and 4.0 Hz), 8.02 (dd, 1H, J=1.2 and 8.4 Hz), 7.50 (d, 1H, J=8.8 Hz), 7.27 (d, 1H, J=8.8 Hz), 7.21 (dd, 1H, J=4.0 and 8.0 Hz), 6.84 (s, 1H), 4.39 (br, 1H), 3.90 (s, 3H), 3.56 (m, 2H), 3.51 (m, 2H), 3.42 (m, 2H), 3.20-3.00 (m, 3H), 2.88 (m, 1H), 2.78 (m, 1H), 2.62 (t, 2H, J=6.0 Hz), 2.54 (br s, 4H), 2.29 (m, 1H), 2.02 (m, 4H), 1.79 (br s, 4H), 1.13 (m, 2H), 1.04 (m, 2H). MS (ES) m/z 549.5 (M+H$^+$).

Example 13

(±)-3-[2-(4-Hydroxy-piperidin-1-yl)-thiazol-4-yl]-3-[4-(7-methoxy-quinolin-8-yl)-[1,4]diazepan-1-yl]-1-(4-methyl-piperazin-1-yl)-propan-1-one Step 1: (±)-3-[2-(4-Hydroxy-piperidin-1-yl)-thiazol-4-yl]-3-[4-(7-methoxy-quinolin-8-yl)-[1,4]diazepan-1-yl]-propionic acid methyl ester

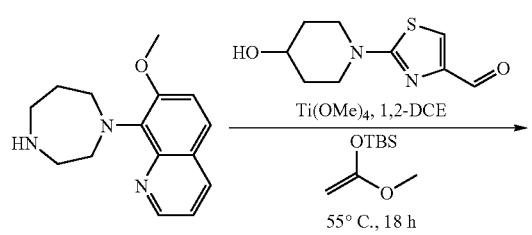

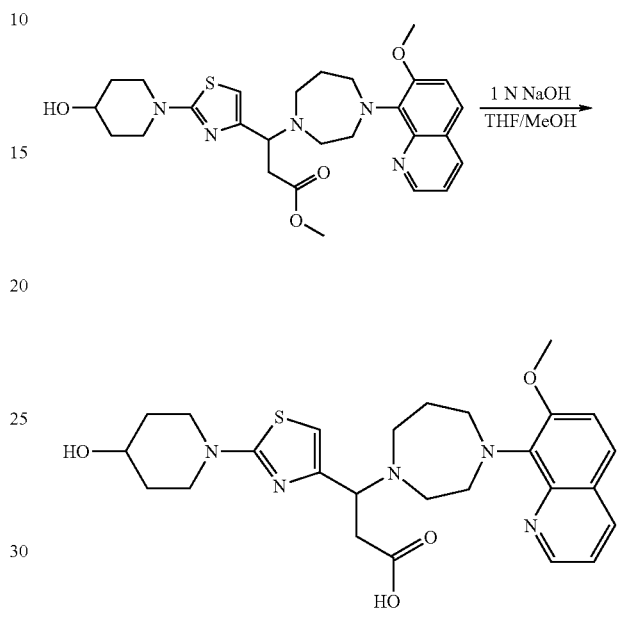

1,2-Dichloroethane (1.02 mL) was added to a mixture of 8-[1,4]diazepan-1-yl-7-methoxy-quinoline (1.00 g, 3.88 mmol) and 2-(4-hydroxy-piperidin-1-yl)-thiazole-4-carbaldehyde (824 mg, 3.88 mmol). The reaction was heated to 55° C. and stirred until homogeneous. Freshly crushed Ti(OMe)$_4$ (1.00 g, 5.82 mmol) was then added and the reaction was stirred at 55° C. for 1 h. tert-Butyl-(1-methoxy-vinyloxy)-dimethyl-silane (1.02 mL, 4.66 mmol) was then added and the reaction was stirred at 55° C. for 18 h. CH$_2$Cl$_2$ was then added, followed by sat. aq. NaHCO$_3$, then 1 N aq. NaOH. This mixture was then stirred for 5 min and filtered through celite, washing the filter cake with CH$_2$Cl$_2$. The filtrate was then washed once with H$_2$O, dried over MgSO$_4$, filtered, and concentrated. The crude product was purified on silica gel (99:1 to 90:10 CH$_2$Cl$_2$:(9:1 MeOH:NH$_4$OH)) to give the product (660 mg, 38% yield).

Step 2: (±)-3-[2-(4-Hydroxy-piperidin-1-yl)-thiazol-4-yl]-3-[4-(7-methoxy-quinolin-8-yl)-[1,4]diazepan-1-yl]-propionic acid The product from step 1 (660 mg, 1.26 mmol) was dissolved in THF (4.20 mL) and 1 N aq. NaOH (2.52 mL, 2.52 mmol) was added, followed by MeOH (2.10 mL). The reaction was stirred at room temp for 3 h, then concentrated. The product was taken up in CH$_2$Cl$_2$ and water, then acidified to pH 4 with AcOH. NH$_4$OH was added to bring the pH to 9, then the aqueous was extracted with CH$_2$Cl$_2$ (3×50 mL). The combined organic was dried over MgSO$_4$, filtered, and concentrated to give the product, which was used without further purification.

Step 3: (±)-3-[2-(4-Hydroxy-piperidin-1-yl)-thiazol-4-yl]-3-[4-(7-methoxy-quinolin-8-yl)-[1,4]diazepan-1-yl]-1-(4-methyl-piperazin-1-yl)-propan-1-one

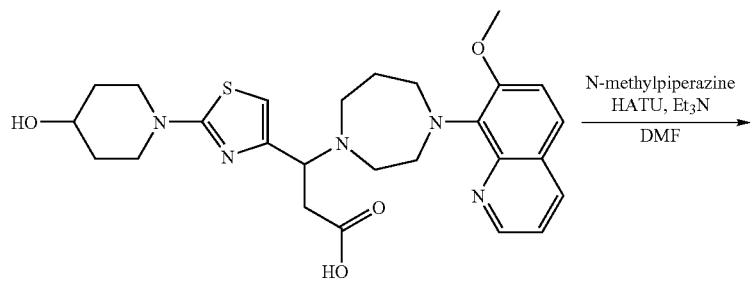

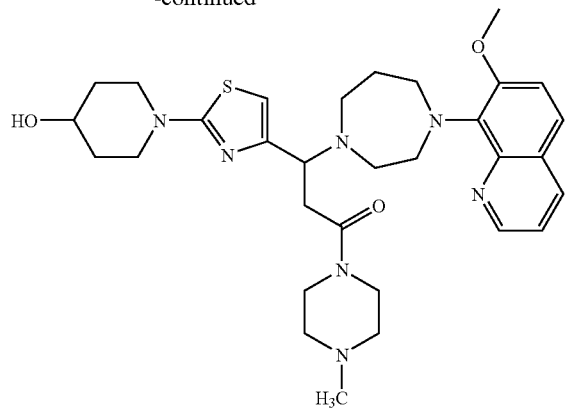

DMF (3.0 mL) was added to the product from step 2 (309 mg, 0.60 mmol), followed by N-methylpiperazine (0.08 mL, 0.72 mmol), and Et$_3$N (0.17 mL, 1.20 mmol). HATU (274 mg, 0.72 mmol) was then added to the mixture, and the reaction was stirred for 2 h at room temperature. The solution was then diluted with CH$_2$Cl$_2$ and washed with H$_2$O (4×50 mL), then brine. The organic was dried over MgSO$_4$, filtered, and concentrated to give the crude. This was purified by silica gel chromatography (99:1 to 90:10 CH$_2$Cl$_2$:(9:1 MeOH:NH$_4$OH)) and lyophilized from MeCN/H$_2$O to give the product (122 mg, 34% yield) as a pale yellow solid. $^1$H NMR (400 MHz, CDCl$_3$) δ 8.84 (dd, 1H, J=1.4, 4.2 Hz), 8.02 (dd, 1H, J=2.0, 8.0 Hz), 7.51 (d, 1H, J=8.8 Hz), 7.29 (d, 1H, J=8.8 Hz), 7.21 (dd, 1H, J=4.2, 8.2 Hz), 6.44 (s, 1H), 4.35 (bs, 1H), 3.95 (s, 3H), 3.95-3.76 (m, 2H), 3.67-3.45 (m, 7H), 3.24-2.78 (m, 8H), 2.42-2.33 (m, 2H), 2.28 (s, 3H), 2.32-2.10 (m, 5H), 2.02-1.92 (m, 4H), 1.68-1.58 (m, 2H). MS (ES) m/z 594.5 (M+H$^+$).

Example 14

(±)-3-[4-(7-Methoxy-quinolin-8-yl)-[1,4]-diazepan-1-yl]-3-(2-morpholino-4-yl-thiazol-4-yl)-1-pyrrolidin-1-yl-propane Step 1: (±)-3-[4-(7-Methoxy-quinolin-8-yl)-[1,4]-diazepan-1-yl]-3-(2-morpholino-4-yl-thiazol-4-yl)-1-pyrrolidin-1-yl-proan-1-one

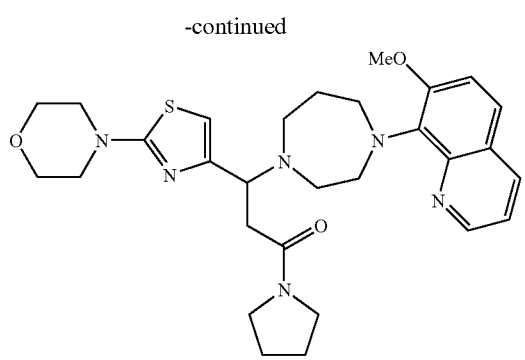

To a solution of (±)-methyl 3-[4-(7-methoxyquinolin-8-yl)-[1,4]-diazepan-1-yl]-3-(2-morpholinothiazol-4-yl)-N-[2-(pyrrolidin-1-yl)ethyl]propanoic acid (0.35 g, 0.70 mmol), pyrrolidine (0.10 g, 1.40 mmol) and triethylamine (0.25 ml, 1.75 mmol) in DMF (3 ml) was added HATU (0.29 g, 0.77 mmol). The mixture was stirred for 1 hr at rt. It was then quenched with water. The mixture was extracted with iPrOH/CHCl$_3$ (1:2)/sat. NaHCO$_3$. The organic layer was separated, dried over anhydrous Na$_2$SO$_4$, concentrated on a rotary evaporator and purified by chromatography with a gradient elution of 0.2-0.6% NH$_4$OH in 2-6% MeOH/DCM to yield (±)-3-[4-(7-methoxy-quinolin-8-yl)-[1,4]-diazepan-1-yl]-3-(2-morpholino-4-yl-thiazol-4-yl)-1-pyrrolidin-1-yl-proan-1-one (0.355 g, 64%) as a yellow solid.

Step 2: (±)-3-[4-(7-Methoxy-quinolin-8-yl-[1,4]-diazepan-1-yl]-3-(2-morpholino-4-yl-thiazol-4-yl)-1-pyrrolidin-1-yl-propane

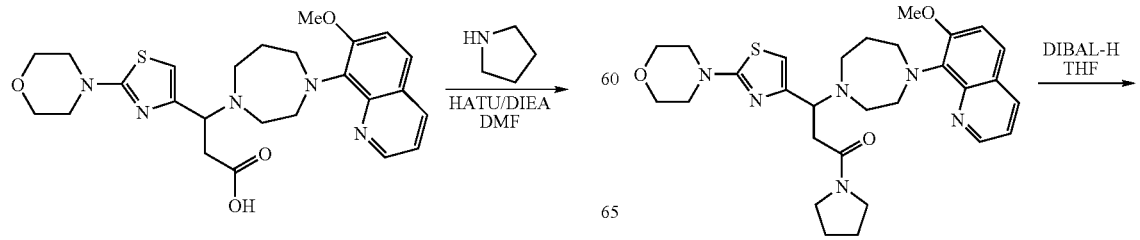

-continued

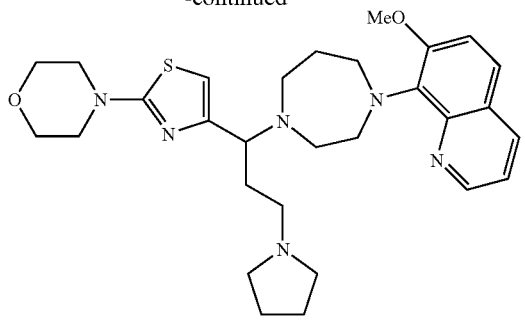

DIBAL-H (0.40 ml, 1M/toluene) was added to a solution of (±)-3-[4-(7-methoxy-quinolin-8-yl)-[1,4]-diazepan-1-yl]-3-(2-morpholino-4-yl-thiazol-4-yl)-1-pyrrolidin-1-yl-proan-1-one (0.10 g, 0.18 mmol) in THF (1.5 ml) at rt. The mixture was stirred at rt for 1 min and quenched with MeOH. It was then extracted with IPA/CHCl₃ (1:2)/sat. NaHCO₃. The organic layer was separated, dried over anhydrous Na₂SO₄, concentrated on a rotary evaporator and purified by chromatography with a gradient elution of 0.2-1% NH₄OH in 2-10% MeOH/DCM to yield (±)-3-[4-(7-methoxy-quinolin-8-yl)-[1,4]-diazepan-1-yl]-3-(2-morpholino-4-yl-thiazol-4-yl)-1-pyrrolidin-1-yl-propane (9 mg) as a yellow solid. $^1$H NMR (400 MHz, CDCl₃): δ 8.84 (dd, 1H, J=4.0, 1.6 Hz), 8.02 (dd, 1H, J=8.0, 1.2 Hz), 7.50 (d, 1H, J=8.8 Hz), 7.28 (d, 1H, J=8.8 Hz), 7.20 (m, 1H), 6.39 (s, 1H), 3.94 (s, 3H), 3.80 (m, 5H), 3.4-3.55 (m, 8H), 2.8-3.1 (m, 4H), 2.4-2.6 (m, 6H), 1.9-2.2 (m, 8H); LC/MS (ES) [M+H]⁺ m/z 537.5.

Example 15

1-(2-{6-Methyl-8-[4-(1-phenyl-1H-pyrazol-3-ylmethyl)-[1,4]diazepan-1-yl]-quinolin-7-yloxy}-acetyl)-azetidine-3-carboxylic acid Step 1: 6-Methyl-7-methoxy-quinoline

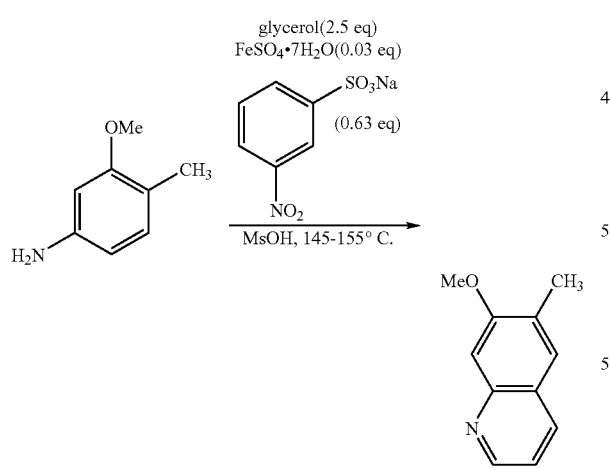

Using a minimal amount of dioxane, 3-methoxy-4-methylaniline (5.00 g, 36.5 mmol) was slowly added to a mixture of sodium m-nitrobenzenesulfonate (6.62 g, 29.4 mmol), MsOH (20 mL), and FeSO₄·7H₂O (0.39 g, 1.4 mmol) in a 100 mL round bottom flask heated to an internal temperature of 145-155° C. Glycerol (10.75 g, 116.8 mmol) was then added dropwise via addition funnel while keeping the internal temperature at 145-155° C. After addition, the reaction was stirred in a 150° C. oil bath until LCMS indicated completion (4-6 h). After being cooled to rt, ice (20 g) was added, then the solution was neutralized with 10 N NaOH (calculated to same eq of MsOH) at a speed to keep the internal temperature below 40° C. A thick suspension appeared after addition, and this was extracted with EtOAc (50 mL×3). The organic layer was filtered through a Celite pad to remove insoluble black particles and then purified by flash column chromatography on silica gel to give the desired product (5.0 g, 79%). MS (ES) m/z 174.1 (M+H⁺).

Step 2: 8-Bromo-7-methoxy-6-methyl-quinoline

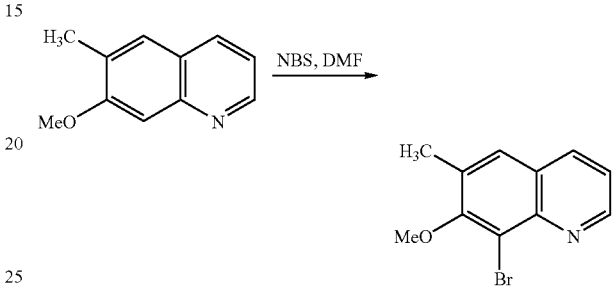

To a stirred solution of 6-methyl-7-methoxy-quinoline (3.0 g, 17.3 mmol) in DMF (20 ml) was added NBS (3.4 g, 19 mmol). The resulting suspension was stirred for 3 h at 60° C. and monitored by LCMS. The reaction mixture was diluted with EtOAc (100 ml) and filtered. The organic layer was washed with saturated aqueous NaHCO₃ and brine, dried over Na₂SO₄ and then purified by flash column chromatography on silica gel to give the desired product (2.9 g, 67%). MS (ES) m/z 251.6 (M+H⁺).

Step 3: 4-(7-Hydroxy-6-methyl-quinolin-8-yl)-[1,4]diazepane-1-carboxylic acid tert-butyl ester

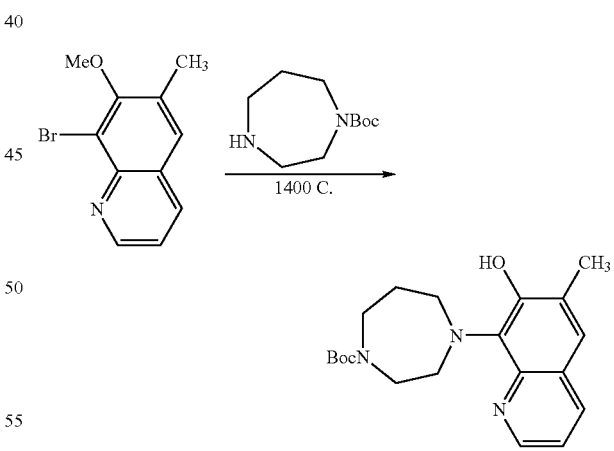

A mixture of product from step 2 (1.66 g, 6.58 mmol) and [1,4]Diazepane-1-carboxylic acid tert-butyl ester (4 g, 20 mmol) was heated via microwave to 140° C. for 1 h. After being cooled to rt, it was diluted with ethyl acetate, washed with saturated NaHCO₃ and brine, dried over Na₂SO₄ and then purified by flash column chromatography on silica gel to give the desired product (0.8 g, 35%). MS (ES) m/z 358 (M+H⁺).

Step 4: (8-[1,4]Diazepan-1-yl-6-methyl-quinolin-7-yloxy)-acetic acid ethyl ester

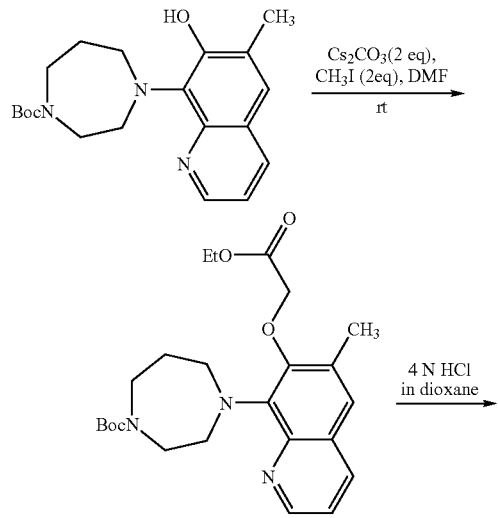

A mixture of 4-(7-hydroxy-6-methyl-quinolin-8-yl)-[1,4]diazepane-1-carboxylic acid tert-butyl ester (0.5 g, 1.4 mmol), Cs$_2$CO$_3$ (1.4 g, 4.1 mmol) and ethyl bromoacetate (0.235 g, 1.41 mmol) in DMF (3 ml) was stirred at rt for 5 hrs. After LCMS indicated completion, the reaction was diluted with water (10 ml) and extracted with EtOAc (20 ml×3). The organic layer was washed with brine, dried over Na$_2$SO$_4$, concentrated, treated with 4 N HCl in dioxane and evaporated to give the HCl salt of the desired product which was then dissolved in 20% iPrOH in CH$_2$Cl$_2$ (30 mL) and neutralized with saturated aq. NaHCO$_3$. The organic layer was dried over magnesium sulfate and concentrated to afford the free base (0.4 g, 80%). MS (ES) m/z 344.2 (M+H$^+$).

Step 5: {6-Methyl-8-[4-(1-phenyl-1H-pyrazol-3-ylmethyl)-[1,4]diazepan-1-yl]-quinolin-7-yloxy}-acetic acid ethyl ester

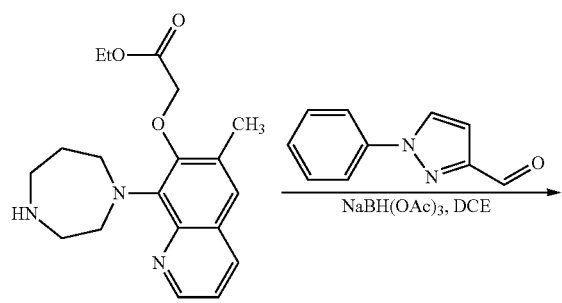

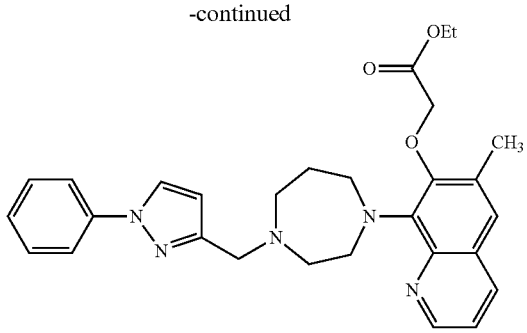

A mixture of (8-[1,4]diazepan-1-yl-6-methyl-quinolin-7-yloxy)-acetic acid ethyl ester (600 mg, 1.75 mmol), 1-Phenyl-1H-pyrazole-3-carbaldehyde (300.8 mg, 1.75) and NaBH(OAc)$_3$ (408 mg, 1.92 mmol) in DCE (5 ml) was stirred at rt for 3 hrs. The reaction was then diluted with DCE (20 ml), filtered, and purified by flash column chromatography on silica gel to give the desired product (500 mg, 57%). MS (ES) m/z 500.2 (M+H$^+$).

Step 6: {6-Methyl-8-[4-(1-phenyl-1H-pyrazol-3-ylmethyl)-[1,4]diazepan-1-yl]-quinolin-7-yloxy}-acetic acid

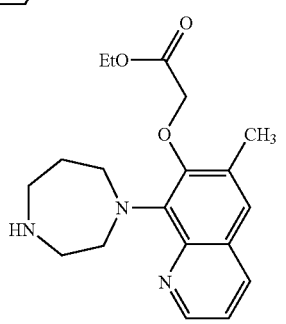

A mixture of {6-methyl-8-[4-(1-phenyl-1H-pyrazol-3-yl-methyl)-[1,4]diazepan-1-yl]-quinolin-7-yloxy}-acetic acid ethyl ester (500 mg, 1.0 mmol) and 2 N NaOH (1 ml, 2 mmol) in THF (3 ml) was stirred at rt for 3 hrs. The solution was then neutralized with 1 N HCl, extracted with mixed solvent (CH$_2$Cl$_2$:iPrOH 80:20) and purified by flash column chromatography on silica gel to give a light yellow solid (300 mg, 64%). MS (ES) m/z 472.2 (M+H$^+$).

Step 7: 1-(2-{6-Methyl-8-[4-(1-phenyl-1H-pyrazol-3-ylmethyl)-[1,4]diazepan-1-yl]-quinolin-7-yloxy}-acetyl)-azetidine-3-carboxylic acid methyl ester

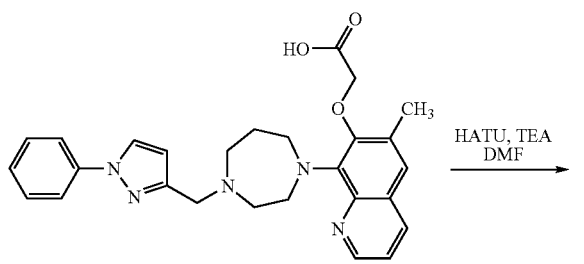

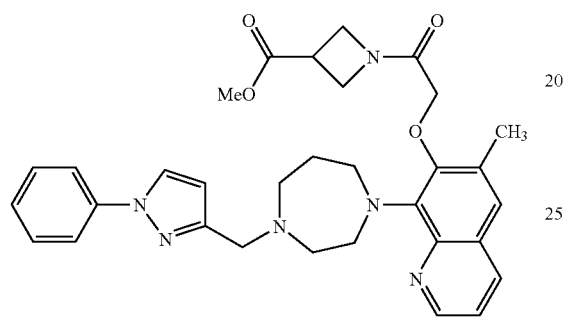

A mixture of {6-Methyl-8-[4-(1-phenyl-1H-pyrazol-3-ylmethyl)-[1,4]diazepan-1-yl]-quinolin-7-yloxy}-acetic acid (100 mg, 0.21 mmol), 3-Azetidinecarboxylic methyl ester HCl salt (35.4 mg, 0.23 mmol), HATU (97 mg, 0.25 mmol) and DIEA (0.222 ml) in DMF (1 ml) was stirred at rt for 2 hrs. After an aqueous workup, the mixture was purified by flash chromatography to give a light yellow solid (70 mg, 59%). MS (ES) m/z 569.3 (M+H⁺).

Step 8: 1-(2-{6-Methyl-8-[4-(1-phenyl-1H-pyrazol-3-ylmethyl)-[1,4]diazepan-1-yl]-quinolin-7-yloxy}-acetyl)-azetidine-3-carboxylic acid

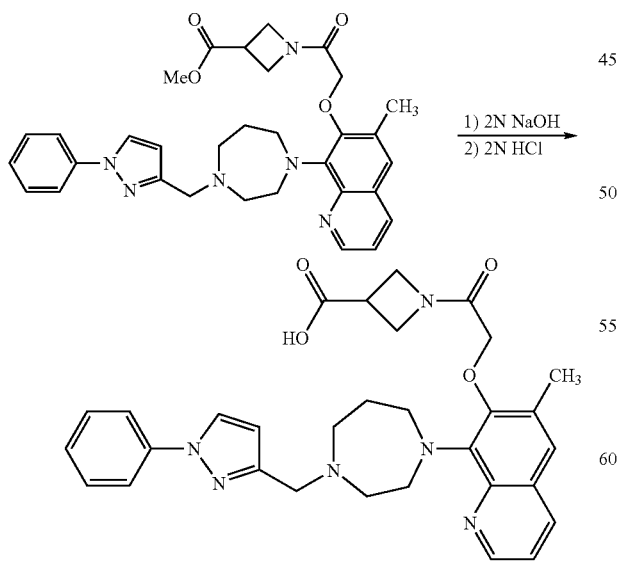

1-(2-{6-Methyl-8-[4-(1-phenyl-1H-pyrazol-3-ylmethyl)-[1,4]diazepan-1-yl]-quinolin-7-yloxy}-acetyl)-azetidine-3-carboxylic acid methyl ester (70 mg, 0.12 mmol) was hydrolyzed with 2 N NaOH (0.15 mL) in THF (1 ml). After hydrolysis was complete, 2 N HCl (ca. 0.15 mL) was added to bring the pH to 7 and the mixture was extracted with 20% iPrOH in CH₂Cl₂ (3×10 mL). The combined organic layer was dried over MgSO₄ and concentrated. The residue was purified by reverse phase HPLC to afford the title compound (45 mg, 66%) as a light yellow solid. ¹H NMR (400 MHz, DMSO) δ 8.75 (d, 1H, J=4.4 Hz), 8.42 (d, 1H, J=2.4 Hz), 8.14 (dd, 1H, J=1.6 and 8.4 Hz), 7.78 (d, 2H, J=8.0 Hz), 7.48-7.42 (m, 3H), 7.35 (q, 1H, J=4.4 Hz), 7.25 (t, 1H, J=7.2 Hz), 6.51 (d, 1H, J=2.8 Hz), 4.77 (s, 2H), 4.40 (t, 1H, J=10.0 Hz), 4.31 (t, 1H, J=6.4 Hz), 4.08 (t, 1H, J=9.2 Hz), 3.97-3.93 (m, 1H), 3.82 (s, 2H), 3.48-3.38 (m, 5H), 2.88 (s, 4H), 2.38 (s, 3H), 1.92 (m, 2H). MS (ES) m/z 555.5 (M+H⁺).

Example 16

4-(8-{4-[2-(4-Hydroxy-piperidin-1-yl)-thiazol-4-ylmethyl]-[1,4]diazepan-1-yl}-6-methyl-quinolin-7-yloxy)-butyric acid Step 1: 4-[7-(3-Methoxycarbonyl-propoxy)-6-methyl-quinolin-8-yl]-[1,4]diazepane-1-carboxylic acid tert-butyl ester

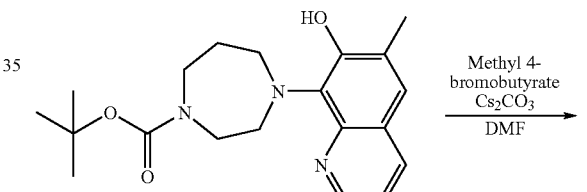

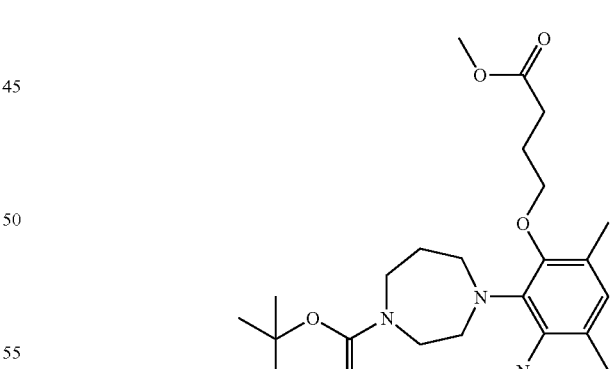

4-(7-Hydroxy-6-methyl-quinolin-8-yl)-[1,4]diazepane-1-carboxylic acid tert-butyl ester (1.3 g, 3.8 mmol) and methyl 4-bromobutyrate (680 mg, 3.8 mmol) were dissolved in DMF (7.5 mL). To this solution was added Cs₂CO₃ (3.7 g, 11.3 mmol) and reaction was stirred at room temperature for 18 h. The reaction was diluted with CH₂Cl₂ and washed with H₂O (4×50 mL), then brine. The organic was then dried over MgSO₄, filtered, and concentrated to give the crude product.

Step 2: 4-(8-[1,4]Diazepan-1-yl-6-methyl-quinolin-7-yloxy)-butyric acid methyl ester

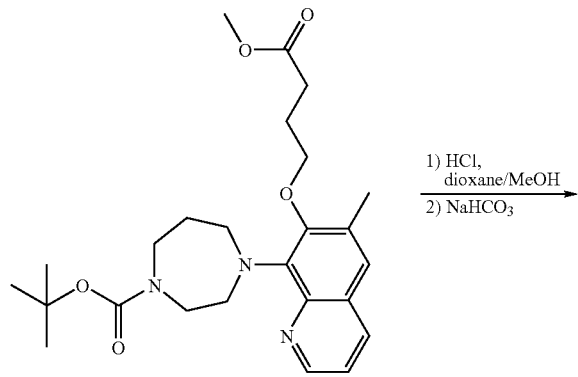

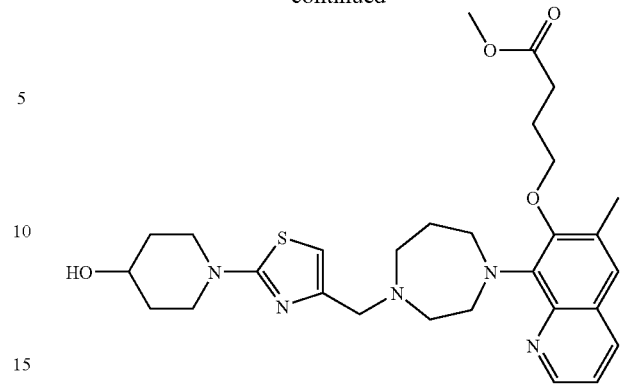

The product from step 2 (3.63 mmol) was dissolved in 1,2-dichloroethane (7.26 mL), and 2-(4-Hydroxy-piperidin-1-yl)-thiazole-4-carbaldehyde (771 mg, 3.63 mmol) was then added. This solution was stirred for 1 h, then NaBH(OAc)$_3$ (1.54 g, 7.26 mmol) was added. The solution was stirred for 2 h, then diluted with CH$_2$Cl$_2$. The solution was washed with sat. aq. NaHCO$_3$, then brine. The organic was dried over MgSO$_4$, filtered, and concentrated to give the crude product. This was carried on without further purification.

Step 4: 4-(8-{4-[2-(4-Hydroxy-piperidin-1-yl)-thiazol-4-yl-methyl]-[1,4]diazepan-1-yl}-6-methyl-quinolin-7-yloxy)-butyric acid

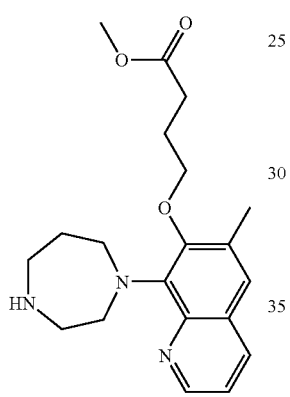

The product from step 1 was dissolved in MeOH (18.8 mL) and HCl was added (4M in dioxane, 18.8 mL, 75.2 mmol). The reaction was stirred at room temperature for 2 h, then concentrated. CH$_2$Cl$_2$ was added and this solution was washed with sat. aq. NaHCO$_3$, then brine. The organic was dried over MgSO$_4$, filtered, and concentrated to give the product (1.30 g, 96% yield) as an oil.

Step 3: 4-(8-{4-[2-(4-Hydroxy-piperidin-1-yl)-thiazol-4-yl-methyl]-[1,4]diazepan-1-yl}-6-methyl-quinolin-7-yloxy)-butyric acid methyl ester

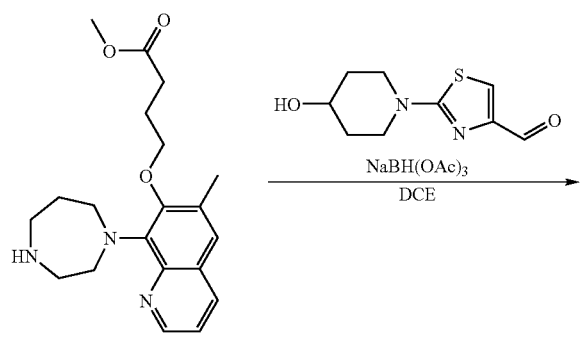

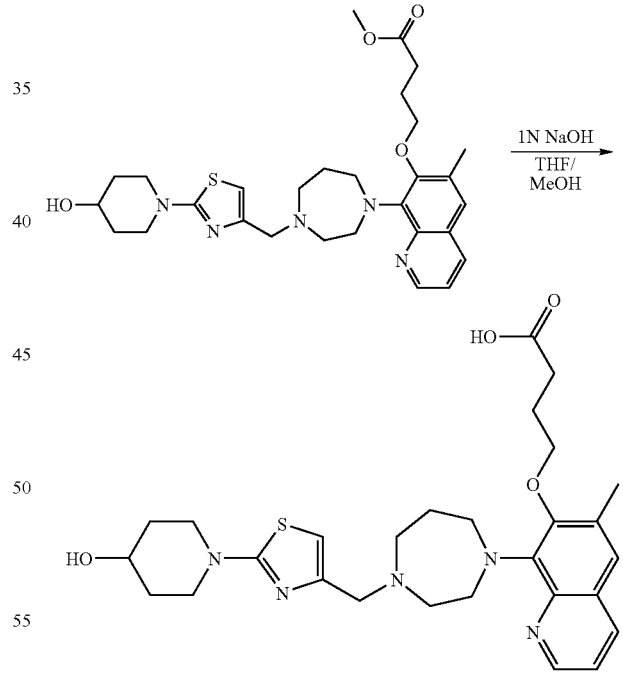

The product from step 3 (3.27 mmol) was dissolved in THF (10.9 mL), and 1 N aq. NaOH (6.54 mL, 6.54 mmol) was added, followed by MeOH (5.5 mL). This solution was allowed to stir for 3 h, then concentrated. The crude product was then purified on a reverse phase column (MeCN:H$_2$O+ 0.1% TFA), and the combined product fractions were basified to pH 9 using NH$_4$OH, then extracted with CH$_2$Cl$_2$ (3×50 mL). The combined organic was then concentrated. The residue was lyophilized from MeCN/H$_2$O to give the product as a white solid. $^1$H NMR (400 MHz, CDCl$_3$) δ 8.70 (dd, 1H, J=1.4, 4.2 Hz), 7.96 (dd, 1H, J=1.4, 8.2 Hz), 7.35 (s, 1H), 7.22 (dd, 1H, J=4.4, 8.0 Hz), 6.71 (s, 1H), 4.12-4.05 (m, 4H), 4.05-3.82 (m, 4H), 3.80-3.72 (m, 4H), 3.62-3.56 (m, 2H), 3.49-3.40 (m, 4H), 3.22-3.15 (m, 2H), 2.58 (t, 2H, J=7.0 Hz), 2.41 (s, 3H), 2.24-2.17 (m, 4H), 1.98-1.90 (m, 2H), 1.69-1.59 (m, 2H). MS (ES) m/z 540.5 (M+H$^+$).

Example 17

6-Isoprpyl-8-[4-(2-phenyl-thiazol-4-ylmethyl)-[1,4]diazepan-1-yl]-quinoline; hydrochloride Step 1: 8-Bromo-6-isopropyl-quinoline

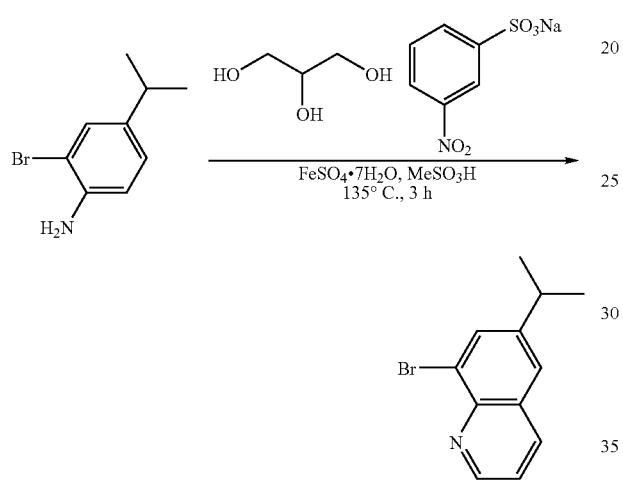

A mixture of 2-bromo-4-isopropyl-phenylamine (1.72 g, 8.0 mmol), propane-1,2,3-triol (1.84 g, 2.5 equiv), FeSO$_4$ (0.067 g, 0.30 equiv), 3-nitrobenzenesulfonic acid sodium salt (1.13 g, 0.63 equiv) in 4.5 mL of methanesulfonic acid was heated to 135° C. for 3 hours and then cooled down to room temperature. 2 N Aqueous NaOH (~40 mL) was added and the mixture was extracted with EtOAc (3×50 mL). The organic layer was washed with saturated aqueous NaHCO$_3$ (200 mL) and brine (200 mL), dried over magnesium sulfate and concentrated. The residue was purified by silica gel chromatography using 5% to 20% EtOAc in hexane to afford the title compound (1.3 g, 65%) as dark brown solid. MS (ES) m/z 250.2 (M+H$^+$).

Step 2: 4-(6-Isopropyl-quinolin-8-yl)[1,4]-diazepan-1-carboxylic acid tert-butyl ester

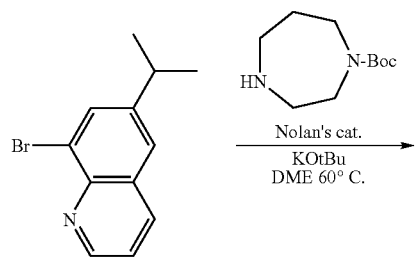

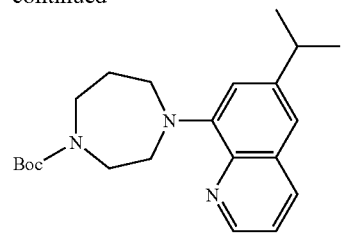

A mixture of 8-Bromo-6-isopropyl-quinoline (1.38 g, 5.51 mmol, 1.04 equiv) and 1-(tert-butoxycarbonyl)homopiperazine (1.06 g, 1.0 equiv) in 5.5 mL of DME was degassed with compressed nitrogen gas for 5 minutes. To the mixture was added t-BuOK (0.83 g, 1.4 equiv). After degassing for another 2 minutes, allylchloro[1,3-(2,6-di-isopropylphenyl)imidazol-2-ylidene]palladium (II) (Nolan's catalyst, 61 mg, 0.02 equiv) was added and the resulting mixture was heated to 60° C. overnight, then cooled down to room temperature. EtOAc (~70 mL) was added and the mixture was filtered through celite. The filtrate was washed with saturated aqueous NaHCO$_3$ (70 mL) and brine (70 mL), dried over magnesium sulfate and concentrated. The residue was purified by silica gel chromatography using 5% to 20% EtOAc in hexane to afford the title compound (1.3 g, 64%). MS (ES) m/z 370.2 (M+H$^+$).

Step 3: 8-[1,4]-Diazepan-1-yl-6-isopropyl-quinoline dihydrochloride

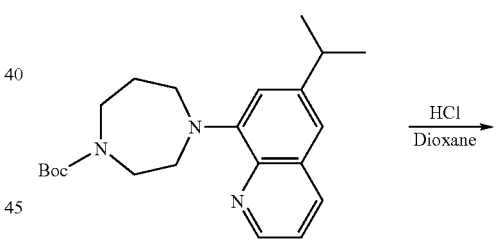

4-(6-Isopropyl-quinolin-8-yl)[1,4]-diazepan-1-carboxylic acid tert-butyl ester (1.3 g, 1.0 equiv) was dissolved in MeOH (5 mL) and 1.0 M HCl in 1,4-dioxane (10 mL) was added to the mixture. After stirring at room temperature for 1 hour, the mixture was concentrated to dryness to afford the title compound (1.2 g, 100%). MS (ES) m/z 270.1 (M+

Step 4: 6-Isopropyl-8-[4-(2-phenyl-thiazol-4-ylmethyl)-[1,4]diazepan-1-yl]-quinoline

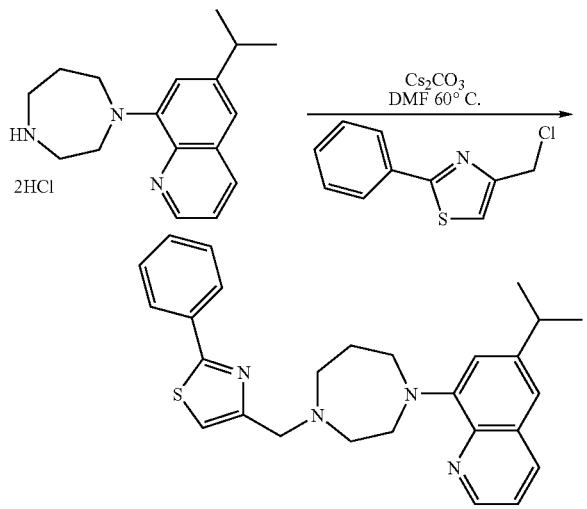

A mixture of 8-[1,4]-diazepan-1-yl-6-isopropyl-quinoline dihydrochloride (0.34 g, 1 mmol, 1 equiv), 4-chloromethyl-2-phenyl-thiazole (0.21 g, 1 equiv) and $Cs_2CO_3$ (1.63 g, 5 equiv) in 5 mL of DMF was heated to 60° C. for 3 hours and then cooled to room temperature. EtOAc (~70 mL) was added and the mixture washed with saturated aqueous $NaHCO_3$ (70 mL) and brine (70 mL), dried over magnesium sulfate and concentrated. The residue was purified by silica gel flash column chromatography using 5% to 40% EtOAc in hexanes. Silica gel chromatography was repeated using 5% to 10% MeOH in EtOAc to afford the title compound (0.22 g, 50%) as light tan solid. $^1$H NMR (400 MHz, $d^6$-$CD_3OD$) δ 8.66 (dd, 1H, J=1.8 and 4 Hz), 8.07 (dd, 1H, J=1.5 and 8.4 Hz), 7.91 (m, 1H), 7.90 (d, 1H, J=2.2 Hz), 7.41 (m, 3H), 7.36 (s, 1H), 7.31 (dd, 1H, J=4.0 and 8.0 Hz), 7.16 (d, 1H, J=1.6 Hz), 7.04 (d, 1H, J=1.6 Hz), 3.90 (s, 2H), 3.71 (m, 2H), 3.59 (t, 2H, J=5.6 Hz), 3.11 (m, 2H), 2.92 (m, 3H), 2.10 (m, 2H), 1.31 (d, 6H, J=7.2 Hz). MS (ES) m/z 443.2 (M+H$^+$).

Example 18

The compounds in the Table below were prepared as described above. Characterization data (NMR) is provided for each.

| Compound | Characterization Data |
|---|---|
| (structure) | $^1$H NMR (400 MHz, $CDCl_3$) δ 8.84 (dd, 1H, J = 1.4, 4.2 Hz), 8.02 (dd, 1H, J = 2.0, 8.0 Hz), 7.51 (d, 1H, J = 8.8 Hz), 7.29 (d, 1H, J = 8.8 Hz), 7.21 (dd, 1H, J = 4.2, 8.2 Hz), 6.44 (s, 1H), 4.35 (bs, 1H), 3.95 (s, 3H), 3.95-3.76 (m, 2H), 3.67-3.45 (m, 7H), 3.24-2.78 (m, 8H), 2.42-2.33 (m, 2H), 2.28 (s, 3H), 2.32-2.10 (m, 5H), 2.02-1.92 (m, 4H), 1.68-1.58 (m, 2H). |
| (structure) | $^1$H NMR (400 MHz, $CDCl_3$) δ 9.00 (br s, 1H), 8.82 (dd, 1H, J = 1.6 and 4 Hz), 8.05 (d, 1H, J = 8 Hz), 7.53 (d, 1H, J = 8.8 Hz), 7.29 (d, 1H, J = 8.8 Hz), 7.22 (dd, 1H, J = 4 and 8 Hz), 6.46 (s, 1H), 4.25 (m, 1H), 3.93 (s, 3H), 3.78 (t, 4H, J = 4.8 Hz), 3.58 (m, 2H), 3.52 (t, 2H, J = 5.6 Hz), 3.40 (t, 4H, J = 4.8 Hz), 3.22 (m, 2H), 3.05-2.98 (m, 3H), 2.64 (br, 1H), 2.62 (t, 2H, J = 6.4 Hz), 2.53 (hr s, 4H), 2.45 (br s, 2H), 2.02 (m, 2H), 1.78 (br s, 4H). |

| Compound | Characterization Data |
|---|---|
| (structure) | ¹H NMR (400 MHz, CDCl$_3$) δ 9.20 (br, 1H), 8.81 (d, 1H, J = 2.8 Hz), 8.03 (d, 1H, J = 8.4 Hz), 7.51 (d, 1H, J = 8.4 Hz), 7.34 (d, 1H, J = 2.8 Hz), 7.27 (d, 1H, J = 8.8 Hz), 7.21 (dd, 1H, J = 4.0 and 8.0 Hz), 6.16 (s, 1H), 4.52 (septet, 1H, J = 6.8 Hz), 4.34 (br, 1H), 3.90 (s, 3H), 3.58 (m, 2H), 3.52-3.40 (m, 4H), 3.20-2.80 (m, 4H), 2.63 (t, 2H, J = 6.8 Hz), 2.54 (br s, 4H), 2.20 (br s, 2H), 2.02 (m, 2H), 1.78 (br s, 4H), 1.47 (d, 6H, J = 6.8 Hz). |
| (structure) | ¹H NMR (400 MHz, CDCl$_3$): δ 8.84 (dd, 1H, J = 4.0, 1.6 Hz), 8.02 (dd, 1H, J = 8.0, 1.2 Hz), 7.50 (d, 1H, J = 8.8Hz), 7.28 (d, 1H, J = 8.8 Hz), 7.20 (m, 1H), 6.39 (s, 1H), 3.94 (s, 3H), 3.80 (m, 5H), 3.4-3.55 (m, 8H), 2.8-3.1 (m, 4H), 2.4-2.6 (m, 6H), 1.9-2.2 (m, 8H) |
| (structure) | ¹H NMR (400 MHz, DMSO) δ 8.75 (d, 1H, J = 4.4 Hz), 8.42 (d, 1H, J = 2.4 Hz), 8.14 (dd, 1H, J = 1.6 and 8.4 Hz), 7.78 (d, 2 H, J = 8.0 Hz), 7.48-7.42 (m, 3H), 7.35 (q, 1H, J = 4.4 Hz), 7.25 (t, 1H, J = 7.2 Hz), 6.51 (d, 1H, J = 2.8 Hz), 4.77 (s, 2H), 4.40 (t, 1H, J = 10.0 Hz), 4.31 (t, 1H, J = 6.4 Hz), 4.08 (t, 1H, J = 9.2 Hz), 3.97-3.93 (m, 1H), 3.82 (s, 2H), 3.48-3.38 (m, 5H), 2.88 (s, 4H), 2.38 (s, 3H), 1.92 (m, 2H). |
| (structure) | ¹H NMR (400 MHz, CDCl$_3$) δ 8.70 (dd, 1H, J = 1.4, 4.2 Hz), 7.96 (dd, 1H, J = 1.4, 8.2 Hz), 7.35 (s, 1H), 7.22 (dd, 1H, J = 4.4, 8.0 Hz), 6.71 (s, 1H), 4.12-4.05 (m, 4H), 4.05-3.82 (m, 4H), 3.80-3.72 (m, 4H), 3.62-3.56 (m, 2H), 3.49-3.40 (m, 4H), 3.22-3.15 (m, 2H), 2.58 (t, 2H, J = 7.0 Hz), 2.41 (s, 3H), 2.24-2.17 (m, 4H), 1.98-1.90 (m, 2H), 1.69-1.59 (m, 2H). |

-continued

| Compound | Characterization Data |
|---|---|
| [Structure: cyclopropyl-thiazole connected to diazepane, methoxy-quinoline, and amide-ethyl-pyrrolidine] | $^1$H NMR (400 MHz, CDCl$_3$) δ 8.81 (dd, 1H, J = 2.0 and 4.0 Hz), 8.02 (dd, 1H, J = 1.2 and 8.4 Hz), 7.50 (d, 1H, J = 8.8 Hz), 7.27 (d, 1H, J = 8.8 Hz), 7.21 (dd, 1H, J = 4.0 and 8.0 Hz), 6.84 (s, 1H), 4.39 (br, 1H), 3.90 (s, 3H), 3.56 (m, 2H), 3.51 (m, 2H), 3.42 (m, 2H), 3.20-3.00 (m, 3H), 2.88 (m, 1H), 2.78 (m, 1H), 2.62 (t, 2H, J = 6.0 Hz), 2.54 (br s, 4H), 2.29 (m, 1H), 2.02 (m, 4H), 1.79 (br s, 4H), 1.13 (m, 2H), 1.04 (m, 2H). |
| [Structure: methoxy-quinoline connected to diazepane, piperidine with cyclopentylcarbonyl, and amide-ethyl-pyrrolidine] | $^1$H NMR (400 MHz, CDCl$_3$) δ 8.81 (dd, 1H, J = 1.6 and 4 Hz), 8.02 (dd, H, J = 1.6 and 8 Hz), 7.88 (br, 1H), 7.50 (d, 1H, J = 8.8 Hz), 7.29 (d, 1H, J = 8.8 Hz), 7.21 (dd, 1H, J = 4 and 8.4 Hz), 4.65 (br s, 1H), 4.00 (m, 1H), 3.96 (s, 3H), 3.54 (t, 4H, J = 5.2 Hz), 3.37 (m, 3H), 3.20-2.80 (m, 7H), 2.70-2.40 (m, 7H), 2.24 (m, 1H), 1.98 (br s, 1H), 1.80-1.50 (m, 15H), 1.34-1.16 (m, 3H). |

Biological Example 1

To demonstrate that the compounds described above are useful modulators for chemokine binding to CXCR7, the compounds were screened in vitro to determine their ability to displace SDF-1 from the CXCR7 receptor at multiple concentrations. The compounds were combined with cells expressing the CXCR7 receptor (e.g., MCF cells or cells transfected to express CXCR7) in the presence of the $^{125}$I-labeled SDF-1chemokine as detailed in Determination of IC$_{50}$ values, Reagents and Cells (see below). The ability of the compounds to displace the labeled chemokine from the CXCR7 receptor sites at multiple concentrations was then determined with the screening process.

Figure 1B:
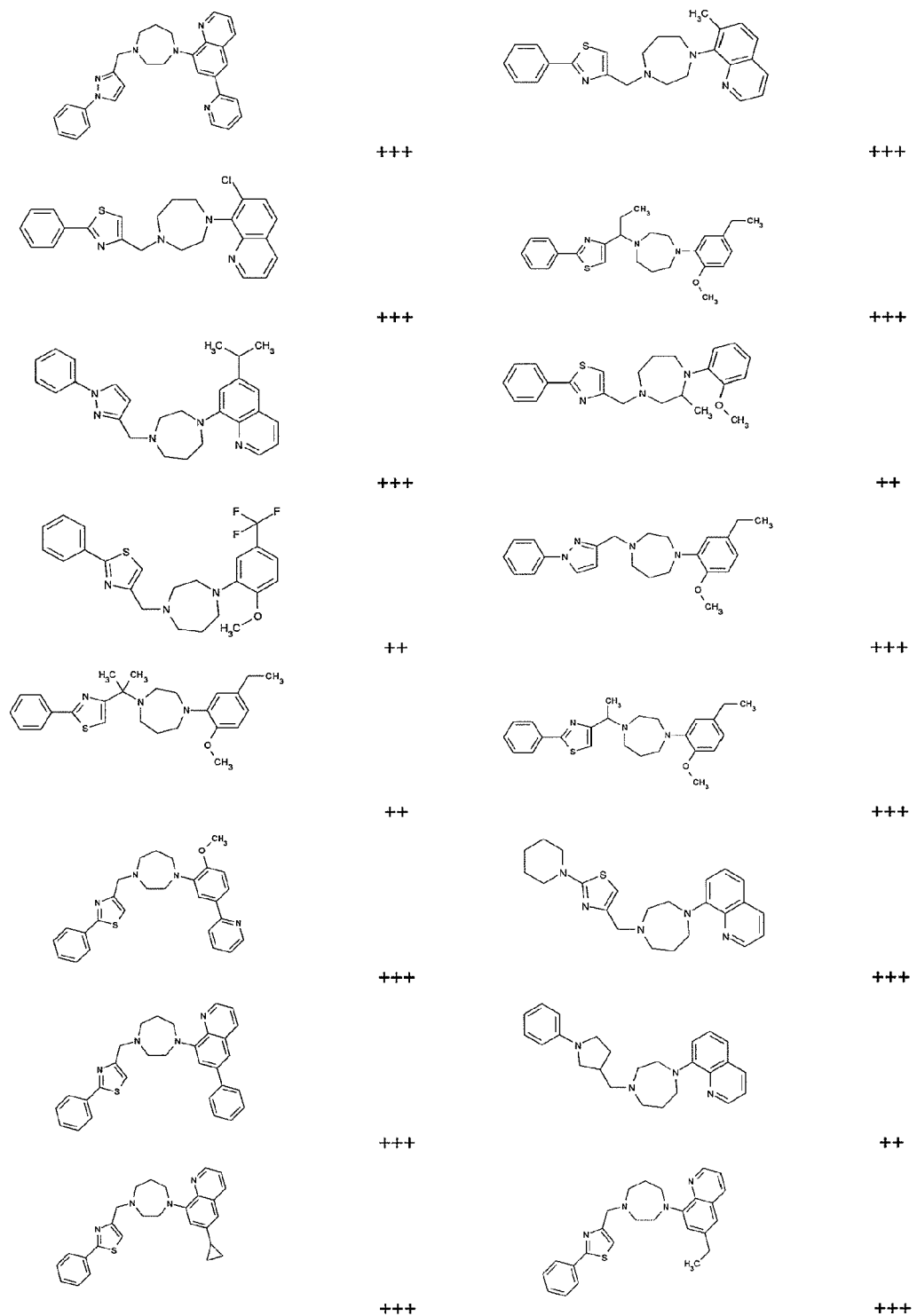
Figure 1C:
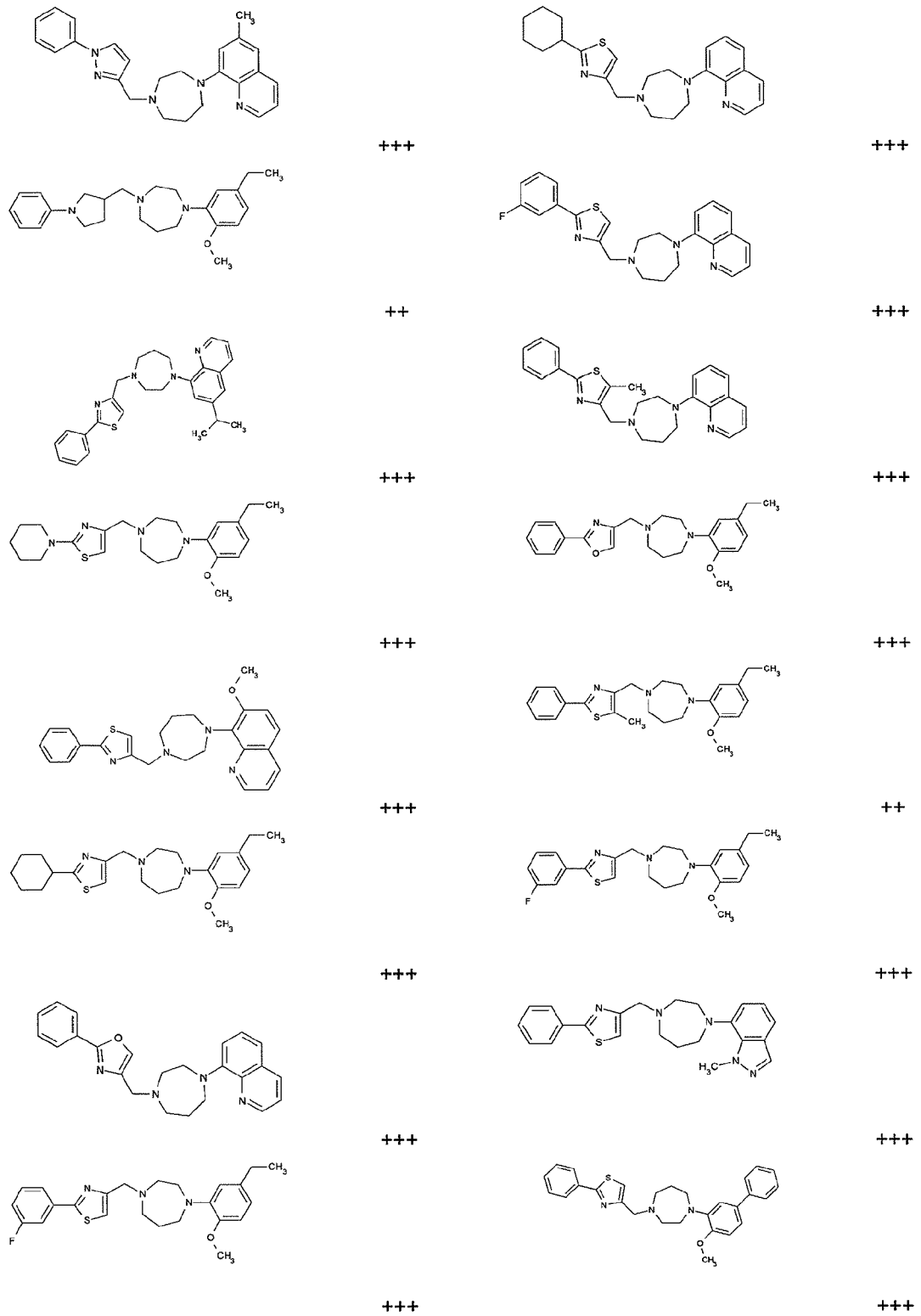
Figure 1D:
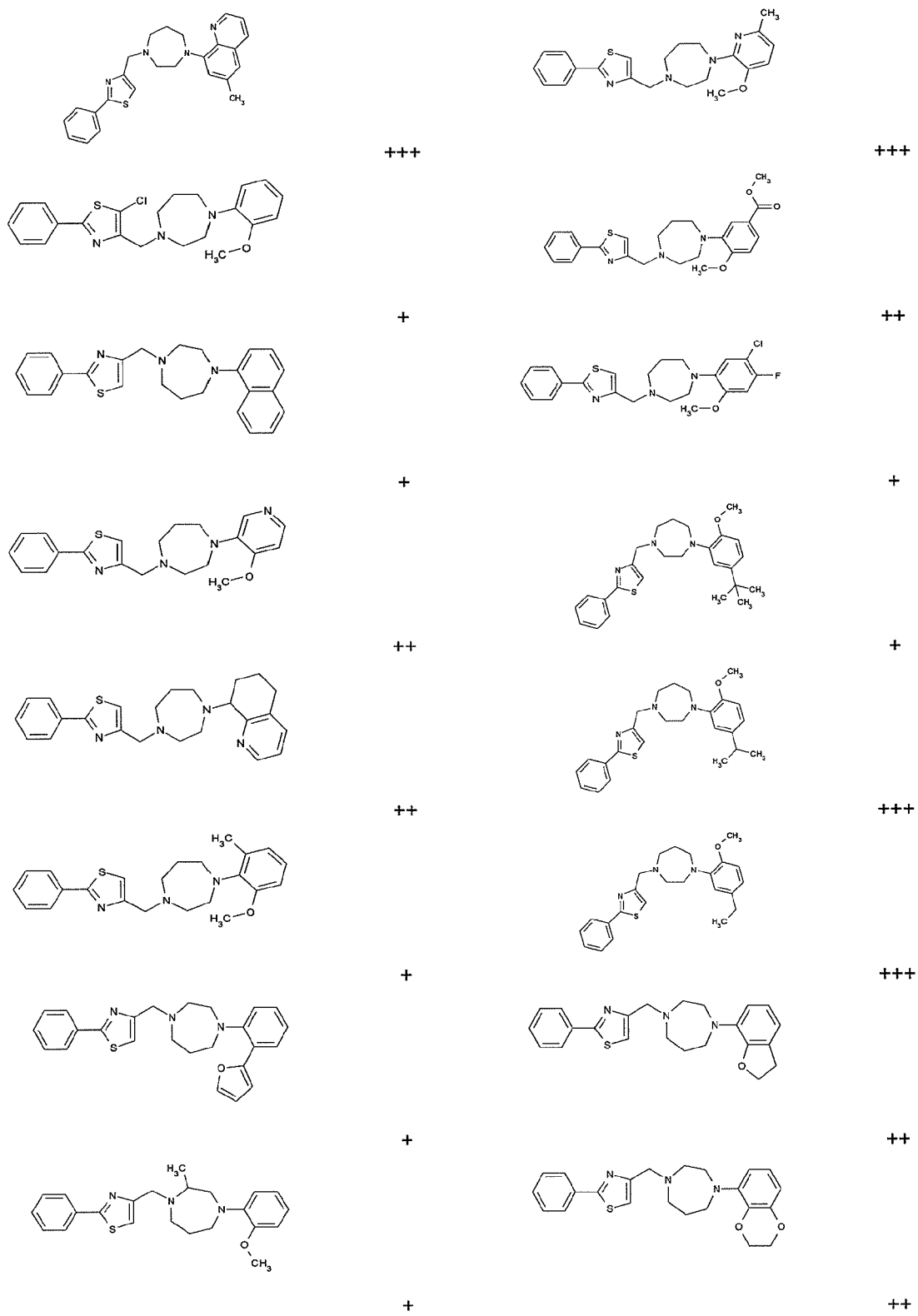
Figure 1E:
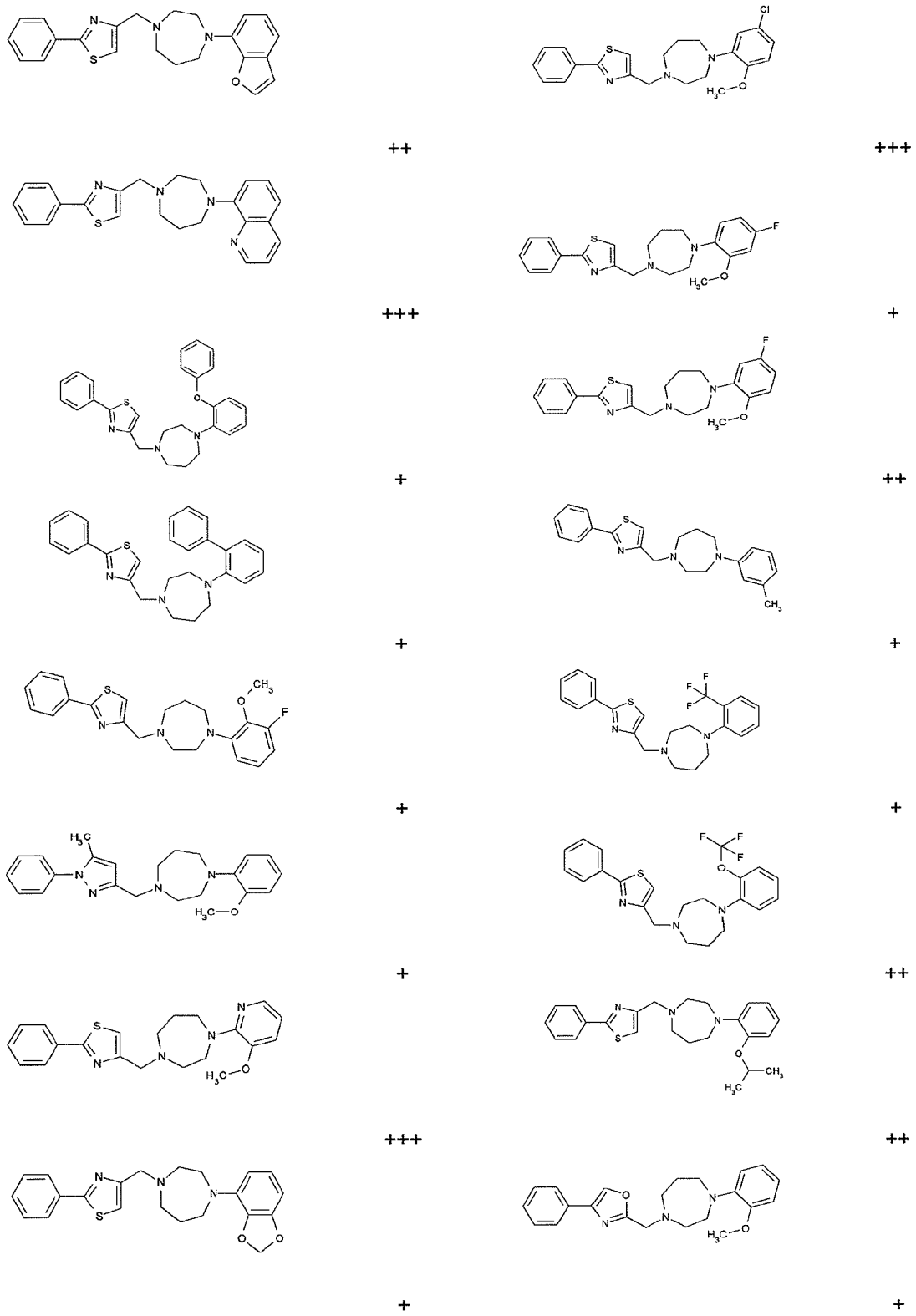
Figure 1F:
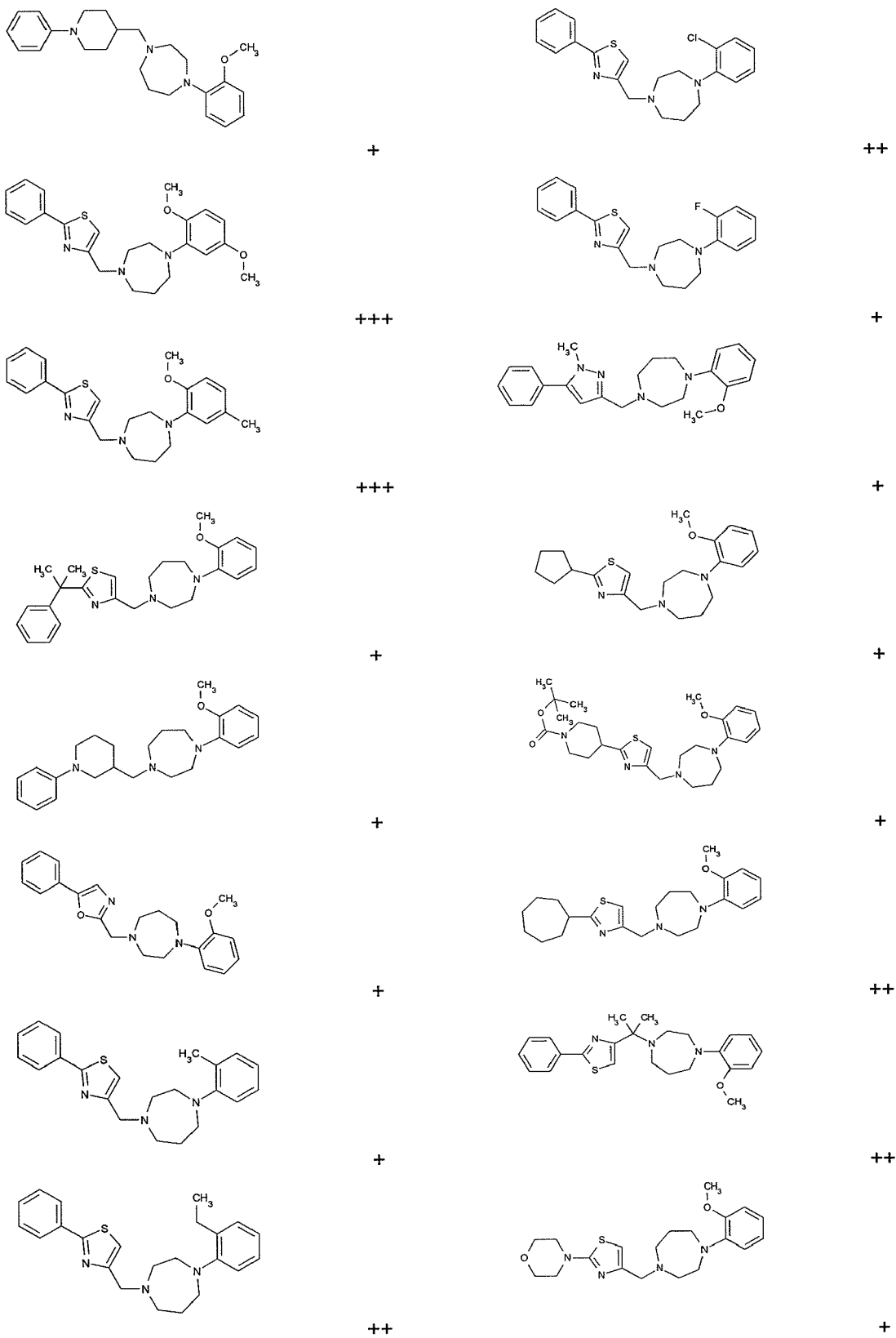
Figure 1G:
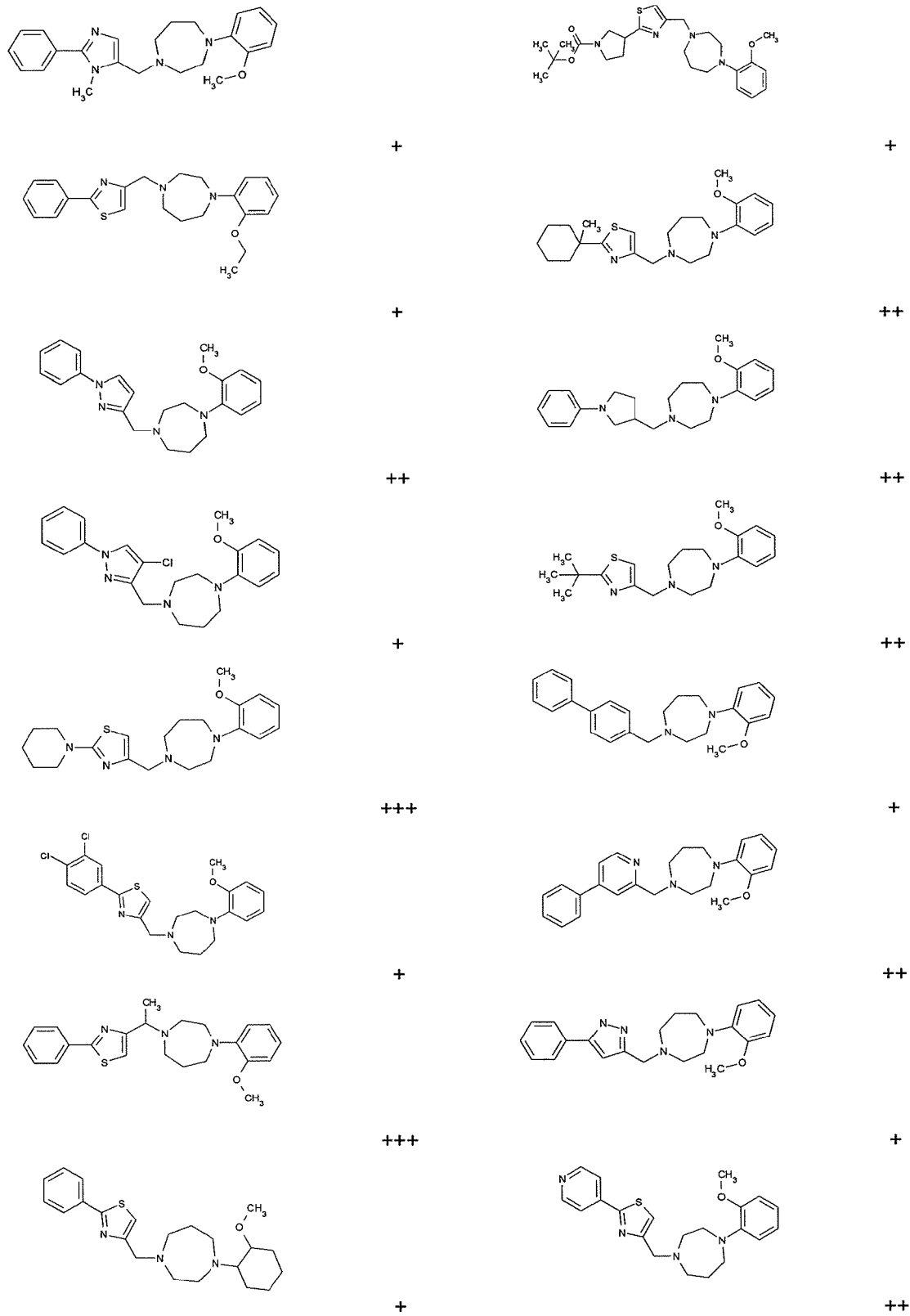
Figure 1H:
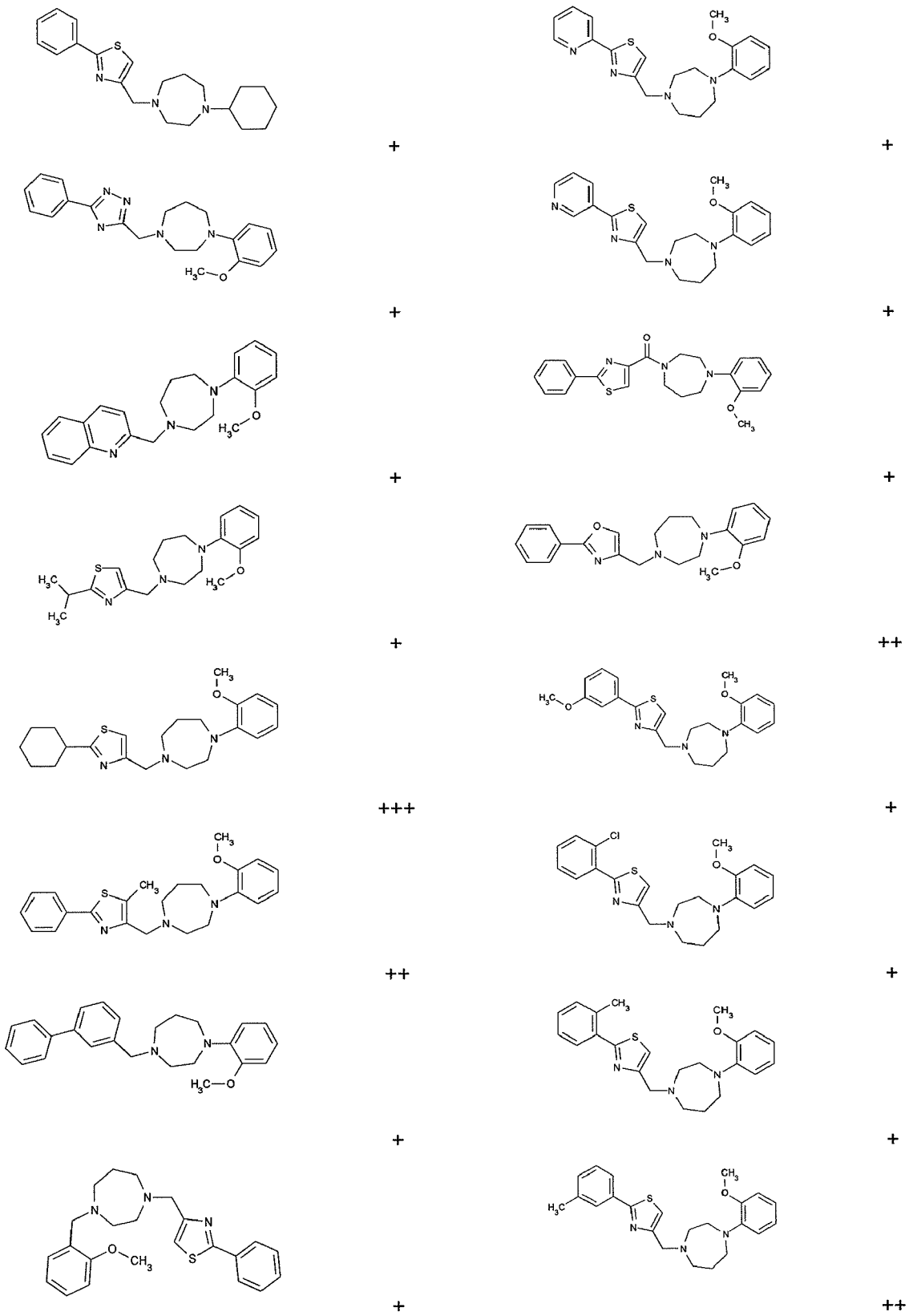
Figure 1I:
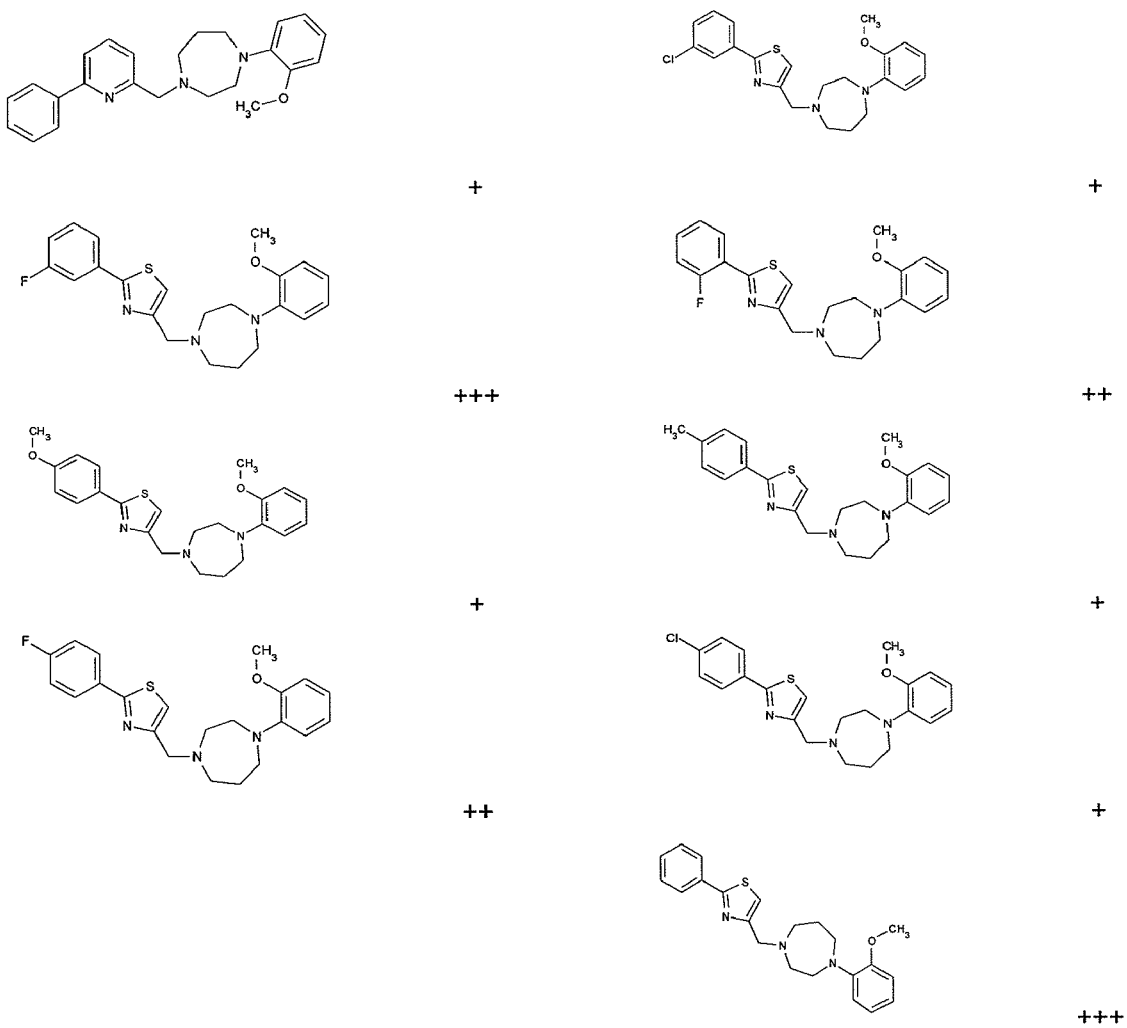
Figure 2A:
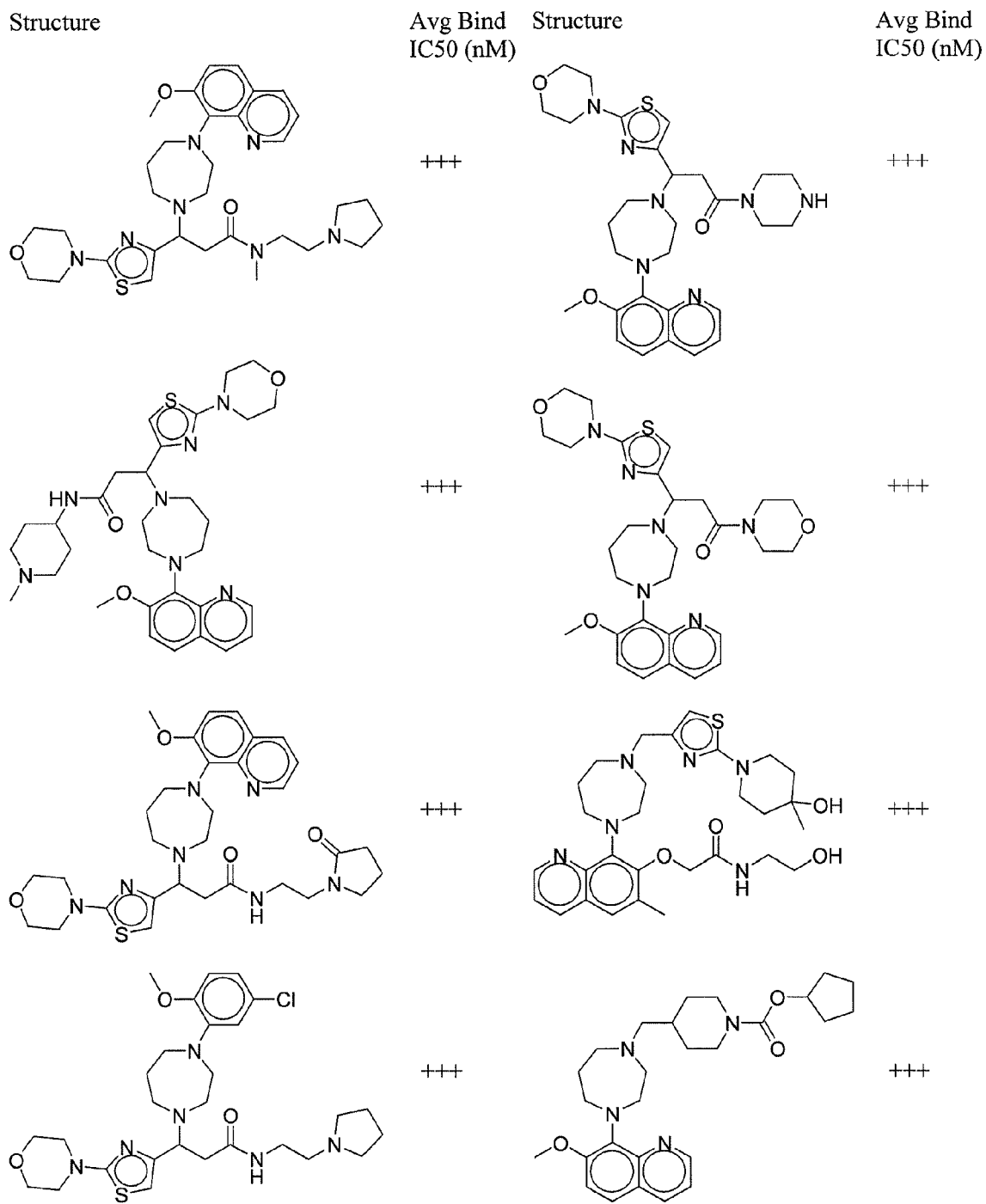
Figure 2B:
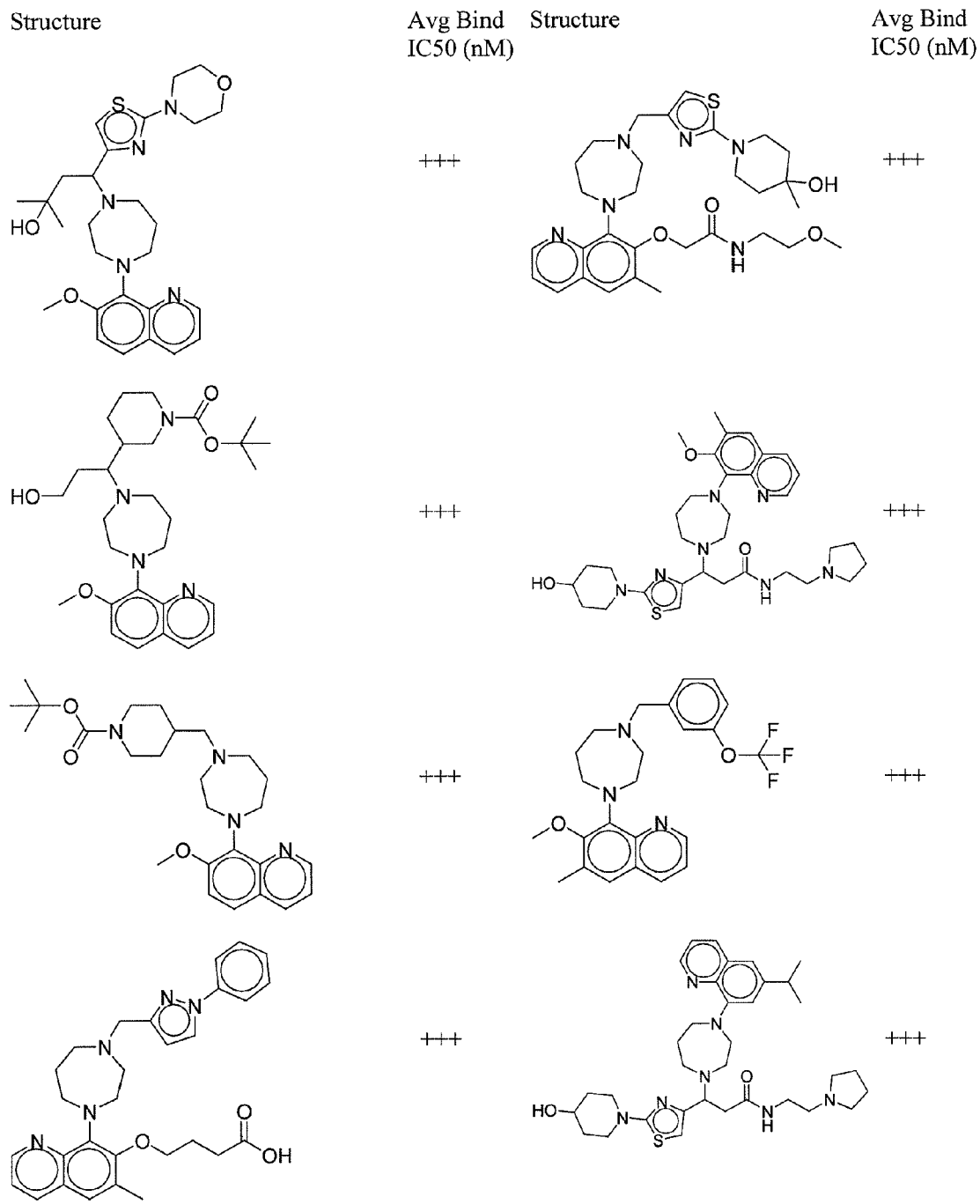
Figure 2C:
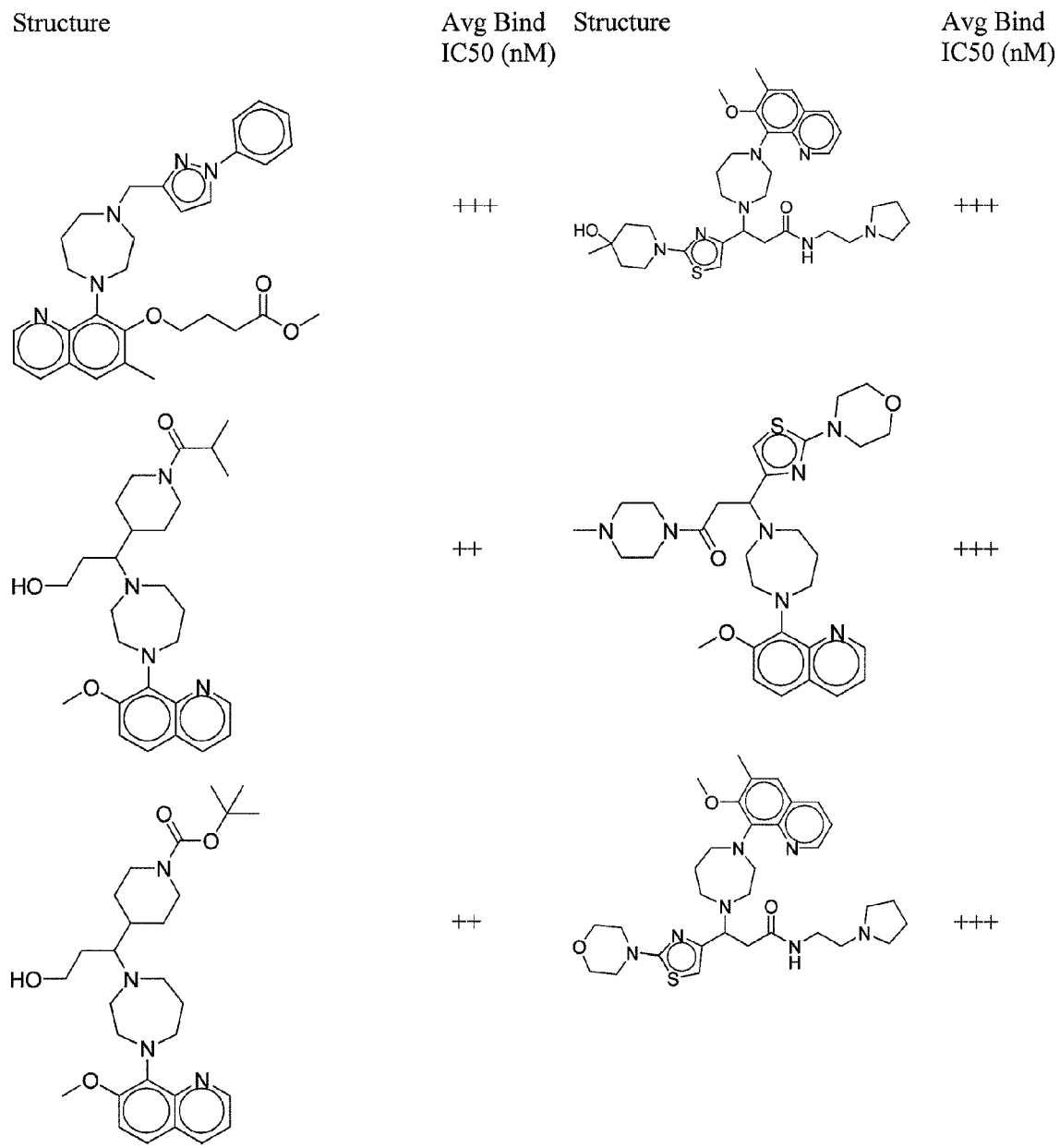
Figure 2D:
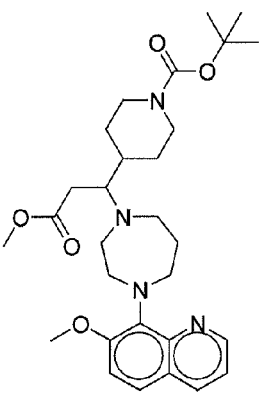
Figure 2D:
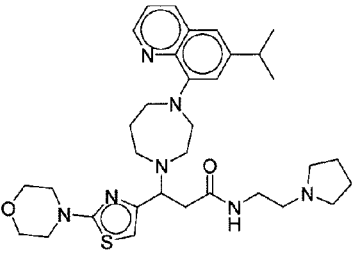
Figure 2D:
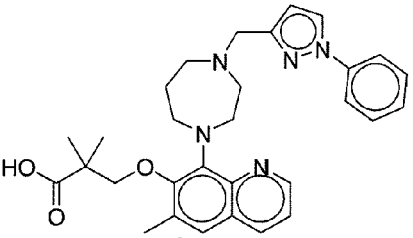
Figure 2D:
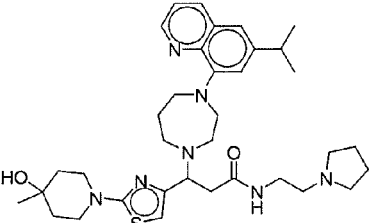
Figure 2D:
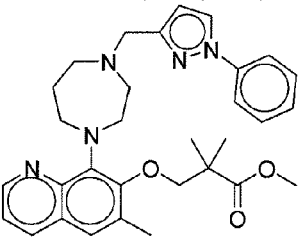
Figure 2D:
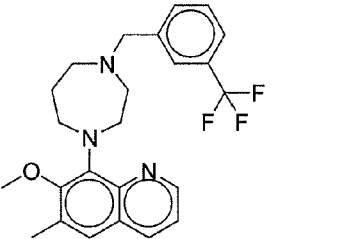
Figure 2D:
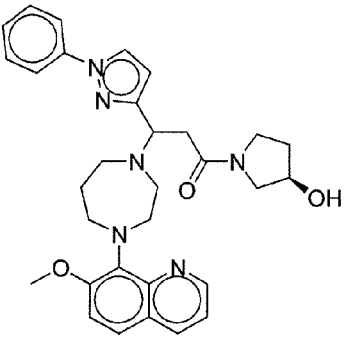
Figure 2D:
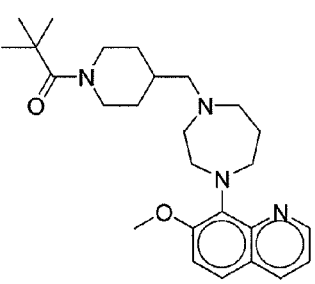
Figure 2E:
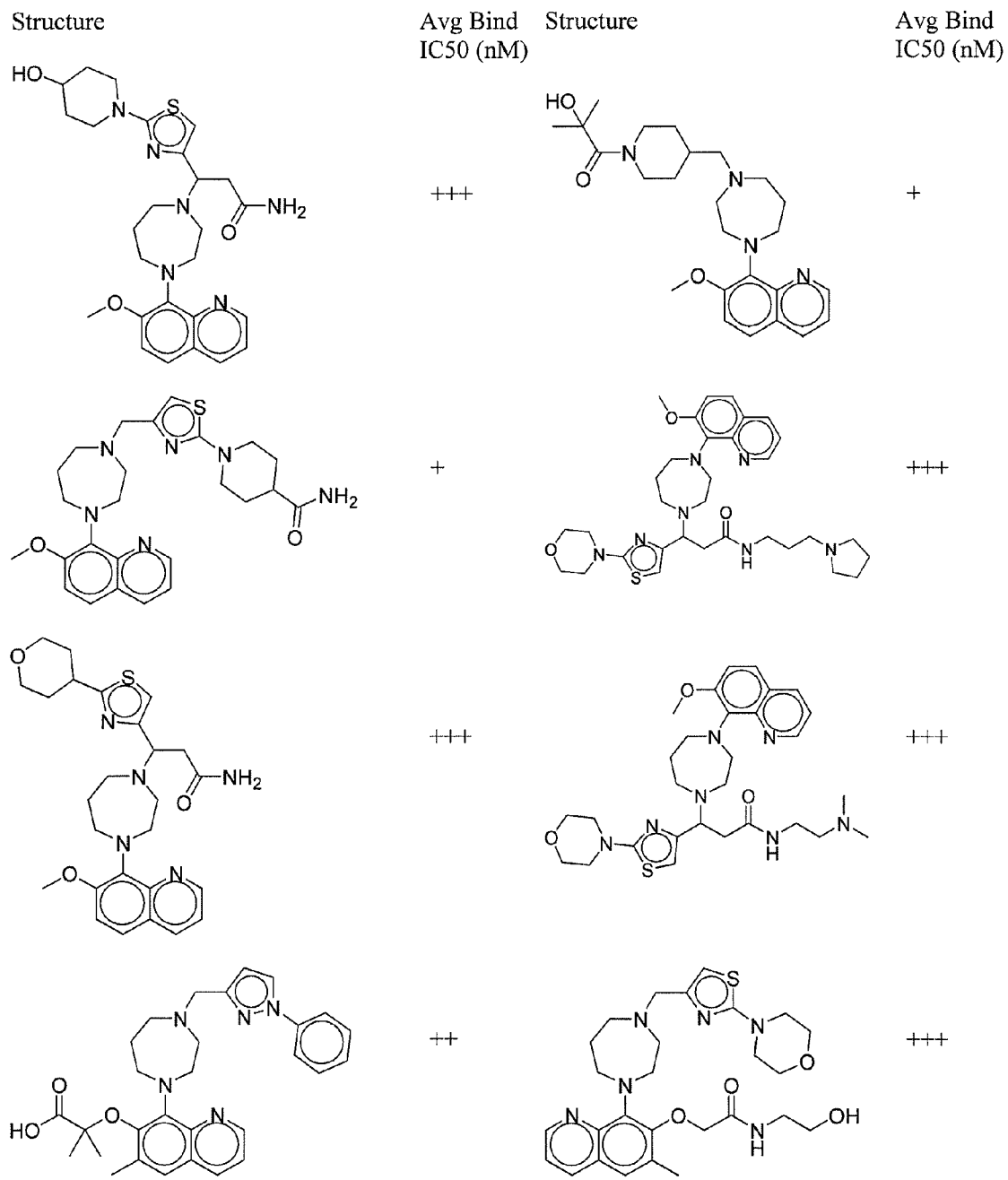
Figure 2F:
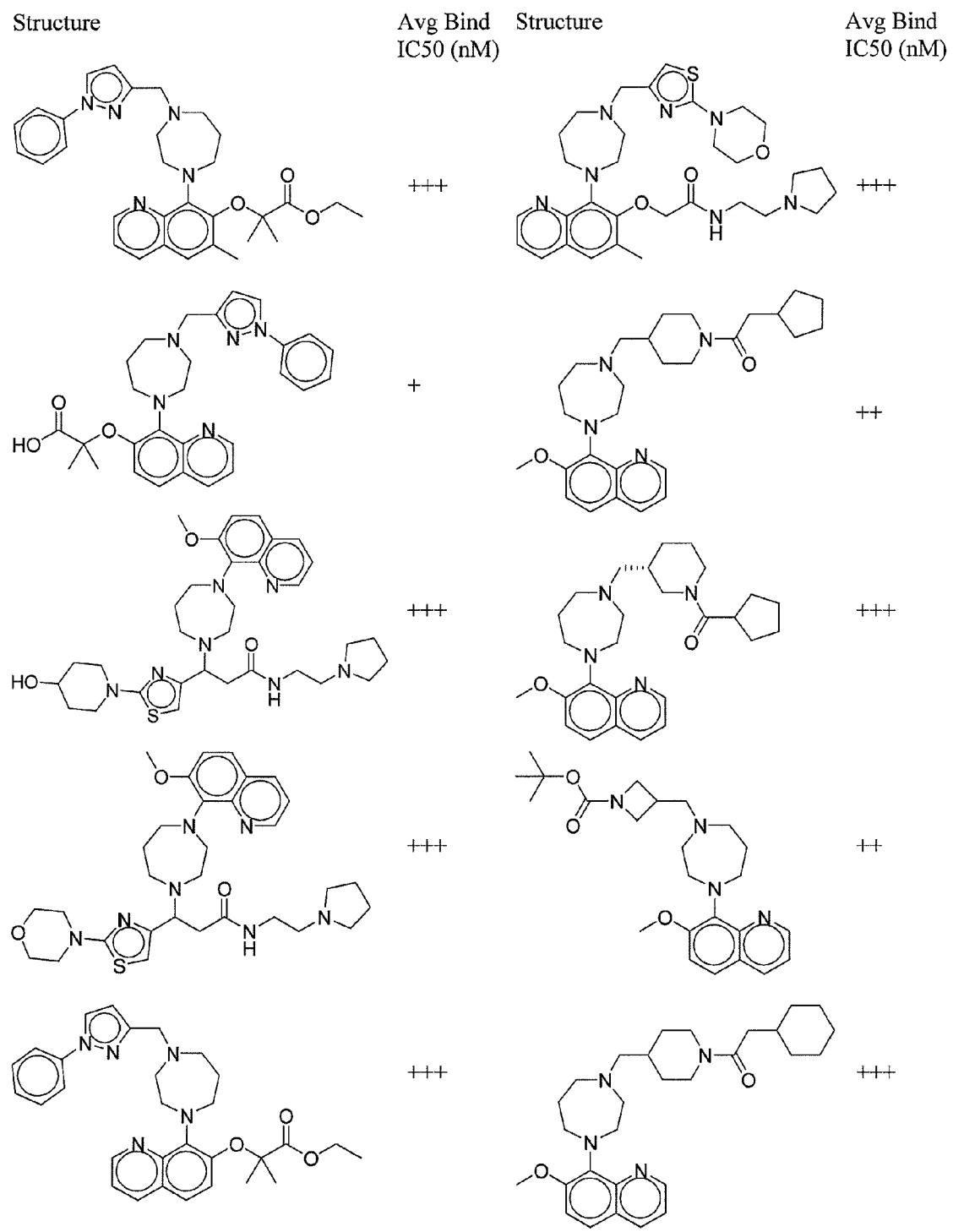
Figure 2G:
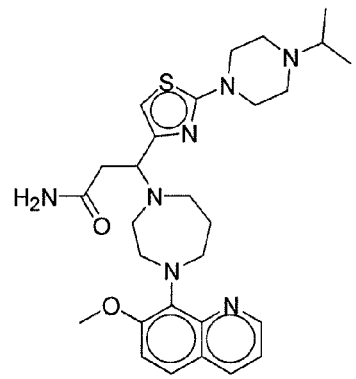
Figure 2G:
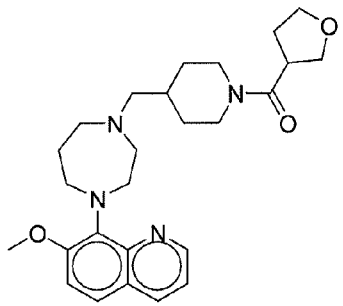
Figure 2G:
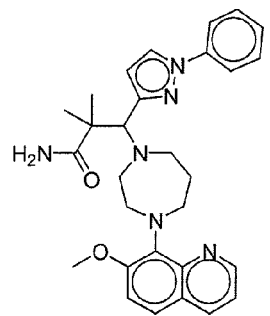
Figure 2G:
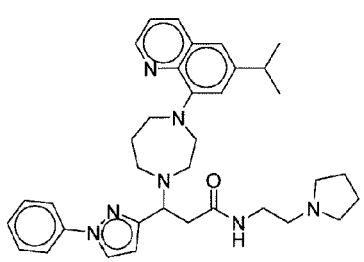
Figure 2G:
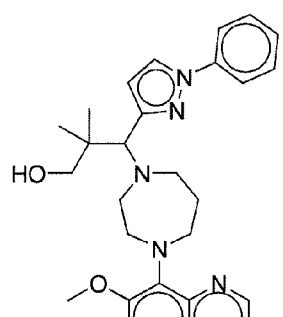
Figure 2G:
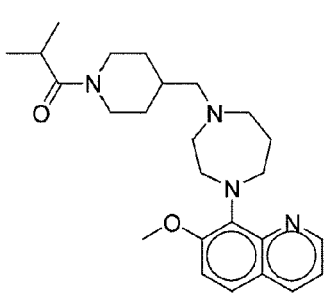
Figure 2G:
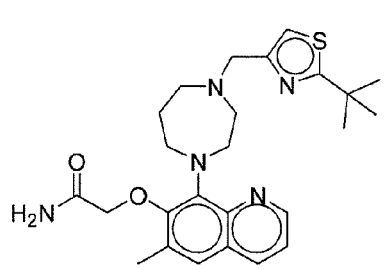
Figure 2G:
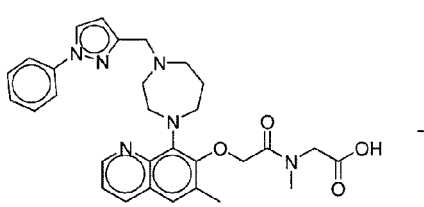
Figure 2H:
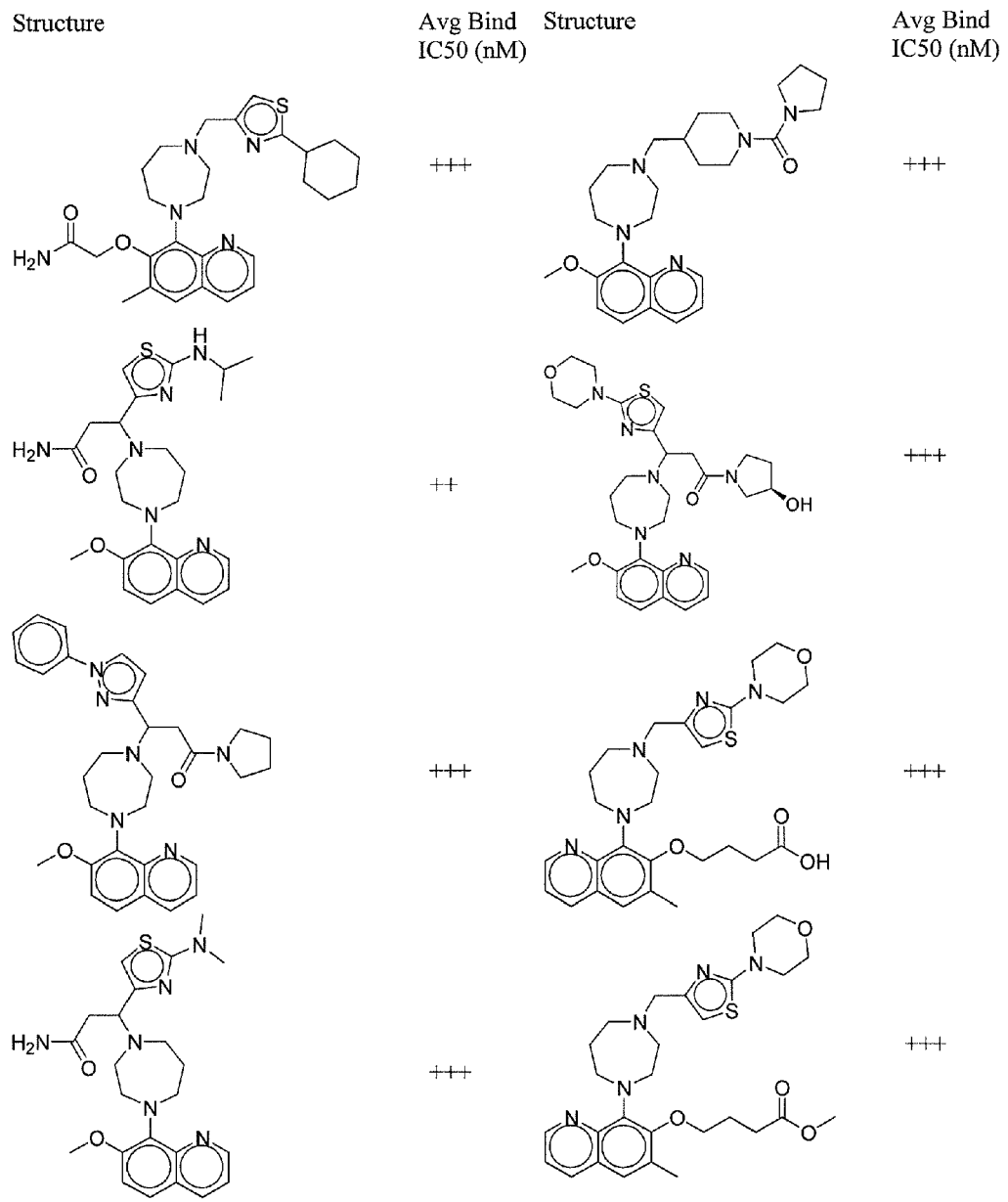
Figure 2I:
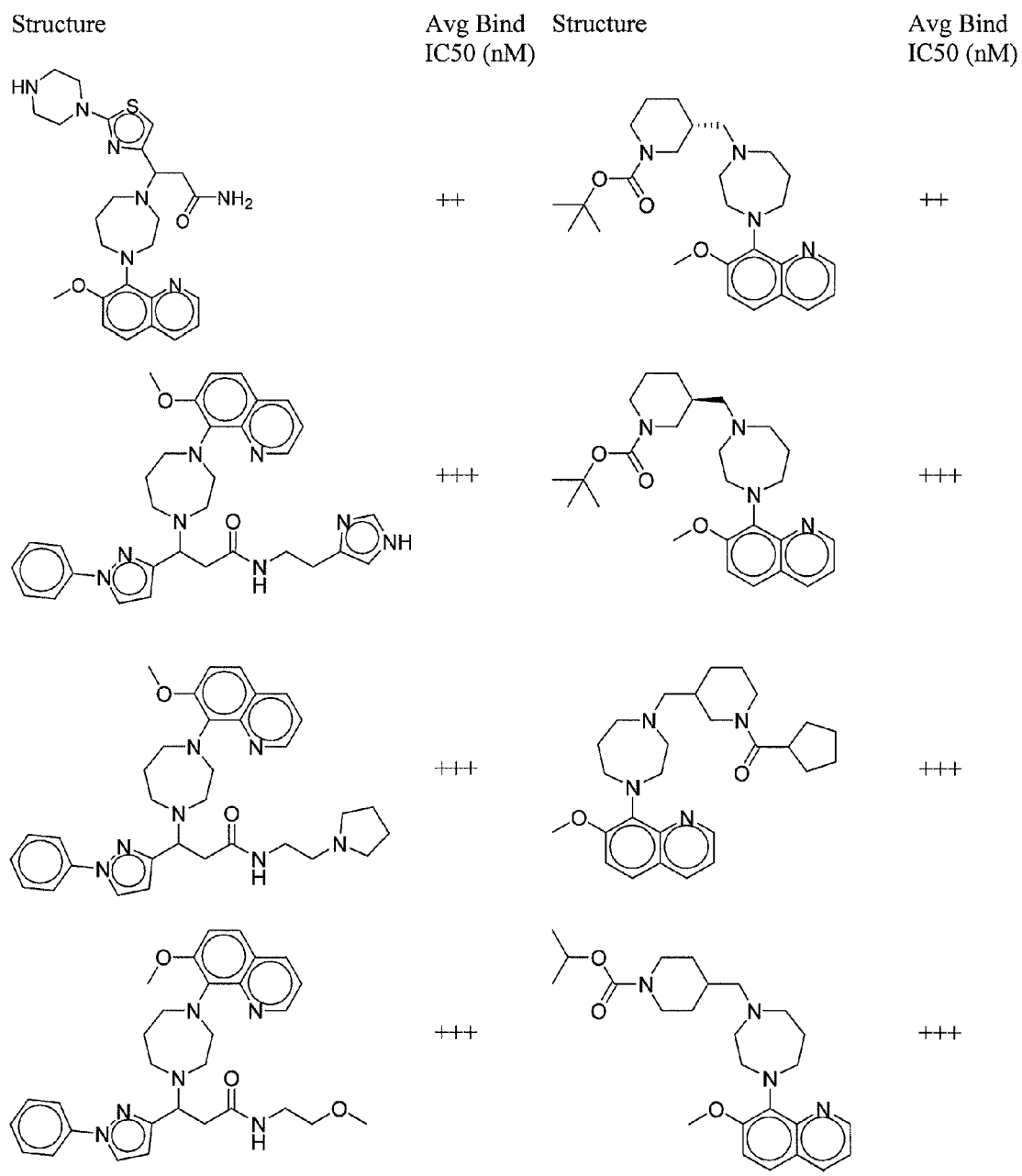
Figure 2J:
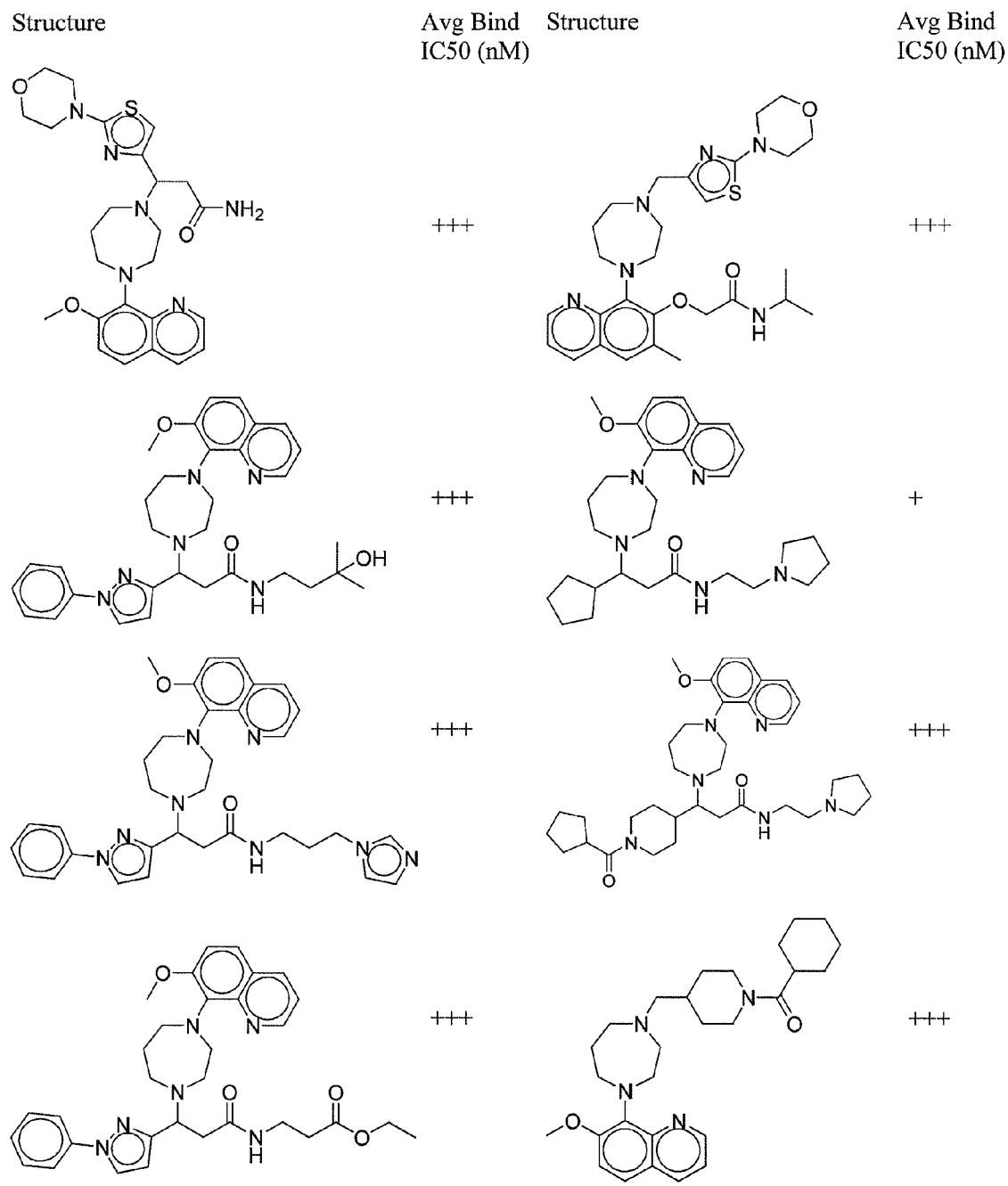
Figure 2K:
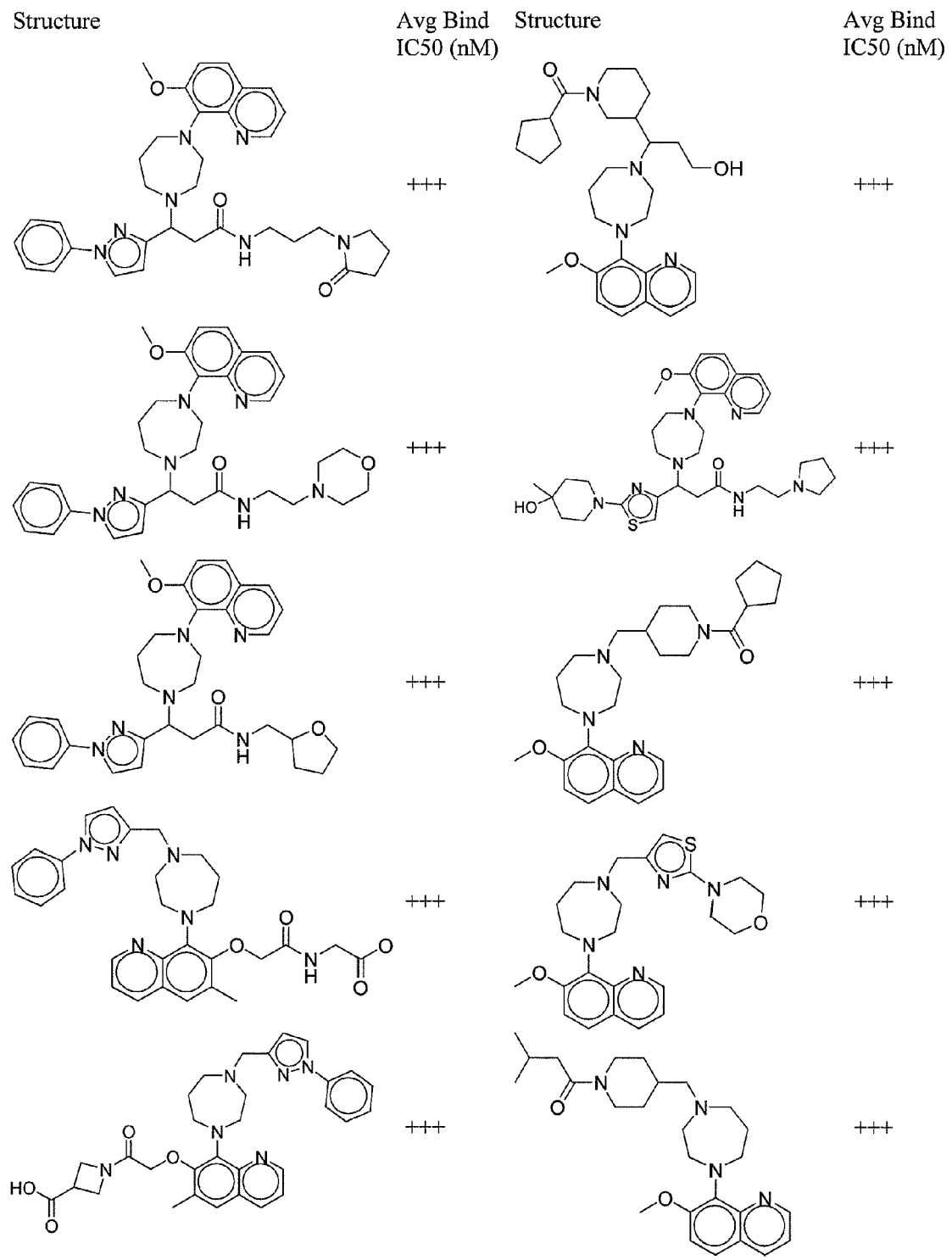
Figure 2M:
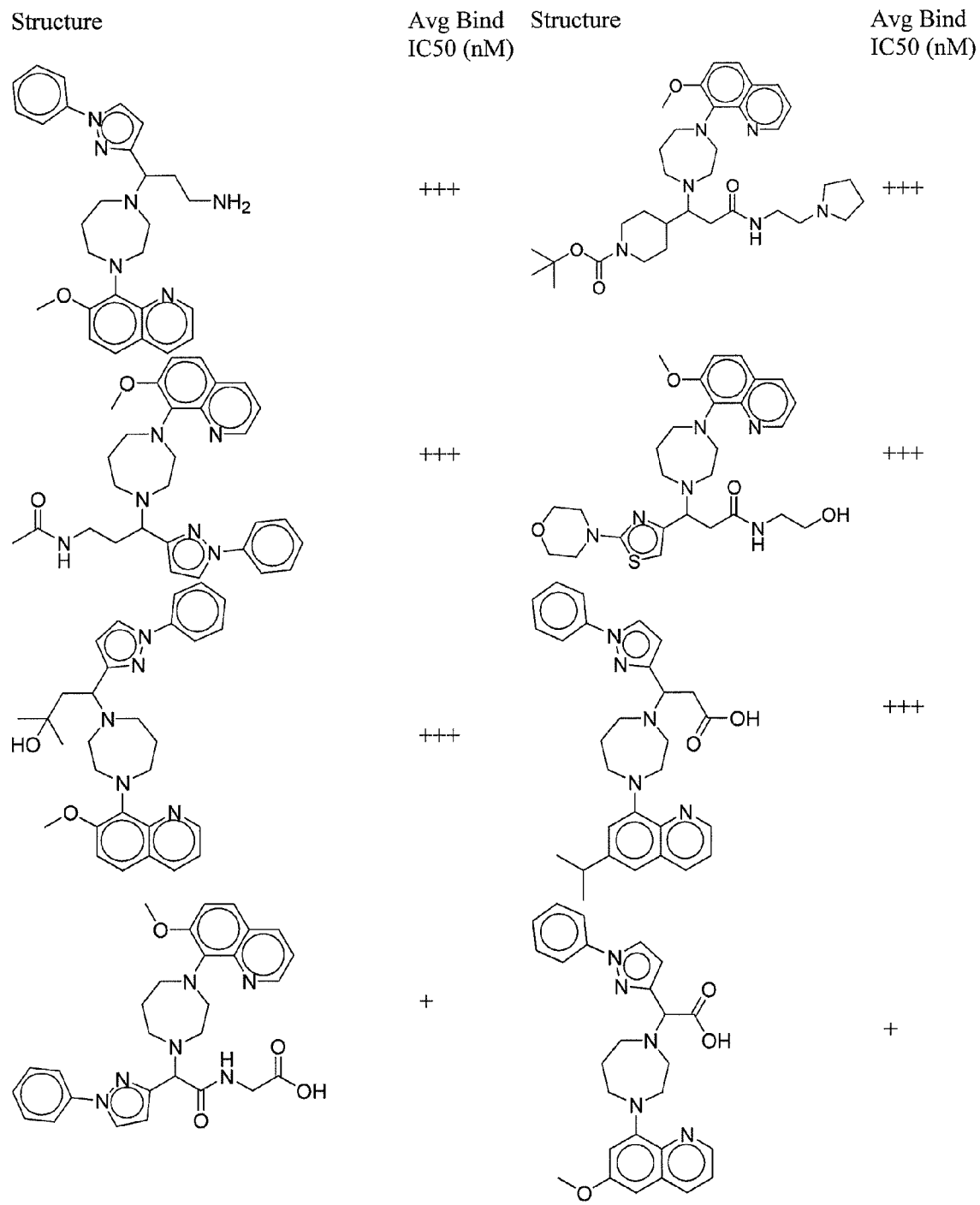
Figure 2N:
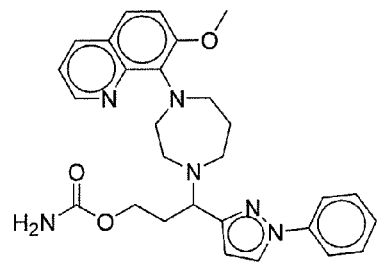
Figure 2N:
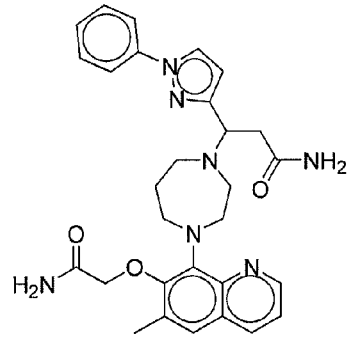
Figure 2N:
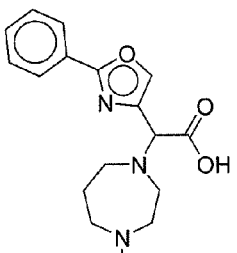
Figure 2N:
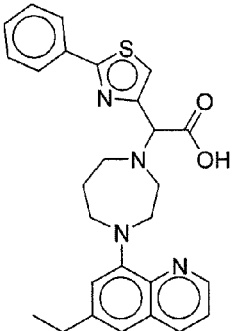
Figure 2N:
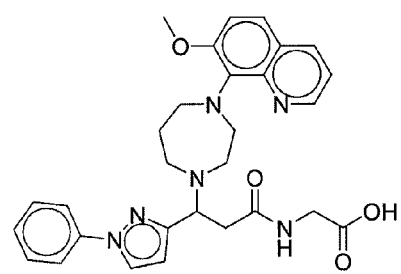
Figure 2N:
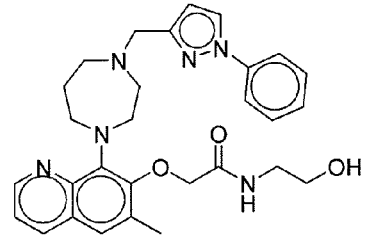
Figure 2N:
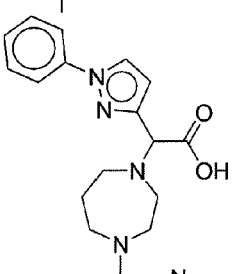
Figure 2N:
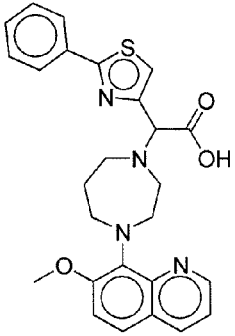
Figure 2O:
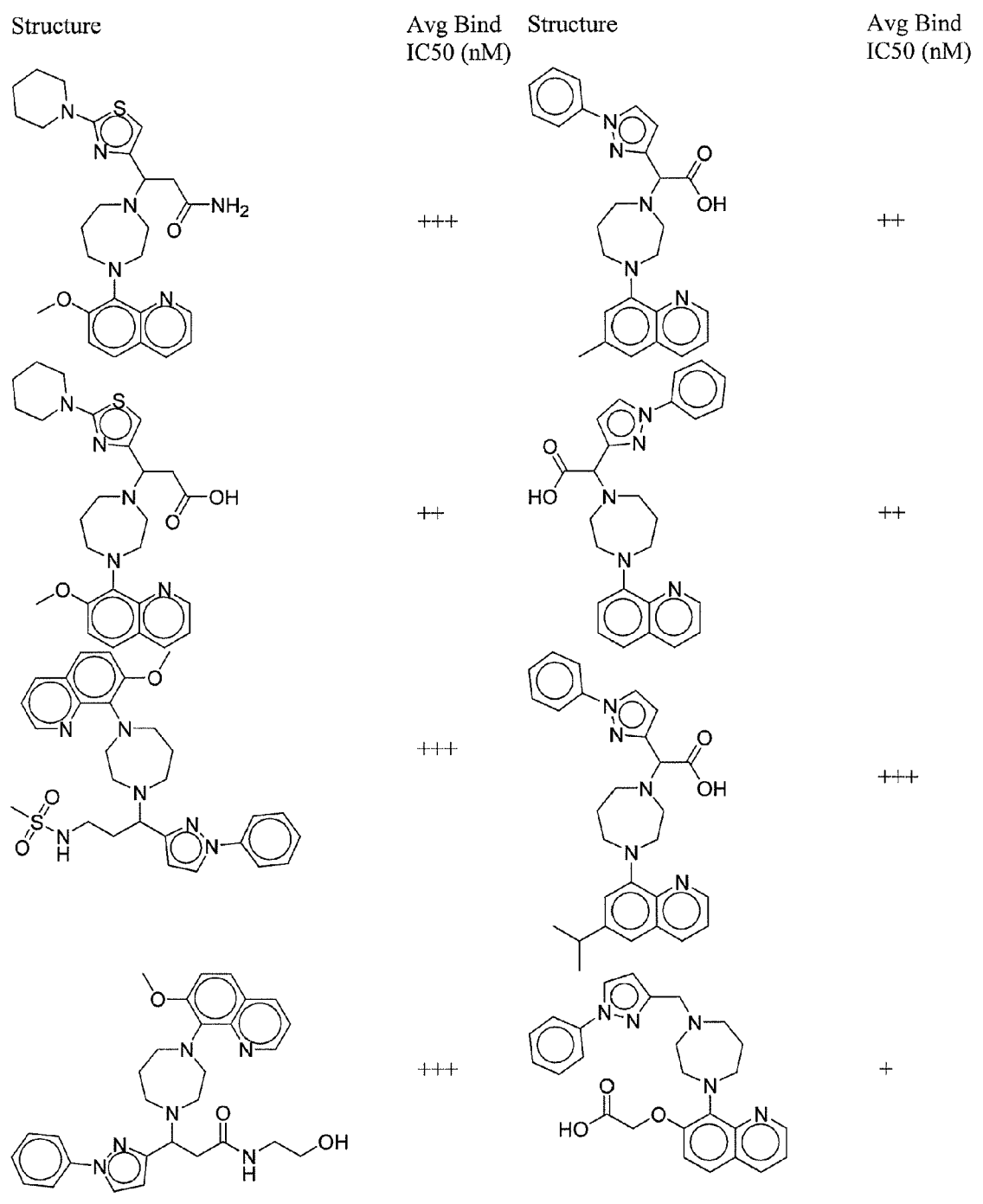
Figure 2P:
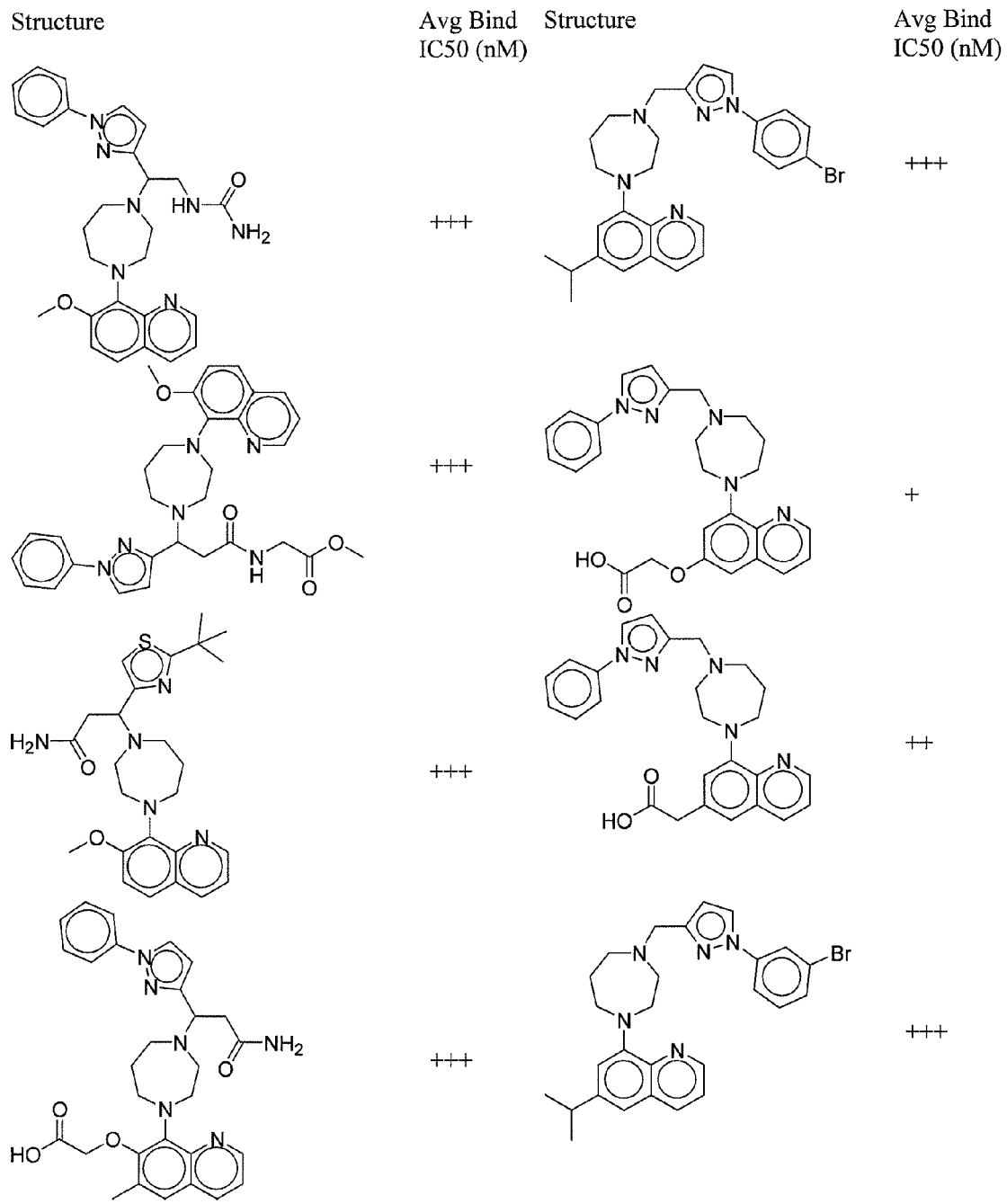
Figure 2Q:
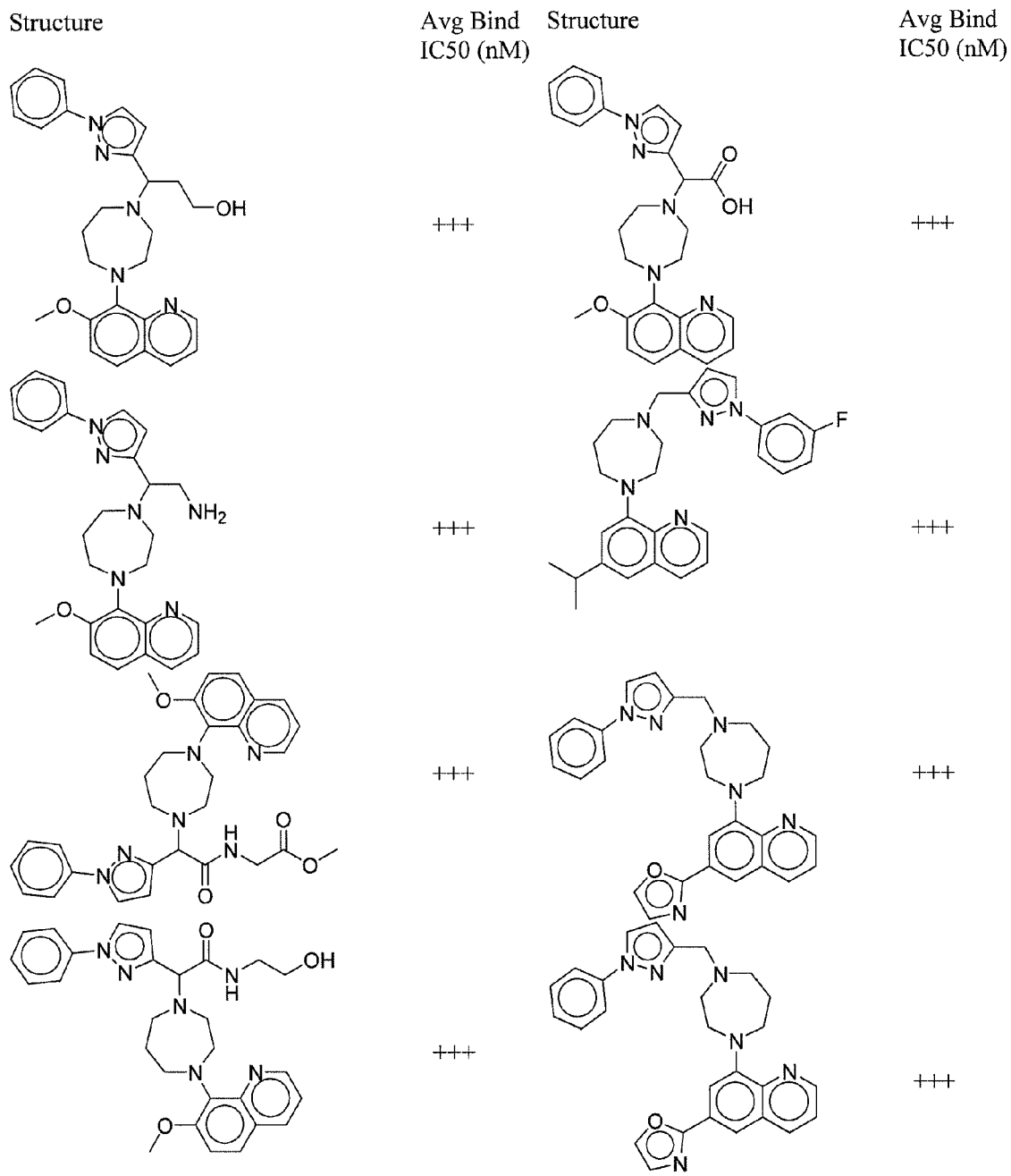
Figure 2R:
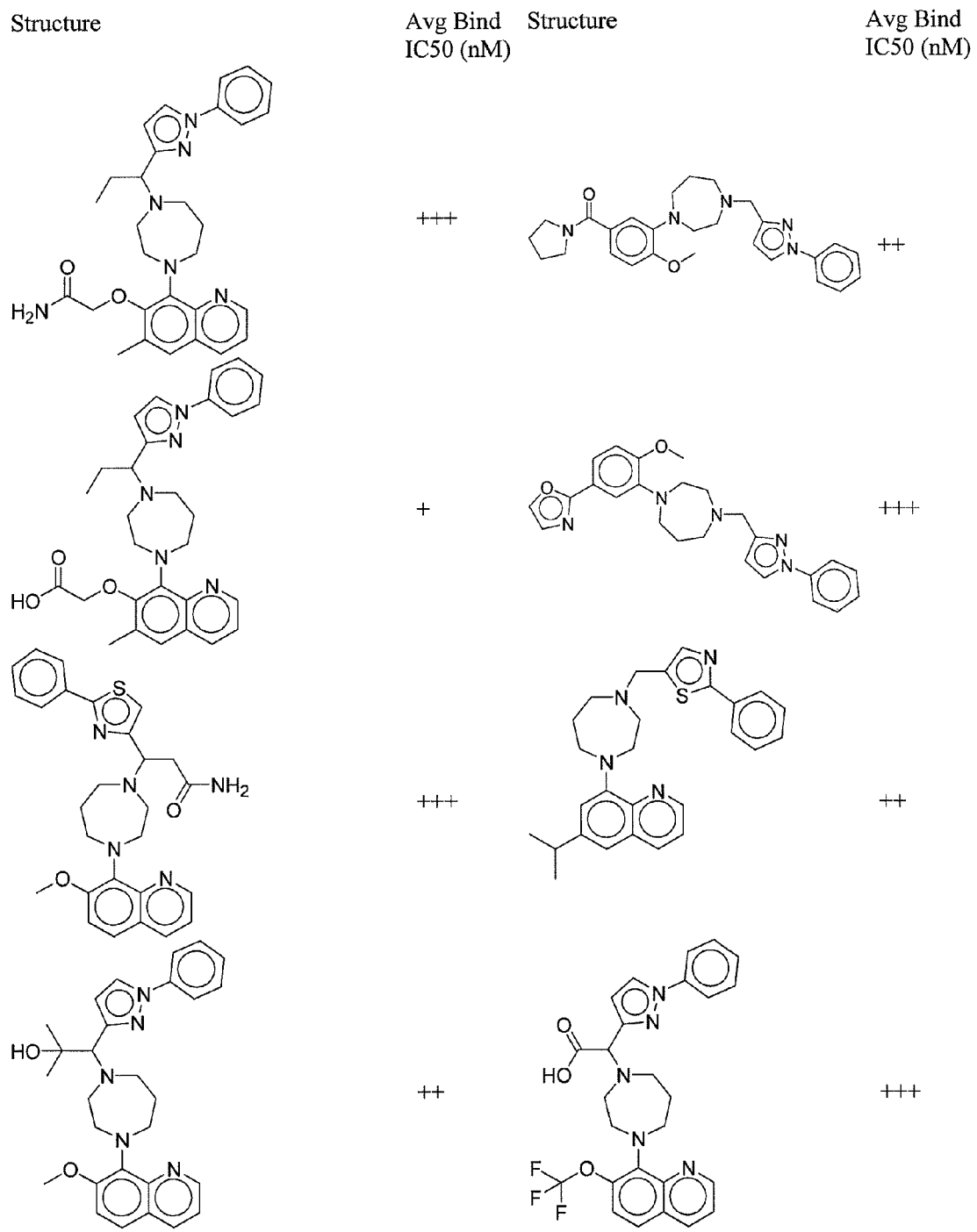
Figure 2S:
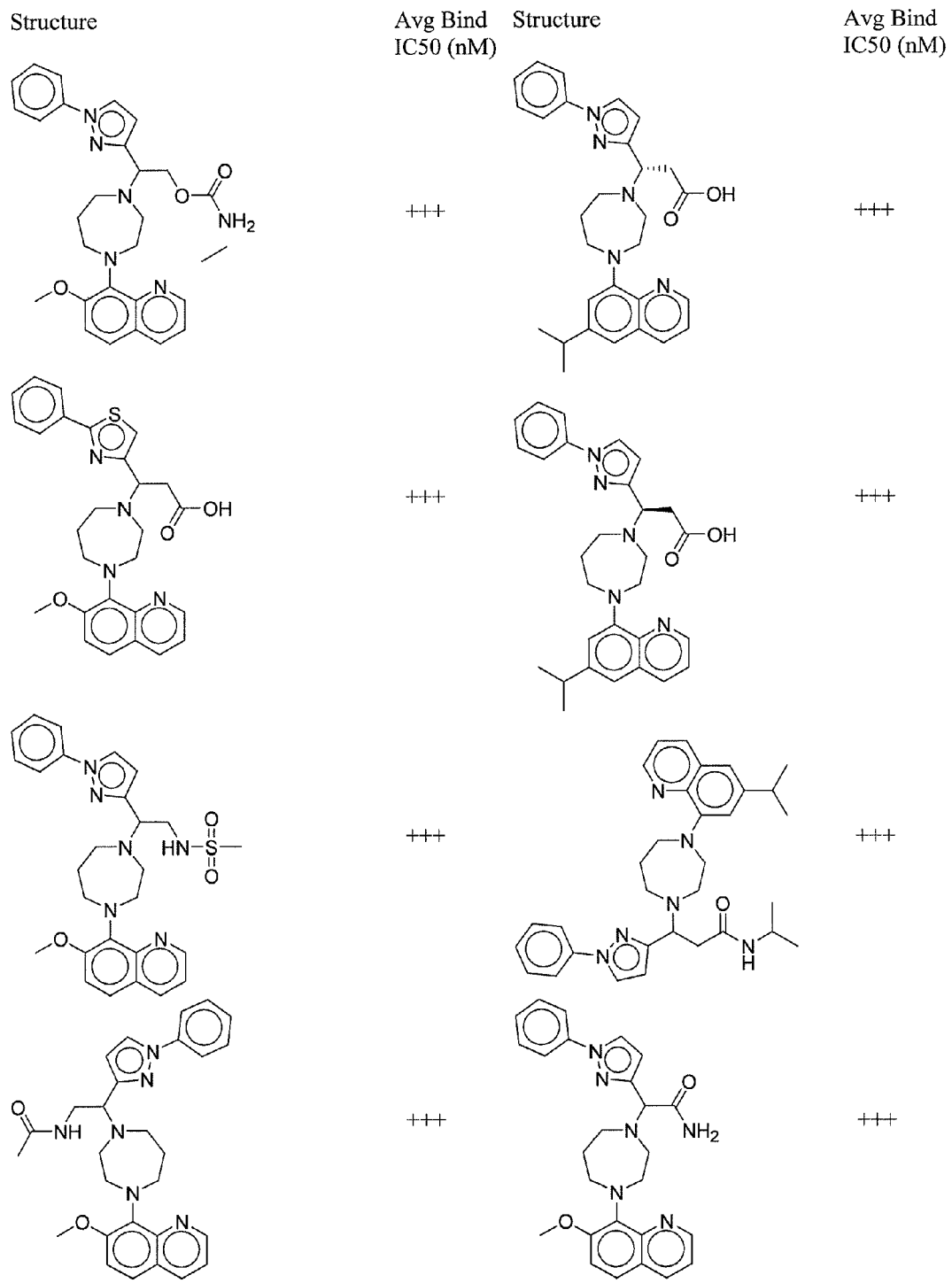
Figure 2T:
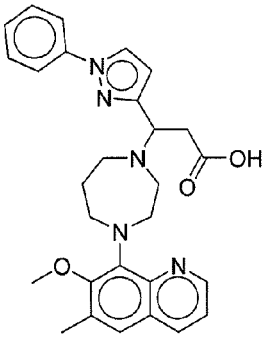
Figure 2T:
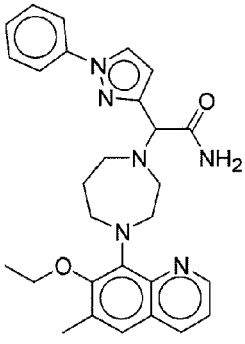
Figure 2T:
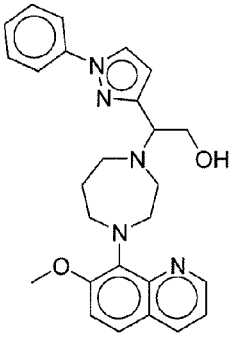
Figure 2T:
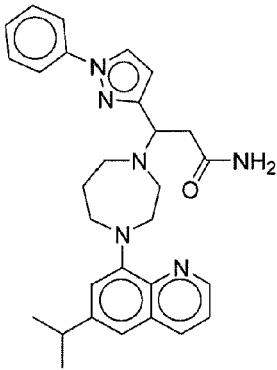
Figure 2T:
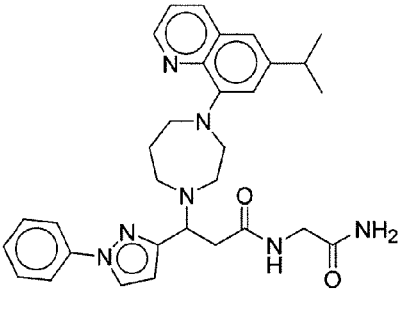
Figure 2T:
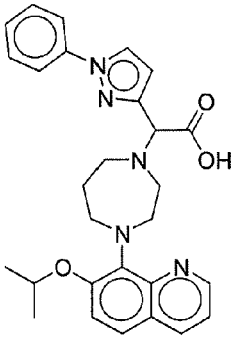
Figure 2U:
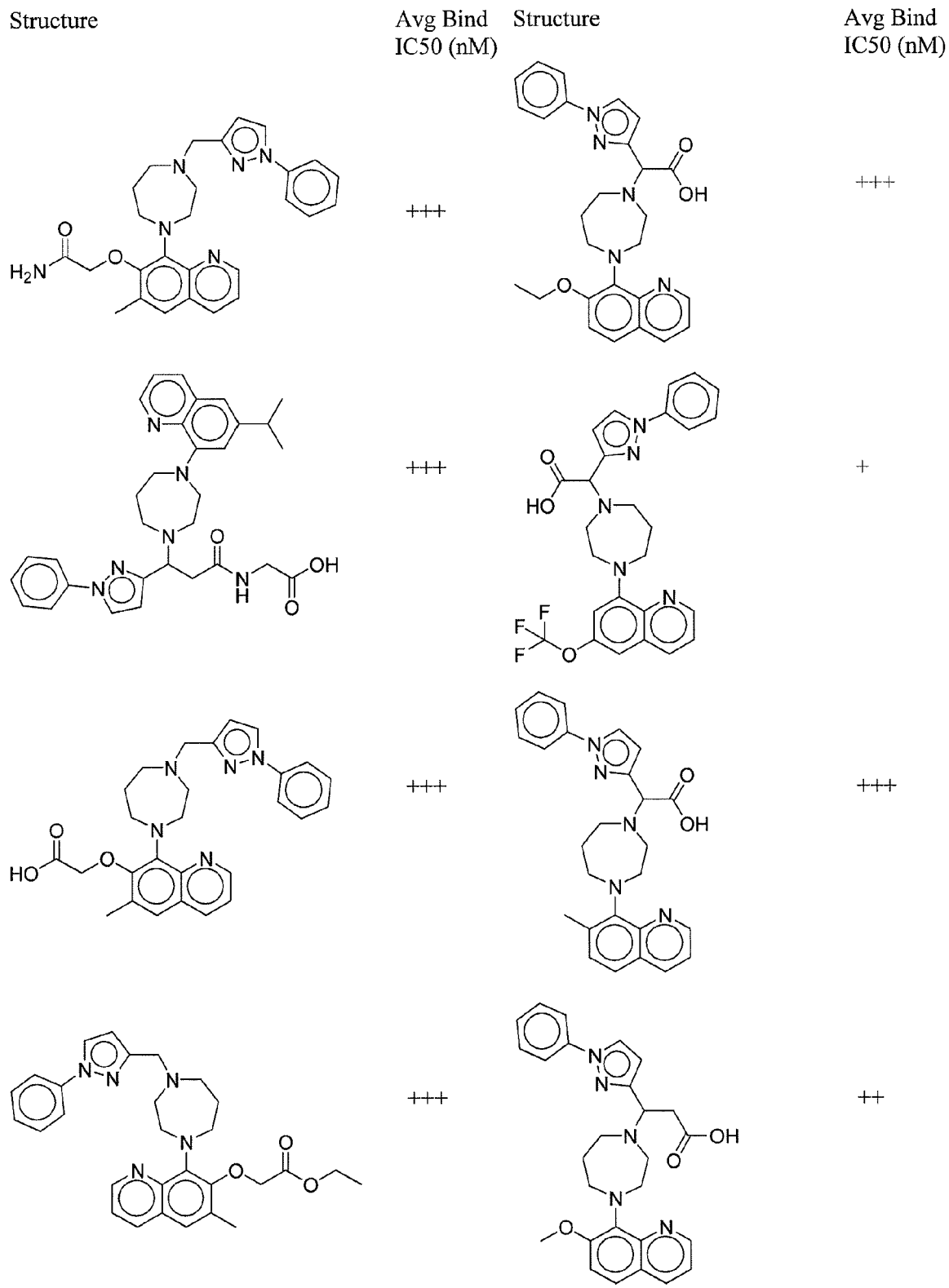
Figure 2V:
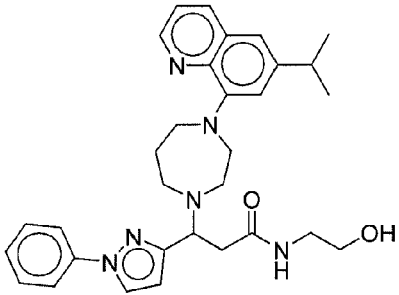
Figure 2V:
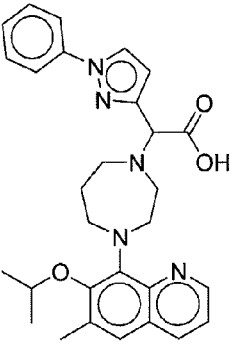
Figure 2V:
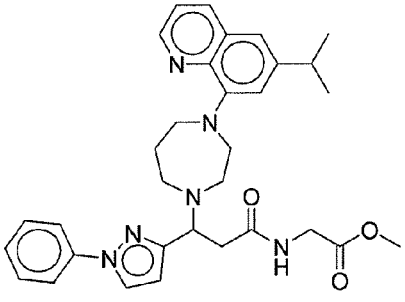
Figure 2V:
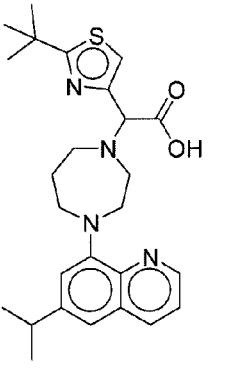
Figure 2V:
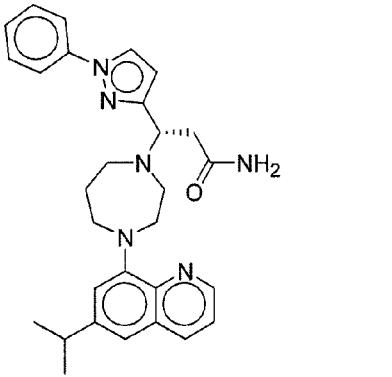
Figure 2V:
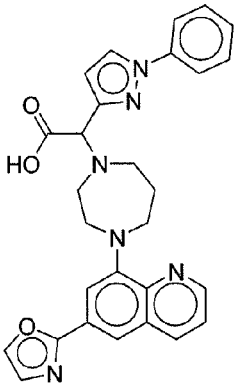
Figure 2W:
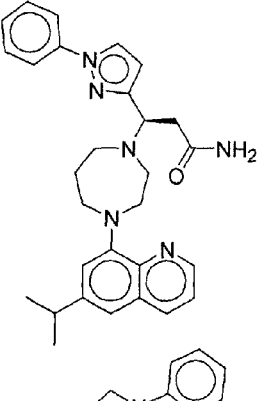
Figure 2W:
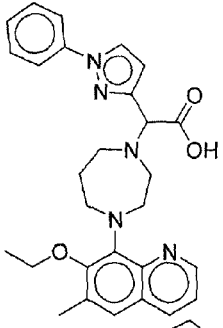
Figure 2W:
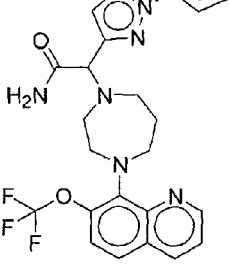
Figure 2W:
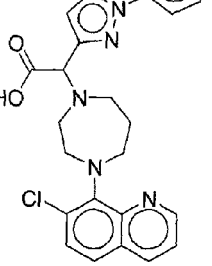
Figure 2W:
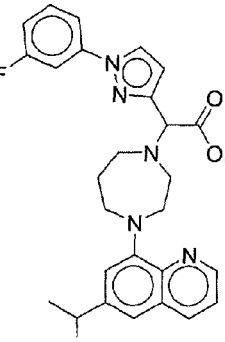
Figure 2W:
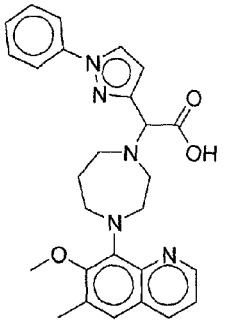
Figure 2X:
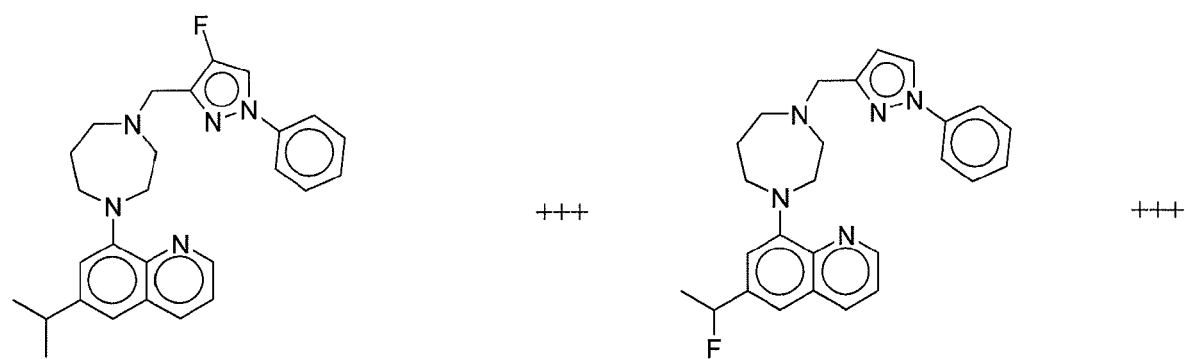
Figure 3A:
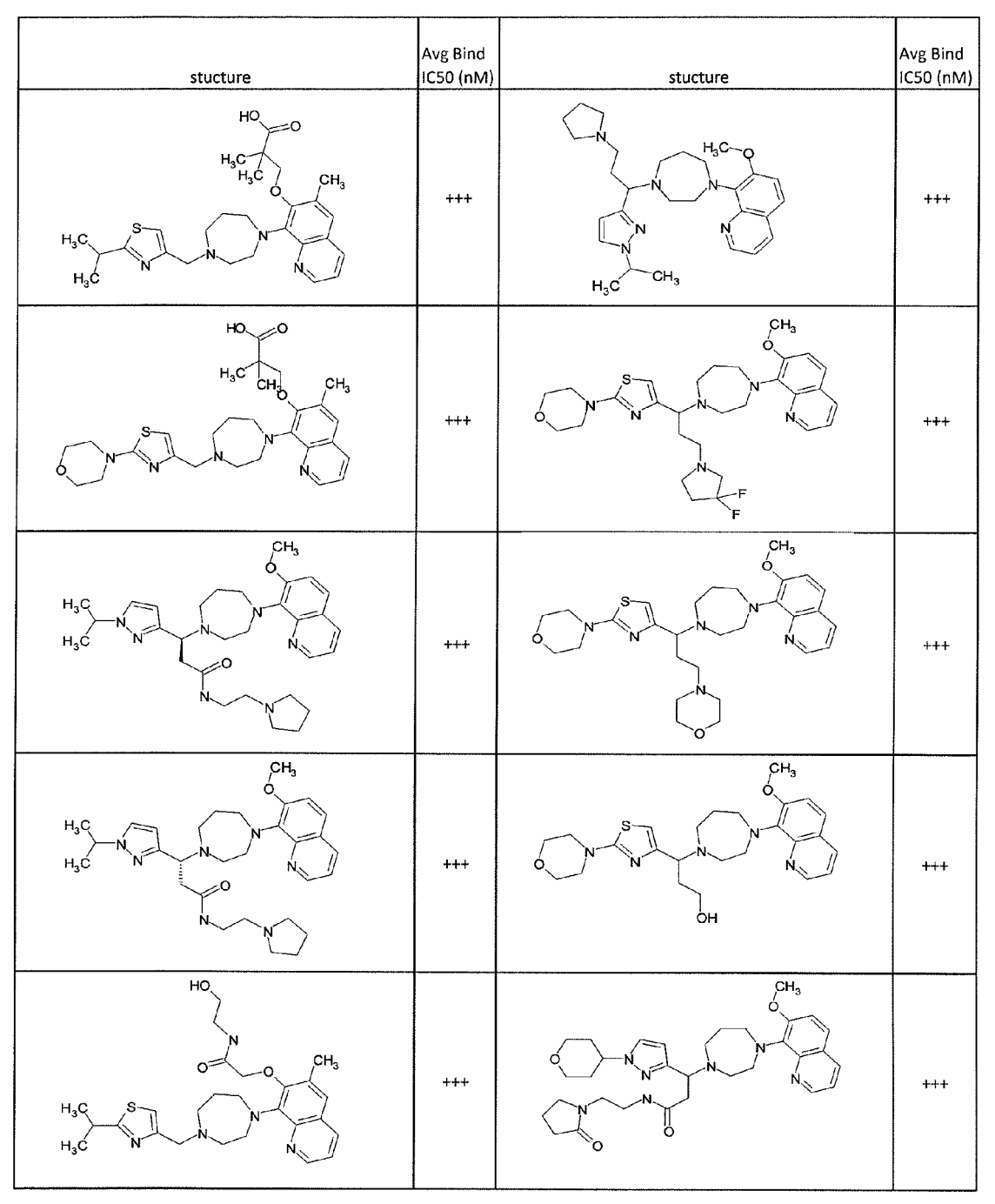
Figure 3C:
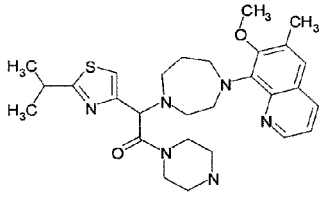
Figure 3D:
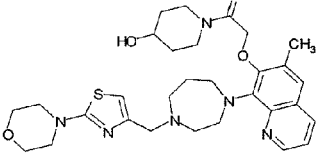
Figure 3D:
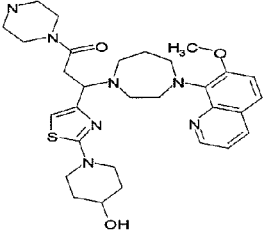
Figure 3D:
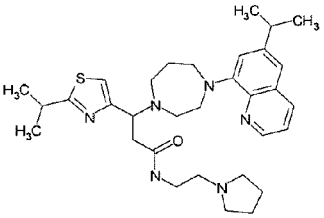
Figure 3D:
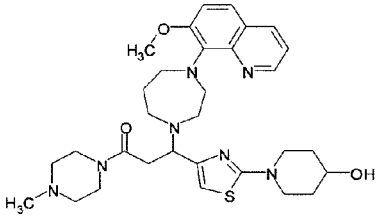
Figure 3D:
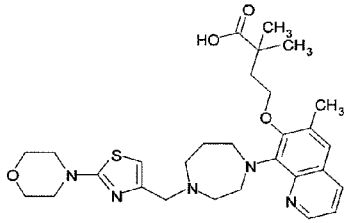
Figure 3D:
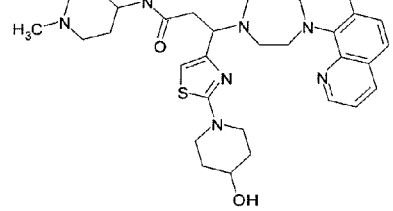
Figure 3D:
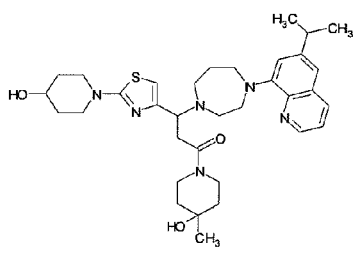
Figure 3D:
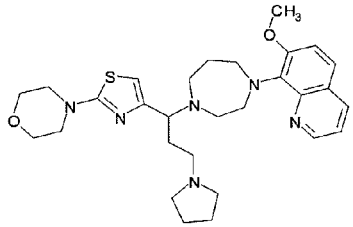
Figure 3D:
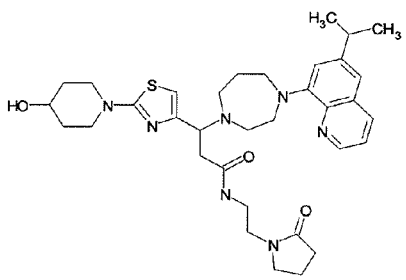
Figure 3D:
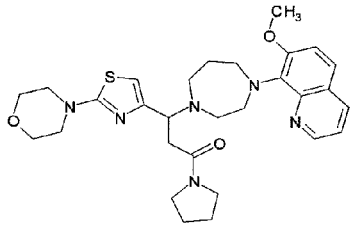
Figure 3E:
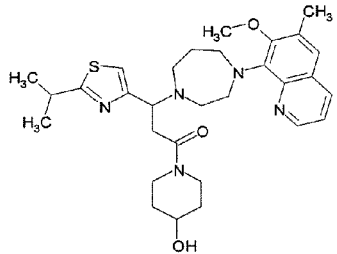
Figure 3E:
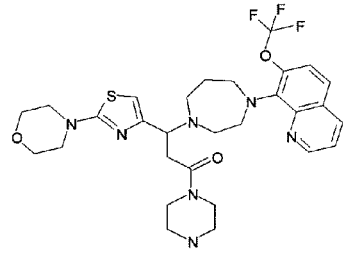
Figure 3E:
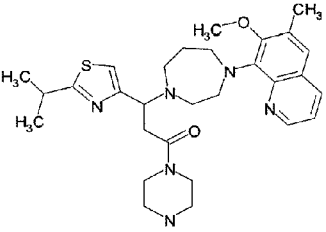
Figure 3E:
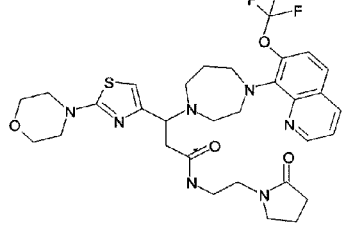
Figure 3E:
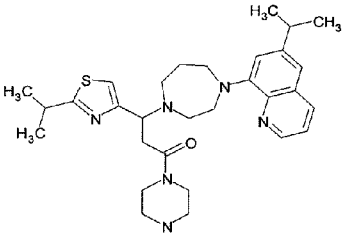
Figure 3E:
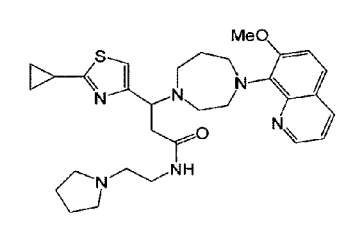
Figure 3E:
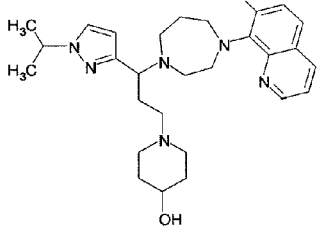
Figure 3E:
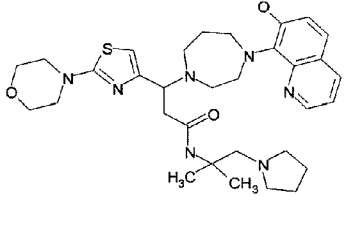
Figure 3E:
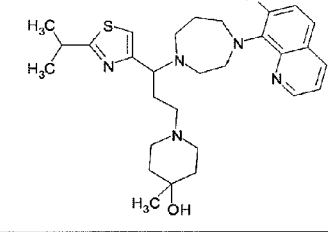
Figure 3E:
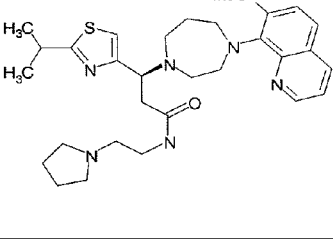
Figure 3G:
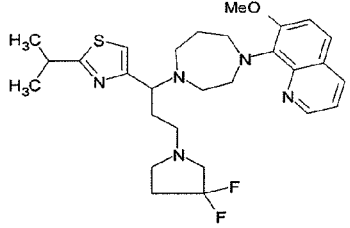
Figure 3H:
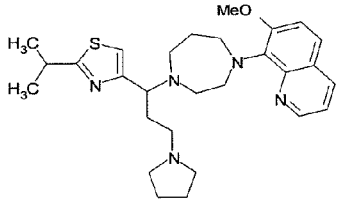

Compounds that were deemed effective modulators were able to displace at least 50% of the SDF-1 from the CXCR7 receptor at concentrations at or below 5 micromolar (µM) but>500 nM (+); and more preferably at concentrations from >100 nM to ≦500 nM (++). At present, especially preferred compounds can displace at least 50% of the SDF-1 from the CXCR7 receptor at concentrations at or below 100 nM (+++). Exemplary compounds that met these criteria are reproduced in FIGS. 1, 2 and 3. All compounds were prepared as described in the Examples above, or by related methods substituting readily available starting materials.

1. Determination of IC$_{50}$ values.

Reagents and Cells. $^{125}$I-labeled SDF-1 was purchased from Perkin-Elmer Life Sciences, Inc. (Boston, MA). The MCF-7 (adenocarcinoma; mammary gland) cell line was obtained from the American Type Culture Collection (ATCC, Manassas, VA) or and was cultured in DMEM (Mediatech, Herndon, VA) supplemented with 10% fetal bovine serum (FBS) (HyClone Logan, UT) and bovine insulin (0.01 mg/mL) (Sigma, St. Louis, MO) at 37° C. in a humidified incubator at a 5% CO$_2$/air mixture. CXCR7 transfected MDA-MB-435S were produced as described below. MDA-MB-435S human breast cancer line, was purchased from ATCC, and cultured in DMEM/10% FBS medium. The complete coding sequence of the gene encoding CXCR7 (a.k.a._CCXCKR2, hRDC1), was isolated from MCF-7 cells using µMACs mRNA isolation kit (Miltenyi Biotec, Auburn, CA). DNA contamination was removed by DNase digestion via RNeasy columns (Qiagen, Inc., Valencia, CA) and cDNA was generated using GeneAmp RNA PCR Core Kit (Applied Biosystems, Foster City, CA). PCR of cDNA samples was performed using Taq PCR Master Mix kit (Qiagen, Inc.) and hRDC1 primers harboring 5' and 3' Not I sites (hRDC1F 5'-GAATGCGGCCGCTATGGATCTG-CATCTCTTCGACT-3' (SEQ ID NO:11)hRDC1R 5'-GAAT-GCGGCCGCTCATTTGGTGCTCTGCTCCAAG-3' (SEQ ID NO:12)) Not I digested PCR product was ligated into Not I digested pcDNA3.1(+)_(Invitrogen, Carlsbad, CA) and screened for orientation and sequence confirmed. Plasmid DNA was then isolated from overnight bacterial cultures by Maxiprep (Qiagen, Inc.). Plasmid DNA (10µg) was added to MDA-MB-435s cells and cells were electroporated (0.22kV, 960uF) via Gene Pulser (Biorad laboratories, Hercules, CA). 48 hr post-electroporation, cells were transferred to selection medium (600ug/ml G418).

Binding Analysis. Target compounds were tested to determine their ability to bind with CXCR7 sites on MCF-7 and/or MDA-MB-435S CXCR7 transfected cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. 1999

Jul. 30; 274(31): 21569-74 and Gosling J, et al., *Cutting edge: identification of a novel chemokine receptor that binds dendritic cell- and T cell-active chemokines including ELC, SLC, and TECK.*, J. Immunol. 2000 Mar. 15; 164(6):2851-6 was used.

In these assays, MCF-7 and/or MDA-MB-435S cells were interrogated with the target compounds and the ability of these compounds to displace $^{125}$I radiolabeled SDF-1 was assessed using the protocol described in Dairaghi and Gosling. The target compounds were added to the plate to the indicated concentration and were then incubated with cells followed by the addition of radiolabeled chemokine ($^{125}$I SDF-1) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using GraphPad Prism (GraphPad Software).

Transendothelial migration assay: The compounds of the invention may be further assessed by their ability to inhibit migration of cells in a transendothelial migration assay. In this assay, the ability of a cell to migrate through a layer of endothelial cells towards a chemokine source is analyzed. In one example of this assay 100,000 human umbillic vein endothelial cells (HUVECs, available from Lonza) are plated into the upper chamber of a transwell culture dish with a 5 uM filter pore size (Corning Costar). Medium is added and plates placed in an incubator overnight with 5% $CO_2$ at 37° C. After HUVECs have adhered to the filter overnight to form a monolayer, medium containing chemokine (eg SDF-1, final concentration 10 nM) is added to the lower chamber. Then 500,000 NC-37 cells (available from ATCC) are added to the upper chamber in the presence or absence of the test compound, and plates are returned to the incubator for 3 hours to overnight. Various concentrations of compound may be added to different wheels to create a dose response. At the end of this incubation the upper chamber is removed and the cells in the lower chamber are quantified. The cells can be quantified for instance, by labeling with a fluorescent dye such as Cyquant® (Invitrogen, CA) and then quantifying fluorescence on an appropriate plate reader. Data can be analyzed and plotted using GraphPad Prism (GraphPad Software). The efficacy of the compound is measured as its ability to inhibit the migration of these cells to the lower chamber.

In Vivo Efficacy a) Rabbit Model of Destructive Joint Inflammation

A rabbit LPS study can be conducted essentially as described in Podolin, et al. ibid., Female New Zealand rabbits (approximately 2 kilograms) are treated intra-articularly in both knees with LPS (10 ng). The compound of interest (e.g. formulated in 1% methocel) or vehicle (1% methocel) are dosed orally at a 5 ml/kg dose volume at two times (2 hours before the intra-articular LPS injection and 4 hours after the intra-articular LPS injection). Sixteen hours after the LPS injection, knees are lavaged and cells counts performed. Beneficial effects of treatment are determined by reduction in the number of inflammatory cells recruited to the inflamed synovial fluid of the knee joints. Treatment with the compound of interest results in a significant reduction in recruited inflammatory cells.

b) Evaluation of a Compound of Interest in a Rat Model of Collagen Induced Arthritis A 17 day developing type II collagen arthritis study can be conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

(c) Evaluation of a Compound of Interest in a Mouse Model of Wound Healing

In the wound healing studies, ICR derived male mice (24±2 g) are used. During the testing period, animals are singly housed in individual cages. Under hexobarbital (90 mg/kg, IP) anesthesia, the shoulder and back region of each animal is shaved. A sharp punch (ID 12 mm) is applied to remove the skin including *panniculus carnosus* and adherent tissues. A test compound or vehicle are each administered topically immediately following cutaneous injury once daily for 10 consecutive days. A positive control, for instance an A2 adenosine receptor agonist (CGS-21680; 10 μg/mouse), may also administered topically daily over the course of the experiment. The wound area, traced onto clear plastic sheets, is measured by use of an Image Analyzer (Life Science Resources Vista, Version 3.0) on days 1, 3, 5, 7, 9 and 11. The percent closure of the wound (%) is calculated, and wound half-closure time (CT50) is determined and analyzed by linear regression using Graph-Pad Prism (Graph Pad Software). Unpaired Student's t test may be applied for comparison between the treated and vehicle groups at each measurement time point. Differences are considered of statistical significance at $P<0.05$ level.

(d) Evaluation of a Compound of Interest in a Mouse Model of Lung Carcinoma

Many tumor models in animals are known in the art, and may be employed to evaluate a compound of instance. For instance, in a lung carcinoma xenograft study, A549 tumor fragments (30-40 mg) are implanted into the sub cutaneous space in nude mice. Tumors are permitted to grow until approximately 150 mg in size (between 100 and 200 mg) at which point mice are enrolled in the study and treatment begins. Mice are treated with a compound of interest or the vehicle control. Melphalan may be included as a positive control (9 mpk/dose, ip administration, Q4Dx3). Tumors are measured twice weekly with a caliper in two dimensions and converted to tumor mass using the formula for a prolate ellipsoid ($a \times b^2/2$), where a is the longer dimension and b is the shorter dimension, and assuming unit density (1 $mm^3$=1 mg). Body weights may also be measured twice weekly to assess any adverse effects of compound dosing. Antitumor activity is assessed by the delay in tumor growth of the treated group in comparison to the vehicle-treated control group.

Validation

Compounds that are initially identified as being of interest by any of the foregoing screening methods can be further tested to validate the apparent activity in vivo. Preferably such studies are conducted with suitable animal models. The basic format of such methods involves administering a lead compound identified during an initial screen to an animal that serves as a disease model for humans and then determining if the disease (e.g., cancer, myocardial infarction, wound healing, inflammatory diseases or other diseases associated with CXCR7) is in fact modulated and/or the disease or condition is ameliorated. The animal models utilized in validation studies generally are mammals of any kind. Specific examples of suitable animals include, but are not limited to, primates, mice, rats and zebrafish.

One of ordinary skill in the art will recognize from the provided description, figures, and examples, that modifications and changes can be made to the various embodiments of the invention without departing from the scope of the invention defined by the following claims and their equivalents.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound having formula I

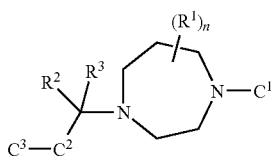

(I)

or a pharmaceutically acceptable salt or hydrate, or N-oxide, or isotopically enriched or enantiomerically enriched versions thereof, wherein
the subscript n is an integer of from 0 to 2;
each $R^1$, when present, is independently selected from the group consisting of $C_{1-4}$ alkyl, $-CO_2R^a$, $-X-CO_2R^a$, $-CONR^aR^b$ and $-X-CONR^aR^b$;
$R^2$ and $R^3$ are each members independently selected from the group consisting of H, $-R^a$, $-XR^a$, $-XNR^aR^b$, $-XNHCONR^aR^b$, $-XNHCOR^a$, $-X-O-CONR^aR^b$, $-XNHSO_2R^a$, $-CO_2R^a$, $-X-CO_2R^a$, $-CONR^aR^b$ and $-X-CONR^aR^b$; or taken together are oxo;
$C^1$ is phenyl or quinolin-8-yl, each optionally substituted with from 1 to 3 $R^4$ substituents;
$C^2$ is monocyclic four-, five-, six- or seven-membered ring selected from the group consisting of benzene, heteroaromatic, cycloalkane, and heterocycloalkane, wherein the heteroaromatic and heterocycloalkane rings have from 1-3 heteroatoms as ring members selected from N, O and S; and wherein each of said monocyclic $C^2$ rings are optionally substituted with from 1 to 3 $R^5$ substituents;
$C^3$ is selected from the group consisting of hydrogen, $C_{1-8}$ alkyl, $C_{3-8}$ cycloalkyl, aryl, aryl-$C_{1-4}$ alkyl, heteroaryl, heteroaryl-$C_{1-4}$ alkyl, and four- to six-membered heterocycloalkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^6$ substituents;
each $R^4$ is independently selected from the group consisting of halogen, $-CN$, $-NO_2$, $-R^c$, $-CO_2R^a$, $-NR^aR^b$, $-OR^a$, $-X-CO_2R^a$, $-CONR^aR^b$ and $-X-CONR^aR^b$;
wherein within each of $R^1$, $R^2$, $R^3$ and $R^4$, each $R^a$ and $R^b$ is independently selected from hydrogen, $C_{1-8}$ alkyl, $C_{3-7}$ cycloalkyl, $C_{1-8}$ haloalkyl, and four- to six-membered heterocycloalkyl, or when attached to the same nitrogen atom can be combined with the nitrogen atom to form a four-, five- or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, aryl and heteroaryl, and wherein the aliphatic and cyclic portions of $R^a$, $R^b$ and $R^c$ are optionally further substituted with from one to three halogen, hydroxy, methyl, alkoxy, amino, alkylamino, dialkylamino, carboxamide, carboxy alkyl ester, carboxylic acid, heteroaryl, and four- to six-membered heterocycloalkyl groups; and wherein the heterocycloalkyl portions of $R^2$, $R^3$ and $R^4$ are optionally substituted with oxo; and optionally when two $R^4$ substituents are on adjacent atoms, are combined to form a fused five or six-membered ring having carbon and oxygen atoms as ring members;

each $R^5$ is independently selected from the group consisting of halogen, —CN, —$NO_2$, —$R^f$, —$CO_2R^d$, —$COR^d$, —$NR^dR^e$, —$OR^d$, —X—$CO_2R^d$, —$CONR^dR^e$ and —X—$CONR^dR^e$; wherein each $R^d$ and $R^e$ is independently selected from hydrogen, $C_{1-8}$ alkyl, $C_{1-8}$ haloalkyl, $C_{3-6}$ cycloalkyl, $C_{3-6}$ cycloalkylalkyl, and four- to six-membered heterocycloalkyl or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, and $C_{3-6}$ cycloalkyl, and wherein the aliphatic and cyclic portions of $R^d$, $R^e$ and $R^f$ are optionally further substituted with from one to three halogen, hydroxy, methyl, alkoxy, amino, alkylamino, dialkylamino, carboxamide, carboxy alkyl ester, carboxylic acid, heteroaryl, four- to six-membered heterocycloalkyl groups;

each $R^6$ is independently selected from the group consisting of halogen, —CN, —$NO_2$, —$R^i$, —$CO_2R^g$, —$COR^g$, —$NR^gR^h$, —$OR^g$, —X—$CO_2R^g$, —X—$COR^g$, —$CONR^gR^h$ and —X—$CONR^gR^h$, wherein each $R^g$ and $R^h$ is independently selected from hydrogen, $C_{1-8}$ alkyl and $C_{1-8}$ haloalkyl; each $R^i$ is independently selected from the group consisting of $C_{1-8}$ alkyl and $C_{1-8}$ haloalkyl; and each X is a $C_{1-4}$ alkylene linking group or a linking group having the formula —$(CH_2)_mO(CH_2)_p$—, wherein the subscripts m and p are integer of from 0 to 5, and m +p is from 0 to 6, wherein any of the methylene portions of X are optionally substituted with one or two methyl groups.

2. The compound of claim 1, wherein X is selected from the group consisting of —$OCH_2$—, —$OCH_2CH_2$—, —$OCH_2CH_2CH_2$—, —$OC(CH_3)_2$—, —$OCH_2C(CH_3)_2$—, —$OCH_2CH_2C(CH_3)_2$—, —$CH_2$—, —$C(CH_3)_2$— and —$CH_2CH_2$—.

3. The compound of claim 1, wherein the subscript n is an integer of from 0 to 2;

each $R^1$, when present, is independently selected from the group consisting of $C_{1-4}$ alkyl, —$CO_2R^a$, —X—$CO_2R^a$, —$CONR^aR^b$ and —X—$CONR^aR^b$;

$R^2$ and $R^3$ are each members independently selected from the group consisting of H, —$R^a$, —$XR^a$, —$XNR^aR^b$, —$XNHCONR^aR^b$, —$XNHCOR^a$, —X—O—$CONR^aR^b$, —$XNHSO_2R^a$, —$CO_2R^a$, —X—$CO_2R^a$, —$CONR^aR^b$ and —X—$CONR^aR^b$; or taken together are oxo;

$C^2$ is monocyclic four-, five-, six- or seven-membered ring selected from the group consisting of benzene, heteroaromatic, cycloalkane, and heterocycloalkane, wherein the heteroaromatic and heterocycloalkane rings have from 1-3 heteroatoms as ring members selected from N, O and S; and wherein each of said monocyclic $C^2$ rings are optionally substituted with from 1 to 3 $R^5$ substituents;

$C^3$ is selected from the group consisting of hydrogen, $C_{1-8}$ alkyl, $C_{3-8}$ cycloalkyl, aryl, aryl-$C_{1-4}$ alkyl, heteroaryl, heteroaryl-$C_{1-4}$ alkyl, and four- to six-membered heterocycloalkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^6$ substituents;

each $R^4$ is independently selected from the group consisting of halogen, —CN, —$NO_2$, —$R^c$, —$CO_2R^a$, —$NR^aR^b$, —$OR^a$, —X—$CO_2R^a$, —$CONR^aR^b$ and —X—$CONR^aR^b$, wherein within each of $R^1$, $R^2$, $R^3$ and $R^4$, each $R^a$ and $R^b$ is independently selected from hydrogen, $C_{1-8}$ alkyl, $C_{3-7}$ cycloalkyl, $C_{1-8}$ haloalkyl, and four- to six-membered heterocycloalkyl, or when attached to the same nitrogen atom can be combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{3-6}$ cycloalkyl, aryl and heteroaryl, and wherein the aliphatic and cyclic portions of $R^a$, $R^b$ and $R^c$ are optionally further substituted with from one to three halogen, hydroxy, methyl, alkoxy, amino, alkylamino, dialkylamino, carboxamide, carboxy alkyl ester, carboxylic acid, heteroaryl, and four- to six-membered heterocycloalkyl groups; and wherein the heterocycloalkyl portions of $R^2$, $R^3$ and $R^4$ are optionally substituted with oxo; and optionally when two $R^4$ substituents are on adjacent atoms, are combined to form a fused five or six-membered ring having carbon and oxygen atoms as ring members;

each $R^5$ is independently selected from the group consisting of halogen, —CN, —$NO_2$, —$R^f$, —$CO_2R^d$, —$COR^d$, —$NR^dR^e$, —$OR^d$, —X—$CO_2R^d$, —$CONR^dR^e$ and —X—$CONR^dR^e$; wherein each $R^d$ and $R^e$ is independently selected from hydrogen, $C_{1-8}$ alkyl, $C_{1-8}$ haloalkyl, $C_{3-6}$ cycloalkyl, $C_{3-6}$ cycloalkylalkyl, and four- to six-membered heterocycloalkyl or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, and $C_{3-6}$ cycloalkyl, and wherein the aliphatic and cyclic portions of $R^d$, $R^e$ and $R^f$ are optionally further substituted with from one to three halogen, hydroxy, methyl, alkoxy, amino, alkylamino, dialkylamino, carboxamide, carboxy alkyl ester, carboxylic acid, heteroaryl, four- to six-membered heterocycloalkyl groups;

each $R^6$ is independently selected from the group consisting of halogen, —CN, —$NO_2$, —$R^i$, —$CO_2R^g$, —$COR^g$, —$NR^gR^h$, —$OR^g$, —X—$CO_2R^g$, —$CONR^gR^h$ and —X—$CONR^gR^h$, wherein each $R^g$ and $R^h$ is independently selected from hydrogen, $C_{1-8}$ alkyl and $C_{1-8}$ haloalkyl; each $R^i$ is independently selected from the group consisting of $C_{1-8}$ alkyl and $C_{1-8}$ haloalkyl; and each X is independently selected from the group consisting of —$OCH_2$—, —$CH_2$—, —$C(CH_3)_2$— and —$CH_2CH_2$—.

4. The compound of claim 1, wherein the subscript n is an integer of from 0 to 2;

each $R^1$, when present, is independently selected from the group consisting of $C_{1-4}$ alkyl, $-CO_2R^a$, $-X-CO_2R^a$, $-CONR^aR^b$ and $-X-CONR^aR^b$;

$R^2$ and $R^3$ are each members independently selected from the group consisting of H, $C_{1-4}$ alkyl, $-CO_2R^a$, $-X-CO_2R^a$, $-CONR^aR^b$ and $-X-CONR^aR^b$; or taken together are oxo;

$C^2$ is monocyclic five-, six- or seven-membered ring selected from the group consisting of benzene, heteroaromatic, cycloalkane, and heterocycloalkane, wherein the heteroaromatic and heterocycloalkane rings have from 1-3 heteroatoms as ring members selected from N, O and S; and wherein each of said monocyclic $C^2$ rings are optionally substituted with from 1 to 3 $R^5$ substituents;

$C^3$ is selected from the group consisting of hydrogen, $C_{1-8}$ alkyl, $C_{3-8}$ cycloalkyl, aryl, aryl-$C_{1-4}$ alkyl, heteroaryl, heteroaryl-$C_{1-4}$ alkyl, and four- to six-membered heterocycloalkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^6$ substituents;

each $R^4$ is independently selected from the group consisting of halogen, $-CN$, $-NO_2$, $-R^c$, $-CO_2R^a$, $-NR^aR^b$, $-OR^a$, $-X-CO_2R^a$, $-CONR^aR^b$ and $-X-CONR^aR^b$, wherein within each of $R^1$, $R^2$, $R^3$ and $R^4$, each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; within $R^4$ each $R^c$ is independently selected from the group consisting of $C_{1-8}$ alkyl, $C_{1-8}$ haloalkyl, $C_{3-6}$ cycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^4$ substituents are on adjacent atoms, are combined to form a fused five or six-membered ring having carbon and oxygen atoms as ring members;

each $R^5$ is independently selected from the group consisting of halogen, $-CN$, $-NO_2$, $-R^f$, $-CO_2R^d$, $-NR^dR^e$, $-OR^d$, $-X-CO_2R^d$, $-CONR^dR^e$ and $-X-CONR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, and $C_{3-6}$ cycloalkyl, and wherein the aliphatic and cyclic portions of $R^d$, $R^e$ and $R^f$ are optionally further substituted with from one to three halogen, hydroxy, methyl, amino, alkylamino and dialkylamino groups;

each $R^6$ is independently selected from the group consisting of halogen, $-CN$, $-NO_2$, $-R^i$, $-CO_2R^g$, $-NR^gR^h$, $-OR^g$, $-X-CO_2R^g$, $-CONR^gR^h$ and $-X-CONR^gR^h$, wherein each $R^g$ and $R^h$ is independently selected from hydrogen, $C_{1-8}$ alkyl and $C_{1-8}$ haloalkyl; each $R^i$ is independently selected from the group consisting of $C_{1-8}$ alkyl and $C_{1-8}$ haloalkyl; and each X is independently selected from the group consisting of $CH_2$ and $CH_2CH_2$.

5. The compound of claim 1, wherein $C^1$ is phenyl, optionally substituted with from 1 to 3 $R^4$ substituents.

6. The compound of claim 1, wherein $C^2$ is a monocyclic five-membered heteroaromatic ring selected from the group consisting of thiazole, triazole, imidazole, pyrazole and oxazole, each of which is optionally substituted with from 1 to 3 $R^5$ substituents.

7. The compound of claim 1, wherein $C^2$ is selected from the group consisting of cyclobutane, cyclopentane, cyclohexane, cycloheptane, azetidine, pyrrolidine and piperidine, each of which is optionally substituted with from 1 to 3 $R^5$ substituents.

8. The compound of claim 7, wherein $C^2$ is selected from the group consisting of cyclopentane, cyclohexane, cycloheptane, pyrrolidine and piperidine, each of which is optionally substituted with from 1 to 3 $R^5$ substituents.

9. The compound of claim 1, wherein $C^2$ is selected from the group consisting of benzene and pyridine, each of which is optionally substituted with from 1 to 3 $R^5$ substituents.

10. The compound of claim 1, wherein $C^3$ is selected from the group consisting of $C_{1-8}$ alkyl and $C_{3-8}$ cycloalkyl, each of which is optionally substituted with from 1 to 3 $R^6$ substituents.

11. The compound of claim 1, wherein $C^3$ is selected from the group consisting of phenyl and phenyl-$C_{1-4}$ alkyl, each of which is optionally substituted with from 1 to 3 $R^6$ substituents.

12. The compound of claim 1, wherein $C^3$ is heteroaryl, which is optionally substituted with from 1 to 3 $R^6$ substituents.

13. The compound of claim 1, wherein $C^3$ is a four- to six-membered heterocycloalkyl, each of which is optionally substituted with from 1 to 3 $R^6$ substituents.

14. The compound of claim 1, wherein $C^1$ is quinolin-8-yl, which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-8}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

15. The compound of claim 1, wherein $C^1$ is quinolin-8-yl, which is optionally substituted with from 1 to 3 $R^4$ substituents; $C^2$ is selected from the group consisting of pyrrolidine, thiazole, pyrazole and benzene, each of which is optionally substituted with from 1 to 2 $R^5$ substituents; and $C^3$ is selected from the group consisting of $C_{3-8}$ alkyl, cyclohexyl, pyrrolidinyl, piperidinyl and phenyl, wherein each of said cyclohexyl, pyrrolidinyl, piperidinyl and phenyl groups are optionally substituted with from 1 to 2 $R^6$ substituents.

16. The compound of claim 1, wherein $C^1$ is phenyl, which is optionally substituted with from 1 to 3 $R^4$ substituents; $C^2$ is selected from the group consisting of pyrrolidine, piperidine, thiazole, pyrazole, oxazole and benzene, each of which is optionally substituted with from 1 to 2 $R^5$ substituents; and $C^3$ is selected from the group consisting of $C_{3-8}$ alkyl, cyclopropyl, cyclohexyl, pyrrolidinyl, piperidinyl, morpholinyl, tetrahydropyranyl and phenyl, wherein each of said cyclopropyl, cyclohexyl, pyrrolidinyl, piperidinyl, morpholinyl, tetrahydropyranyl and phenyl groups are optionally substituted with from 1 to 2 $R^6$ substituents.

17. The compound of claim 1, wherein $C^1$ is phenyl, which is optionally substituted with from 1 to 3 $R^4$ substituents; $C^2$ is selected from the group consisting of pyrrolidine, thiazole, pyrazole and benzene, each of which is optionally substituted with from 1 to 2 $R^5$ substituents; and $C^3$ is selected from the group consisting of $C_{3-8}$ alkyl, cyclohexyl, pyrrolidinyl, piperidinyl and phenyl, wherein each of said cyclohexyl, pyrrolidinyl, piperidinyl and phenyl groups are optionally substituted with from 1 to 2 $R^6$ substituents.

18. The compound of claim 1, selected from the group consisting of:

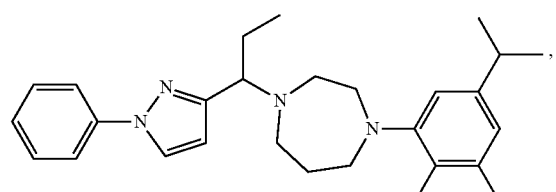

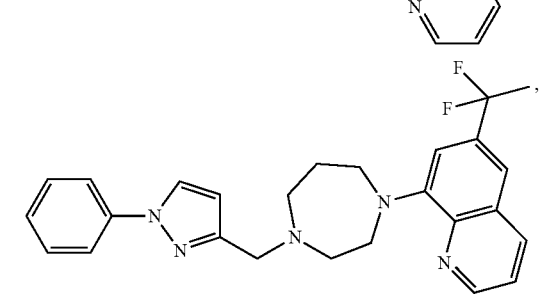

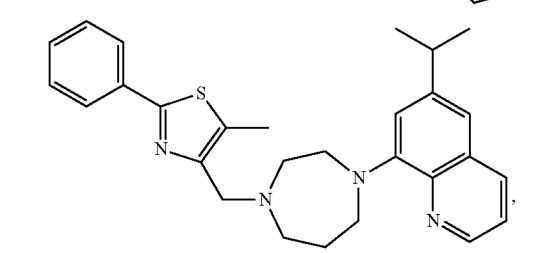

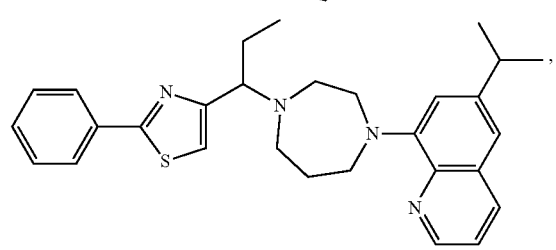

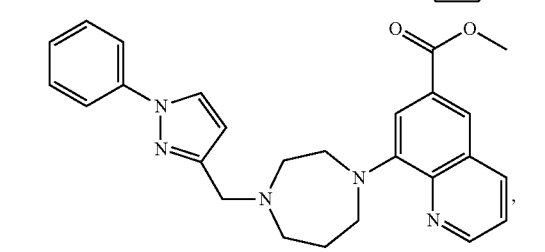

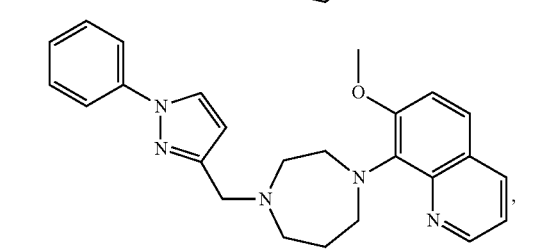

-continued

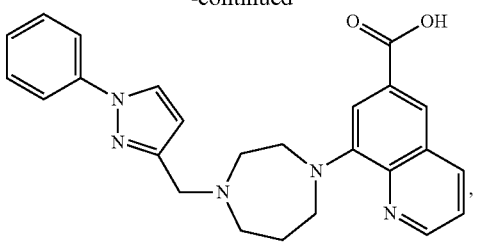

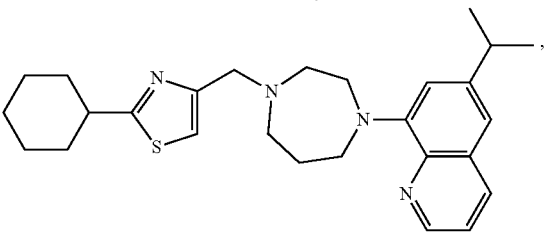

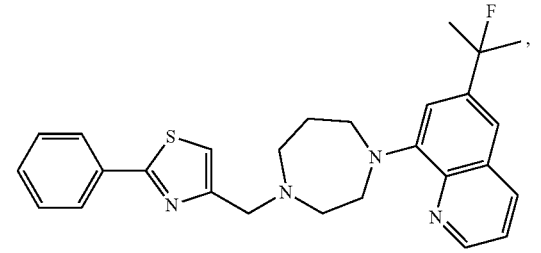

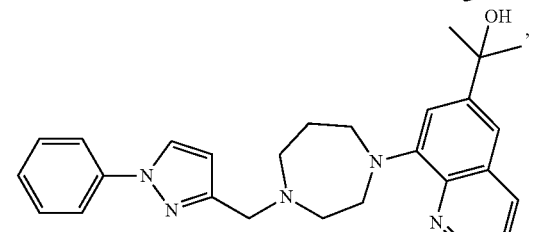

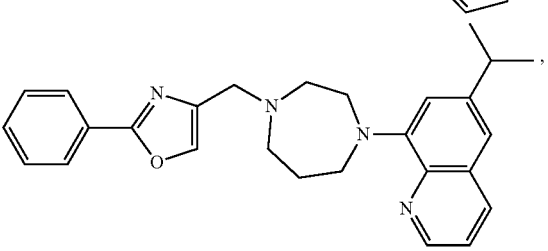

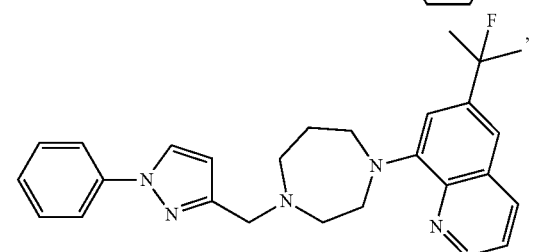

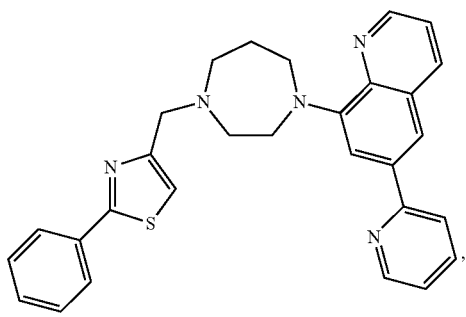
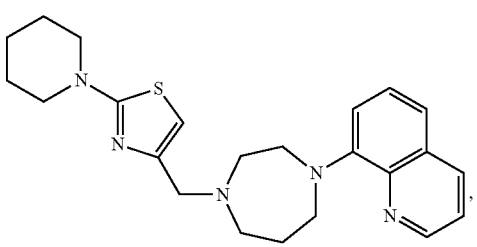
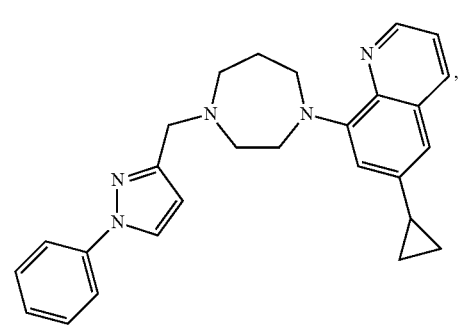
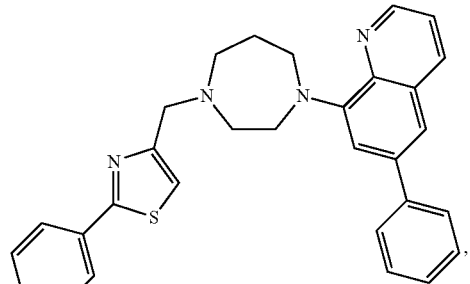
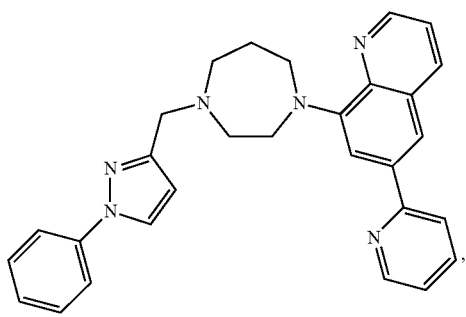
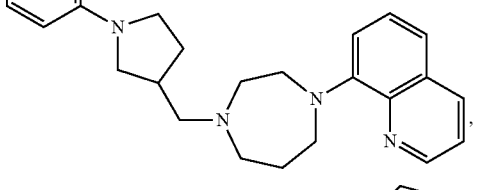
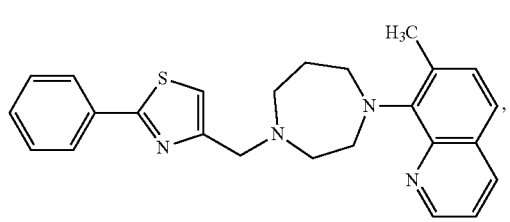
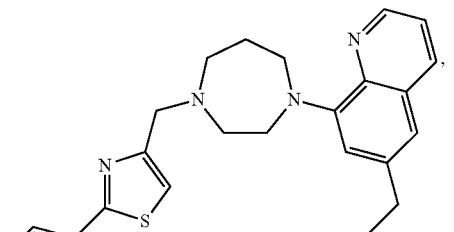
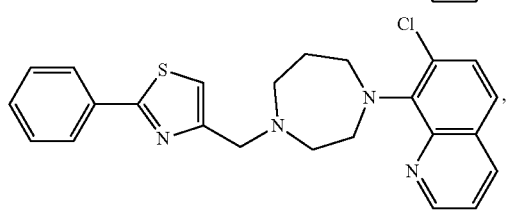
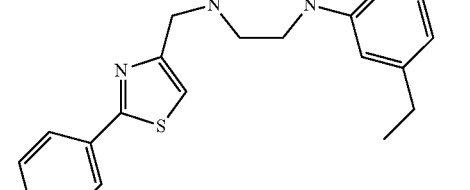
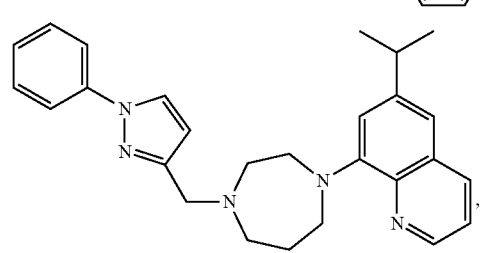
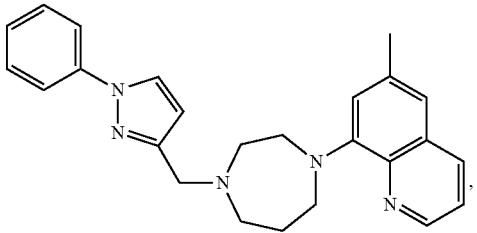

109
-continued
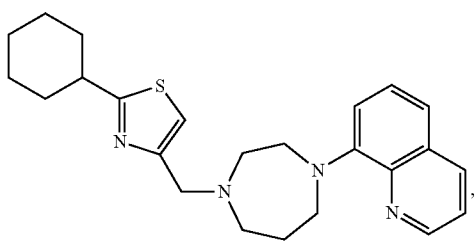
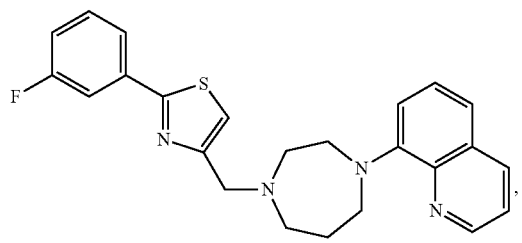
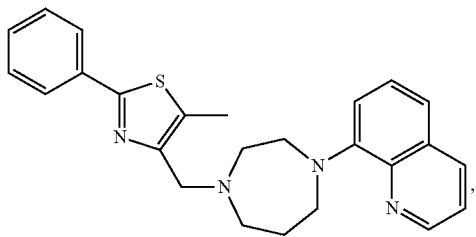
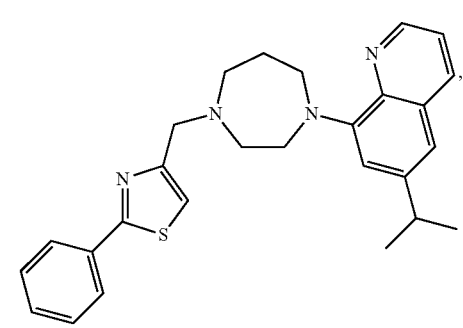
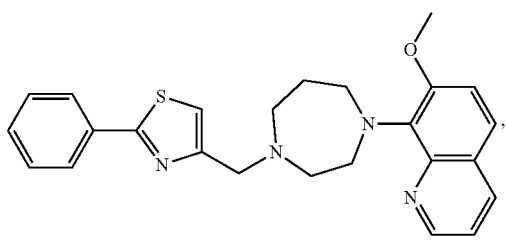
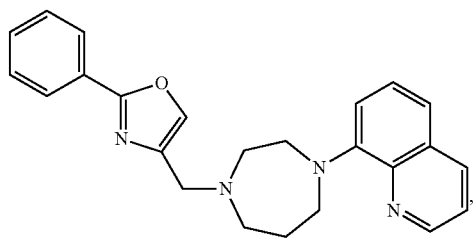
110
-continued
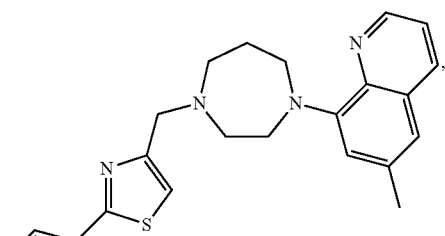
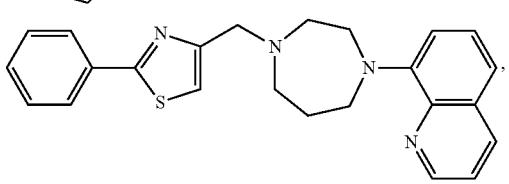
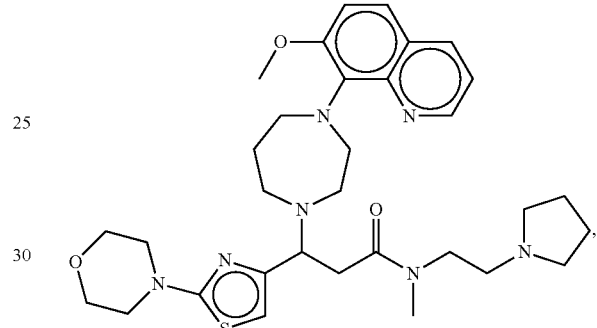
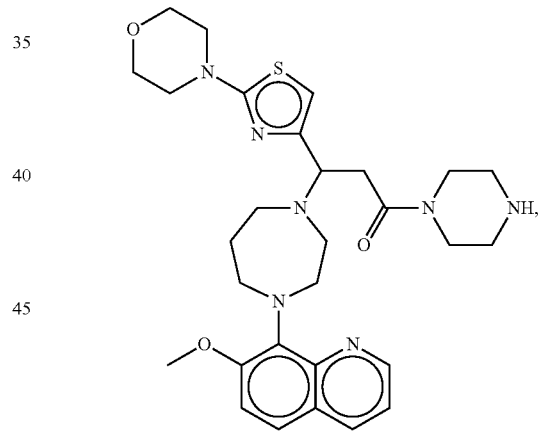
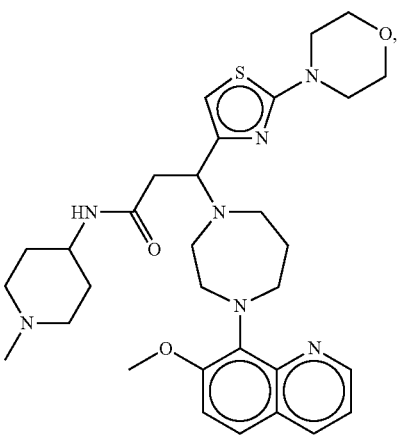

111
-continued
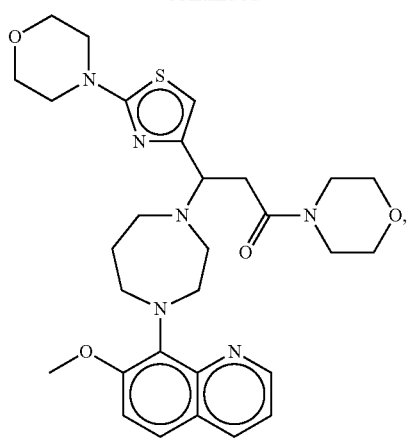
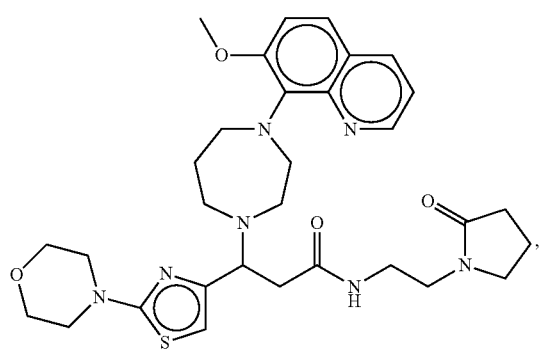
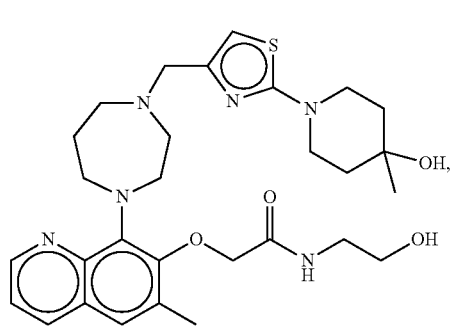
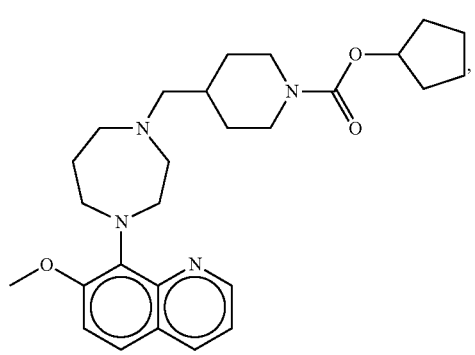
112
-continued
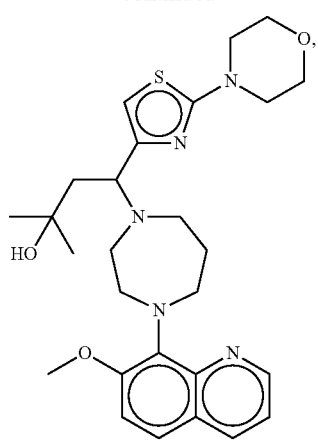
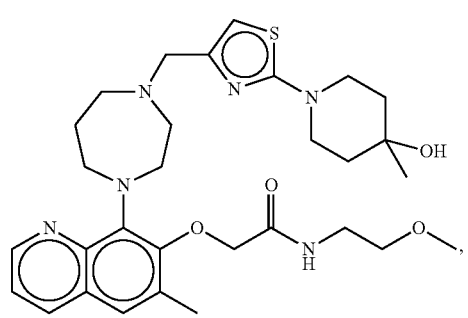
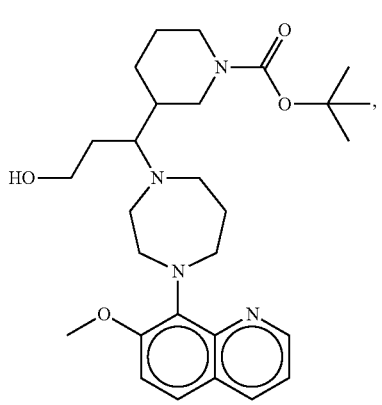
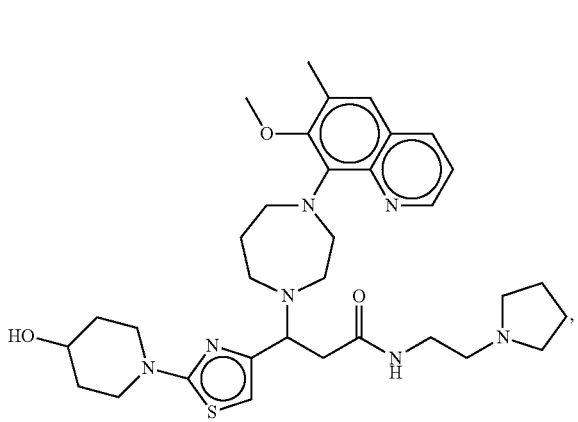

113
-continued
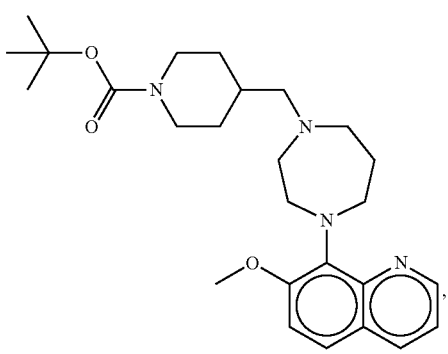
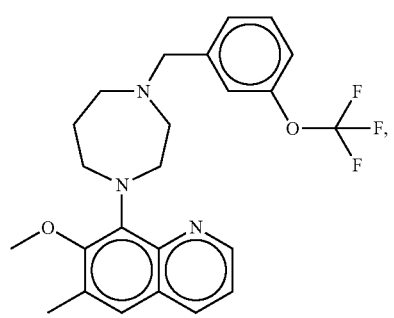
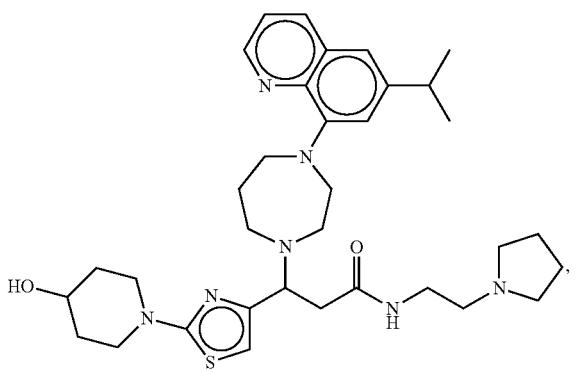
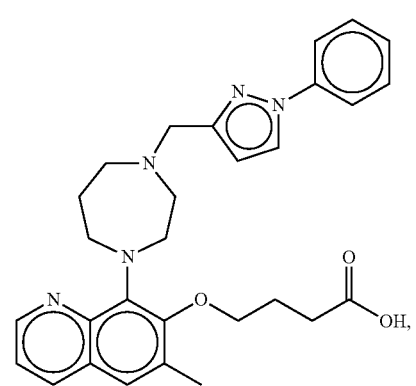
114
-continued
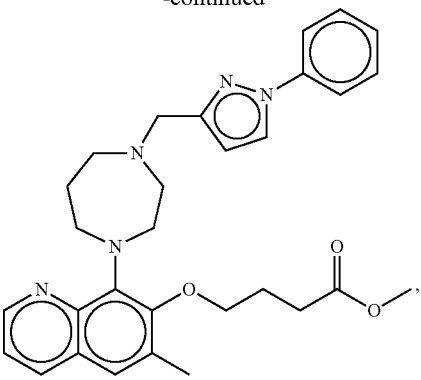
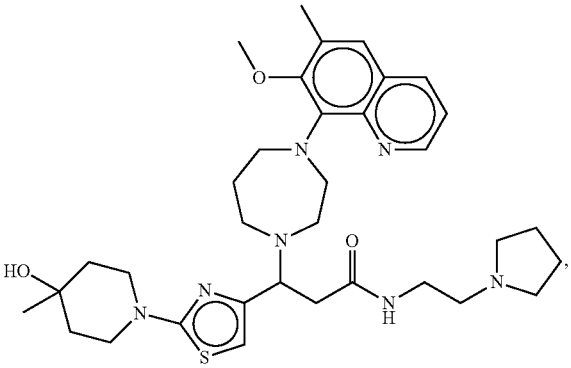
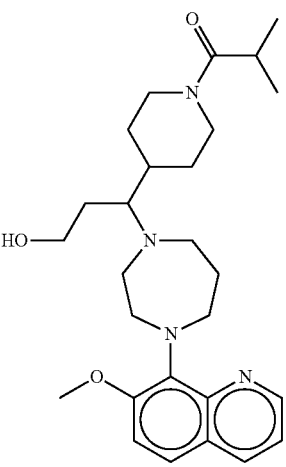
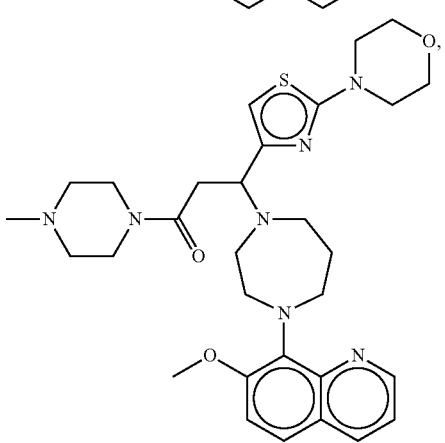

115
-continued
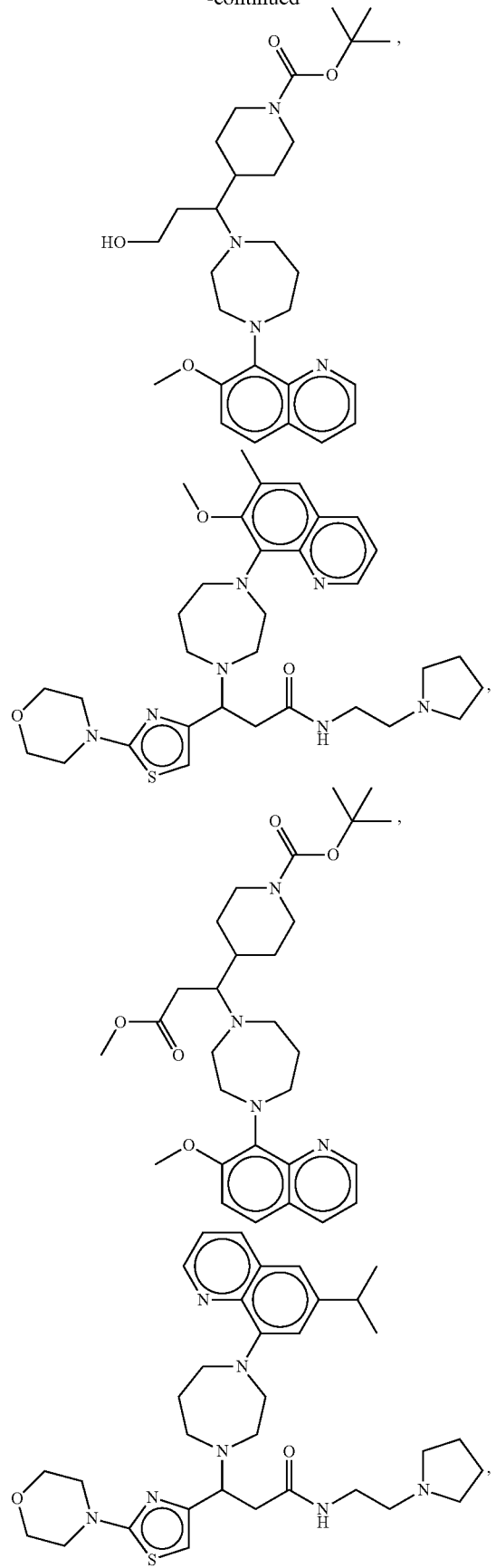
116
-continued
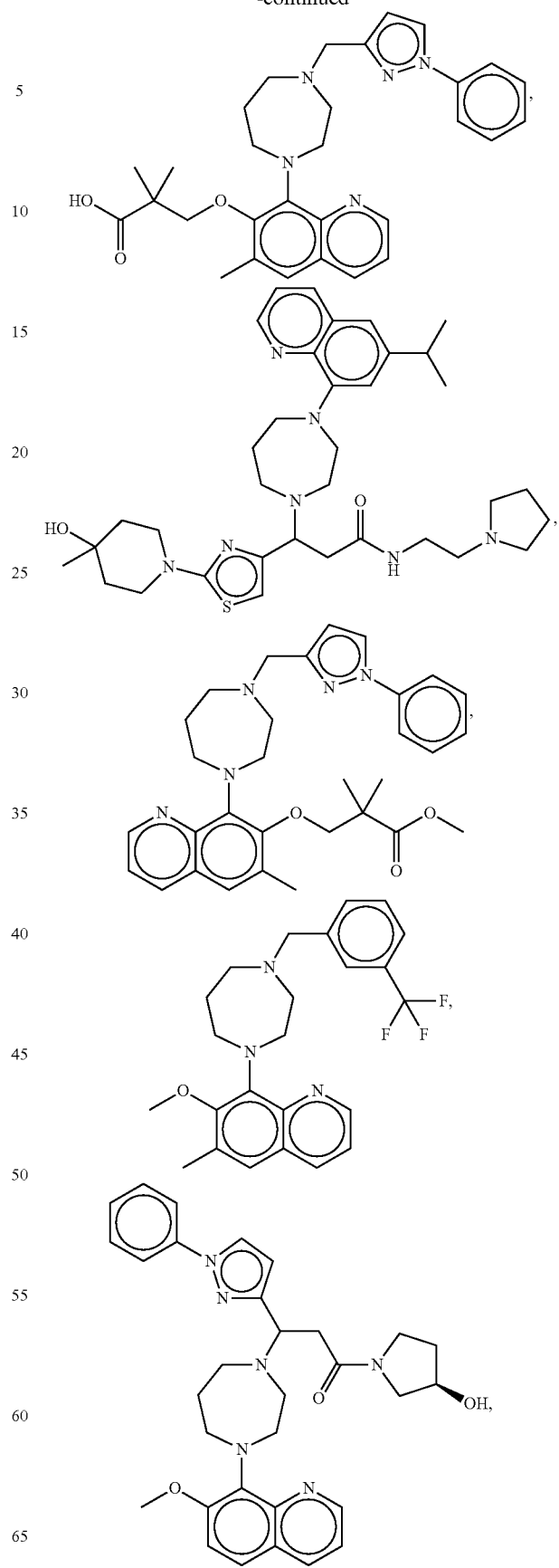

117
-continued
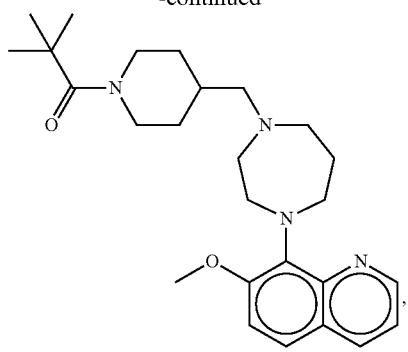
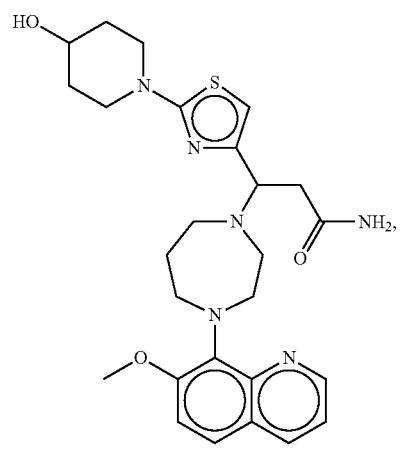
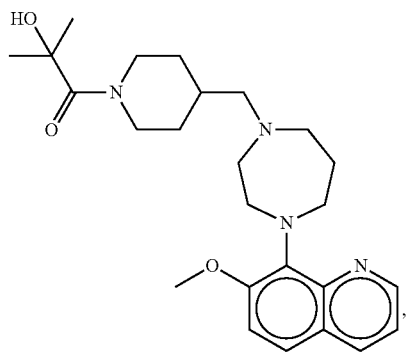
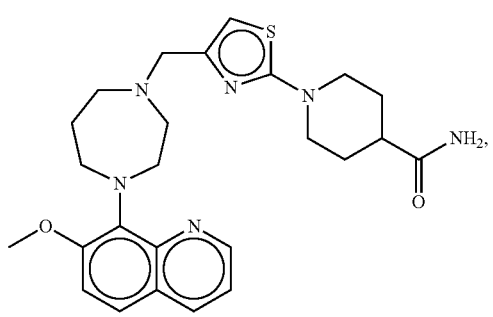
118
-continued
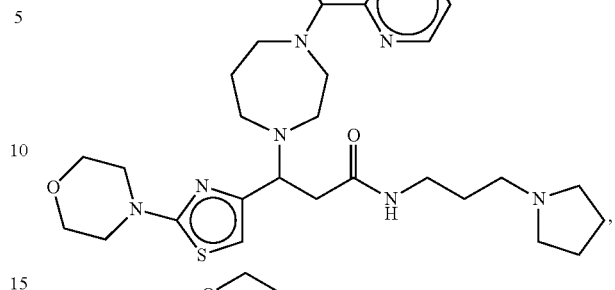
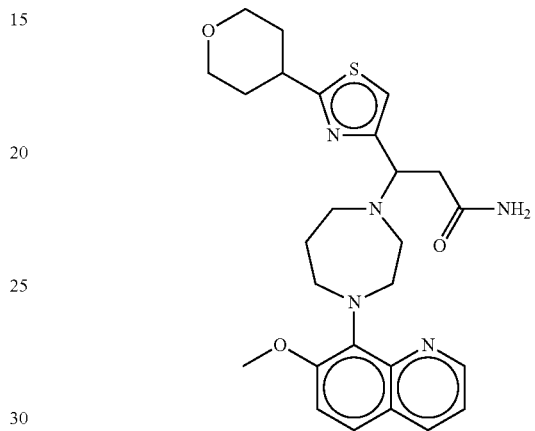
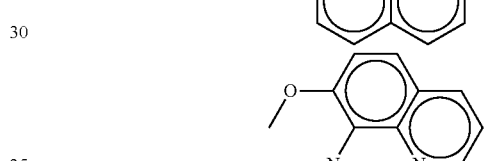
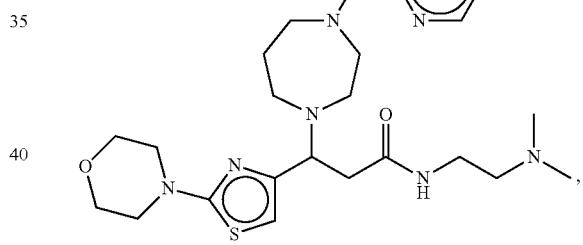
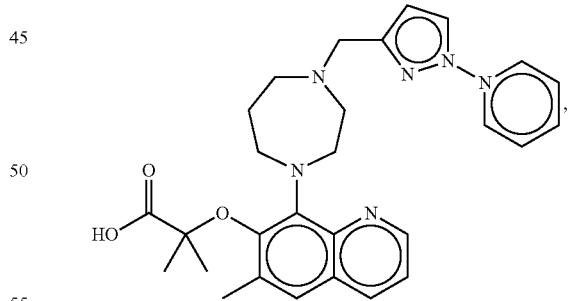
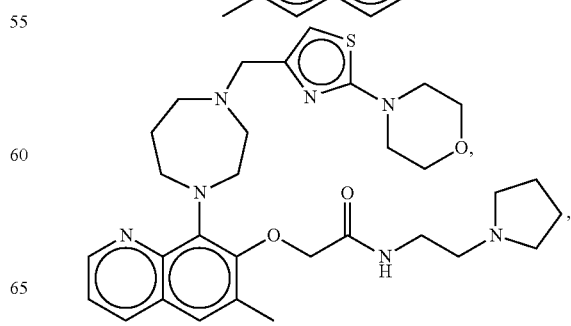

119
-continued
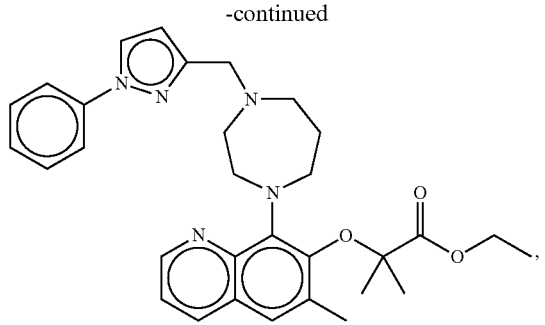
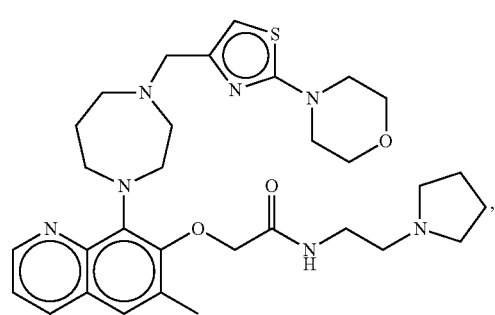
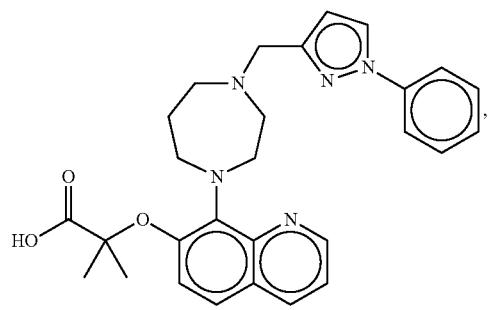
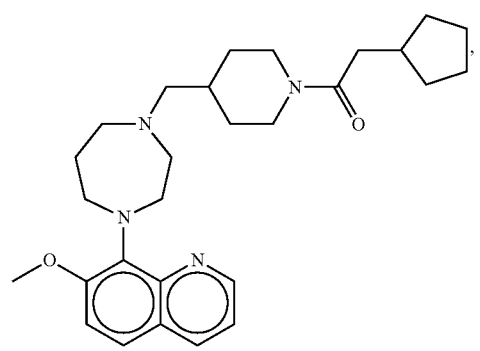
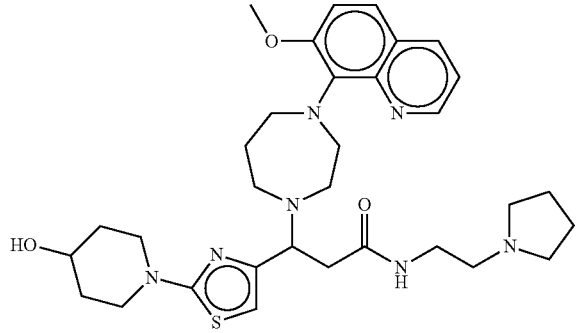
120
-continued
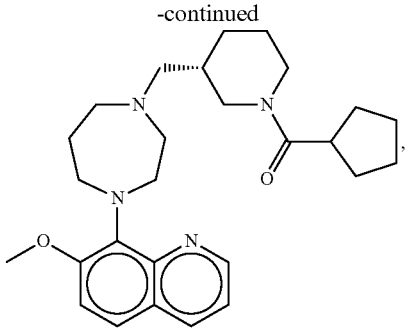
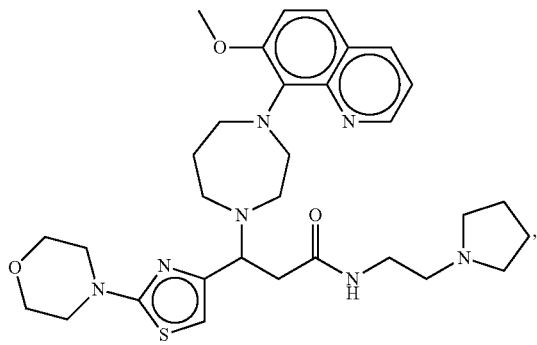
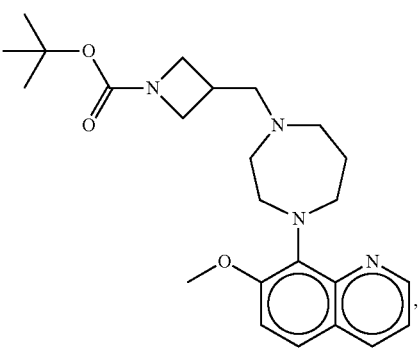
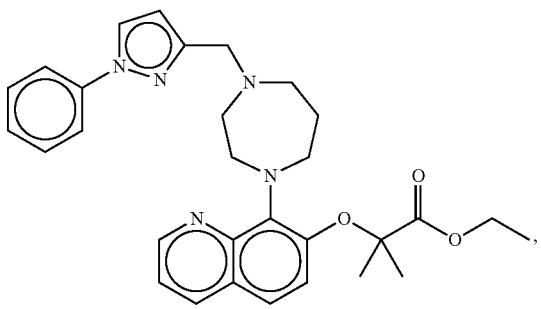
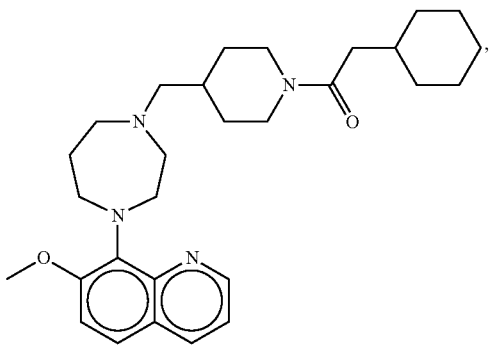

121
-continued
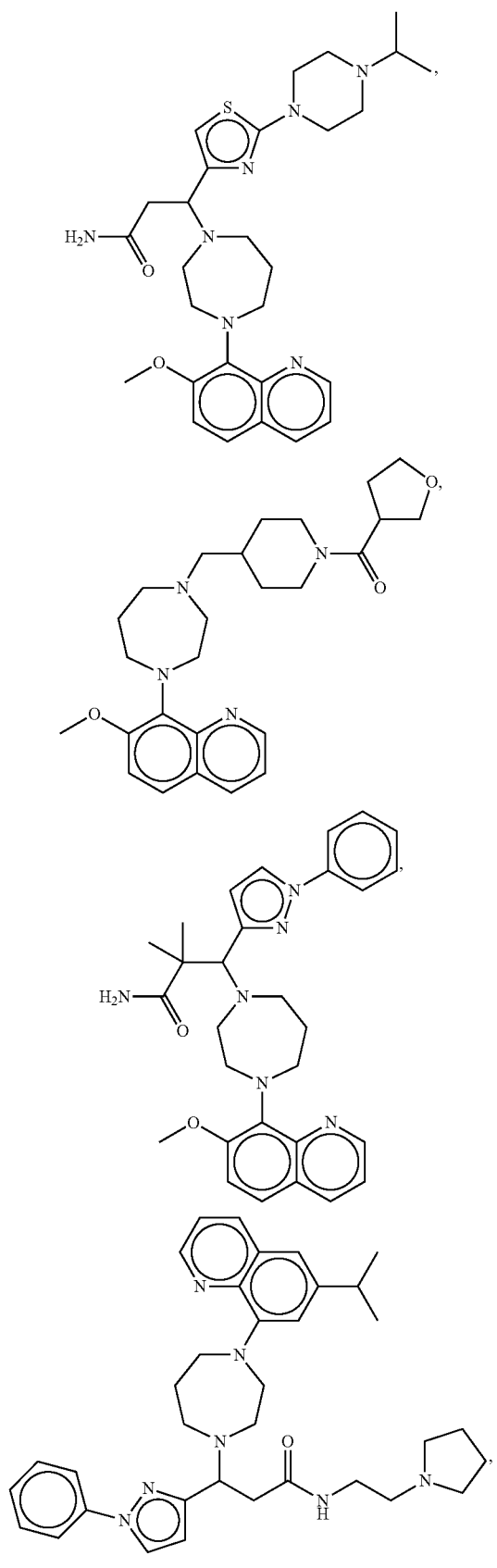
122
-continued
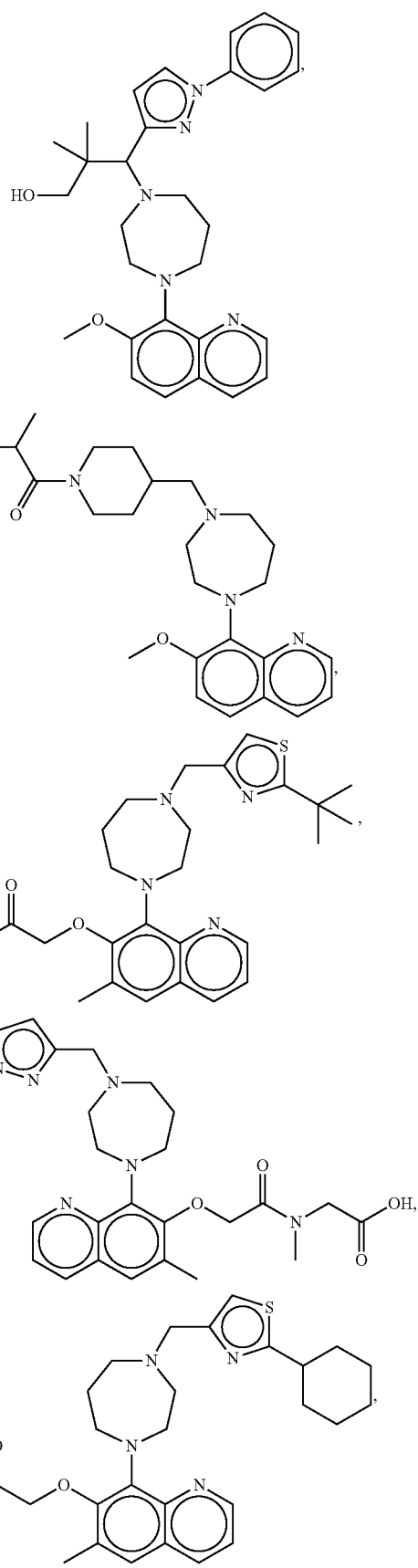

123
-continued
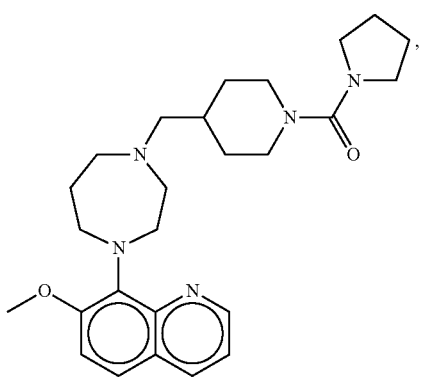
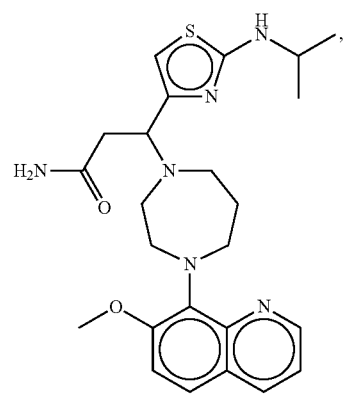
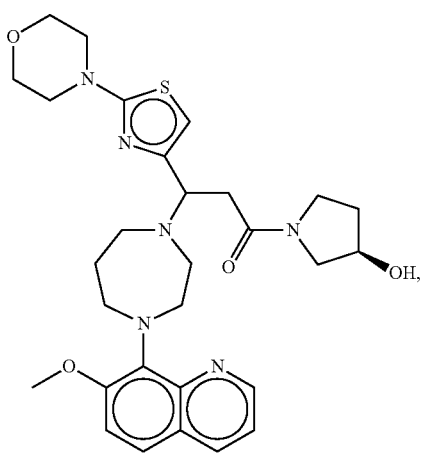
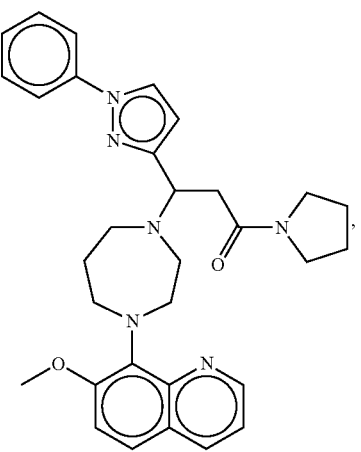
124
-continued
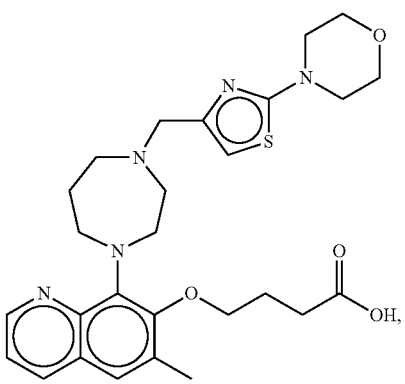
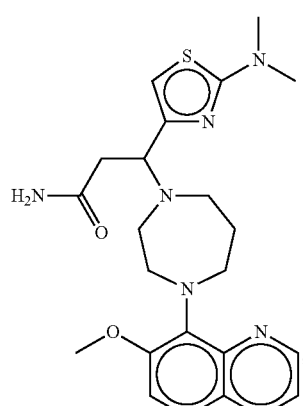
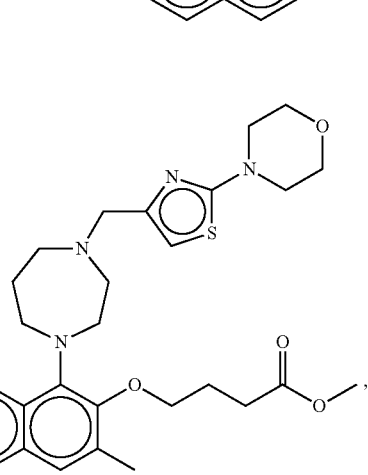
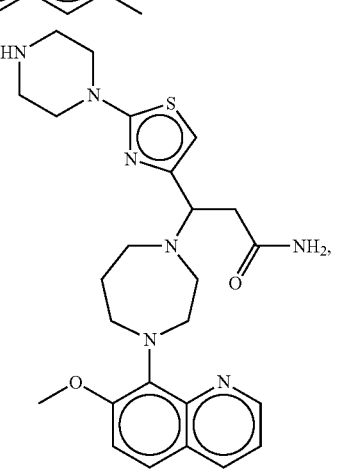

125
-continued
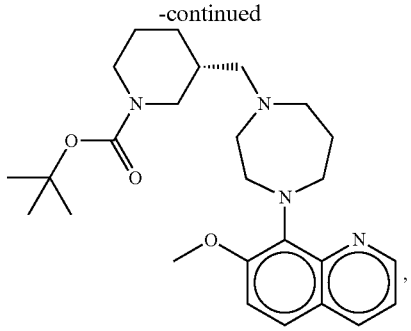
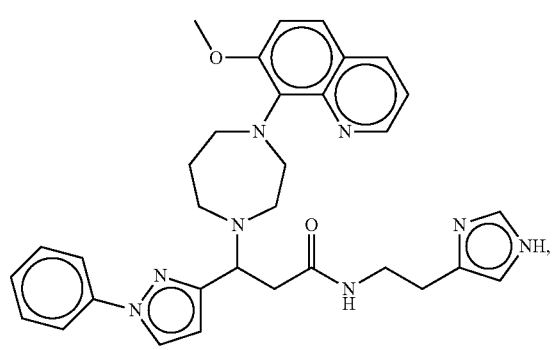
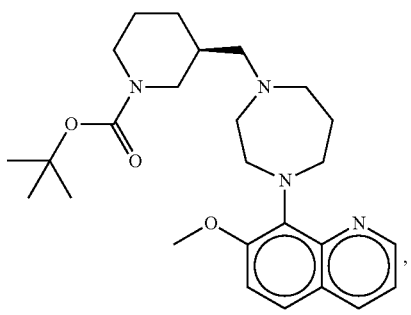
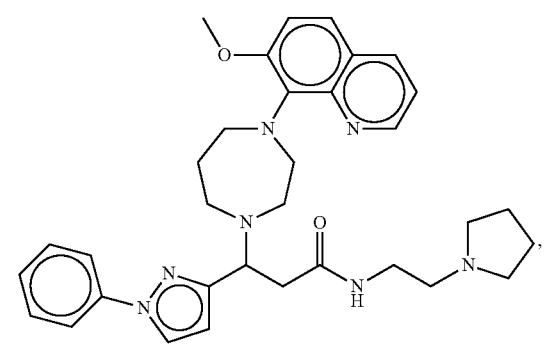
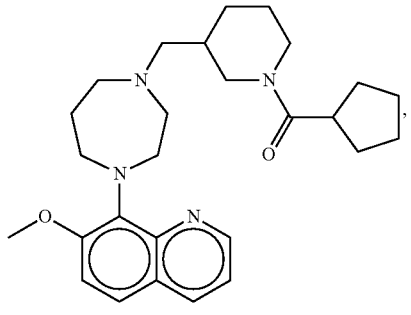
126
-continued
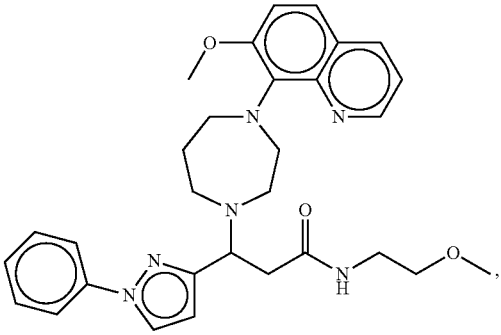
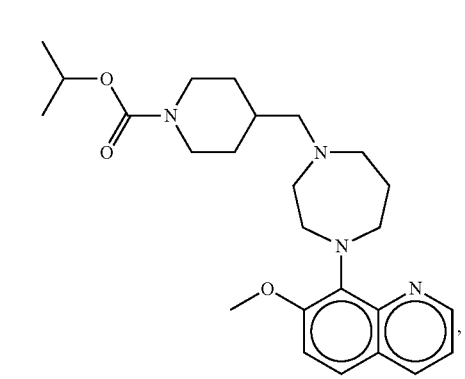
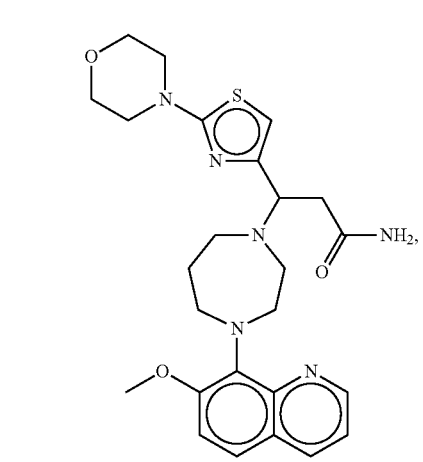
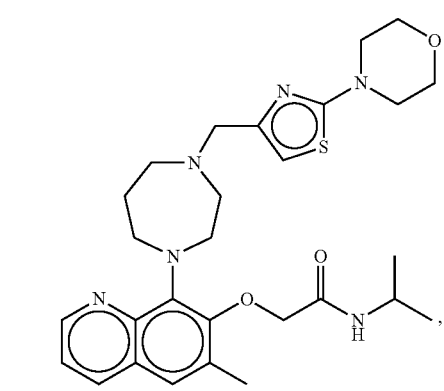

127
-continued
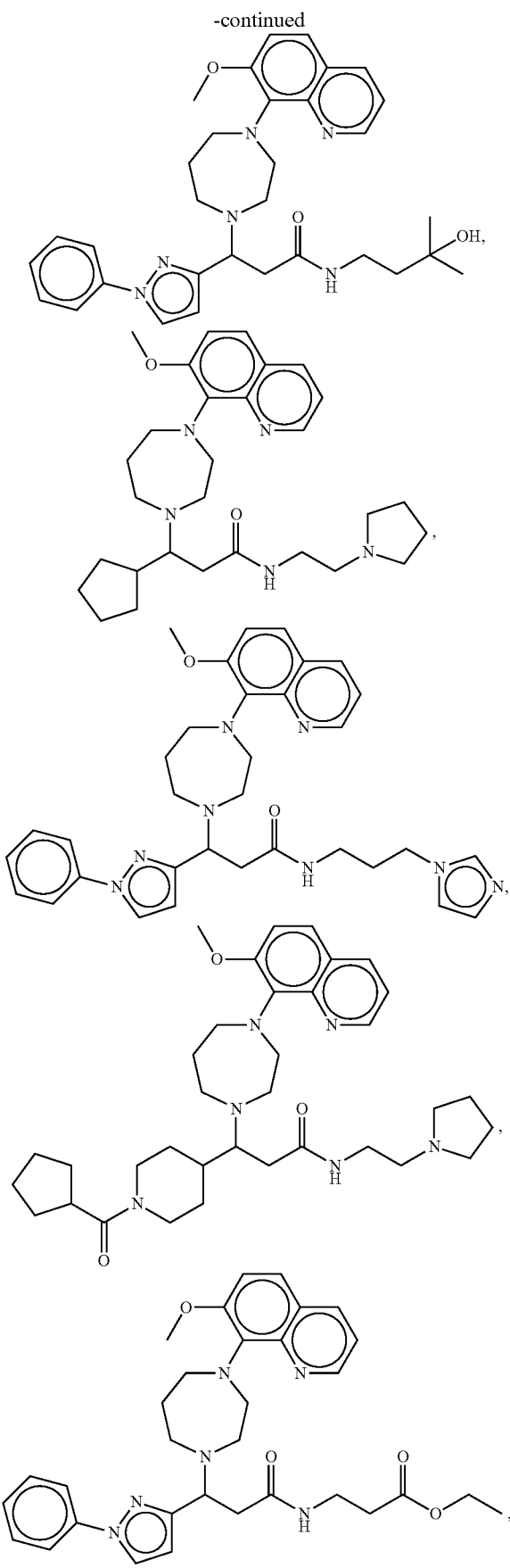
128
-continued
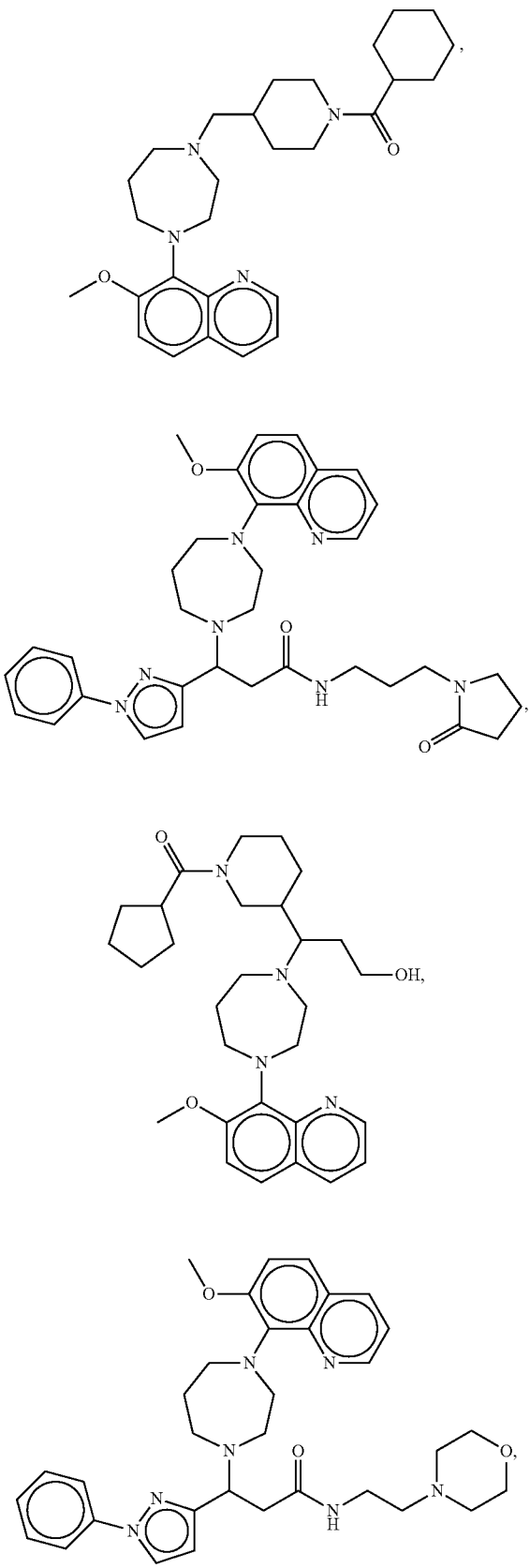

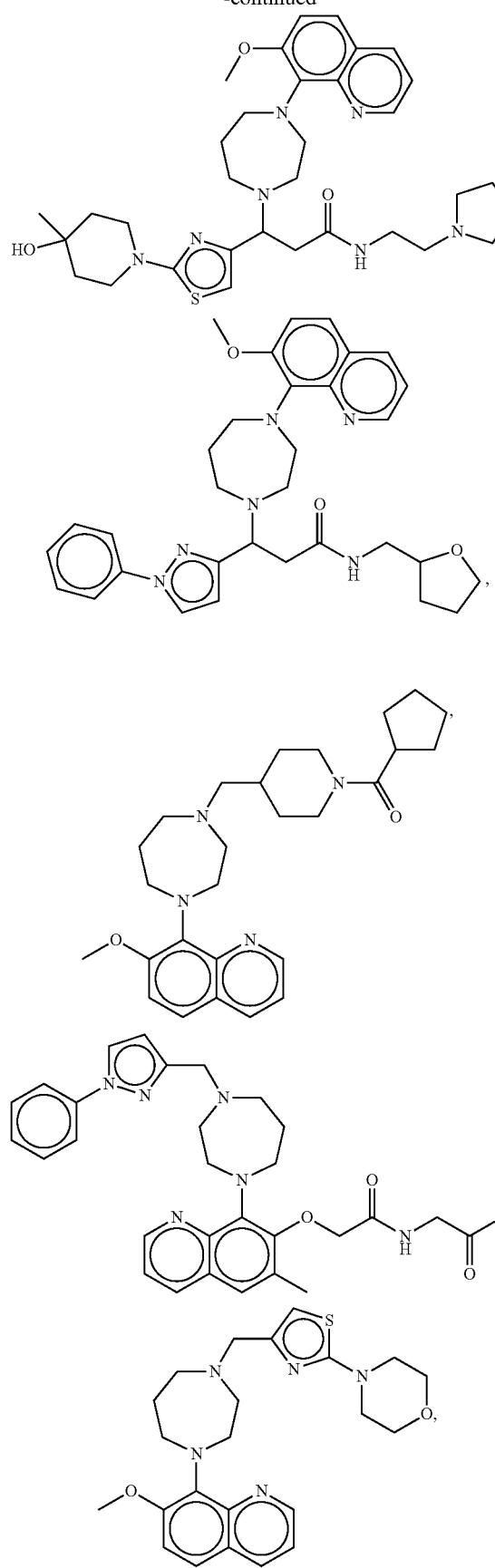
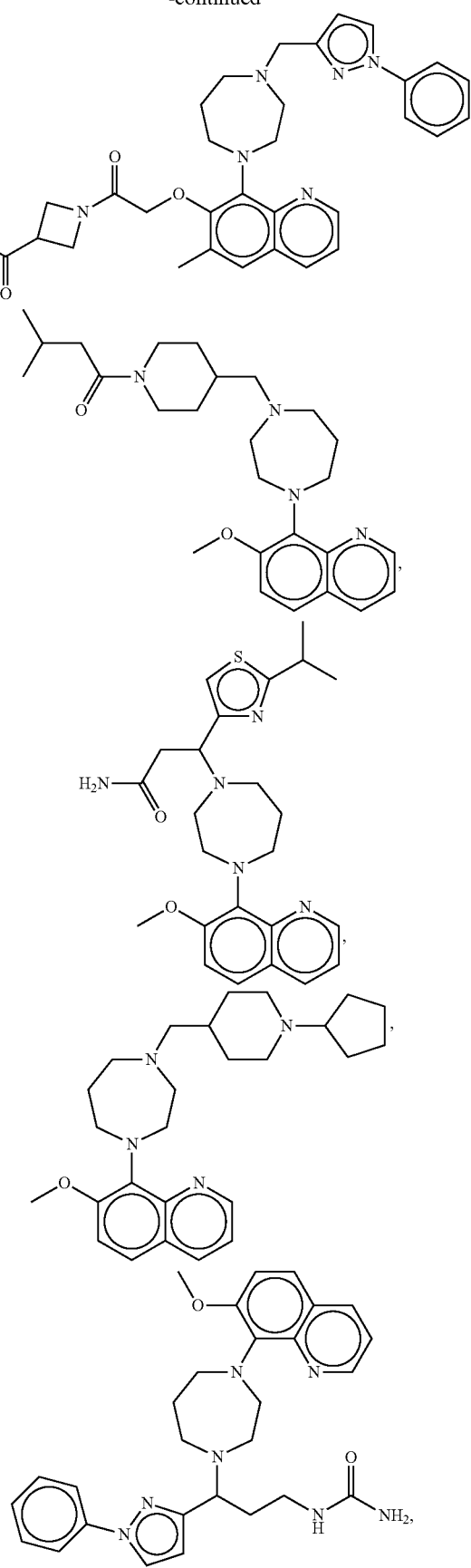

131
-continued
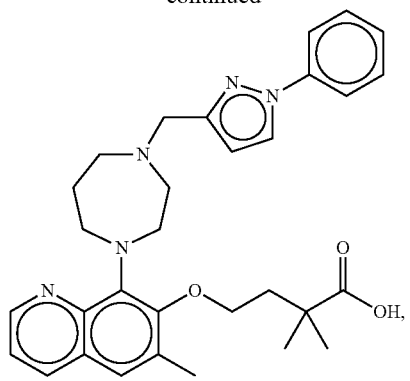
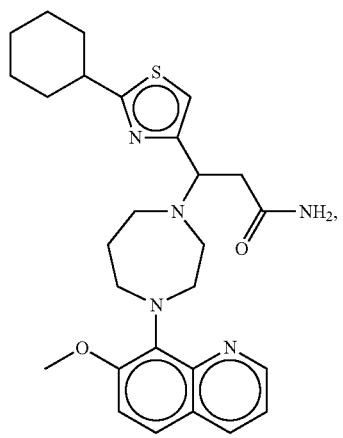
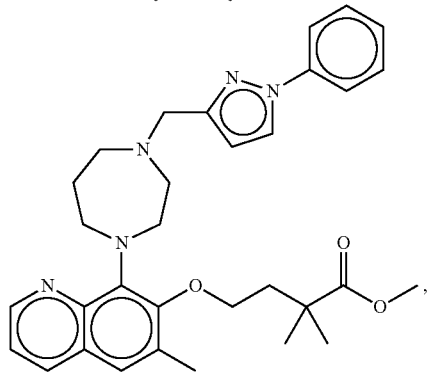
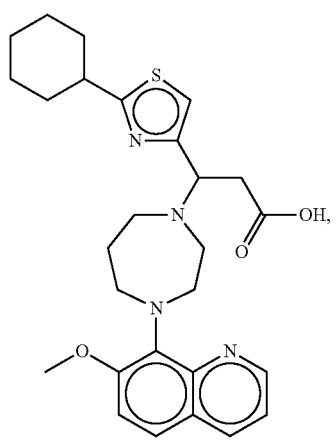
132
-continued
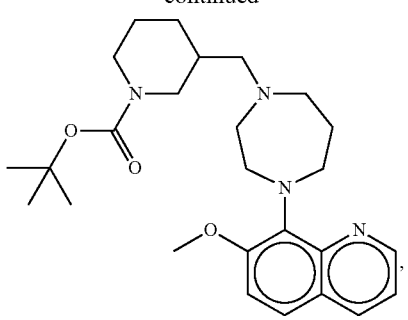
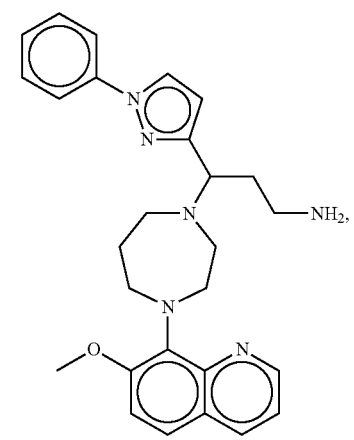
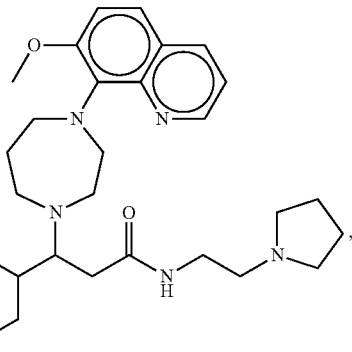
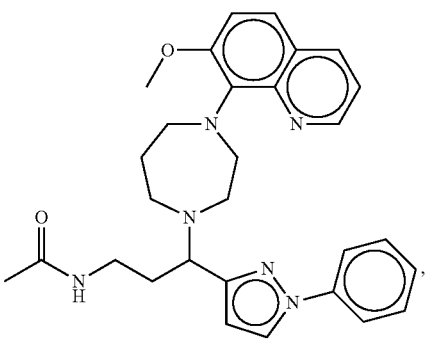

133
-continued
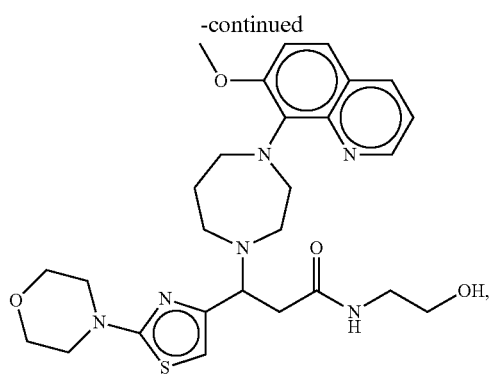
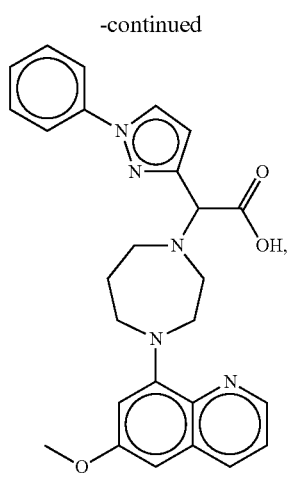
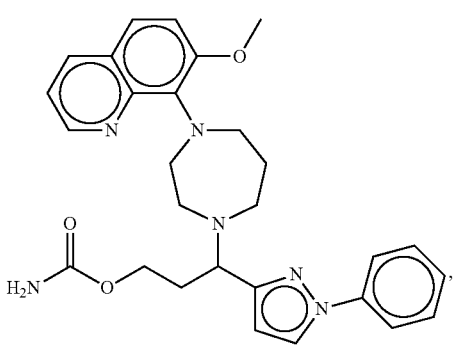
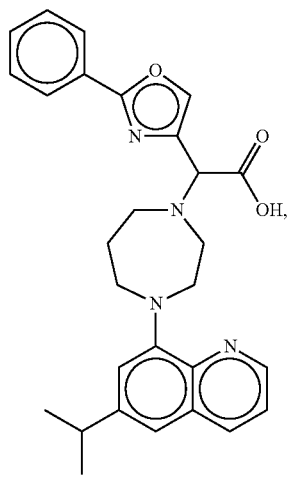
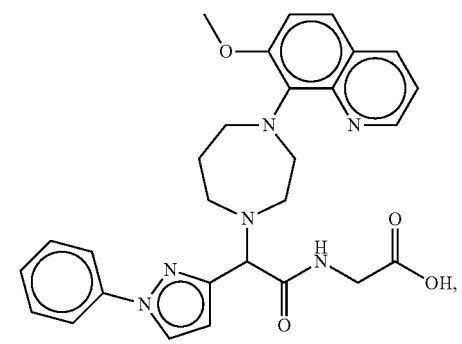
134
-continued
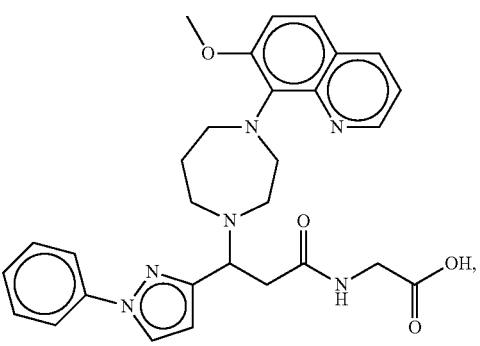

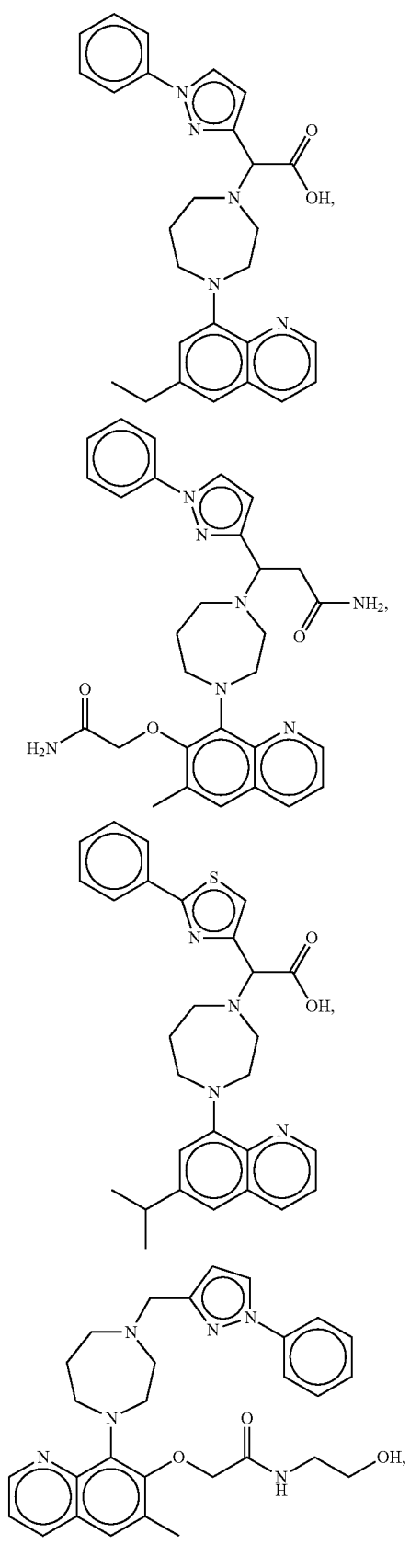
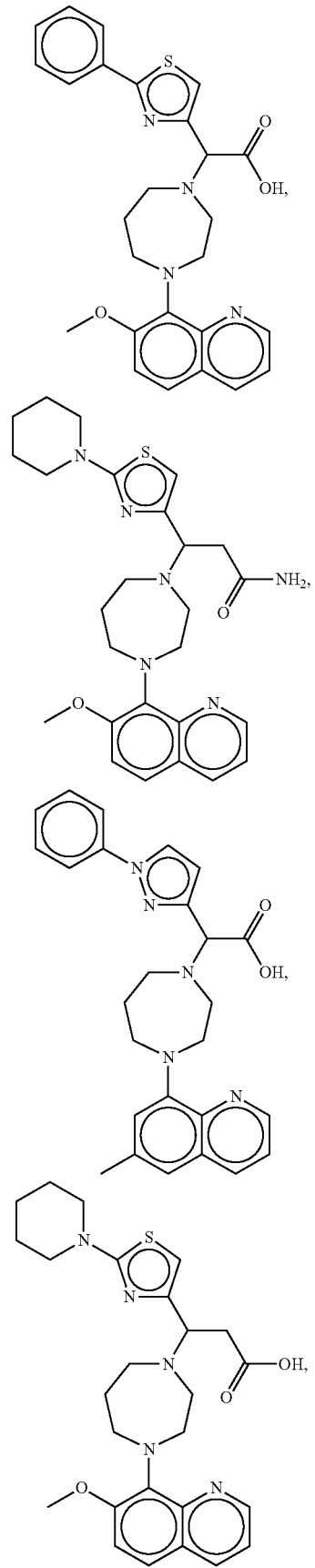

137
-continued
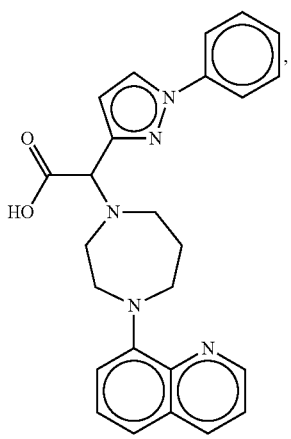
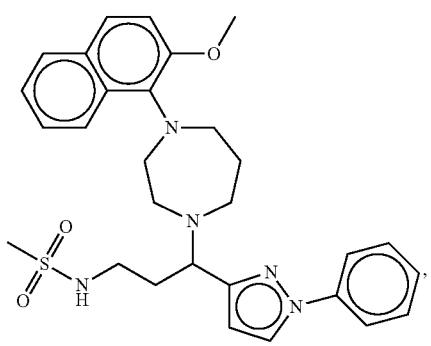
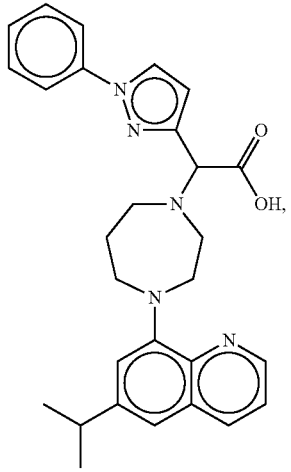
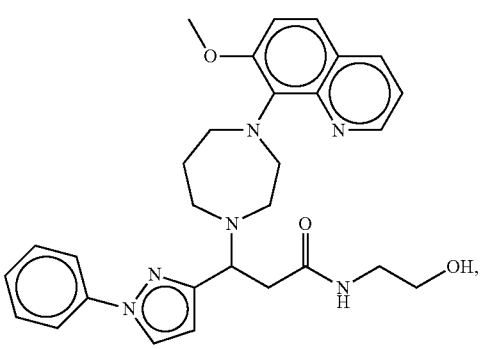
138
-continued
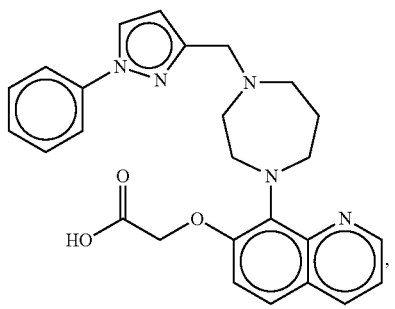
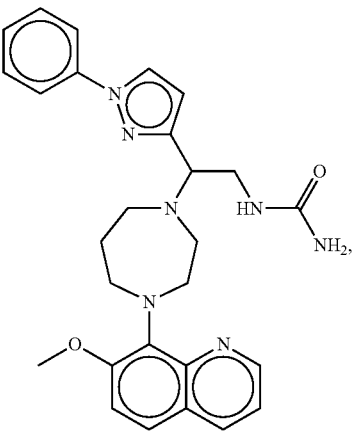
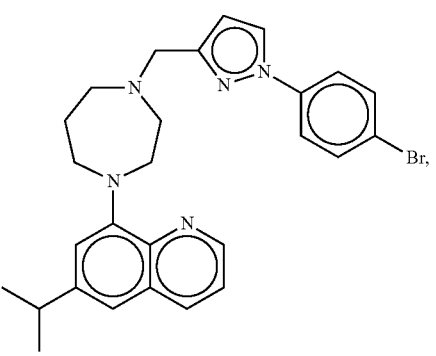
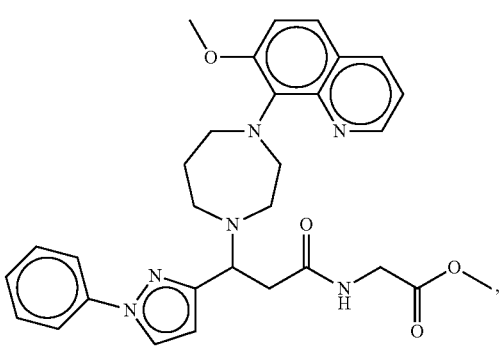

139
-continued
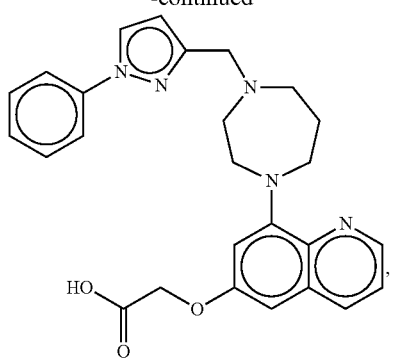
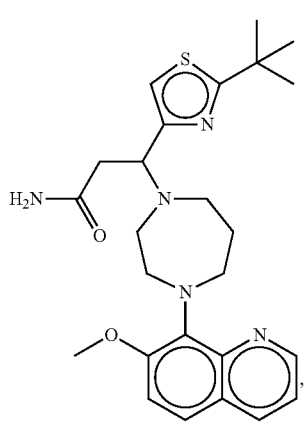
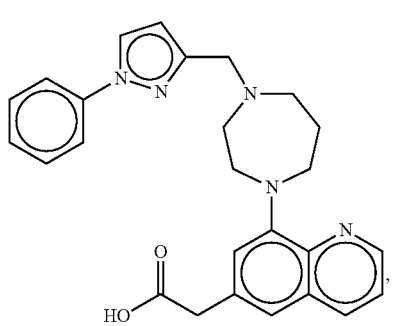
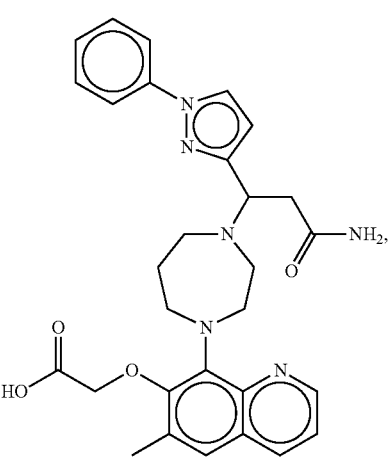
140
-continued
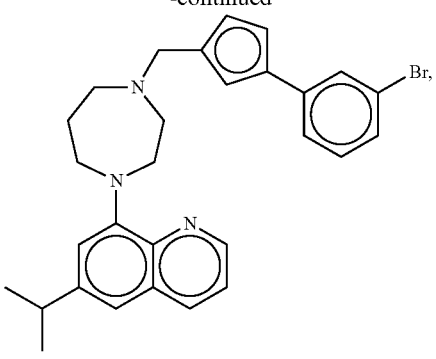
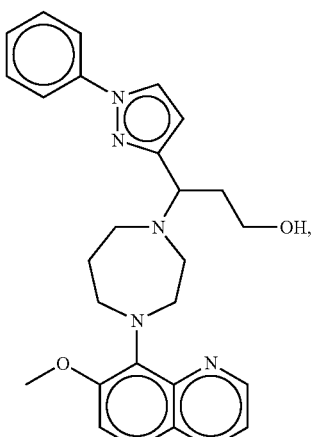
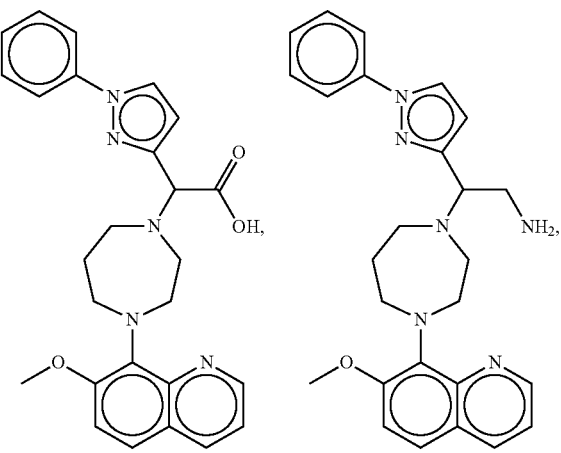
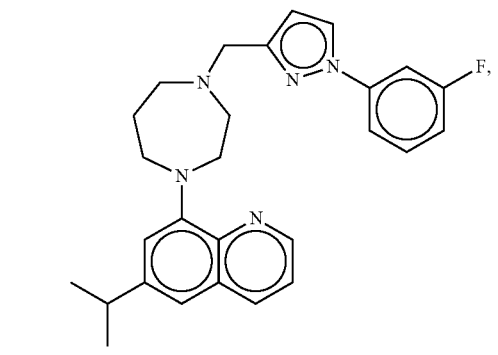

141
-continued
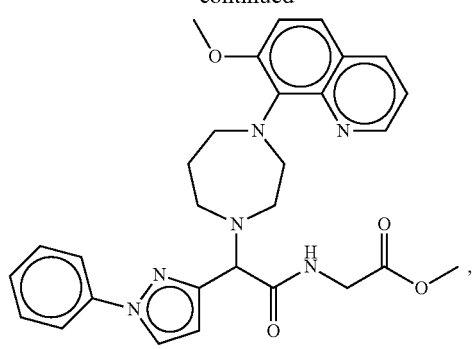,
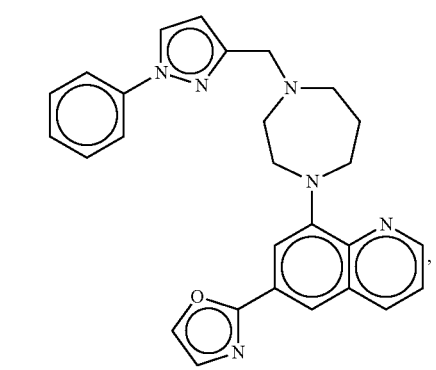,
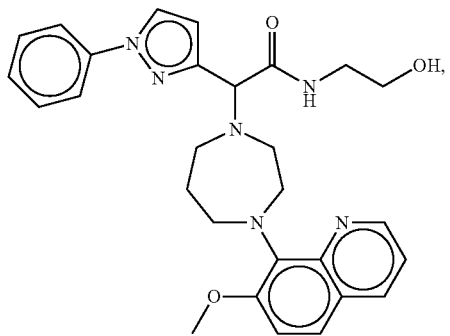,
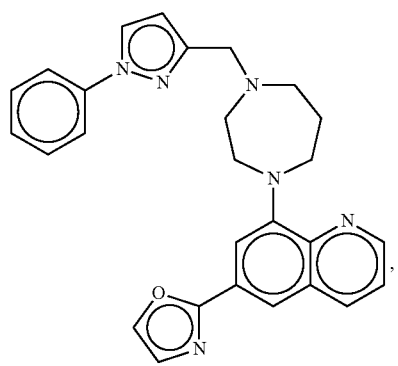,
142
-continued
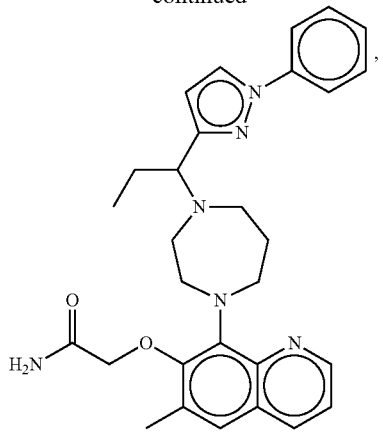,
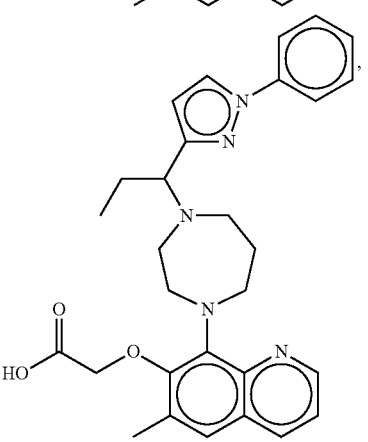,
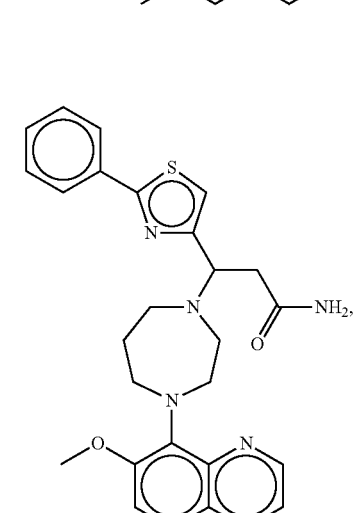,
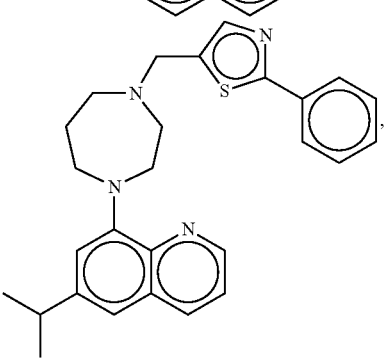, 143
-continued
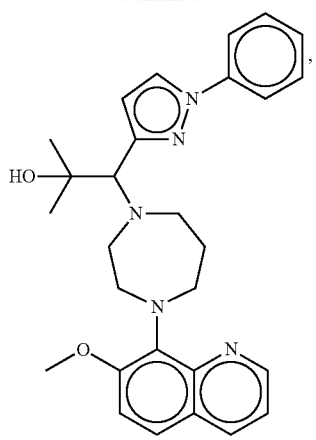
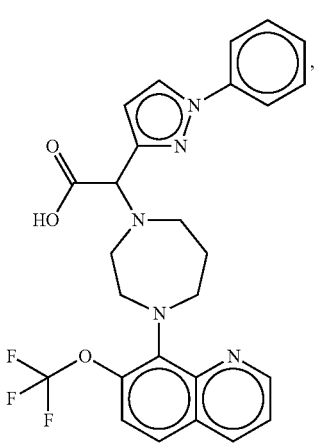
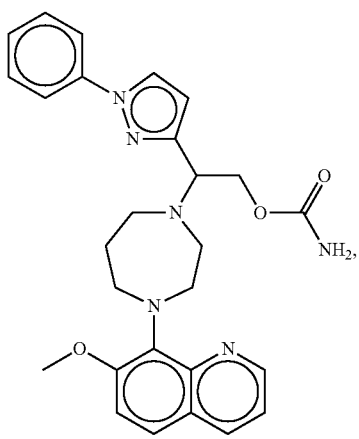
144
-continued
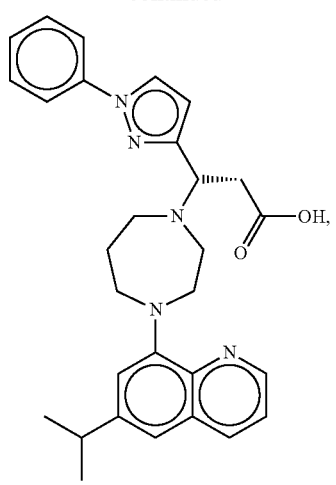
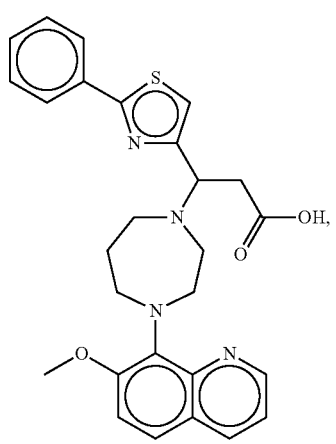
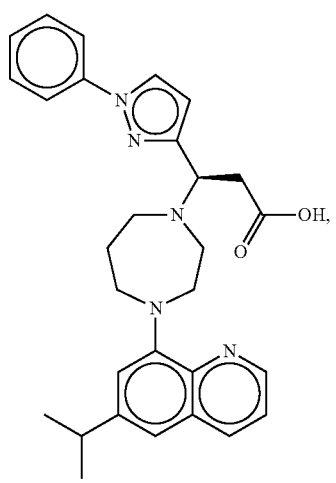

145
-continued
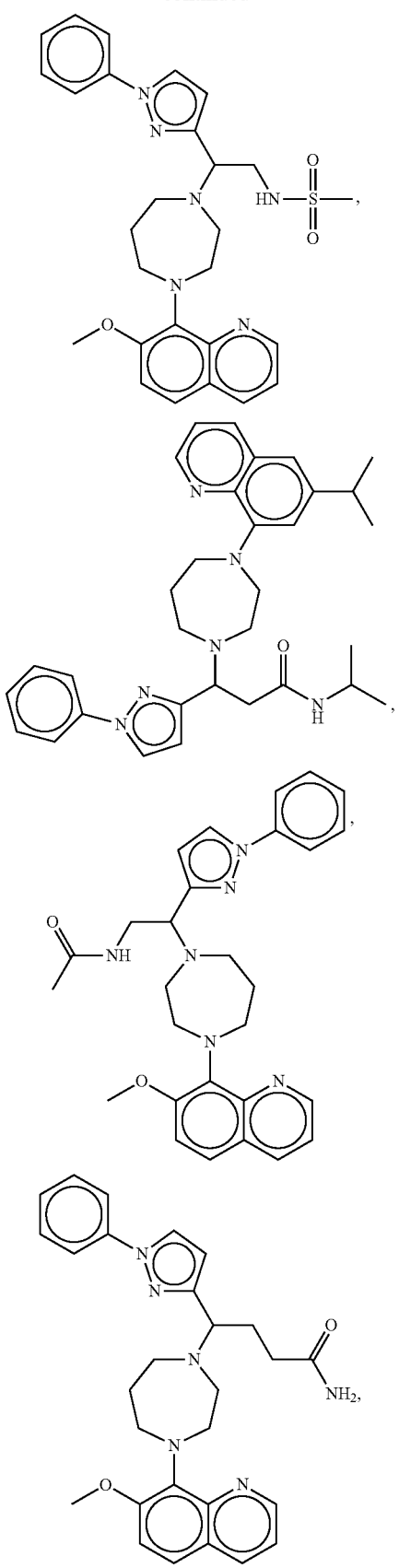
146
-continued
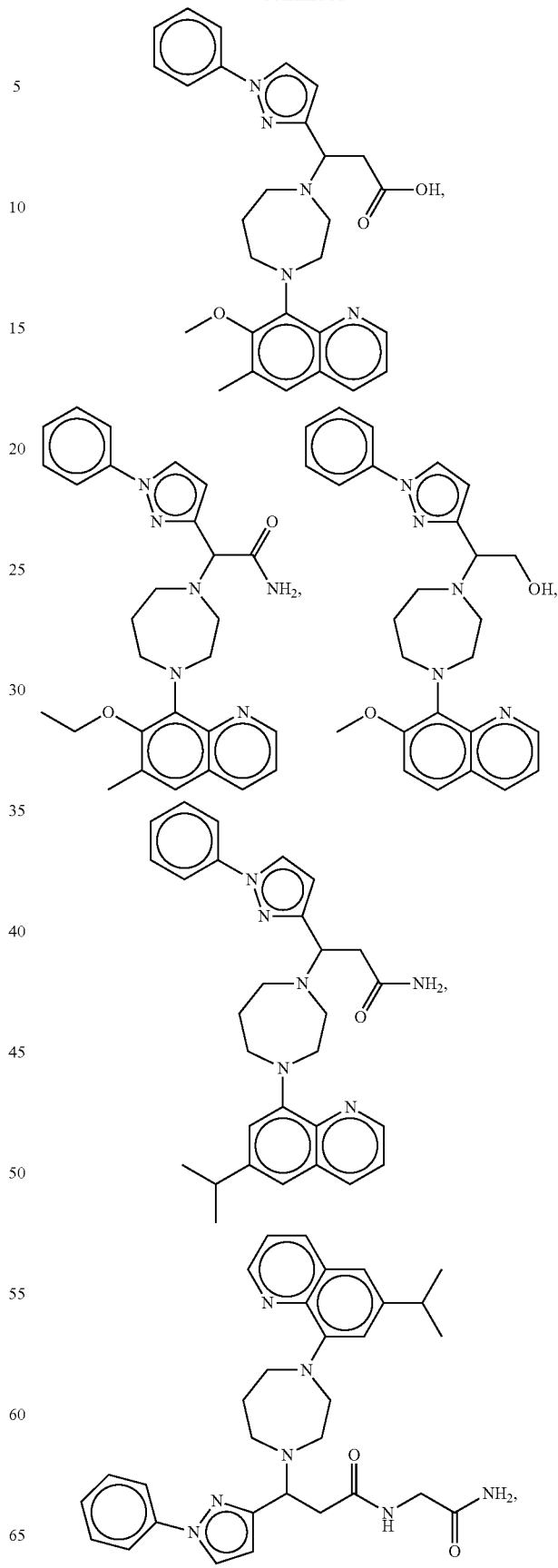

147
-continued
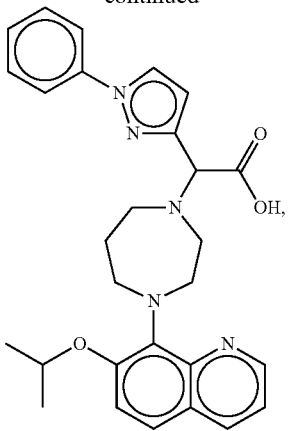
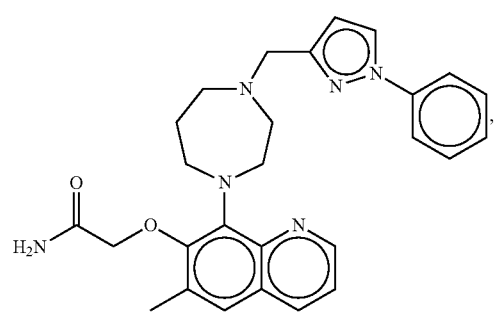
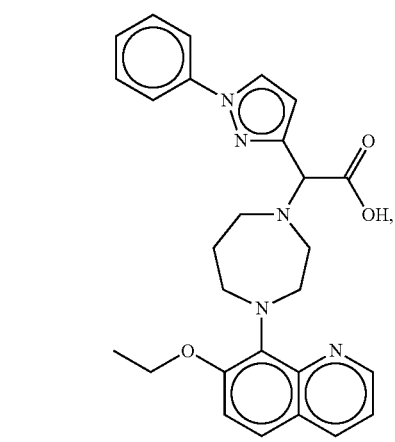
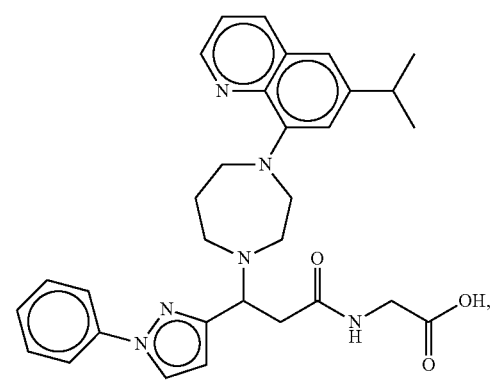
148
-continued
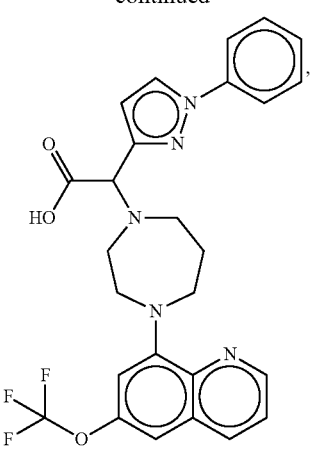
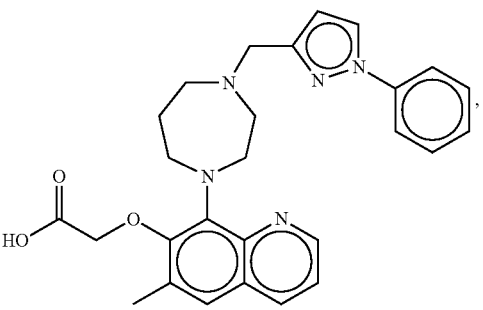
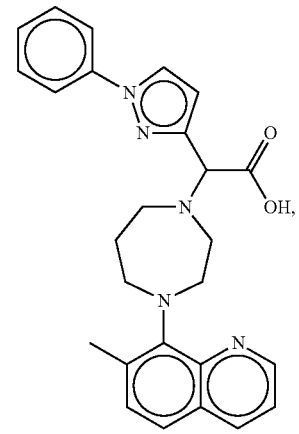
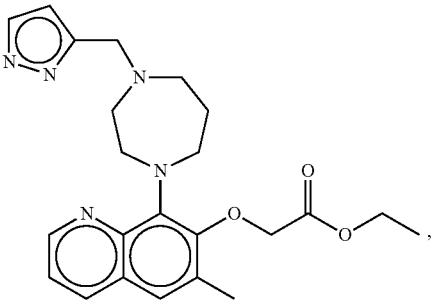

149
-continued
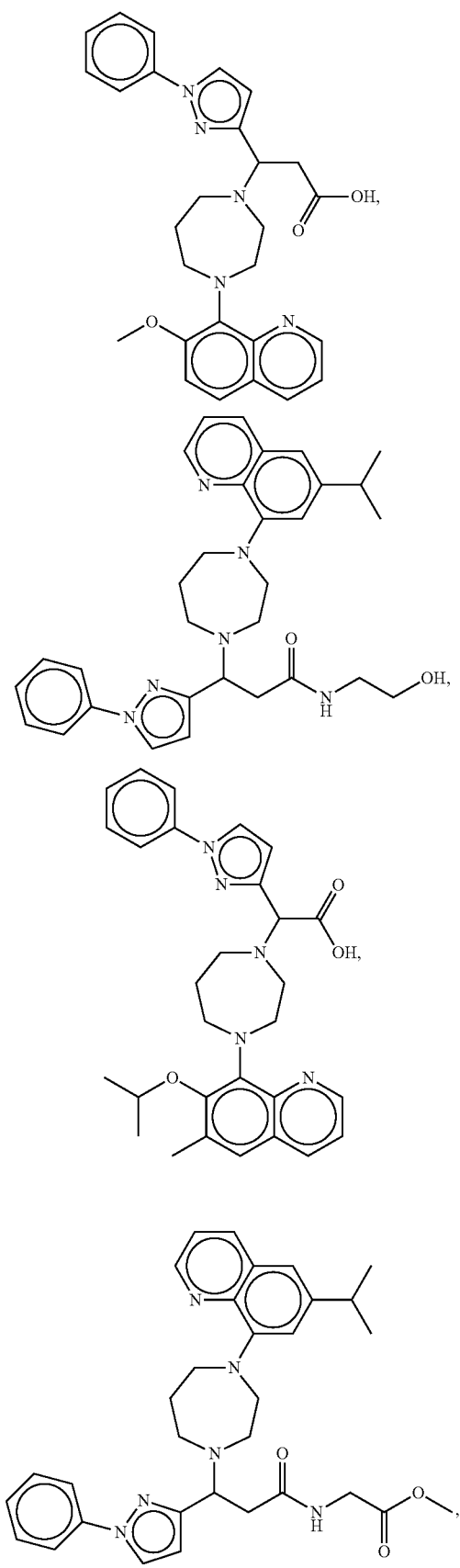
150
-continued
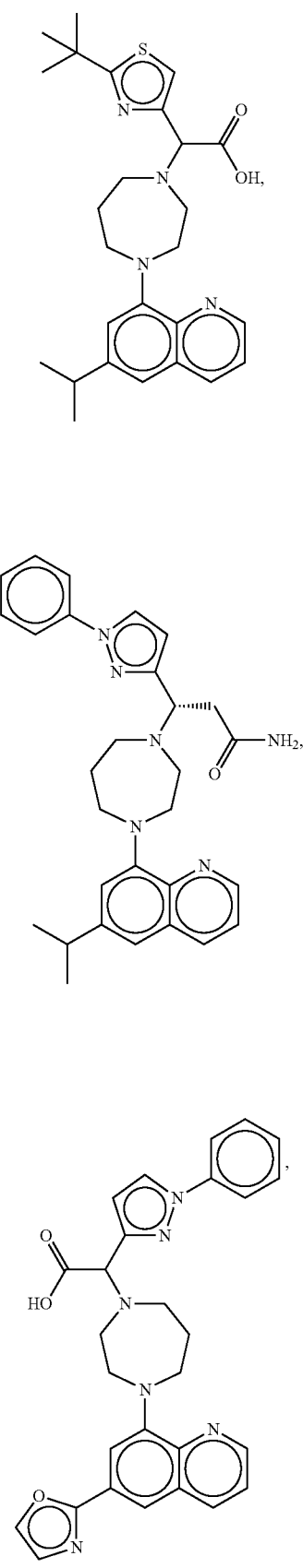

151
-continued
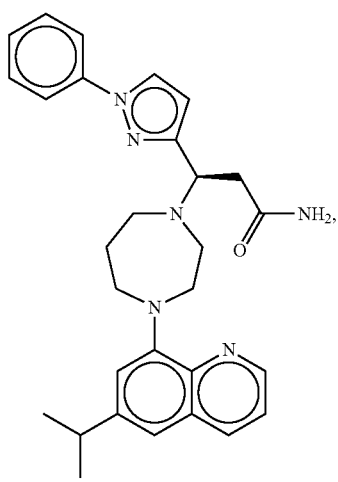
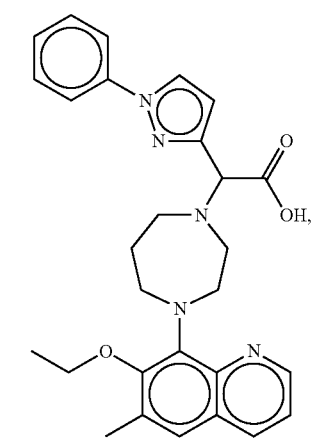
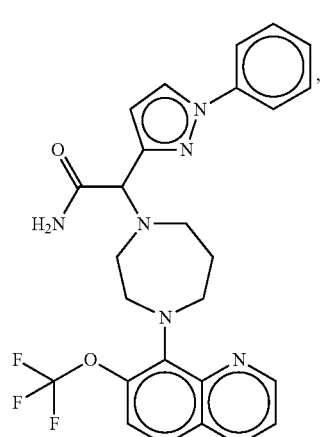
152
-continued
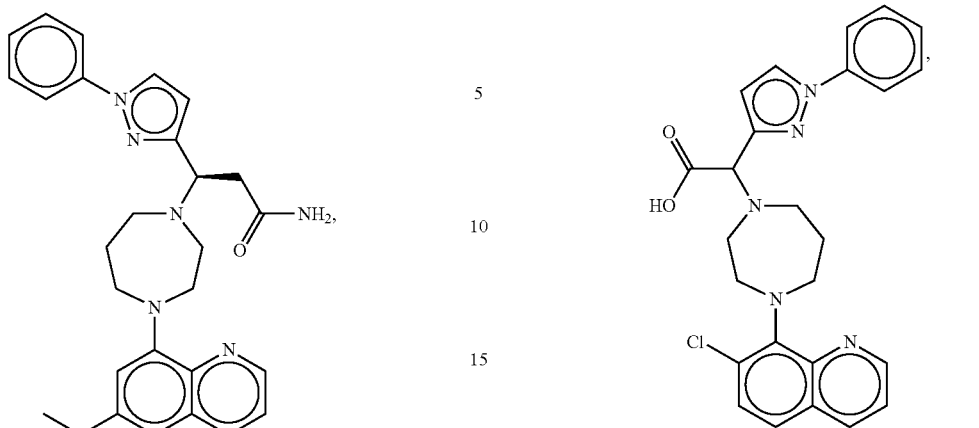
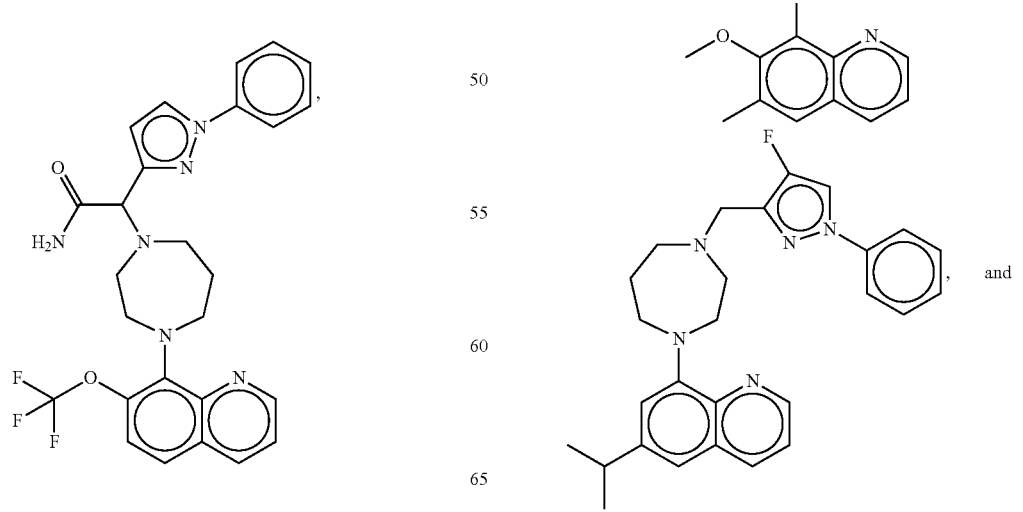

153
-continued
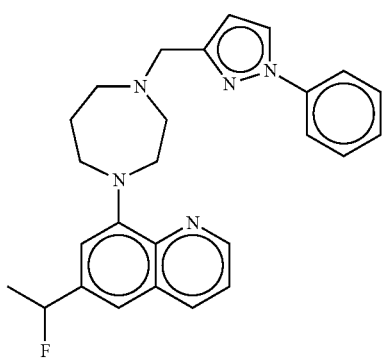
154
-continued
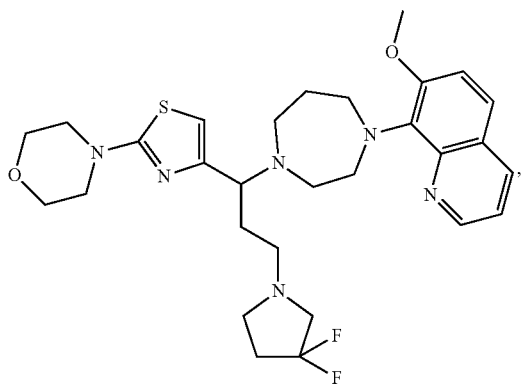
or a pharmaceutically acceptable salt or hydrate thereof.
19. The compound of claim 1, selected from the group consisting of:
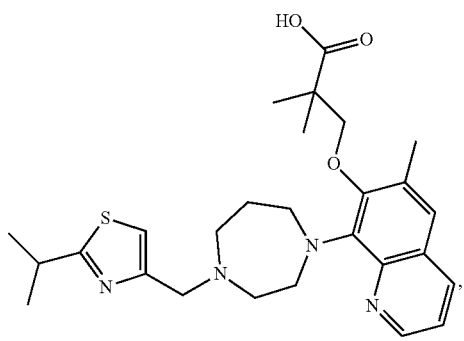
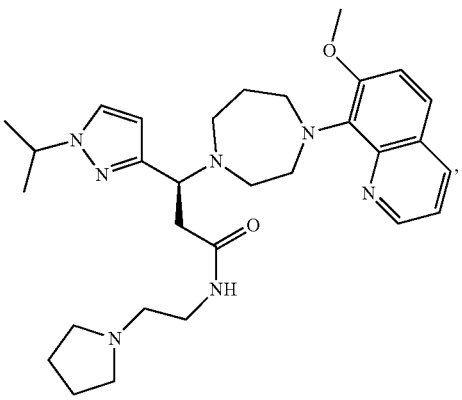
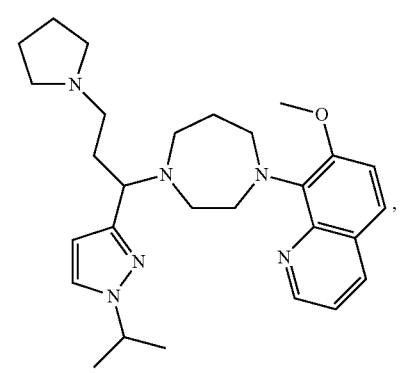
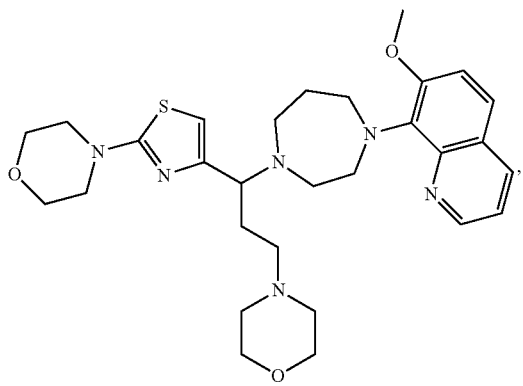
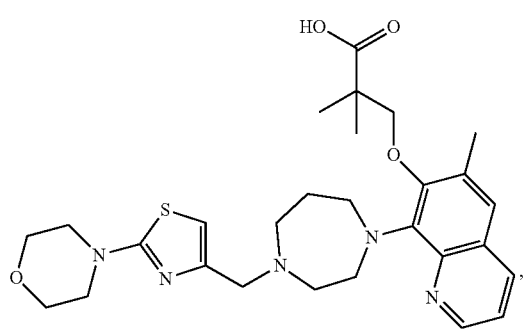
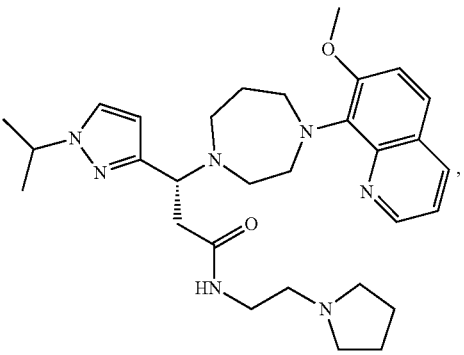

155
-continued
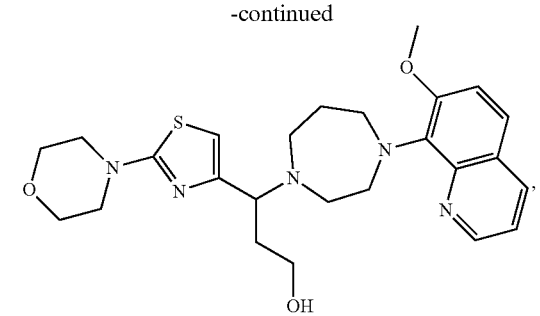
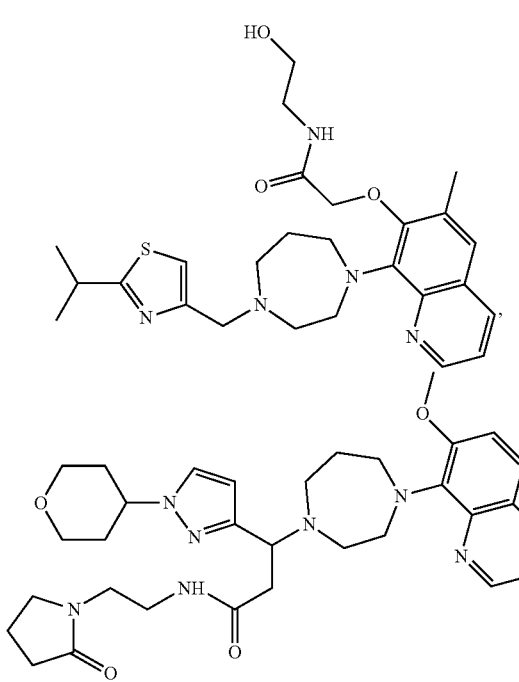
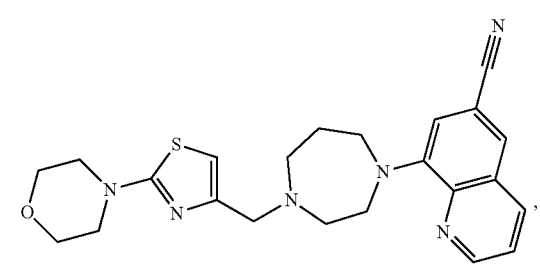
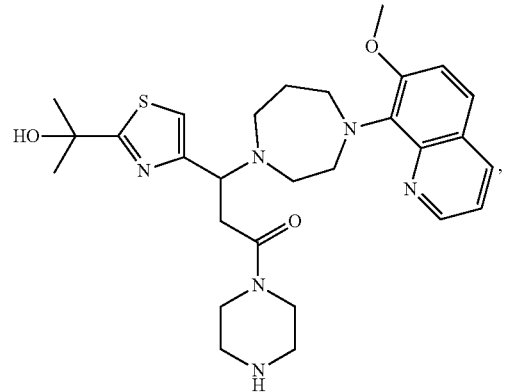
156
-continued
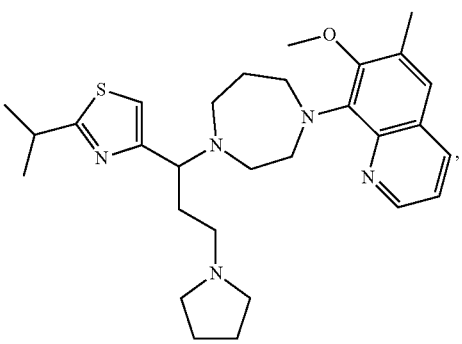
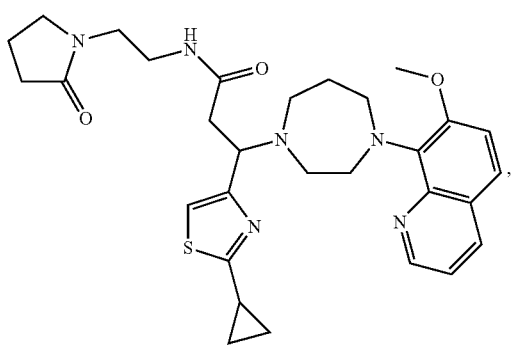
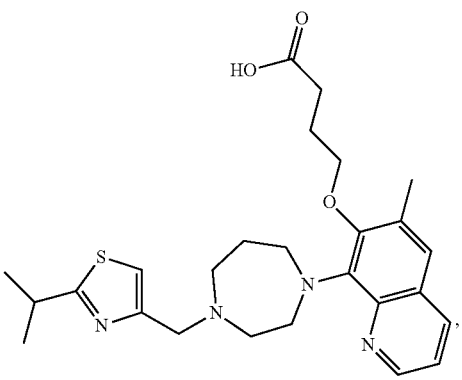
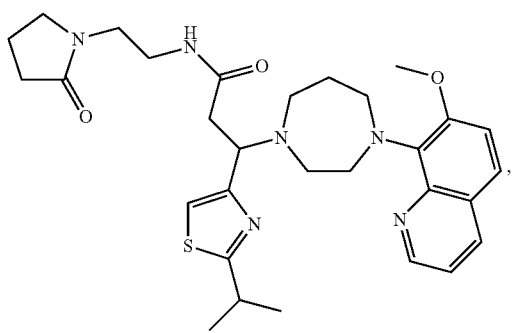

157
-continued
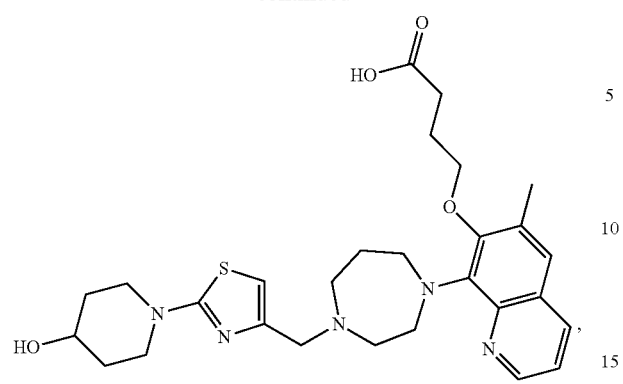
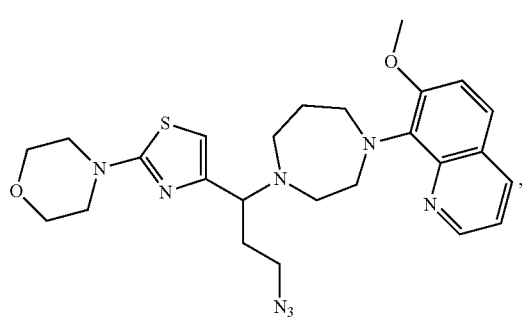
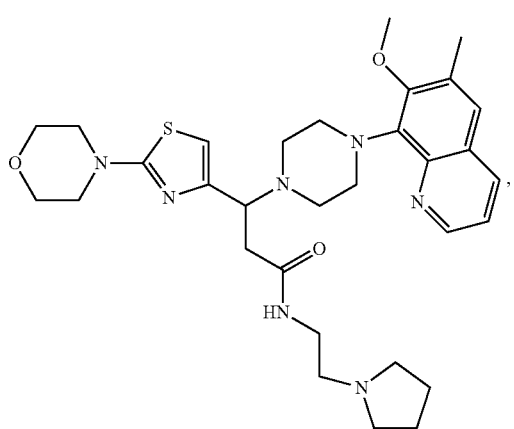
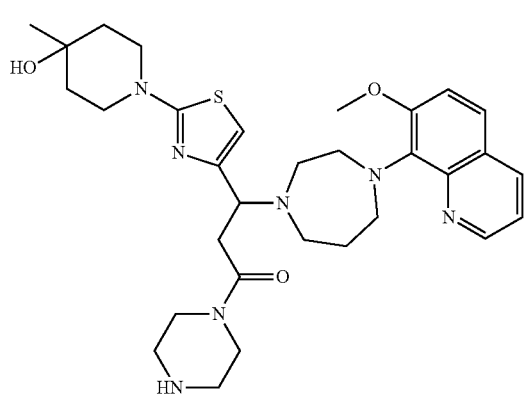
158
-continued
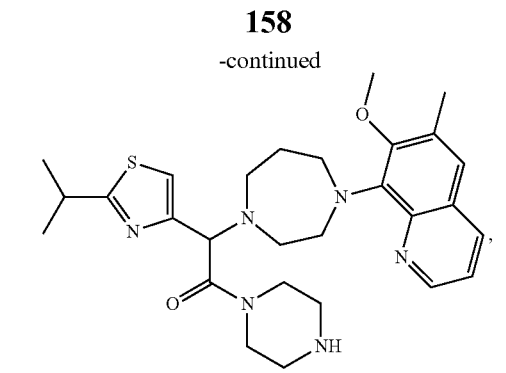
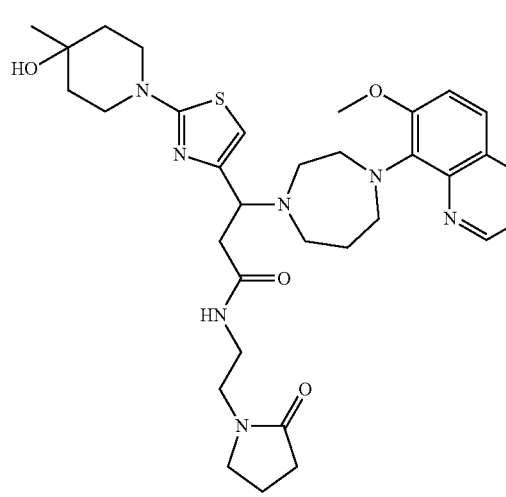
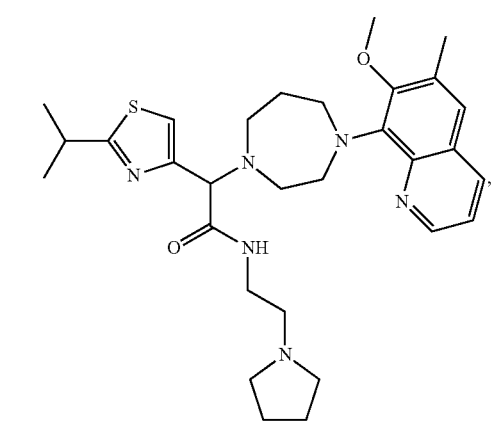
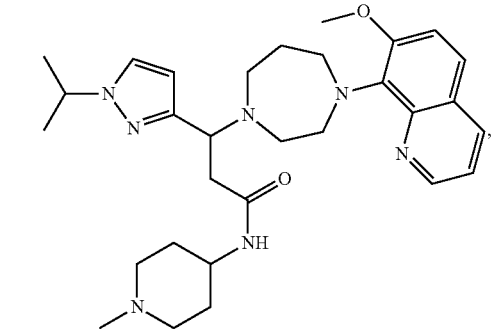

159
-continued
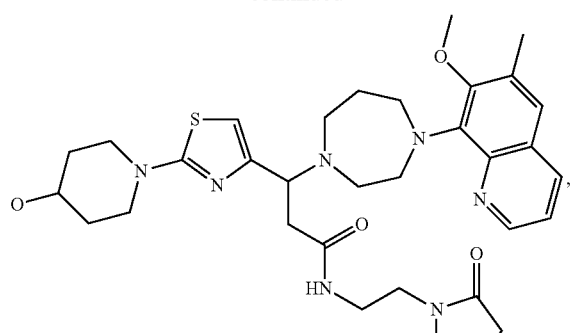
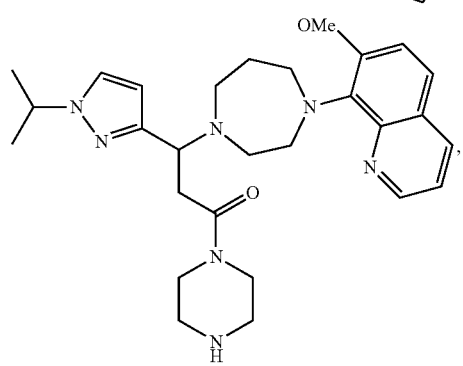
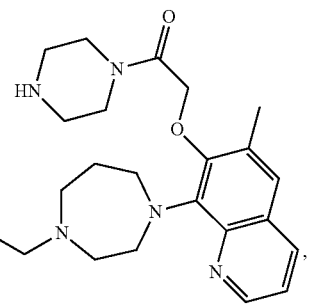
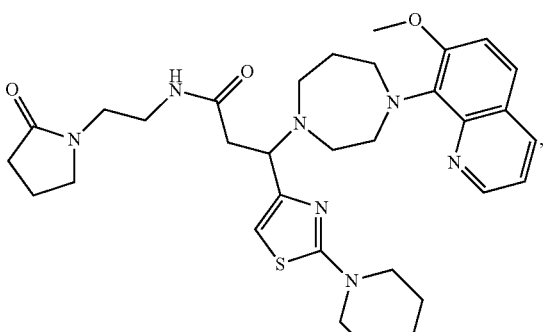
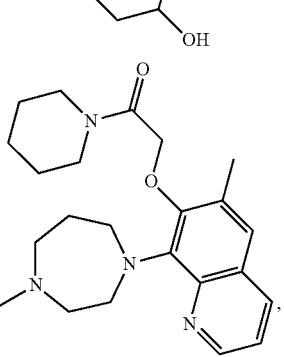
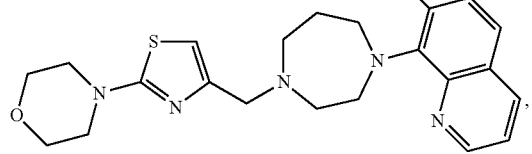
160
-continued
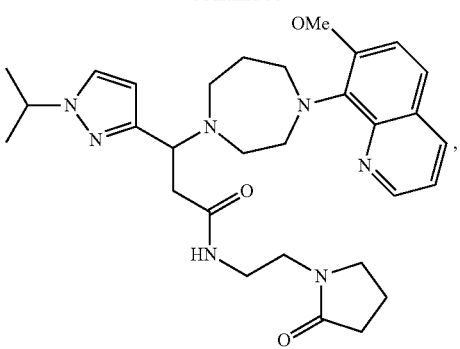
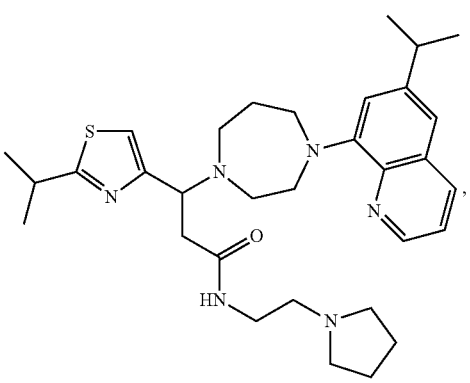
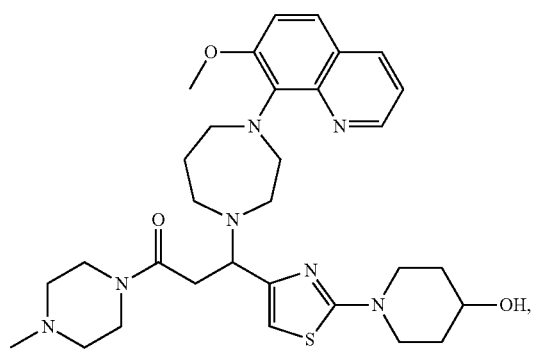
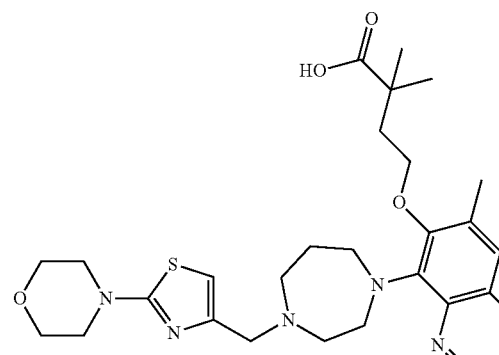
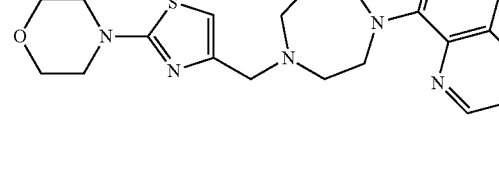

161
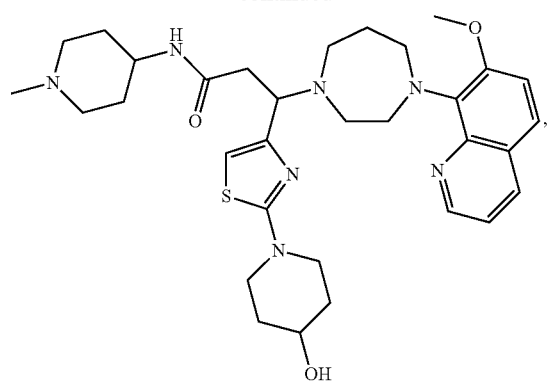
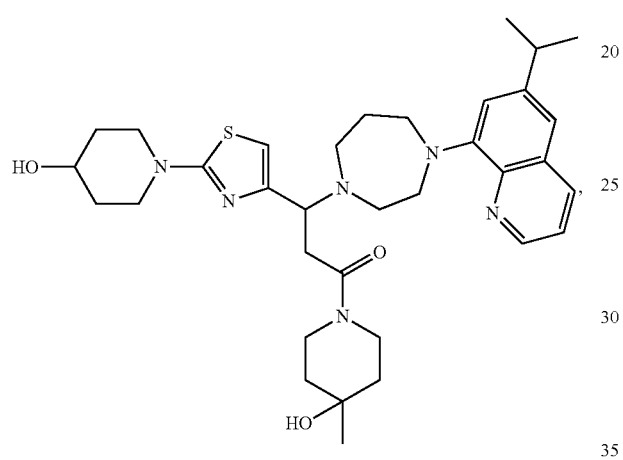
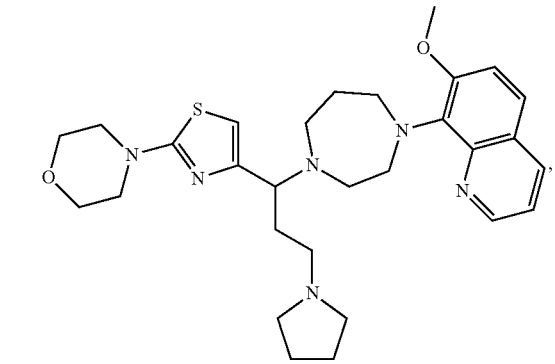
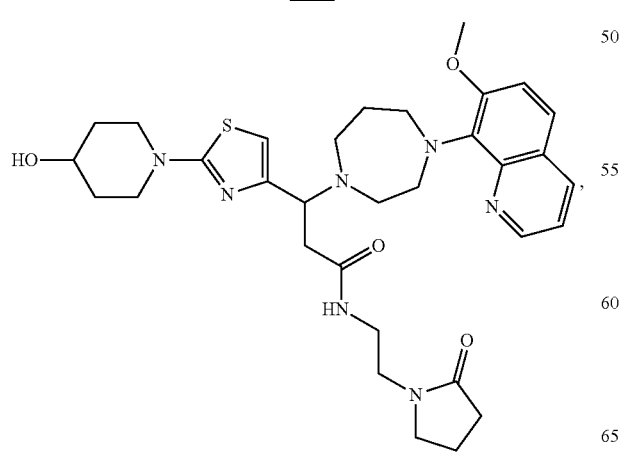
162
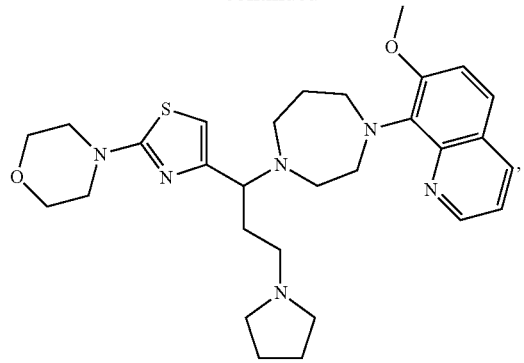
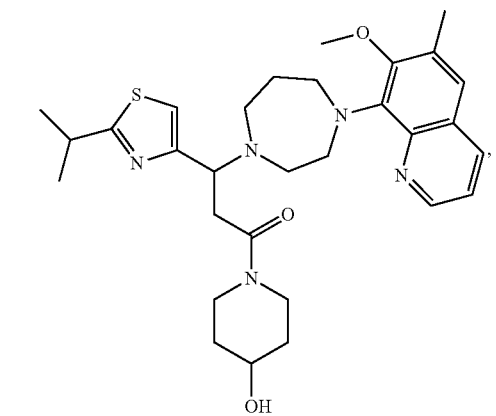
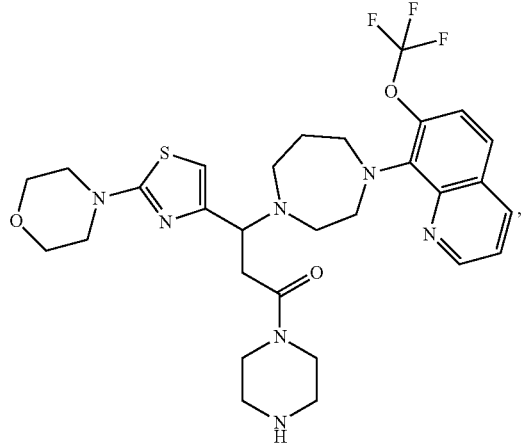
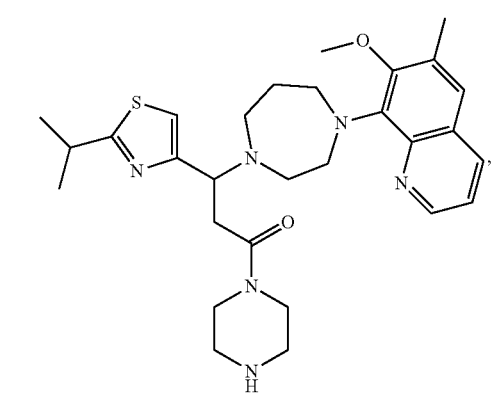

163
-continued
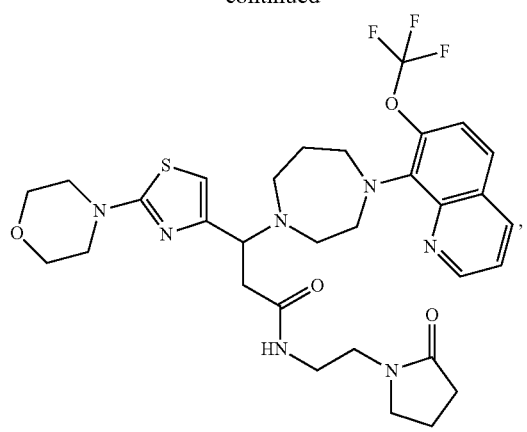
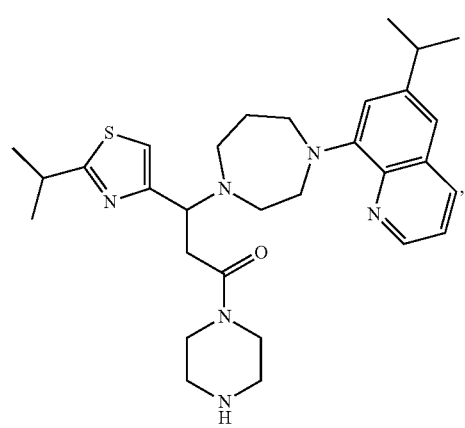
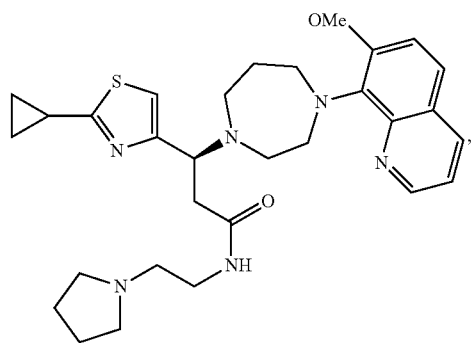
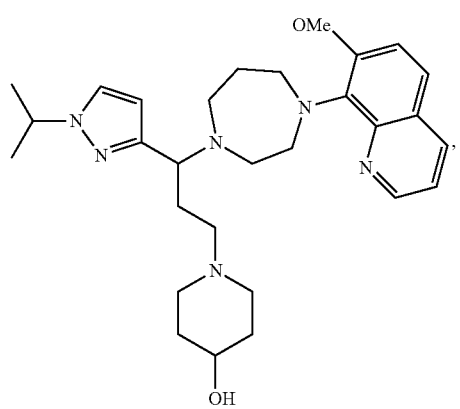
164
-continued
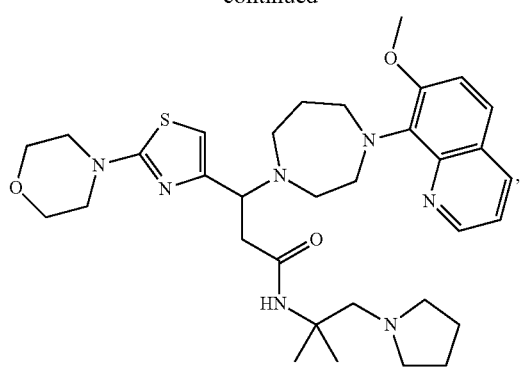
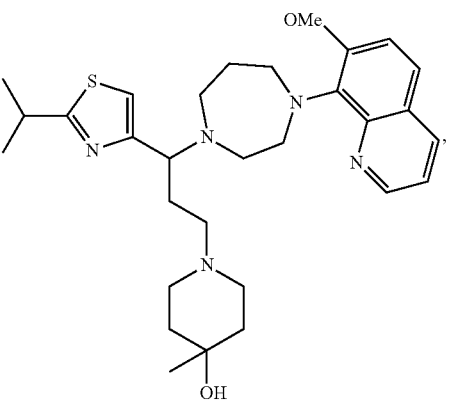
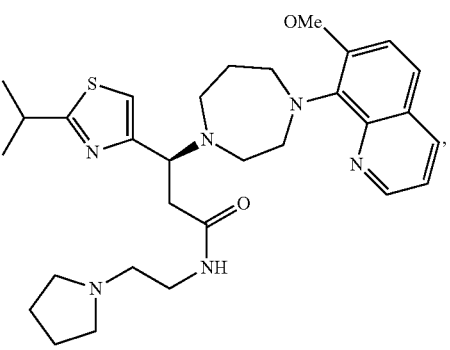
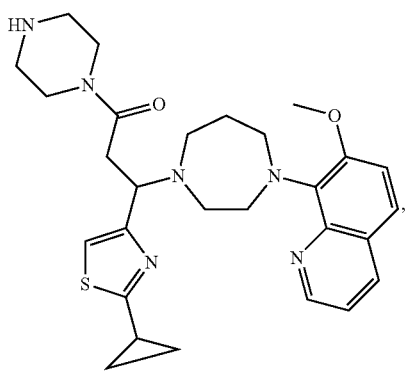

165
-continued
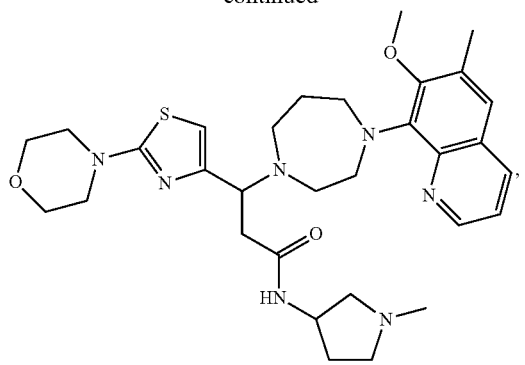
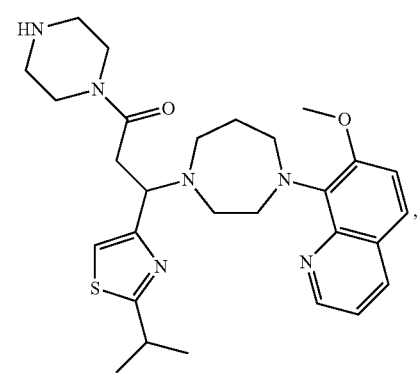
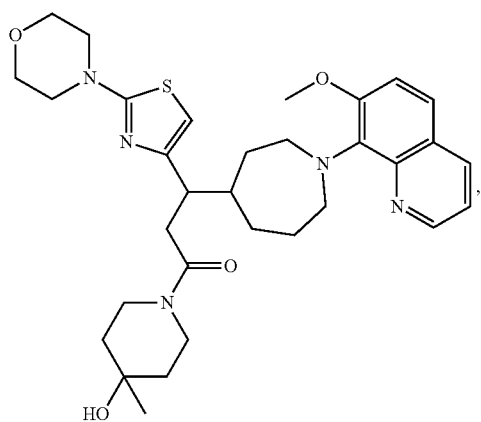
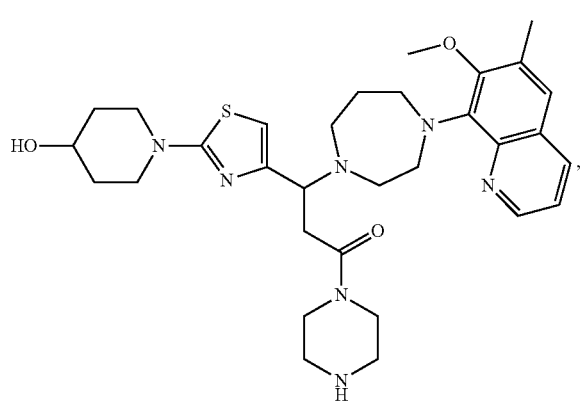
166
-continued
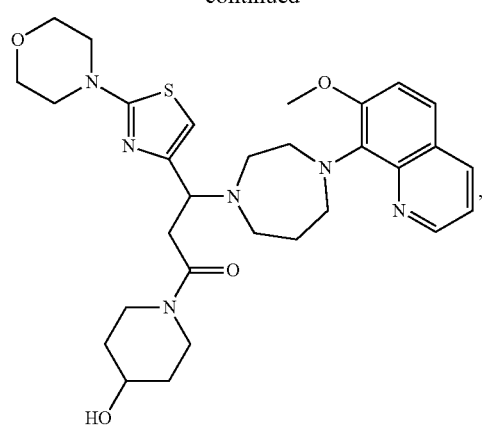
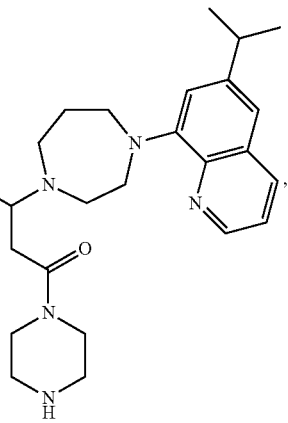
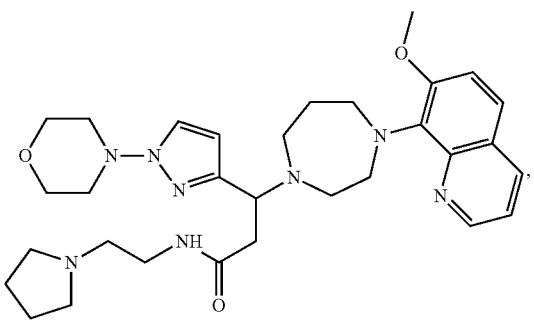
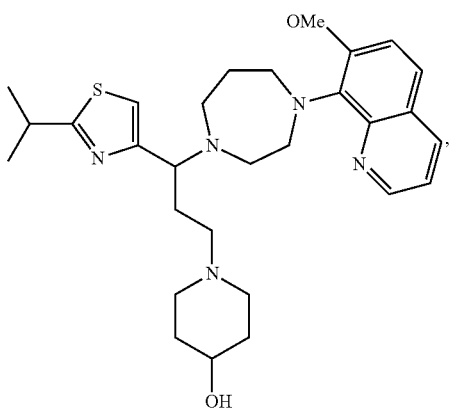

167
-continued
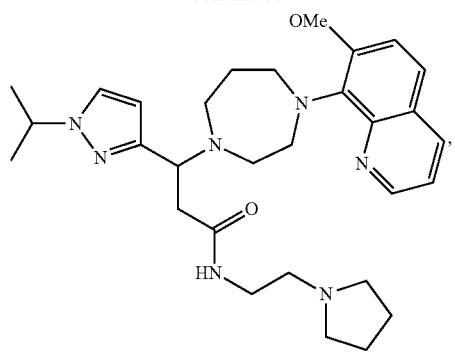
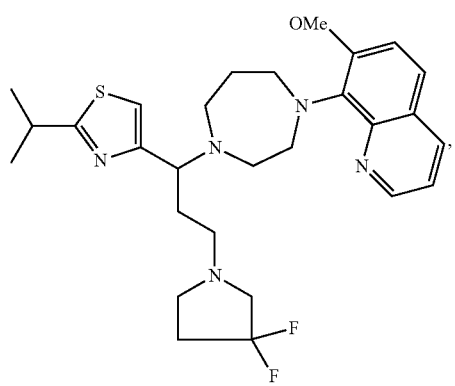
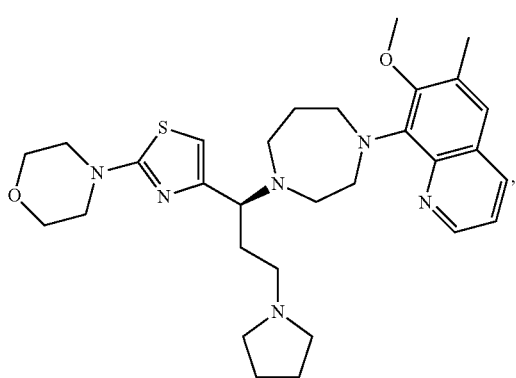
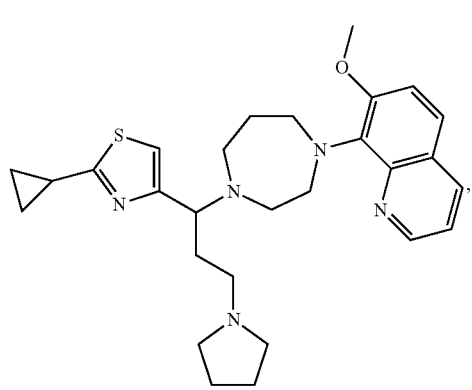
168
-continued
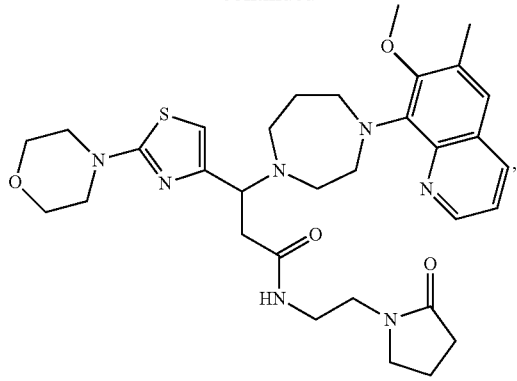
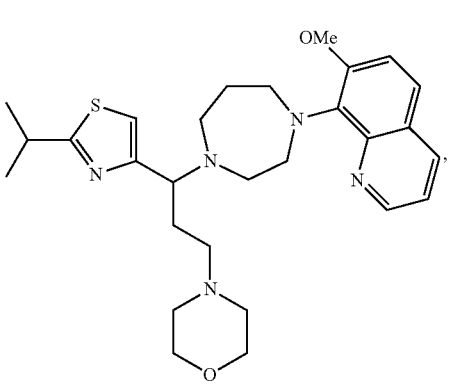
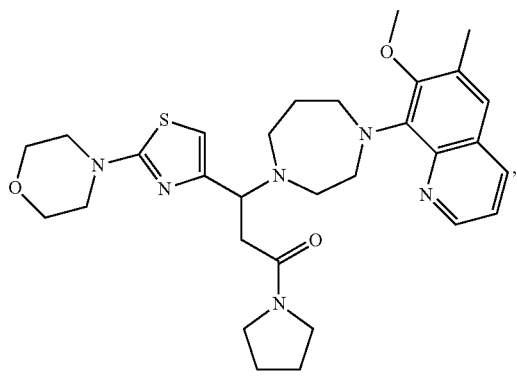
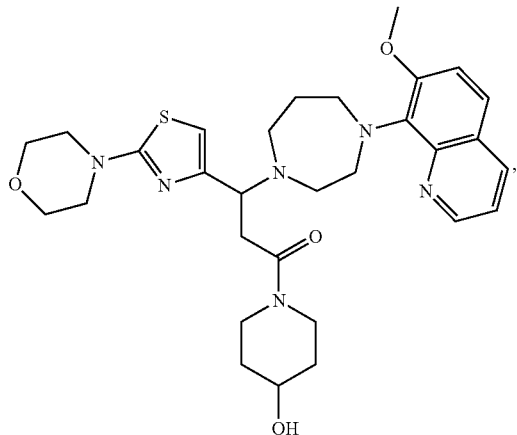

-continued

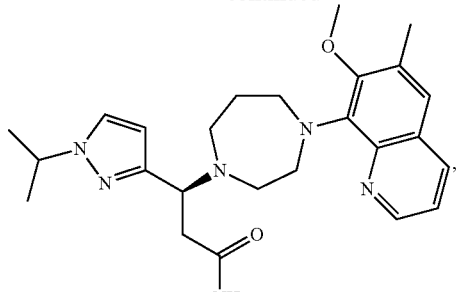
and

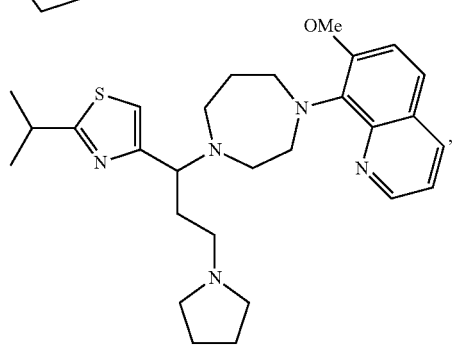

or a pharmaceutically acceptable salt or hydrate thereof.

20. The compound of claim 18 or 19, in isotopically enriched form.

21. The compound of claim 1, wherein n is 0.

22. The compound of claim 1, wherein n is 1, and $R^1$ is methyl.

23. The compound of claim 1, wherein n is 1, and $R^1$ is methyl and each of $R^2$ and $R^3$ is hydrogen.

24. The compound of claim 1, wherein n is 0, and each of $R^2$ and $R^3$ is hydrogen.

25. The compound of claim 1, wherein n is 0, $R^2$ is hydrogen and $R^3$ is selected from the group consisting of methyl, ethyl, —$XR^a$, —$XNR^aR^b$, —$XCONR^aR^b$, —$CO_2H$ and —$CH_2CO_2H$.

26. The compound of claim 1, wherein $R^2$ is hydrogen and $R^3$ is selected from the group consisting of

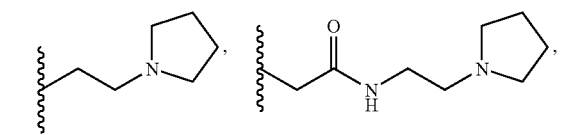

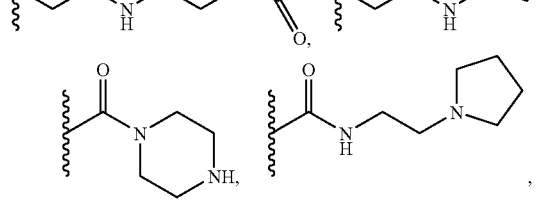

-continued

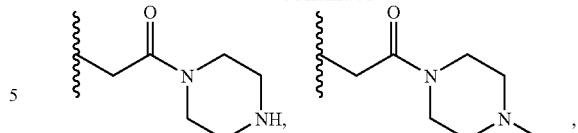

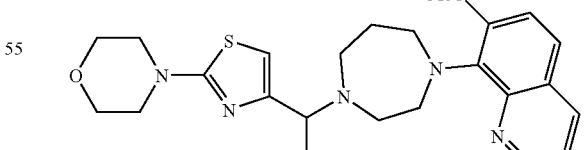

wherein the wavy line indicates the point of attachment to the remainder of the compound.

27. The compound of claim 1, wherein each $R^4$, when present, is selected from the group consisting of methyl, ethyl, isopropyl, 2-fluoroethyl, 2-fluoroisopropyl, 2-hydroxyisopropyl, methoxy, chloro, —$CO_2H$, —$CH_2CO_2H$, oxazolyl and pyridyl.

28. The compound of claim 1, wherein each $R^5$, when present, is selected from the group consisting of methyl, fluoro, chloro, —$CO_2H$ and —$CH_2CO_2H$.

29. The compound of claim 1, wherein each $R^6$, when present, is selected from the group consisting of methyl, fluoro, chloro, —$CO_2H$ and —$CH_2CO_2H$.

30. The compound of claim 1, having the structure:

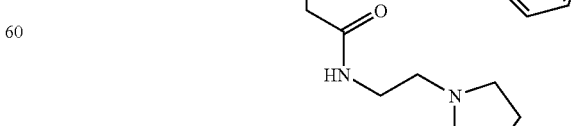

or a pharmaceutically acceptable salt or hydrate thereof.

31. The compound of claim 1, selected from the group consisting of

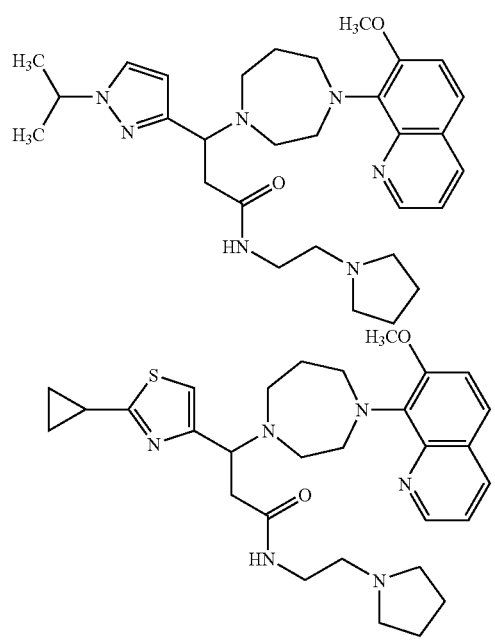

and

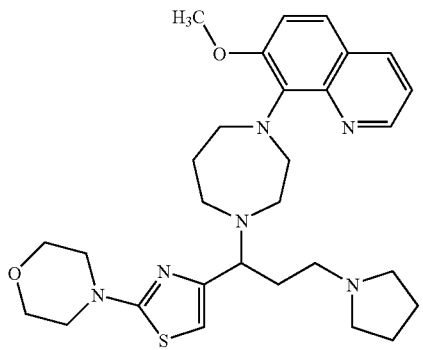

or a pharmaceutically acceptable salt or hydrate thereof.

32. The compound of claim 1, having the structure:

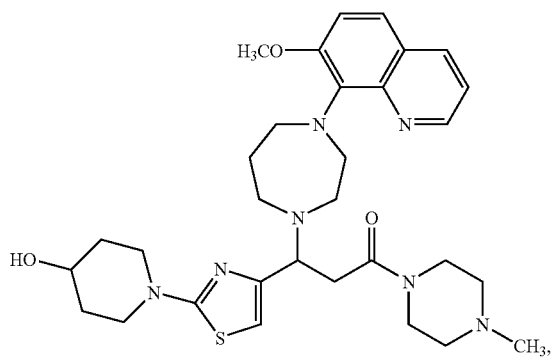

or a pharmaceutically acceptable salt or hydrate thereof.

33. The compound of claim 1, selected from the group consisting of

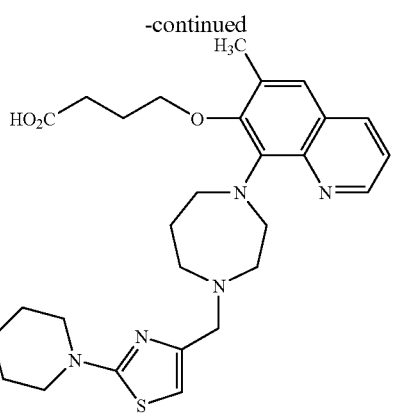

-continued

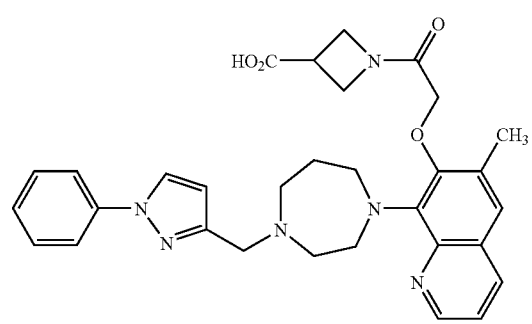

and

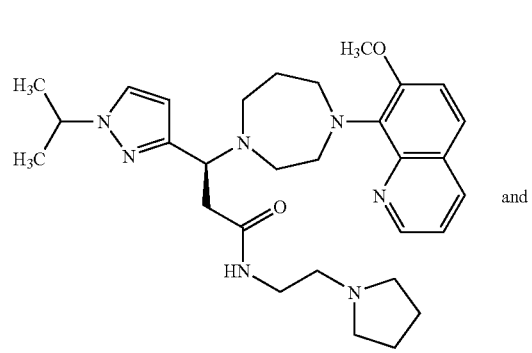

or a pharmaceutically acceptable salt or hydrate thereof.

34. The compound of any one of claims 30 to 33, wherein said compound is in an enantiomerically enriched form.

35. The compound of claim 1, selected from the group consisting of

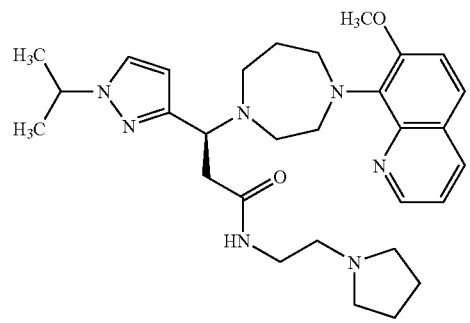

and

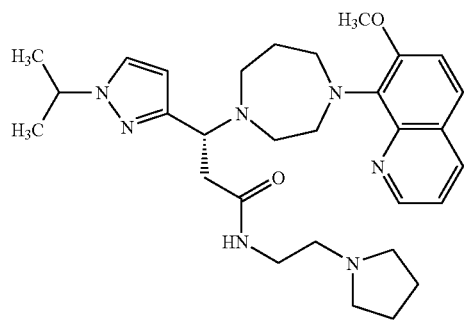

or a pharmaceutically acceptable salt or hydrate thereof.

36. The compound of claim 1, selected from the group consisting of
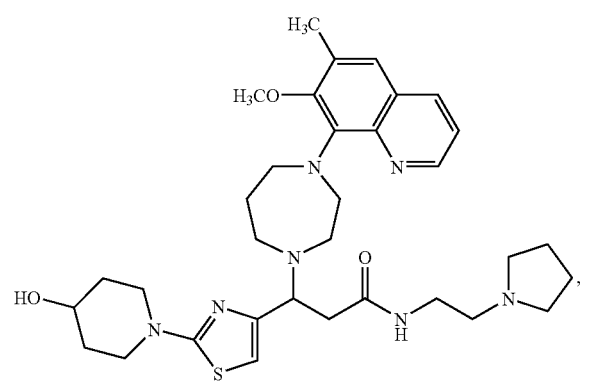
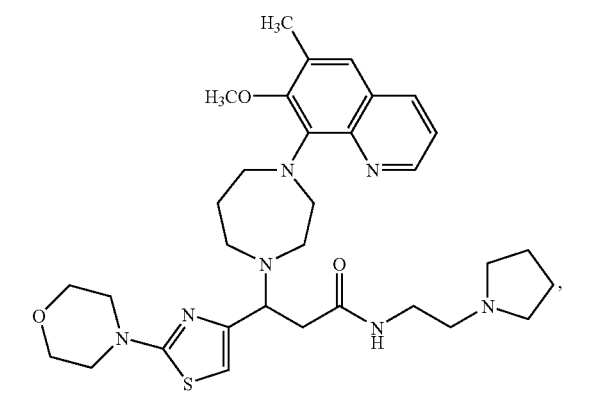
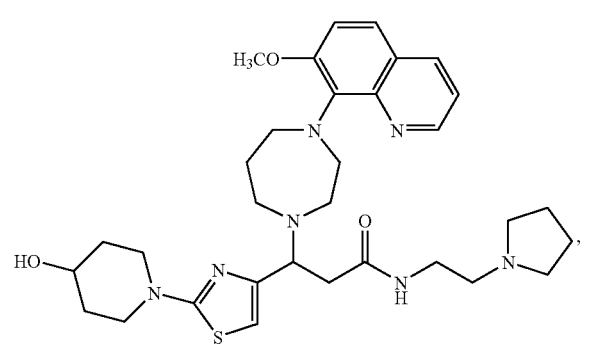
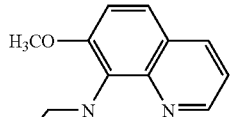
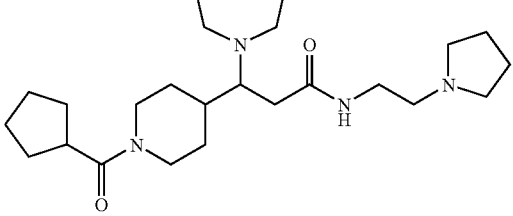
and
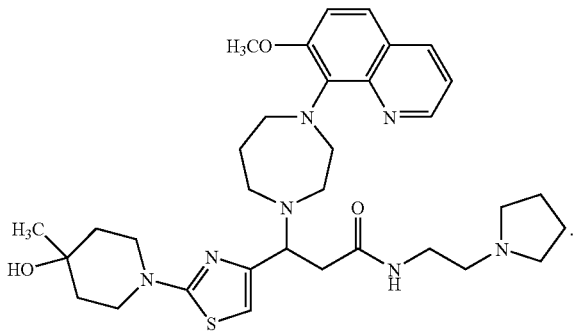
or a pharmaceutically acceptable salt or hydrate thereof.
37. The compound of claim 1, selected from the group consisting of
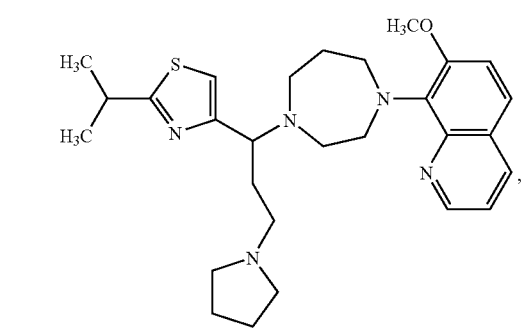
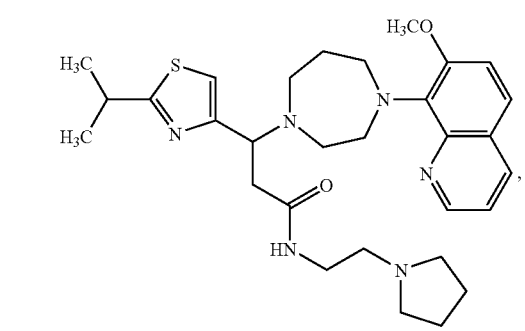

-continued

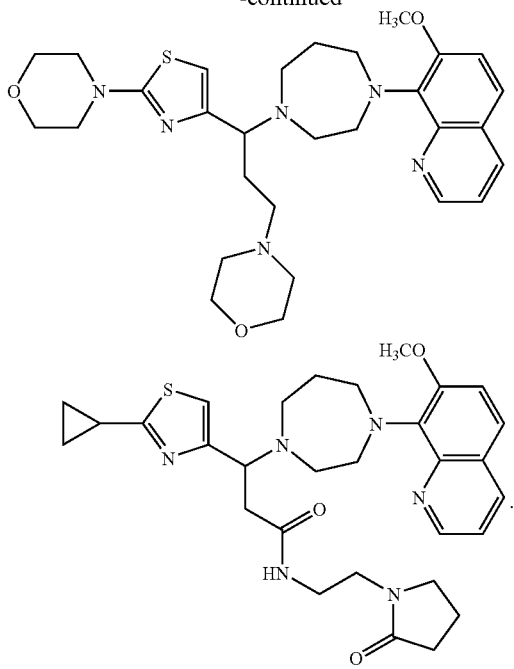

or a pharmaceutically acceptable salt or hydrate thereof.

38. The compound of claim 1, selected from the group consisting of

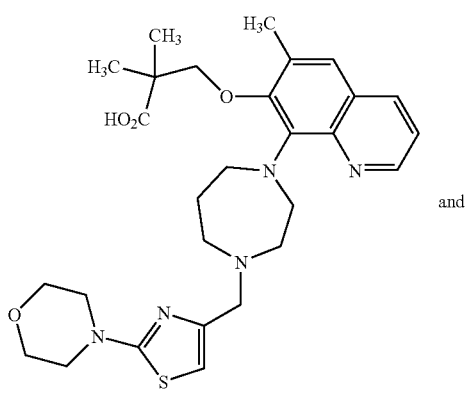

and

-continued

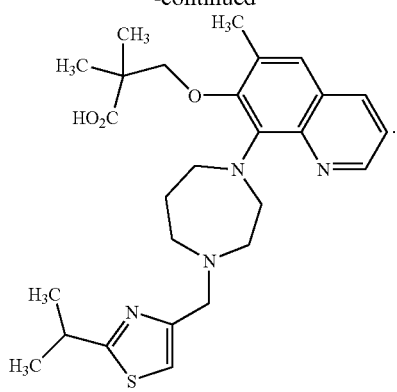

or a pharmaceutically acceptable salt or hydrate thereof.

39. A pharmaceutical composition comprising a compound of claim 1 or a pharmaceutically acceptable salt or hydrate thereof and a pharmaceutically acceptable excipient.

40. A pharmaceutical composition comprising a compound of claim 18 or claim 19, or a pharmaceutically acceptable salt of hydrate thereof and a pharmaceutically acceptable carrier.

41. A method for imaging a tumor, organ, or tissue, said method comprising:
(a) administering to a subject in need of such imaging, a radiolabeled or detectable form of a compound of claim 1; and
(b) detecting said compound to determine where said compound is concentrated in said subject.

42. A method in accordance with claim 41, wherein said compound is radiolabeled.

* * * * *

UNITED STATES PATENT AND TRADEMARK OFFICE
CERTIFICATE OF CORRECTION

| | |
|---|---|
| PATENT NO. | : 8,288,373 B2 |
| APPLICATION NO. | : 12/612638 |
| DATED | : October 16, 2012 |
| INVENTOR(S) | : Chen et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 268 days.

Signed and Sealed this
Twenty-seventh Day of November, 2012

David J. Kappos
*Director of the United States Patent and Trademark Office*

SEQUENCE LISTING

```
<160> NUMBER OF SEQ ID NOS: 12

<210> SEQ ID NO 1
<211> LENGTH: 1089
<212> TYPE: DNA
<213> ORGANISM: Homo sapiens
<220> FEATURE:
<223> OTHER INFORMATION: human chemokine receptor CXCR7 (RDC1, CCXCKR2)

<400> SEQUENCE: 1
atggatctgc atctcttcga ctactcagag ccagggaact tctcggacat cagctggcca        60
tgcaacagca gcgactgcat cgtggtggac acggtgatgt gtcccaacat gcccaacaaa       120
agcgtcctgc tctacacgct ctccttcatt tacattttca tcttcgtcat cggcatgatt       180
gccaactccg tggtggtctg ggtgaatatc caggccaaga ccacaggcta tgacacgcac       240
tgctacatct tgaacctggc cattgccgac ctgtgggttg tcctcaccat cccagtctgg       300
gtggtcagtc tcgtgcagca caaccagtgg cccatgggcg agctcacgtg caaagtcaca       360
cacctcatct tctccatcaa cctcttcggc agcatttttct tcctcacgtg catgagcgtg       420
gaccgctacc tctccatcac ctacttcacc aacacccca gcagcaggaa gaagatggta       480
cgccgtgtcg tctgcatcct ggtgtggctg ctggccttct gcgtgtctct gcctgacacc       540
tactacctga agaccgtcac gtctgcgtcc aacaatgaga cctactgccg gtccttctac       600
cccgagcaca gcatcaagga gtggctgatc ggcatggagc tggtctccgt tgtcttgggc       660
tttgccgttc ccttctccat tatcgctgtc ttctacttcc tgctggccag agccatctcg       720
gcgtccagtg accaggagaa gcacagcagc cggaagatca tcttctccta cgtggtggtc       780
ttccttgtct gctggctgcc ctaccacgtg gcggtgctgc tggacatctt ctccatcctg       840
cactacatcc ctttcacctg ccggctggag cacgccctct tcacggccct gcatgtcaca       900
cagtgcctgt cgctggtgca ctgctgcgtc aaccctgtcc tctacagctt catcaatcgc       960
aactacaggt acgagctgat gaaggccttc atcttcaagt actcggccaa acagggctc      1020 accaagctca tcgatgcctc cagagtctca gagacggagt actctgcctt ggagcagagc      1080
accaaatga                                                              1089

<210> SEQ ID NO 2
<211> LENGTH: 362
<212> TYPE: PRT
<213> ORGANISM: Homo sapiens
<220> FEATURE:
<223> OTHER INFORMATION: human chemokine receptor CXCR7 (RDC1, CCXCKR2)

<400> SEQUENCE: 2
```

```
Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
            115                 120                 125

Phe Gly Ser Ile Phe Phe Leu Thr Cys Met Ser Val Asp Arg Tyr Leu
        130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 3
<211> LENGTH: 1089
<212> TYPE: DNA
<213> ORGANISM: Homo sapiens
<220> FEATURE:
<223> OTHER INFORMATION: human chemokine receptor CXCR7.2

<400> SEQUENCE: 3
```

```
atggatctgc acctcttcga ctacgccgag ccaggcaact tctcggacat cagctggcca    60
tgcaacagca gcgactgcat cgtggtggac acggtgatgt gtcccaacat gcccaacaaa   120
agcgtcctgc tctacacgct ctccttcatt tacattttca tcttcgtcat cggcatgatt   180
gccaactccg tggtggtctg ggtgaatatc caggccaaga ccacaggcta tgacacgcac   240
tgctacatct tgaacctggc cattgccgac ctgtgggttg tcctcaccat cccagtctgg   300
gtggtcagtc tcgtgcagca caaccagtgg cccatgggcg agctcacgtg caaagtcaca   360
cacctcatct tctccatcaa cctcttcagc ggcattttct tcctcacgtg catgagcgtg   420
gaccgctacc tctccatcac ctacttcacc aacacccccaa gcagcaggaa gaagatggta   480
cgccgtgtcg tctgcatcct ggtgtggctg ctggccttct gcgtgtctct gcctgacacc   540
tactacctga agaccgtcac gtctgcgtcc aacaatgaga cctactgccg gtccttctac   600
cccgagcaca gcatcaagga gtggctgatc ggcatggagc tggtctccgt tgtcttgggc   660
tttgccgttc ccttctccat tatcgctgtc ttctacttcc tgctggccag agccatctcg   720
gcgtccagtg accaggagaa gcacagcagc cggaagatca tcttctccta cgtggtggtc   780
ttccttgtct gctggctgcc ctaccacgtg gcggtgctgc tggacatctt ctccatcctg   840
cactacatcc ctttcacctg ccggctggag cacgccctct tcacggccct gcatgtcaca   900
cagtgcctgt cgctggtgca ctgctgcgtc aaccctgtcc tctacagctt catcaatcgc   960
aactacaggt acgagctgat gaaggccttc atcttcaagt actcggccaa acagggctcc  1020
accaagctca tcgatgcctc cagagtgtcg gagacggagt actccgcctt ggagcaaaac  1080
gccaagtga                                                          1089
```

<210> SEQ ID NO 4
<211> LENGTH: 362
<212> TYPE: PRT
<213> ORGANISM: Homo sapiens
<220> FEATURE:
<223> OTHER INFORMATION: human chemokine receptor CXCR7.2

<400> SEQUENCE: 4

```
Met Asp Leu His Leu Phe Asp Tyr Ala Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Gly Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175
```

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Asn Ala Lys
        355                 360

<210> SEQ ID NO 5
<211> LENGTH: 1089
<212> TYPE: DNA
<213> ORGANISM: Homo sapiens
<220> FEATURE:
<223> OTHER INFORMATION: human chemokine receptor CXCR7.3

<400> SEQUENCE: 5

| | | |
|---|---|---|
| atggatctgc atctcttcga ctactcagag ccagggaact tctcggacat cagctggcca | 60 |
| tgcaacagca gcgactgcat cgtggtggac acggtgatgt gtcccaacat gcccaacaaa | 120 |
| agcgtcctgc tctacacgct ctccttcatt tacattttca tcttcgtcat cggcatgatt | 180 |
| gccaactccg tggtggtctg ggtgaatatc caggccaaga ccacaggcta tgacacgcac | 240 |
| tgctacatct tgaacctggc cattgccgac ctgtgggttg tcctcaccat cccagtctgg | 300 |
| gtggtcagtc tcgtgcagca caaccagtgg cccatgggcg agctcacgtg caaagtcaca | 360 |
| cacctcatct tctccatcaa cctcttcggc agcattttct cctcacgtg catgagcgtg | 420 |
| gaccgctacc tctccatcac ctacttcacc aacacccca gcagcaggaa gaagatggta | 480 |
| cgccgtgtcg tctgcatcct ggtgtggctg ctggccttct gcgtgtctct gcctgacacc | 540 |
| tactacctga gaccgtcac gtctgcgtcc aacaatgaga cctactgccg gtccttctac | 600 |
| cccgagcaca gcatcaagga gtggctgatc ggcatggagc tggtctccgt tgtcttgggc | 660 |
| tttgccgttc ccttctccat tgtcgctgtc ttctacttcc tgctggccag agccatctcg | 720 |
| gcgtccagtg accaggagaa gcacagcagc cggaagatca tcttctccta cgtggtggtc | 780 |
| ttccttgtct gctggttgcc ctaccacgtg gcggtgctgc tggacatctt ctccatcctg | 840 |
| cactacatcc ctttcacctg ccggctggag cacgccctct tcacggccct gcatgtcaca | 900 |
| cagtgcctgt cgctggtgca ctgctgcgtc aaccctgtcc tctacagctt catcaatcgc | 960 |
| aactacaggt acgagctgat gaaggccttc atcttcaagt actcggccaa acagggctc | 1020 | accaagctca tcgatgcctc cagagtctca gagacggagt actctgcctt ggagcagagc    1080 accaaatga                                                             1089

<210> SEQ ID NO 6
<211> LENGTH: 362
<212> TYPE: PRT
<213> ORGANISM: Homo sapiens
<220> FEATURE:
<223> OTHER INFORMATION: human chemokine receptor CXCR7.3

<400> SEQUENCE: 6

```
Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Val Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350
```

Glu Tyr Ser Ala Leu Glu Gln Ser Thr Lys
        355                 360

<210> SEQ ID NO 7
<211> LENGTH: 1089
<212> TYPE: DNA
<213> ORGANISM: Homo sapiens
<220> FEATURE:
<223> OTHER INFORMATION: human chemokine receptor CXCR7.4

<400> SEQUENCE: 7

| | | | | | |
|---|---|---|---|---|---|
| atggatctgc | atctcttcga | ctactcagag | ccagggaact | tctcggacat | cagctggcca | 60 |
| tgcaacagca | gcgactgcat | cgtggtggac | acggtgatgt | gtcccaacat | gcccaacaaa | 120 |
| agcgtcctgc | tctacacgct | ctccttcatt | tacattttca | tcttcgtcat | cggcatgatt | 180 |
| gccaactccg | tggtggtctg | ggtgaatatc | caggccaaga | ccacaggcta | tgacacgcac | 240 |
| tgctacatct | tgaacctggc | cattgccgac | ctgtgggttg | tcctcaccat | cccagtctgg | 300 |
| gtggtcagtc | tcgtgcagca | caaccagtgg | cccatgggcg | agctcacgtg | caaagtcaca | 360 |
| cacctcatct | tctccatcaa | cctcttcggc | agcattttct | tcctcacgtg | catgagcgtg | 420 |
| gaccgctacc | tctccatcac | ctacttcacc | aacacccca | gcagcaggaa | gaagatggta | 480 |
| cgccgtgtcg | tctgcatcct | ggtgtggctg | ctggccttct | gcgtgtctct | gcctgacacc | 540 |
| tactacctga | agaccgtcac | gtctgcgtcc | aacaatgaga | cctactgccg | gtccttctac | 600 |
| cccgagcaca | gcatcaagga | gtggctgatc | ggcatggagc | tggtctccgt | tgtcttgggc | 660 |
| tttgccgttc | ccttctccat | tatcgctgtc | ttctacttcc | tgctggccag | agccatctcg | 720 |
| gcgtccagtg | accaggagaa | gcacagcagc | cggaagatca | tcttctccta | cgtggtggtc | 780 |
| ttccttgtct | gctggctgcc | ctaccacgtg | gcggtgctgc | tggacatctt | ctccatcctg | 840 |
| cactacatcc | ctttcacctg | ccggctggag | cacgccctct | tcacggccct | gcatgtcaca | 900 |
| cagtgcctgt | cgctggtgca | ctgctgcgtc | aaccctgtcc | tctacagctt | catcaatcgc | 960 |
| aactacaggt | acgagctgat | gaaggccttc | atcttcaagt | actcggccaa | aacagggctc | 1020 |
| accaagctca | tcgatgcctc | cagagtctca | gagacggagt | actctgcctt | ggagcagagc | 1080 |
| accaaatga | | | | | | 1089 |

<210> SEQ ID NO 8
<211> LENGTH: 362
<212> TYPE: PRT
<213> ORGANISM: Homo sapiens
<220> FEATURE:
<223> OTHER INFORMATION: human chemokine receptor CXCR7.4

<400> SEQUENCE: 8

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

```
Ile Pro Val Trp Val Ser Leu Val Gln His Asn Gln Trp Pro Met
            100                 105                 110
Gly Glu Leu Thr Cys Lys Val Thr His Leu Ile Phe Ser Ile Asn Leu
        115                 120                 125
Phe Gly Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
            180                 185                 190
Glu Thr Tyr Cys Arg Ser Phe Tyr Pro Glu His Ser Ile Lys Glu Trp
        195                 200                 205
Leu Ile Gly Met Glu Leu Val Ser Val Val Leu Gly Phe Ala Val Pro
    210                 215                 220
Phe Ser Ile Ile Ala Val Phe Tyr Phe Leu Leu Ala Arg Ala Ile Ser
225                 230                 235                 240
Ala Ser Ser Asp Gln Glu Lys His Ser Ser Arg Lys Ile Ile Phe Ser
                245                 250                 255
Tyr Val Val Val Phe Leu Val Cys Trp Leu Pro Tyr His Val Ala Val
            260                 265                 270
Leu Leu Asp Ile Phe Ser Ile Leu His Tyr Ile Pro Phe Thr Cys Arg
        275                 280                 285
Leu Glu His Ala Leu Phe Thr Ala Leu His Val Thr Gln Cys Leu Ser
    290                 295                 300
Leu Val His Cys Cys Val Asn Pro Val Leu Tyr Ser Phe Ile Asn Arg
305                 310                 315                 320
Asn Tyr Arg Tyr Glu Leu Met Lys Ala Phe Ile Phe Lys Tyr Ser Ala
                325                 330                 335
Lys Thr Gly Leu Thr Lys Leu Ile Asp Ala Ser Arg Val Ser Glu Thr
            340                 345                 350
Glu Tyr Ser Ala Leu Glu Gln Ser Thr Lys
        355                 360

<210> SEQ ID NO 9
<211> LENGTH: 1089
<212> TYPE: DNA
<213> ORGANISM: Homo sapiens
<220> FEATURE:
<223> OTHER INFORMATION: human chemokine receptor CXCR7.5

<400> SEQUENCE: 9
atggatctgc atctcttcga ctactcagag ccagggaact tctcggacat cagctggccg     60
tgcaacagca gcgactgcat cgtggtggac acggtgatgt gtcccaacat gcccaacaaa    120
agcgtcctgc tctacacgct ctccttcatt tacattttca tcttcgtcat cggcatgatt    180
gccaactccg tggtggtctg ggtgaatatc caggccaaga ccacaggcta tgacacgcac    240
tgctacatct tgaacctggc cattgccgac ctgtgggttg tcctcaccat cccagtctgg    300
gtggtcagtc tcgtgcagca caaccagtgg cccatgggcg agctcacgtg caaagtcaca    360
cacctcatct tctccatcaa cctcttcagc agcattttct tcctcacgtg catgagcgtg    420
gaccgctacc tctccatcac ctacttcacc aacaccccca gcagcaggaa gaagatggta    480
cgccgtgtcg tctgcatcct ggtgtggctg ctggccttct gcgtgtctct gcctgacacc    540
tactacctga agaccgtcac gtctgcgtcc aacaatgaga cctactgccg gtccttctac    600
```

```
cccgagcaca gcatcaagga gtggctgatc ggcatggagc tggtctccgt tgtcttgggc    660
tttgccgttc ccttctccat tatcgctgtc ttctacttcc tgctggccag agccatctcg    720
gcgtccagtg accaggagaa gcacagcagc cggaagatca tcttctccta cgtggtggtc    780
ttccttgtct gctggttgcc ctaccacgtg gcggtgctgc tggacatctt ctccatcctg    840
cactacatcc ctttcacctg ccggctggag cacgccctct tcacggccct gcatgtcaca    900
cagtgcctgt cgctggtgca ctgctgcgtc aaccctgtcc tctacagctt catcaatcgc    960
aactacaggt acgagctgat gaaggccttc atcttcaagt actcggccaa aacagggctc   1020
accaagctca tcgatgcctc cagagtctca gagacggagt actccgcctt ggagcagagc   1080
accaaatga                                                           1089
```

<210> SEQ ID NO 10
<211> LENGTH: 362
<212> TYPE: PRT
<213> ORGANISM: Homo sapiens
<220> FEATURE:
<223> OTHER INFORMATION: human chemokine receptor CXCR7.5

<400> SEQUENCE: 10

```
Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270
```

```
Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
                340                 345                 350

Glu Tyr Ser Ala Leu Glu Gln Ser Thr Lys
        355                 360

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:synthetic
      PCR primer hRDC1F

<400> SEQUENCE: 11
gaatgcggcc gctatggatc tgcatctctt cgact                              35

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:synthetic
      PCR primer hRDC1R

<400> SEQUENCE: 12
gaatgcggcc gctcatttgg tgctctgctc caag                               34
```